United States Patent
Sasu et al.

(10) Patent No.: US 12,296,012 B2
(45) Date of Patent: *May 13, 2025

(54) CHIMERIC ANTIGEN RECEPTORS TARGETING FLT3

(71) Applicant: Pfizer Inc., New York, NY (US)

(72) Inventors: Barbra Johnson Sasu, San Francisco, CA (US); Danielle Elizabeth Dettling, San Francisco, CA (US); Cesar Adolfo Sommer, San Mateo, CA (US); Yik Andy Yeung, South San Francisco, CA (US); Moustafa Marc Hamze, Nogent-sur-Marne (FR)

(73) Assignee: PFIZER INC., New York, NY (US)

( * ) Notice: Subject to any disclaimer, the term of this patent is extended or adjusted under 35 U.S.C. 154(b) by 1448 days.

This patent is subject to a terminal disclaimer.

(21) Appl. No.: 16/617,487

(22) PCT Filed: May 31, 2018

(86) PCT No.: PCT/US2018/035492
§ 371 (c)(1),
(2) Date: Nov. 26, 2019

(87) PCT Pub. No.: WO2018/222935
PCT Pub. Date: Dec. 6, 2018

(65) Prior Publication Data
US 2023/0181634 A1    Jun. 15, 2023

Related U.S. Application Data

(60) Provisional application No. 62/660,908, filed on Apr. 20, 2018, provisional application No. 62/514,634, filed on Jun. 2, 2017, provisional application No. 62/514,574, filed on Jun. 2, 2017.

(51) Int. Cl.
| | |
|---|---|
| *A61K 45/06* | (2006.01) |
| *A61K 38/00* | (2006.01) |
| *A61K 39/00* | (2006.01) |
| *A61K 39/395* | (2006.01) |
| *A61P 35/02* | (2006.01) |
| *C07K 14/705* | (2006.01) |
| *C07K 14/715* | (2006.01) |
| *C07K 14/725* | (2006.01) |
| *C07K 16/28* | (2006.01) |

(52) U.S. Cl.
CPC .......... *A61K 45/06* (2013.01); *A61K 39/3955* (2013.01); *A61K 39/4611* (2023.05); *A61K 39/4631* (2023.05); *A61K 39/464462* (2023.05); *A61P 35/02* (2018.01); *C07K 14/7051* (2013.01); *C07K 14/70517* (2013.01); *C07K 14/7151* (2013.01); *C07K 16/2863* (2013.01); *A61K 38/00* (2013.01); *A61K 2239/31* (2023.05); *A61K 2239/38* (2023.05); *A61K 2239/48* (2023.05); *C07K 2317/622* (2013.01); *C07K 2317/92* (2013.01)

(58) Field of Classification Search
CPC .... A61K 35/17; A61K 35/02; A61K 39/3955; C07K 14/7051
See application file for complete search history.

(56) References Cited

U.S. PATENT DOCUMENTS

| | | | |
|---|---|---|---|
| 11,421,040 B2* | 8/2022 | Dettling | ................ A61P 35/02 |
| 2012/0328612 A1 | 12/2012 | Grosse-hovest et al. | |
| 2016/0297884 A1 | 10/2016 | Kuo et al. | |
| 2016/0297885 A1 | 10/2016 | Kuo et al. | |
| 2017/0037149 A1 | 2/2017 | Raum et al. | |
| 2023/0059489 A1* | 2/2023 | Dettling | ............. C07K 16/2809 |

FOREIGN PATENT DOCUMENTS

| | | |
|---|---|---|
| CN | 102046659 A | 5/2011 |
| CN | 104203981 A | 12/2014 |
| CO | 2018011804 A2 | 2/2019 |
| EP | 3029067 A1 | 6/2016 |
| JP | 2017513478 A | 6/2017 |
| RU | 2220979 C2 | 1/2004 |
| WO | WO-2009/155015 A1 | 12/2009 |
| WO | WO-2014/011988 A2 | 1/2014 |
| WO | WO-2014/011988 A3 | 1/2014 |
| WO | 2014039523 A1 | 3/2014 |
| WO | 2015142675 A2 | 9/2015 |

(Continued)

OTHER PUBLICATIONS

Rudikoff et al., Single amino acid substitution altering antigen-binding specificity, PNAS, USA, 1982, 79: 1979-1983 (Year: 1982).*
Riemer et al., Matching of trastuzumab (Herceptin®) epitope mimics onto the surface of Her-2/neu—a new method of epitope definition, Mol Immunol, 2005 42(9): 1121-1124 (Year: 2005).*
Edwards et al. The Remarkable Flexibility of the Human Antibody Repertoire; Isolation of Over One Thousand Different Antibodies to a Single Protein, BLyS, J. Mol. Biol. 2003, 334:103-118. (Year: 2003).*
Lloyd et al. Modelling the human immune response: performance of a 1011 human antibody repertoire against a broad panel of therapeutically relevant antigens, Protein Engineering Design & Selection. 2009, 22;3: 159-168) (Year: 2009).*

(Continued)

*Primary Examiner* — Peter J Reddig
*Assistant Examiner* — Cheng Lu
(74) *Attorney, Agent, or Firm* — Mintz Levin Cohn Ferris Glovsky and Popeo, P.C.

(57) ABSTRACT

Provided herein are antibodies that specifically bind to Fms-like tyrosine kinase 3 (FLT3), chimeric antigen receptors (CARs) that specifically bind to FLT3, and engineered immune cells expressing such CARs (e.g. FLT3-specific CAR-T cells). The invention also provides making such antibodies, CARs, and engineered immune cells. The invention also provides using such antibodies, CARs, and engineered immune cells, for example for the treatment of a condition associated with malignant cells expressing FLT3 (e.g., cancer).

24 Claims, 9 Drawing Sheets
Specification includes a Sequence Listing.

(56) References Cited

FOREIGN PATENT DOCUMENTS

| WO | 2015158671 A1 | 10/2015 |
| WO | 2016075612 A1 | 5/2016 |
| WO | 2016120220 A1 | 8/2016 |
| WO | WO-2016/120216 A1 | 8/2016 |
| WO | 2016142532 A1 | 9/2016 |
| WO | 2016145099 A1 | 9/2016 |
| WO | 2016166630 A1 | 10/2016 |
| WO | 2016210293 A1 | 12/2016 |
| WO | 2017001572 A1 | 1/2017 |
| WO | 2017015427 A1 | 1/2017 |
| WO | 2017021362 A1 | 2/2017 |
| WO | WO-2017/053889 A2 | 3/2017 |
| WO | WO-2017/053889 A3 | 3/2017 |
| WO | 2017059196 A2 | 4/2017 |
| WO | WO-2017/173410 A9 | 10/2017 |
| WO | WO-2018/119279 A1 | 6/2018 |

OTHER PUBLICATIONS

Sterner et al., CAR-T cell therapy: current limitations and potential strategies, Blood Cancer Journal, (2021) 11:69 (Year: 2021).*
Zabel et al., The making and function of CAR cells, Immunology Letters, 212 (2019): 53-69 (Year: 2019).*
Bridgeman et al., "The Optimal Antigen Response of Chimeric Antigen Receptors Harboring the CD3 *(symbol needed here)* Transmembrance Domain Is Dependent upon Incorporation of the Receptor into the Endogenous TCR/CD3 Complex," J Immunol 2010; 184:6938-6949; Prepublished online May 17, 2010; doi:10.4049/jimmunol.0901766; http://www.jimmunol.org/content/184/12/6938.
Edwards et al., "The Remarkable Flexibility of the Human Antibody Repertoire; Isolation of Over One Thousand Different Antibodies to a Single Protein, BLySm" J. Mol. Biol. (2003) 334, 103-118; doi:10.1016/j.jmb.2003.09.54.
Fujiwara et al., "Impact of scFv structure in chimeric antigen receptor on receptor expression efficiency and antigen recognition properties," Biochemical and Biophysical Research Communications, http:doi.org10.1016/j.bbrc.2020.03.071, 8 pgs.
Fujiwara et al., "Hinge and Transmembrane Domains of Chimeric Antigen Receptor Regulate Receptor Expression and Signaling Threshold," Cells: 2020, 9,1182; doi:10.3390/cells9051182; www.mdpi.com/journal/cells, 17 pgs.
Lloyd et al., "Modelling the human immune response: performance of a 10" human antibody repertoire against a broad panel of therapeutically relevant antigens," Protein Engineering, Design & Selection, vol. 22. No. 3, 3 pp., 159-168 (2009); Published online Oct. 29, 2008 doi:10.1093/protein/gzn058.
Zhao et al., "Structural design of engineered costimulation determines tumor rejection kinetics and persistence of CAR T cells," Cancer cell, Oct. 12, 2015; 28(4): 415-428. doi:10.1016/j.ccell.2015.09.004.
Zhong et al., "Chimeric Antigen Receptors Combining 4-1BB and CDBB Signaling Domains Augment PI3kinase/AKT/Bcl-XL, Activation and CD8+ T Cell-medidated Tumor Eradication," Molecular Therapy, vol. 18, No. 2, 413-420, Feb. 2010.
Roitt et al., Immunology (5th edition) (Russian edition; Moscow, Russia) 2000, pp. 110-111.
RU Application No. 201914341, Office Action dated Nov. 9, 2021, English translation, 11 pgs.
RU Application No. 201914341, Office Action dated Nov. 9, 2021,12 pgs.
SA Application No. 519410496, Office Action dated Oct. 4, 2021, English Translation, 6 pgs.
SA Application No. 519410496, Office Action dated Oct. 4, 2021, 7 pgs.
Examination Report for CA Application No. 3062328 dated Jun. 6, 2023 (5 pages).
Examination Report for EP Application No. 18732621.0 dated Oct. 5, 2023 (10 pages).
Examination Report for NZ Application No. 759042 dated Oct. 10, 2023 (1 page).
Examination Report for NZ Application No. 759042 dated Jul. 7, 2023 (3 pages).
Hudecek et al., "Receptor affinity and extracellular domain modifications affect tumor recognition by ROR1-specific chimeric antigen receptor T-cells," Clin Cancer Res. Jun. 15, 2013; 19(12): 3153-3164. doi: 10.1158/1078-0432.CCR-13-0330.
New Zealand Examination Report for NZ Application No. 759042 dated Jan. 18, 2023, 5 pgs.
Chen, L. et al. (2017). "Targeting FLT3 by chimeric antigen receptor T cells for the treatment of acute myeloid leukemia," Leukemia 31:1830-1834.
Chien, C.D. et al. (2016). "Preclinical Development of FLT3-Redirected Chimeric Antigen Receptor T Cell Immunotherapy for Acute Myeloid Leukemia," Blood 128:1072.
Jetani, H. et al. (2018). "CAR T-cells targeting FLT3 have potent activity against FLT3-ITD+AML and act synergistically with the FLT3-inhibitor crenolanib," Leukemia 32:1168-1179.
Hofmann, M et al. (2012). "Generation, selection and preclinical characterization of an Fe-optimized FLT3 antibody for the treatment of myeloid leukemia," Leukemia 26:1228-1237.
Philip, B. et al. (2014). "A highly compact epitope-based marker/suicide gene for easier and safer T-cell therapy," Blood 124:1277-1287.
International Search Report mailed on Aug. 2, 2018, for PCT Application No. PCT/US2018/035492, filed on May 31, 2018, 8 Pages.
Written Opinion of the International Searching Authority mailed on Aug. 2, 2018, for PCT Application No. PCT/US2018/035492, filed on May 31, 2018, 8 Pages.
JP Office Action for JP Application No. 2019-566197, dated Jun. 7, 2022, 12 pgs.
English Translation of JP Office Action for JP Application No. 2019-566197, dated Jun. 7, 2022, 14 pgs.
Examination Report for PH Application No. 1-2019-502637 dated Nov. 28, 2023 (5 pages).
Notice of Acceptance for NZ Application No. 759042 dated Jan. 18, 2024 (2 pages).
Office Action Issued in European Patent Application No. 18732621.0, Mailed on: Oct. 5, 2023, 10 Pages.
International Preliminary Report on Patentability Issued in PCT Application No. PCT/US2018/035492, Mailed on: Dec. 3, 2019, 9 Pages.
International Search Report and Written Opinion Issued in PCT Application No. PCT/US2018/035492, Mailed on: Aug. 2, 2018, 16 Pages.
Notice of Allowance Issued in Singapore Patent Application No. 11201911461W, Mailed on: Jun. 20, 2024, 4 Pages.
Office Action Issued in Australia Patent Application No. 2018278321, Mailed on: May 31, 2024, 5 Pages.
Office Action Issued in Canadian Patent Application No. 3062328, Mailed on: Sep. 6, 2024, 4 Pages.
Office Action Issued in New Zealand Patent Application No. 759042, Mailed on: Oct. 10, 2023, 1 Page.
Office Action Issued in New Zealand Patent Application No. 759042, Mailed on: Jul. 7, 2023, 3 Pages.
Office Action Issued in New Zealand Patent Application No. 759042, Mailed on: Jan. 18, 2023, 5 Pages.
Abu-Duhier et al., (2000) "FLT3 Internal Tandem Duplication Mutations in Adult Acute Myeloid Leukemia Define a High-Risk Group", British Journal of Haematology, 111(1): 190-195.
Birg et al., (Nov. 1992) "Expression of the FMS/KIT-Like Gene FLT3 in Human Acute Leukemias of the Myeloid and Lymphoid Lineages", Blood, 80(10):2584-2593.
Brenner et al., (Apr. 2010) "Adoptive T Cell Therapy of Cancer", Current Opinion in Immunology, 22(2):251-257 (11 pages).
Carow et al., (Feb. 1996) "Expression of the Hematopoietic Growth Factor Receptor FLT3 (STK-1/FIK2) in Human Leukemias", Blood, 87(3):1089-1096.
Eshhar et al., (Jan. 1993) "Specific Activation and Targeting of Cytotoxic Lymphocytes Through Chimeric Single Chains Consisting of Antibody-binding Domains and the gamma or zeta Subunits

(56) References Cited

OTHER PUBLICATIONS of the Immunoglobulin and T-cell Receptors", Proceedings of the National Academy of Sciences of the United States of America, 90(2):720-724.

Rosenberg et al., (2008) "Adoptive Cell Transfer: a Clinical Path To Effective Cancer Immunotherapy", Nature Reviews Cancer, 8(4):299-308 (22 Pages).

Sadelain et al., (Apr. 2009) "The Promise and Potential Pitfalls of Chimeric Antigen Receptors", Current Opinion in Immunology, 21(2):215-223 (18 Pages).

Yamamoto et al., (Apr. 2001) "Activating Mutation of D835 within the Activation Loop of FLT3 in Human Hematologic Malignancies", Blood, 97(8):2434-2439.

* cited by examiner

CHIMERIC ANTIGEN RECEPTORS TARGETING FLT3

CROSS REFERENCE TO RELATED APPLICATIONS

The present application is a U.S. National Stage Application under 35 U.S.C. § 371 of International Application No. PCT/US2018/035492, filed on May 31, 2018, which claims the benefit of priority to U.S. Provisional Application No. 62/514,634, filed Jun. 2, 2017, U.S. Provisional Application No. 62/514,574, filed Jun. 2, 2017, and U.S. Provisional Application No. 62/660,908, filed Apr. 20, 2018, the contents of which are hereby incorporated by reference in their entirety.

The contents of PCT Application PCT/IB2018/053908, entitled "ANTIBODIES SPECIFIC FOR FLT3 AND THEIR USES", filed on May 31, 2018, which discloses FLT3 specific antibodies, is hereby incorporated by reference in its entirety.

REFERENCE TO SEQUENCE LISTING

This application is being filed electronically via EFS-Web and includes an electronically submitted sequence listing in .txt format. The .txt file contains a sequence listing entitled ALGN_010_01US_SeqList_ST25.txt" created on Mar. 26, 2020, and having a size of 238 KB. The sequence listing contained in this .txt file is part of the specification and is incorporated herein by reference in its entirety.

FIELD

Provided herein are Fms-like tyrosine kinase 3 (FLT3)-specific antibodies, chimeric antigen receptors (CARs) that specifically bind to FLT3 (FLT3 CARs), polynucleotides encoding FLT3 CARs, and engineered immune cells comprising the FLT3-specific CARs (e.g. FLT3-specific CAR-T cells). The invention further relates to methods for engineering immune cells to express FLT3 specific CARs and methods of using the FLT3-specific antibodies and FLT3-specific CAR-T cells for treating conditions associated with FLT3 (e.g., malignant cells expressing FLT3).

BACKGROUND

Adoptive transfer of immune cells genetically modified to recognize malignancy-associated antigens is showing promise as a new approach to treating cancer (see, e.g., Brenner et al., Current Opinion in Immunology, 22(2): 251-257 (2010); Rosenberg et al., Nature Reviews Cancer, 8(4): 299-308 (2008)). T cells can be genetically modified to express chimeric antigen receptors (CARs), fusion proteins comprised of an antigen recognition moiety and T cell activation domains (see, e.g., Eshhar et al., Proc. Natl. Acad. Sci. USA, 90(2): 720-724 (1993), and Sadelain et al., Curr. Opin. Immunol, 21(2): 215-223 (2009)).

FLT3 is an Acute Myeloid Leukemia (AML) target antigen, is over-expressed on AML patient blasts when compared to healthy cells, and is expressed on the majority of patient cells (Carow et al, Feb. 2, 1996 Blood: 87(3); Birg et al. November 1992 Blood: 80(10)). FLT3 is a frequently mutated gene in AML patients, and mutations are associated with poor prognosis (Abu-Duhier et al. Br J Haematol. 2000 October; 111(1):190-5, Yamamoto et al. Apr. 15, 2001; Blood: 97 (8)). Small-molecule FLT3 inhibitors have shown activity in clinical trials; however, the responses are usually transient due to the acquisition of resistance. Additionally kinase inhibitors treat only a percentage of patients expressing the mutated form of FLT3, highlighting the urgent need for improved therapies.

Accordingly, there is a need for alternative treatments for cancer and in particular malignancies involving aberrant expression of FLT3. Provided herein are methods and compositions addressing this need.

SUMMARY

Provided herein are antibodies or antigen binding fragments thereof that specifically bind to Fms-like tyrosine kinase 3 (FLT3), chimeric antigen receptors (CARs) that specifically bind to FLT3, and engineered immune cells expressing such CARs (e.g. FLT3-specific CAR-T cells). Also provided are making such antibodies, CARs and immune cells. Further provided are using such antibodies, CARs and engineered immune cells, for example for the treatment of a condition associated with malignant cells expressing FLT3 (e.g., cancer). In one aspect, provided herein is an isolated antibody which specifically binds to FLT3, wherein the antibody comprises a heavy chain variable (VH) region having any one of the partial VH sequences listed in Table 2 and/or a light chain variable (VL) region having any one of the partial VL sequences listed in Table 2.

In another aspect, provided herein is an isolated antibody which specifically binds to FLT3, wherein the antibody comprises (a) a heavy chain variable (VH) region comprising complementarity determining region one (CDR1), CDR2, and CDR3 sequences listed in Table 3 and/or (b) a light chain variable (VL) region comprising CDR1, CDR2, and CDR3 sequences listed in Table 3.

Also provided herein are Chimeric antigen receptors (CARs) that bind to FLT3 It is demonstrated that the expression of FLT3 specific CARs in T cells is effective to activate the T cells upon contact with FLT3. The FLT3 specific CARs provided herein bind human FLT3and exhibit cytotoxic activity upon contact with FLT3-expressing cells.

Accordingly, in another aspect, provided herein is a FLT3 specific chimeric antigen receptor (CAR) comprising an extracellular ligand-binding domain, a first transmembrane domain, and an intracellular signaling domain, wherein the extracellular domain comprises a single chain variable fragment (scFv) binding to the extracellular domain of FLT3. In some embodiments, provided herein are FLT3 CARs comprising an extracellular ligand-binding domain, a first transmembrane domain, and an intracellular signaling domain, wherein the extracellular domain comprises a scFv binding to particular domains of the FLT3 target, e.g. binding to SEQ ID NO: 199 (Domain 1), SEQ ID NO: 200 (Domain 2), SEQ ID NO: 201 (Domain 3), SEQ ID NO: 254 (Domain 2-3), SEQ ID NO: 202 (Domain 4) or SEQ ID NO: 203 (Domain 5), SEQ ID NO: 254 (Domain 2-3) or SEQ ID NO: 202 (Domain 4).

In some embodiments, the FLT3 specific CARs comprise an extracellular domain comprising a scFv, wherein the scFv binds to Domain 4 of the FLT3 target (SEQ ID NO: 202).

In some embodiments, the FLT3 specific CARs comprise an extracellular domain comprising a scFv, wherein the scFv binds to Domain 2 of the FLT3 target (SEQ ID NO: 200).

The extracellular domain of FLT3 specific CARs comprises a scFv, wherein the scFv comprises a heavy chain variable (VH) region and a light chain variable (VL) region, the VH and VL regions each comprising three complementarity determining regions (CDRs) specific for FLT3.

In some embodiments, the VH region comprises (i) a VH complementarity determining region one (CDR1) having the amino acid sequence shown in SEQ ID NO: 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 294, 295, 296, 300, 301, 305, 306, 307, 311, 312, 316, 317, or 318; (ii) a VH complementarity determining region two (CDR2) having the amino acid sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 297, 298, 302, 303, 308, 309, 313, 314, 319, 320, or 322; and (iii) a VH complementarity determining region three (CDR3) having the amino acid sequence shown in SEQ ID NO: 42, 48, 53, 59, 65, 71, 77, 83, 89, 95, 101, 107, 113, 119, 125, 131, 137, 143, 299, 304, 310, 315, or 321; and/or the VL region comprises (i) a VL complementarity determining region one (CDR1) having the amino acid sequence shown in SEQ ID NO: 144, 147, 150, 153, 156, 159, 162, 165, 168, 171, 174, 177, 180, 183, 186, 189, 192, 195, 323, 326, 328, 331, 336, 338, 340, 343, 345, 348, or 350; (ii) a VL complementarity determining region two (CDR2) having the amino acid sequence shown in SEQ ID NO: 145, 148, 151, 154, 157, 160, 163, 166, 169, 172, 175, 178, 181, 184, 187, 190, 193, 196, 324, 329, 332, 334, 341, or 346; and (iii) a VL complementarity determining region three (CDR3) having the amino acid sequence shown in SEQ ID NO: 146, 149, 152, 155, 158, 161, 164, 167, 170, 173, 176, 179, 182, 185, 188, 191, 194, 197, 325, 327, 330, 333, 335, 337, 339, 342, 344, 347, or 349.

In some embodiments, provided are FLT3 specific CARs comprising a scFv, wherein the scFv comprises a VH region having the sequence shown in SEQ ID NO: 2, 4, 6, 8, 10, 12, 14, 16, 18, 20, 22, 24, 26, 28, 30, 32, 34, 36, 265, 267, 269, 271, 273, 275, 277, 279, 281, 283, 285, 287, 289, 291, or 293.

In some embodiments, provided are FLT3 specific CARs comprising a scFV, wherein the scFv comprises a VL region having the sequence shown in SEQ ID NO: 1, 3, 5, 7, 9, 11, 13, 15, 17, 19, 21, 23, 25, 27, 29, 31, 33, 35, 264, 266, 268, 270, 272, 274, 276, 278, 280, 282, 284, 286, 288, 290, or 292.

In some embodiments, provided are FLT3 specific CARs comprising a scFV comprising a VH region and a VL region, wherein the VH region has the sequence shown in SEQ ID NO: 2, 4, 6, 8, 10, 12, 14, 16, 18, 20, 22, 24, 26, 28, 30, 32, 34, 36, 265, 267, 269, 271, 273, 275, 277, 279, 281, 283, 285, 287, 289, 291, or 293; and the VL region has the sequence shown in SEQ ID NOs: 1, 3, 5, 7, 9, 11, 13, 15, 17, 19, 21, 23, 25, 27, 29, 31, 33, 35, 264, 266, 268, 270, 272, 274, 276, 278, 280, 282, 284, 286, 288, 290, or 292.

In some embodiments, the VH region comprises the sequence shown in SEQ ID NO: 2, 4, 6, 8, 10, 12, 14, 16, 18, 20, 22, 24, 26, 28, 30, 32, 34, 36, 265, 267, 269, 271, 273, 275, 277, 279, 281, 283, 285, 287, 289, 291, or 293, or a variant thereof with one or several conservative amino acid substitutions in residues that are not within a CDR and/or the VL region comprises the amino acid sequence shown in SEQ ID NO: 1, 3, 5, 7, 9, 11, 13, 15, 17, 19, 21, 23, 25, 27, 29, 31, 33, 35, 264, 266, 268, 270, 272, 274, 276, 278, 280, 282, 284, 286, 288, 290, or 292, or a variant thereof with one or several amino acid substitutions in amino acids that are not within a CDR.

In some embodiments, the VH region comprises a VH CDR1 comprising the amino acid sequence shown in SEQ ID NO: 90, 91, or 92; a VH CDR2 comprising the amino acid sequence shown in SEQ ID NO: 93 or 94; and a VH CDR3 comprising the amino acid sequence shown in SEQ ID NO: 95; and a light chain variable region (VL) comprising the following CDRs: a VL CDR1 comprising the amino acid sequence shown in SEQ ID NO: 171; a VL CDR2 comprising the amino acid sequence shown in SEQ ID NO: 172; and a VL CDR3 comprising the amino acid sequence shown in SEQ ID NO: 173.

In some embodiments, the VH region comprises the amino acid sequence shown in SEQ ID NO: 20 and the VL region comprises the amino acid sequence shown in SEQ ID NO: 19.

In some embodiments, the VH region comprises a VH CDR1 comprising the amino acid sequence shown in SEQ ID NO: 43, 44, or 45; a VH CDR2 comprising the amino acid sequence shown in SEQ ID NO: 46 or 47; and a VH CDR3 comprising the amino acid sequence shown in SEQ ID NO: 48; and a light chain variable region (VL) comprising the following CDRs: a VL CDR1 comprising the amino acid sequence shown in SEQ ID NO: 147; a VL CDR2 comprising the amino acid sequence shown in SEQ ID NO: 148; and a VL CDR3 comprising the amino acid sequence shown in SEQ ID NO: 149.

In some embodiments, the VH region comprises the amino acid sequence shown in SEQ ID NO: 4 and the VL region comprises the amino acid sequence shown in SEQ ID NO: 3.

In some embodiments, the VH region comprises a VH CDR1 comprising the amino acid sequence shown in SEQ ID NO: 49, 44, or 50; a VH CDR2 comprising the amino acid sequence shown in SEQ ID NO: 51 or 52; and a VH CDR3 comprising the amino acid sequence shown in SEQ ID NO: 53; and a light chain variable region (VL) comprising the following CDRs: a VL CDR1 comprising the amino acid sequence shown in SEQ ID NO: 150; a VL CDR2 comprising the amino acid sequence shown in SEQ ID NO: 151; and a VL CDR3 comprising the amino acid sequence shown in SEQ ID NO: 152.

In some embodiments, the VH region comprises the amino acid sequence shown in SEQ ID NO: 6 and the VL region comprises the amino acid sequence shown in SEQ ID NO: 5.

In some embodiments, the VH region comprises a VH CDR1 comprising the amino acid sequence shown in SEQ ID NO: 60, 61, or 62; a VH CDR2 comprising the amino acid sequence shown in SEQ ID NO: 63 or 64; and a VH CDR3 comprising the amino acid sequence shown in SEQ ID NO: 65; and a light chain variable region (VL) comprising the following CDRs: a VL CDR1 comprising the amino acid sequence shown in SEQ ID NO: 156; a VL CDR2 comprising the amino acid sequence shown in SEQ ID NO: 157; and a VL CDR3 comprising the amino acid sequence shown in SEQ ID NO: 158.

In some embodiments, the VH region comprises the amino acid sequence shown in SEQ ID NO: 10 and the VL region comprises the amino acid sequence shown in SEQ ID NO: 9.

In some embodiments, each CDR is defined in accordance with the Kabat definition, the Chothia definition, the combination of the Kabat definition and the Chothia definition, the AbM definition, or the contact definition of CDR.

In some embodiments, the intracellular signaling domain comprises a CD3 signalling domain. In some embodiments, the intracellular signaling domain comprises a 4-1BB domain. In some embodiments, the FLT3 specific CAR comprises a second intracellular signaling domain. In some embodiments, the second intracellular signaling domain comprises a 4-1BB domain.

In some embodiments, the FLT3 specific CARs disclosed herein may comprise a stalk domain between the extracellular ligand-binding domain and the first transmembrane domain. In some embodiments, the stalk domain is selected from the group consisting of: a CD8α hinge, an IgG1 hinge, and an FcγRIIIα hinge. In some embodiments, the stalk domain is a human CD8α hinge, a human IgG1 hinge, or a human FcγRIIIα hinge.

In some embodiments, the FLT3 specific CARs disclosed herein may comprise one or more epitopes specific for one or more monoclonal antibodies. In some embodiments, the epitope specific for a monoclonal antibody is a CD20 epitope. In some embodiments, the CD20 epitope comprises the amino acid sequence shown in SEQ ID NO: 229 or SEQ ID NO: 230.

In some embodiments, the FLT3 specific CAR comprises the amino acid sequence shown in SEQ ID NO: 235, 236, 237 or 242. In some embodiments, the FLT3 specific CAR comprises the amino acid sequence shown in SEQ ID NO: 235. In some embodiments, the FLT3 specific CAR comprises the amino acid sequence shown in SEQ ID NO: 236.

In some embodiments, the first transmembrane domain comprises a CD8α chain transmembrane domain.

In some embodiments, the FLT3 specific CAR can comprise another extracellular ligand-binding domain which is not specific for FLT3.

In some embodiments, the extracellular ligand-binding domain(s), the first transmembrane domain, and intracellular signaling domain(s) are on a single polypeptide.

In some embodiments, the CAR can comprise a second transmembrane domain, wherein the first transmembrane domain and the extracellular ligand-binding domain(s) are on a first polypeptide, and wherein the second transmembrane domain and the intracellular signaling domain(s) are on a second polypeptide. In an exemplary embodiment, the first transmembrane domain comprises a transmembrane domain from the α chain of the high-affinity IgE receptor (FcεRI) and the second transmembrane domain comprises a transmembrane domain from the γ or β chain of FcεRI.

In some embodiments, the CAR can comprise a third polypeptide comprising a third transmembrane domain fused to an intracellular signaling domain from a co-stimulatory molecule, wherein the third transmembrane domain comprises a transmembrane domain from the γ or β chain of FcεRI.

In another aspect, provided herein is an isolated polynucleotide comprising a nucleic acid sequence encoding the FLT3 specific CAR described herein.

In another aspect, provided herein is an expression vector comprising the polynucleotide encoding the FLT3 specific CAR described herein.

In another aspect, provided herein is an engineered immune cell expressing at its cell surface membrane a FLT3 specific CAR described herein. In some embodiments, the engineered immune cell can comprise another CAR which is not specific for FLT3. In some embodiments, the engineered immune cell can comprise a polynucleotide encoding a suicide polypeptide. In some embodiments, the suicide polypeptide is RQR8.

In some embodiments, the engineered immune cell is derived from an inflammatory T-lymphocyte, a cytotoxic T-lymphocyte, a regulatory T-lymphocyte, or a helper T-lymphocyte.

In some embodiments, the engineered immune cell can comprise a disruption one or more endogenous genes, wherein the endogenous gene encodes TCRα, TCRβ, CD52, glucocorticoid receptor (GR), deoxycytidine kinase (dCK), or an immune checkpoint protein such as for example programmed death-1 (PD-1).

In some embodiments, the engineered immune cell is obtained from a healthy donor. In some embodiments, the engineered immune cell is obtained from an individual afflicted with a disease or disorder.

In another aspect, provided herein is an engineered immune cell expressing at its cell surface membrane a FLT3 specific CAR as described herein for use as a medicament. In another aspect, provided herein is a FLT3 specific antibody for use as a medicament. In some embodiments, the medicament comprising the FLT3 specific CAR expressing immune cells or FLT3 specific antibodies is for use in treatment of a FLT3 associated disease or disorder. In one embodiment, the FLT3 associated disease or disorder is a cancer of hematopoietic origin, such as a lymphoma or leukemia. In some embodiments, the cancer is selected from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulinemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmacytic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cells related cancer, e.g. ALL or AML.

In one aspect, provided herein is a population of cells comprising engineered immune cells expressing FLT specific CARs described herein, wherein (ii) said population of cells comprises a percentage of stem cell memory and central memory cells greater than 20%, 30% or 40%, and/or (iii) said population of cells achieves a percentage lysis of FLT3 expressing cells greater than 10%, 20%, 30% or 40%.

In another aspect, provided herein is a method of engineering an immune cell expressing any one of the FLT3 specific CARs described herein, the method comprising: providing an immune cell; and introducing into the cell at least one polynucleotide encoding said FLT3 specific CAR; whereby said immune cell expresses said FLT3 specific CAR.

In some embodiments, the method comprises providing an immune cell; introducing into the cell at least one polynucleotide encoding said FLT3 specific CAR; and introducing at least one polynucleotide encoding a CAR which is not specific for FLT3.

In another aspect, provided herein is a method of treating a subject suffering from a FLT3 associated disease or disorder, the method comprising: providing an immune cell expressing at the surface a FLT3 specific CAR as described herein; and administering said immune cells to said subject. The invention also provides methods of treating subjects suffering from a FLT3 associated disease or disorder, the method comprising providing FLT3 specific antibodies described herein and administering said antibodies to said subject.

In some embodiments, provided herein is a pharmaceutical composition comprising an engineered immune cell expressing FLT3 specific CARs as described herein. In other embodiments, the invention provides pharmaceutical compositions comprising any of the FLT3 specific antibodies described herein.

In another aspect, provided herein is a method of treating a condition associated with malignant cells expressing FLT3 in a subject comprising administering to a subject in need thereof an effective amount of the pharmaceutical composition comprising an engineered immune cell as described herein or FLT3 specific antibodies as described herein. In some embodiments, the condition is a cancer. In some embodiments, the cancer is a cancer of hematopoietic origin, such as a lymphoma or leukemia. In some embodiments the cancer is selected from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulinemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmacytic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cells related cancer, e.g. ALL or AML.

In another aspect, provided herein is a method of inhibiting tumor growth or progression in a subject who has malignant cells expressing FLT3, comprising administering to the subject in need thereof an effective amount of the pharmaceutical composition comprising an engineered immune cell as described herein or a FLT3 specific antibody as described herein to the subject.

In another aspect, provided herein is a method of inhibiting metastasis of malignant cells expressing FLT3 in a subject, comprising administering to the subject in need thereof an effective amount of the pharmaceutical composition comprising an engineered immune cell as described herein or a FLT3 specific antibody as described herein to the subject.

In another aspect, provided herein is a method of inducing tumor regression in a subject who has malignant cells expressing FLT3, comprising administering to the subject in need thereof an effective amount of the pharmaceutical composition comprising an engineered immune cell as described herein or a FLT3 specific antibody as described herein to the subject.

In some embodiments, any of the above methods further comprises administering one or more additional therapies, such as for example, a monoclonal antibody and/or a chemotherapeutic. In some embodiments, the monoclonal antibody can be, for example, an antibody that binds to a checkpoint inhibitor such as, for example, an anti-PD-1 antibody or an anti-PD-L1 antibody. In some embodiments, any of the above methods further comprises administering a Receptor Tyrosine Kinase inhibitor, an mTOR inhibitor, an epigenetic modulator, a proteasome inhibitor, an immunomodulatory agent such as lenalidomide, a Hedgehog inhibitor or an Isocitrate Dehydrogenase (IDH) inhibitors, to the subject.

DETAILED DESCRIPTION

Figure 1:
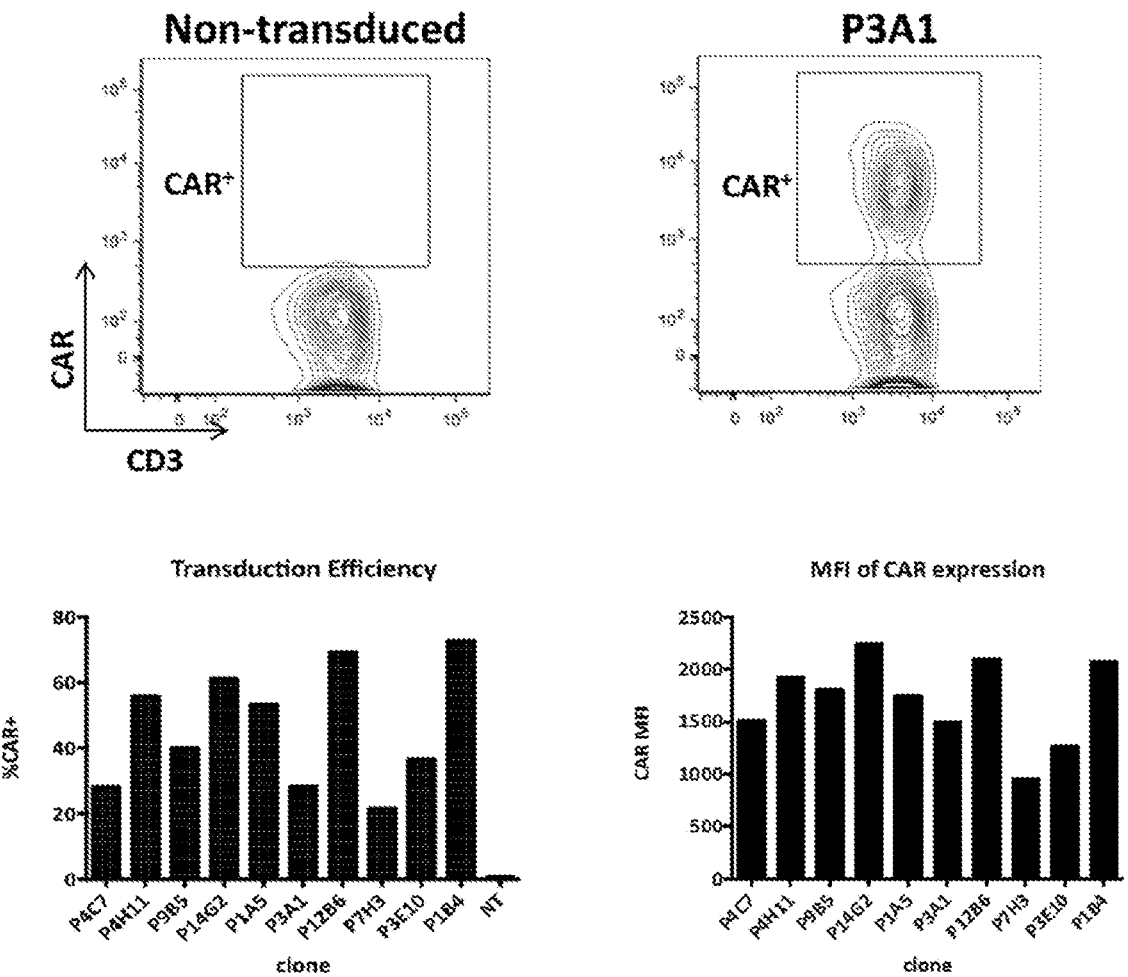
FIG. 1 shows representative FACS plots demonstrating efficient transduction of activated T cells with the P3A1 CAR construct relative to a non-transduced control, and the transduction efficiencies for all constructs as percentage of CAR-expressing T cells and mean fluorescence intensities (MFI).

In one aspect, the invention disclosed herein provides chimeric antigen receptors (CARs) and immune cells comprising CARs (e.g. CAR-T cells) that specifically bind to FLT3 (e.g., human FLT3). The invention also provides polynucleotides encoding these CARs, compositions comprising immune cells expressing these CARs, and methods of making and using these CARs and CAR expressing immune cells. The invention also provides methods for treating a condition associated with FLT3 mediated pathologies in a subject, such as cancer mediated by malignant cells expressing FLT3, using the FLT3 specific CARs and immune cells expressing these CARs as described herein.

In one aspect, the invention disclosed herein provides antibodies that specifically bind to FLT3 (e.g., human FLT3). The invention also provides compositions comprising these antibodies and methods of using these antibodies. For example, provided herein are methods for treating a condition associated with FLT3-mediated pathologies in a subject, such as cancer, using these antibodies.

General Techniques

The practice of the invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-1998) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel et al., eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Definitions

The term "extracellular ligand-binding domain" as used herein refers to a polypeptide that is capable of binding a ligand or capable of interacting with a cell surface molecule. For example, the extracellular ligand-binding domain may be chosen to recognize a ligand that acts as a cell surface marker on target cells associated with a particular disease state.

The term "stalk domain" or "hinge domain" are used interchangeably herein to refer to any polypeptide that functions to link the transmembrane domain to the extracellular ligand-binding domain. In particular, stalk domains are used to provide more flexibility and accessibility for the extracellular ligand-binding domain.

The term "intracellular signaling domain" refers to the portion of a protein which transduces the effector signal function signal and directs the cell to perform a specialized function.

A "co-stimulatory molecule" as used herein refers to the cognate binding partner on immune cells, e.g. T cells, that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

A "co-stimulatory ligand" refers to a molecule on an antigen presenting cell that specifically binds a cognate co-stimulatory signal molecule on a T cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin β receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-1BB, OX40, CD30, CD40, PD-1, ICOS, lymphocyte function-associated antigen-1 (LFA-1), CD2, CD7, LTGHT, NKG2C, B7-H3, a ligand that specifically binds with CD83.

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (scFv) and domain antibodies (including, for example, shark and camelid antibodies), and fusion proteins comprising an antibody, and any other modified configuration of the immunoglobulin molecule that comprises an antigen recognition site. An antibody includes an antibody of any class, such as IgG, IgA, IgE, IgD, or IgM (or sub-class thereof), and the antibody need not be of any particular class. Depending on the antibody amino acid sequence of the constant region of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant regions that correspond to the different classes of immunoglobulins are called alpha, delta, epsilon, gamma, and mu, respectively. The subunit structures and three-dimensional configurations of different classes of immunoglobulins are well known.

The term "antigen binding fragment" or "antigen binding portion" of an antibody, as used herein, refers to one or more fragments of an intact antibody that retain the ability to specifically bind to a given antigen (e.g., FLT3). Antigen binding functions of an antibody can be performed by fragments of an intact antibody. Examples of binding fragments encompassed within the term "antigen binding fragment" of an antibody include Fab; Fab'; F(ab')$_2$; an Fd fragment consisting of the VH and CH1 domains; an Fv fragment consisting of the VL and VH domains of a single arm of an antibody; a single domain antibody (dAb) fragment (Ward et al., Nature 341:544-546, 1989), and an isolated complementarity determining region (CDR).

An antibody, an antigen binding fragment, an antibody conjugate, or a polypeptide that "specifically binds" to a target (e.g., FLT3 protein) is a term well understood in the art, and methods to determine such specific binding are also well known in the art. A molecule is said to exhibit "specific binding" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances. For example, an antibody that specifically binds to a FLT3 epitope is an antibody that binds this epitope with greater affinity, avidity, more readily, and/or with greater duration than it binds to other FLT3 epitopes or non-FLT3 epitopes. It is also understood that by reading this definition, for example, an antibody (or moiety or epitope) that specifically binds to a first target may or may not specifically bind to a second target. As such, "specific binding" does not necessarily require (although it can include) exclusive binding. Generally, but not necessarily, reference to binding means specific binding.

A "variable region" of an antibody refers to the variable region of the antibody light chain or the variable region of the antibody heavy chain, either alone or in combination. As known in the art, the variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda MD)); and (2) an approach based on crystallographic studies of antigen-antibody complexes (Al-lazikani et al., 1997, J. Molec. Biol. 273:927-948). As used herein, a CDR may refer to CDRs defined by either approach or by a combination of both approaches.

A "CDR" of a variable domain are amino acid residues within the variable region that are identified in accordance with the definitions of the Kabat, Chothia, the accumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., Nature 342:877-883, 1989. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., J. Mol. Biol., 262:732-745, 1996. In another approach, referred to herein as the "conformational definition" of CDRs, the positions of the CDRs may be identified as the residues that make enthalpic contributions to antigen binding. See, e.g., Makabe et al., Journal of Biological Chemistry, 283:1156-1166, 2008. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the invention may be made by the hybridoma method first described by Kohler and Milstein, Nature 256:495, 1975, or may be made by recombinant DNA methods such as described in U.S. Pat. No. 4,816,567. The monoclonal antibodies may also be isolated from phage libraries generated using the techniques described in McCafferty et al., Nature 348:552-554, 1990, for example.

As used herein, "humanized" antibody refers to forms of non-human (e.g. murine) antibodies that are chimeric immunoglobulins, immunoglobulin chains, or fragments thereof (such as Fv, Fab, Fab', F(ab')2 or other antigen binding subsequences of antibodies) that contain minimal sequence derived from non-human immunoglobulin. In one aspect, humanized antibodies are human immunoglobulins (recipient antibody) in which residues from a complementarity determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (CDR L1, CDR L2, CDR L3, CDR H1, CDR H2, or CDR H3) which are altered with respect to the original antibody, which are also termed one or more CDRs "derived from" one or more CDRs from the original antibody.

As used herein, "human antibody" means an antibody having an amino acid sequence corresponding to that of an antibody produced by a human and/or which has been made using any of the techniques for making human antibodies known to those skilled in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., Nature Biotechnology, 14:309-314, 1996; Sheets et al., Proc. Natl. Acad. Sci. (USA) 95:6157-6162, 1998; Hoogenboom and Winter, J. Mol. Biol., 227:381, 1991; Marks et al., J. Mol. Biol., 222:581, 1991). Human antibodies can also be made by immunization of animals into which human immunoglobulin loci have been transgenically introduced in place of the endogenous loci, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or from single cell cloning of the cDNA, or may have been immunized in vitro). See, e.g., Cole et al. Monoclonal Antibodies and Cancer Therapy, Alan R. Liss, p. 77, 1985; Boerner et al., J. Immunol., 147 (1):86-95, 1991; and U.S. Pat. No. 5,750,373.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

A "monovalent antibody" comprises one antigen binding site per molecule (e.g., IgG or Fab). In some instances, a monovalent antibody can have more than one antigen binding sites, but the binding sites are from different antigens.

A "bivalent antibody" comprises two antigen binding sites per molecule (e.g., IgG). In some instances, the two binding sites have the same antigen specificities. However, bivalent antibodies may be bispecific.

Antibodies of the invention can be produced using techniques well known in the art, e.g., recombinant technologies, phage display technologies, synthetic technologies or combinations of such technologies or other technologies readily known in the art (see, for example, Jayasena, S. D., Clin. Chem., 45: 1628-50, 1999 and Fellouse, F. A., et al, J. Mol. Biol., 373(4):924-40, 2007).

As known in the art, "polynucleotide," or "nucleic acid," as used interchangeably herein, refer to chains of nucleotides of any length, and include DNA and RNA. The nucleotides can be deoxyribonucleotides, ribonucleotides, modified nucleotides or bases, and/or their analogs, or any substrate that can be incorporated into a chain by DNA or RNA polymerase. A polynucleotide may comprise modified nucleotides, such as methylated nucleotides and their analogs. If present, modification to the nucleotide structure may be imparted before or after assembly of the chain. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha- or beta-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As known in the art, a "constant region" of an antibody refers to the constant region of the antibody light chain or the constant region of the antibody heavy chain, either alone or in combination.

As used herein, "substantially pure" refers to material which is at least 50%, at least 60%, at least 70%, at least 80%, at least 90%, at least 95%, at least 97%, at least 98%, or even at least 99% pure (i.e., free from contaminants).

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As known in the art, the term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant regions, CH2 and CH3.

As used in the art, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, Ann. Rev. Immunol., 9:457-92, 1991; Capel et al., Immunomethods, 4:25-34, 1994; and de Haas et al., J. Lab. Clin. Med., 126:330-41, 1995. "FcR" also includes the neonatal receptor, FcRn, which is responsible for the transfer of maternal IgGs to the fetus (Guyer et al., J. Immunol., 117:587, 1976; and Kim et al., J. Immunol., 24:249, 1994).

The term "compete", as used herein with regard to an antibody, means that a first antibody, or an antigen binding fragment (or portion) thereof, binds to an epitope in a manner sufficiently similar to the binding of a second antibody, or an antigen binding portion thereof, such that the result of binding of the first antibody with its cognate epitope is detectably decreased in the presence of the second antibody compared to the binding of the first antibody in the absence of the second antibody. The alternative, where the binding of the second antibody to its epitope is also detectably decreased in the presence of the first antibody, can, but need not be the case. That is, a first antibody can inhibit the binding of a second antibody to its epitope without that second antibody inhibiting the binding of the first antibody to its respective epitope. However, where each antibody detectably inhibits the binding of the other antibody with its cognate epitope or ligand, whether to the same, greater, or lesser extent, the antibodies are said to "cross-compete" with each other for binding of their respective epitope(s). Both competing and cross-competing antibodies are encompassed by the invention. Regardless of the mechanism by which such competition or cross-competition occurs (e.g., steric hindrance, conformational change, or binding to a common epitope, or portion thereof), the skilled artisan would appreciate, based upon the teachings provided herein, that such competing and/or cross-competing antibodies are encompassed and can be useful for the methods disclosed herein.

As used herein "autologous" means that cells, a cell line, or population of cells used for treating patients are originating from said patient.

As used herein "allogeneic" means that cells or population of cells used for treating patients are not originating from said patient but from a donor.

As used herein, "treatment" is an approach for obtaining beneficial or desired clinical results. For purposes of this invention, beneficial or desired clinical results include, but are not limited to, one or more of the following: reducing the proliferation of (or destroying) neoplastic or cancerous cells, inhibiting metastasis of neoplastic cells, shrinking or decreasing the size of FLT3 expressing tumor, remission of a FLT3 associated disease (e.g., cancer), decreasing symptoms resulting from a FLT3 associated disease (e.g., cancer), increasing the quality of life of those suffering from a FLT3 associated disease (e.g., cancer), decreasing the dose of other medications required to treat a FLT3 associated disease (e.g., cancer), delaying the progression of a FLT3 associated disease (e.g., cancer), curing a FLT3 associated disease (e.g., cancer), and/or prolong survival of patients having a FLT3 associated disease (e.g., cancer).

"Ameliorating" means a lessening or improvement of one or more symptoms as compared to not administering a FLT3 specific CAR or a FLT3 specific CAR-T-cell. "Ameliorating" also includes shortening or reduction in duration of a symptom.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as reducing incidence or amelioration of one or more symptoms of various FLT3 associated diseases or conditions (such as for example multiple myeloma), decreasing the dose of other medications required to treat the disease, enhancing the effect of another medication, and/or delaying the progression of the FLT3 associated disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual", "patient" or a "subject" are used interchangeably herein and is a mammal. Mammals include, but are not limited to, humans, monkeys, pigs, other farm animals, sport animals, pets, primates, horses, dogs, cats, rodents including mice, rats, guinea pigs, etc. An subject is a mammal and are used interchangeably herein. In some embodiments, the subject is a human. In some embodiments, the subject is a non-human primate. In some embodiments, the subject is a human or a monkey, e.g. a cynomolgus monkey.

As used herein, "vector" means a construct, which is capable of delivering, and, in some embodiments, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" or "pharmaceutical acceptable excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Exemplary diluents for aerosol or parenteral administration include phosphate buffered saline (PBS) or normal (0.9%) saline. Compositions comprising such carriers are formulated by well known conventional methods (see, for example, Remington's Pharmaceutical Sciences, 18th edition, A. Gennaro, ed., Mack Publishing Co., Easton, PA, 1990; and Remington, The Science and Practice of Pharmacy 21st Ed. Mack Publishing, 2005).

The term "$k_{on}$", as used herein, refers to the rate constant for association of an antibody or scFv of a CAR to an antigen.

The term "$k_{off}$", as used herein, refers to the rate constant for dissociation of an antibody or scFv of a CAR from the antibody/antigen complex.

The term "$K_D$", as used herein, refers to the equilibrium dissociation constant of an antibody-antigen interaction or an scFv-antigen interaction.

Reference to "about" a value or parameter herein includes (and describes) embodiments that are directed to that value or parameter per se. For example, description referring to "about X" includes description of "X." Numeric ranges are inclusive of the numbers defining the range.

It is understood that wherever embodiments are described herein with the language "comprising," otherwise analogous embodiments described in terms of "consisting of" and/or "consisting essentially of" are also provided.

Where aspects or embodiments of the invention are described in terms of a Markush group or other grouping of alternatives, the invention encompasses not only the entire group listed as a whole, but each member of the group individually and all possible subgroups of the main group, but also the main group absent one or more of the group members. The invention also envisages the explicit exclusion of one or more of any of the group members in the claimed invention.

Unless otherwise defined, all technical and scientific terms used herein have the same meaning as commonly understood by one of ordinary skill in the art to which this invention belongs. In case of conflict, the present specification, including definitions, will control. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular.

Exemplary methods and materials are described herein, although methods and materials similar or equivalent to those described herein can also be used in the practice or testing of the invention. The materials, methods, and examples are illustrative only and not intended to be limiting.

FLT3 Antibodies

The present disclosure provides antibodies that bind to FLT3 [e.g., human FLT3 (e.g., accession number: NP_004110 or SEQ ID NO: 198)] and characterized by any one or more of the following characteristics: (a) treat, prevent, ameliorate one or more symptoms of a condition associated with malignant cells expressing FLT3 in a subject (e.g., cancer such as AML); (b) inhibit tumor growth or progression in a subject (who has a malignant tumor expressing FLT3); (c) inhibit metastasis of cancer (malignant) cells expressing FLT3 in a subject (who has one or more malignant cells expressing FLT3); (d) induce regression (e.g., long-term regression) of a tumor expressing FLT3; (e) exert cytotoxic activity in malignant cells expressing FLT3; (f) block FLT3 interaction with other yet to be identified factors; and/or (g) induce bystander effect that kill or inhibit growth of non-FLT3 expressing malignant cells in the vicinity.

In one aspect, provided is an isolated antibody which specifically binds to FLT3, wherein the antibody comprises (a) a heavy chain variable (VH) region comprising (i) a VH complementarity determining region one (CDR1) comprising the sequence shown in 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 246, or 247; (ii) a VH CDR2 comprising the sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 248, 249, 251, 252, 253, or 255; and iii) a VH CDR3 comprising the sequence shown in SEQ ID NO: 42, 48, 53, 59, 65, 71, 77, 83, 89, 95, 101, 107, 113, 119, 125, 131, 137, 143, 245, 250, or 254; and/or a light chain variable (VL) region comprising (i) a VL CDR1 comprising the sequence shown in SEQ ID NO: 144, 147, 150, 153, 156, 159, 162, 165, 168, 171, 174, 177, 180, 183, 186, 189, 192, 195, 257, 261, 263, 265, 268, 270, 273, or 275; (ii) a VL CDR2 comprising the sequence shown in SEQ ID NO: 145, 148, 151, 154, 157, 160, 163, 166, 169, 172, 175, 178, 181, 184, 187, 190, 193, 196, 259, 266, or 271; and (iii) a VL CDR3 comprising the sequence shown in SEQ ID NO: 146, 149, 152, 155, 158, 161, 164, 167, 170, 173, 176, 179, 182, 185, 188, 191, 194, 197, 256, 258, 260, 262, 264, 267, 269, 272, or 274.

In another aspect, provided is an isolated antibody which specifically binds to FLT3, wherein the antibody comprises: a VH region comprising the sequence shown in SEQ ID NO: 2, 4, 6, 8, 10, 12, 14, 16, 18, 20, 22, 24, 26, 28, 30, 32, 34, 36, 265, 267, 269, 271, 273, 275, 277, 279, 281, 283, 285, 287, 289, 291, or 293; and/or a VL region comprising the sequence shown in SEQ ID NO: 1, 3, 5, 7, 9, 11, 13, 15, 17, 19, 21, 23, 25, 27, 29, 31, 33, 35, 264, 266, 268, 270, 272, 274, 276, 278, 280, 282, 284, 286, 288, 290, or 292.

In some embodiments, provided is an isolated antibody which specifically binds to FLT3, wherein the antibody comprises: a VH region comprising the sequence shown in SEQ ID NO: 275, 289, or 291; and/or a VL region comprising the sequence shown in SEQ ID NO: 274, 288, or 290.

In some embodiments, provided is an antibody having any one of partial light chain sequence as listed in Table 2 and/or any one of partial heavy chain sequence as listed in Table 2.

In some embodiments, the antibodies described herein comprise a constant region. In some embodiments, the antibodies described herein are of the human IgG1, IgG2 or IgG2Δa, IgG3, or IgG4 subclass. In some embodiments, the antibodies described herein comprise a glycosylated constant region. In some embodiments, the antibodies described herein comprise a constant region having decreased binding affinity to one or more human Fc gamma receptor(s).

The antibodies provided herein can encompass monoclonal antibodies, polyclonal antibodies, antibody fragments (e.g., Fab, Fab', F(ab')2, Fv, Fc, etc.), chimeric antibodies, single chain (ScFv), and/or humanized antibodies. The antibodies may be murine, rat, human, or any other origin (including chimeric or humanized antibodies).

FLT3 Specific CARs and Methods of Making Thereof

Provided herein are CARs that bind to FLT3 (e.g., human FLT3 (e.g., SEQ ID NO: 198) or accession number: NP_004110). FLT3 specific CARs provided herein include single chain CARS and multichain CARs. The CARs have the ability to redirect T cell specificity and reactivity toward FLT3 in a non-MHC-restricted manner, exploiting the antigen-binding properties of monoclonal antibodies. The non-MHC-restricted antigen recognition gives T cells expressing CARs the ability to recognize an antigen independent of antigen processing, thus bypassing a major mechanism of tumor escape.

In some embodiments, CARs provided herein comprise an extracellular ligand-binding domain (e.g., a single chain variable fragment (scFv)), a transmembrane domain, and an intracellular signaling domain. In some embodiments, the extracellular ligand-binding domain, transmembrane domain, and intracellular signaling domain are in one polypeptide, i.e., in a single chain. Multichain CARs and polypeptides are also provided herein. In some embodiments, the multichain CARs comprise: a first polypeptide comprising a transmembrane domain and at least one extracellular ligand-binding domain, and a second polypeptide comprising a transmembrane domain and at least one intracellular signaling domain, wherein the polypeptides assemble together to form a multichain CAR.

In some embodiments, a FLT3 specific multichain CAR is based on the high affinity receptor for IgE (FcεRI). The FcεRI expressed on mast cells and basophils triggers allergic reactions. FcεRI is a tetrameric complex composed of a single α subunit, a single β subunit, and two disulfide-linked γ subunits. The α subunit contains the IgE-binding domain. The β and γ subunits contain ITAMs that mediate signal transduction. In some embodiments, the extracellular domain of the FcRα chain is deleted and replaced by a FLT3 specific extracellular ligand-binding domain. In some embodiments, the multichain FLT3 specific CAR comprises an scFv that binds specifically to FLT3, the CD8α hinge, and the ITAM of the FcRβ chain. In some embodiments, the CAR may or may not comprise the FcRγ chain.

In some embodiments, the extracellular ligand-binding domain comprises an scFv comprising the light chain variable (VL) region and the heavy chain variable (VH) region of a target antigen specific monoclonal antibody joined by a flexible linker. Single chain variable region fragments are made by linking light and/or heavy chain variable regions by using a short linking peptide (Bird et al., Science 242:423-426, 1988). An example of a linking peptide is the GS linker having the amino acid sequence (GGGGS)$_3$ (SEQ ID NO: 232), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides, e.g. comprised of about 20 or fewer amino acid residues. Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The FLT3 extracellular domain is composed of 5 immunoglobulin domains, with Domain 5 being closest in proximity to the cell membrane, and domain 1 being furthest out (in linear fashion; Verstraete, Jul. 7, 2011; Blood: 118 (1)). The sequences of the five FLT3 extracellular domains are listed in Table 1 below.

TABLE 1

| FLT3 extra-cellular domain No. | Sequence |
|---|---|
| 1 | NQDLPVIKCVLINHKNNDSSVGKSSSYPMVSES PEDLGCALRPQSSGTVYEAAAVEVDVSASITLQ VLVDAPGNISCLWVFKHSSLNCQPHFDLQNRGV VSMVILKMTETQA GEYLLFIQSEATNYTILFT VSIR (SEQ ID NO: 199) |
| 2 | NTLLYLRRPYFRKMENQDALVCISESVPEPIVE WVLCDSQGESCKEESPAVVKKEEKVLHELFGTD IRCCARNELGRECTRL (SEQ ID NO: 200) |
| 3 | FTIDLNQTPQTTLPQLFLKVGEPLWIRCKAVHV NHGFGLTWELENKALEEGNYFEMSTYSTNRTMI RILFAFVSSVARNDTGYYTCSSSKHPSQSALVT IVE (SEQ ID NO: 201) |
| 4 | KGFINATNSSEDYEIDQYEEFCFSVRFKAYPQI RCTWTFSRKSFPCEQKGLDNGYSISKFCNHKHQ PGEYIFHAENDDAQFTKMFTLN (SEQ ID NO: 202) |
| 5 | IRRKPQVLAEASASQASCFSDGYPLPSWTWKKC SDKSPNCTEEITEGVWNRKANRKVFGQWVSSST LNMSEAIKGFLVKCCAYNSLGTSCETILLNSPG PFPFIQDN (SEQ ID NO: 203) |

Domain 2-3 comprises the sequence of Domain 2 and Domain 3 (SEQ ID NO: 254).

In some embodiments, the extracellular ligand-binding domain of FLT3 specific CARs described herein binds to Domain 1, 2, 3, 4 or 5 of the FLT3 extracellular domain.

In some embodiments, the extracellular ligand-binding domain of FLT3 specific CARs described herein binds to Domain 1 of the FLT3 extracellular domain.

In some embodiments, the extracellular ligand-binding domain of FLT3 specific CARs described herein binds to Domain 2 of the FLT3 extracellular domain.

In some embodiments, the extracellular ligand-binding domain of FLT3 specific CARs described herein binds to Domain 3 of the FLT3 extracellular domain.

In some embodiments, the extracellular ligand-binding domain of FLT3 specific CARs described herein binds to Domain 4 of the FLT3 extracellular domain.

In some embodiments, the extracellular ligand-binding domain of FLT3 specific CARs described herein binds to Domain 5 of the FLT3 extracellular domain.

In some embodiments, the extracellular ligand-binding domain of FLT3 specific CARs described herein binds to Domain 2-3 of the FLT3 extracellular domain.

In some embodiments, the extracellular ligand-binding domain of FLT3 specific CARs described herein binds to Domain 2-3 or 4 of the FLT3 extracellular domain.

In another aspect, provided is a CAR, which specifically binds to FLT3, wherein the CAR comprises an extracellular ligand-binding domain comprising: a VH region having the sequence shown in SEQ ID NO: 2, 4, 6, 8, 10, 12, 14, 16, 18, 20, 22, 24, 26, 28, 30, 32, 34, 265, 267, 269, 271, 273, 275, 277, 279, 281, 283, 285, 287, 289, 291, or 293; and/or a VL region having the sequence shown in SEQ ID NO: 1, 3, 5, 7, 9, 11, 13, 15, 17, 19, 21, 23, 25, 27, 29, 31, 33, 35, 264, 266, 268, 270, 272, 274, 276, 278, 280, 282, 284, 286, 288, 290, or 292. In some embodiments, the VH and VL are linked together by a flexible linker. In some embodiments, a flexible linker comprises the amino acid sequence shown in SEQ ID NO: 232.

In another aspect, provided is a FLT3 specific chimeric antigen receptor (CAR) comprising an extracellular ligand-binding domain, a first transmembrane domain, and an intracellular signaling domain, wherein the extracellular domain comprises a single chain Fv fragment (scFv) comprising a heavy chain variable (VH) region and a light chain variable (VL) region, wherein the VH region comprises (i) a VH complementarity determining region one (CDR1) having the amino acid sequence shown in SEQ ID NO: 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 294, 295, 296, 300, 301, 305, 306, 307, 311, 312, 316, 317, or 318; (ii) a VH complementarity determining region two (CDR2) having the amino acid sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 297, 298, 302, 303, 308, 309, 313, 314, 319, 320, or 322; and (iii) a VH complementarity determining region three (CDR3) having the amino acid sequence shown in SEQ ID NO: 42, 48, 53, 59, 65, 71, 77, 83, 89, 95, 101, 107, 113, 119, 125, 131, 137, 143, 299, 304, 310, 315, or 321.

In another aspect, provided is a FLT3 specific chimeric antigen receptor (CAR) comprising an extracellular ligand-binding domain, a first transmembrane domain, and an intracellular signaling domain, wherein the extracellular domain comprises a single chain Fv fragment (scFv) comprising a heavy chain variable (VH) region and a light chain variable (VL) region, wherein the VL region comprises (i) a VL complementarity determining region one (CDR1) having the amino acid sequence shown in SEQ ID NO: 144, 147, 150, 153, 156, 159, 162, 165, 168, 171, 174, 177, 180, 183, 186, 189, 192, 195, 323, 326, 328, 331, 336, 338, 340, 343, 345, 348, or 350; (ii) a VL complementarity determining region two (CDR2) having the amino acid sequence shown in SEQ ID NO: 145, 148, 151, 154, 157, 160, 163, 166, 169, 172, 175, 178, 181, 184, 187, 190, 193, 196, 324, 329, 332, 334, 341, or 346; and (iii) a VL complementarity determining region three (CDR3) having the amino acid sequence shown in SEQ ID NO: 146, 149, 152, 155, 158, 161, 164, 167, 170, 173, 176, 179, 182, 185, 188, 191, 194, 197, 325, 327, 330, 333, 335, 337, 339, 342, 344, 347, or 349.

In another aspect, provided is a FLT3 specific chimeric antigen receptor (CAR) comprising an extracellular ligand-binding domain, a first transmembrane domain, and an intracellular signaling domain, wherein the extracellular domain comprises a single chain Fv fragment (scFv) comprising a heavy chain variable (VH) region and a light chain variable (VL) region, wherein (a) the VH region comprises (i) a VH complementarity determining region one (CDR1) having the amino acid sequence shown in SEQ ID NO: 37, 38, 39, 43, 44, 45, 49, 50, 54, 55, 56, 60, 61, 62, 66, 67, 68, 72, 73, 74, 78, 79, 80, 84, 85, 86, 90, 91, 92, 96, 97, 98, 102, 103, 104, 108, 109, 110, 114, 115, 116, 120, 121, 122, 126, 127, 128, 132, 133, 134, 138, 139, 140, 294, 295, 296, 300, 301, 305, 306, 307, 311, 312, 316, 317, or 318; (ii) a VH complementarity determining region two (CDR2) having the amino acid sequence shown in SEQ ID NO: 40, 41, 46, 47, 51, 52, 57, 58, 63, 64, 69, 70, 75, 76, 81, 82, 87, 88, 93, 94, 99, 100, 105, 106, 111, 112, 117, 118, 123, 124, 129, 130, 135, 136, 141, 142, 297, 298, 302, 303, 308, 309, 313, 314, 319, 320, or 322; and (iii) a VH complementarity determining region three (CDR3) having the amino acid sequence shown in SEQ ID NO: 42, 48, 53, 59, 65, 71, 77, 83, 89, 95, 101, 107, 113, 119, 125, 131, 137, 143, 299, 304, 310, 315, or 321; and (b) the VL region comprises (i) a VL complementarity determining region one (CDR1) having the amino acid sequence shown in SEQ ID NO: 144, 147, 150, 153, 156, 159, 162, 165, 168, 171, 174, 177, 180, 183, 186, 189, 192, 195, 323, 326, 328, 331, 336, 338, 340, 343, 345, 348, or 350; (ii) a VL complementarity determining region two (CDR2) having the amino acid sequence shown in SEQ ID NO: 145, 148, 151, 154, 157, 160, 163, 166, 169, 172, 175, 178, 181, 184, 187, 190, 193, 196, 324, 329, 332, 334, 341, or 346; and (iii) a VL complementarity determining region three (CDR3) having the amino acid sequence shown in SEQ ID NO: 146, 149, 152, 155, 158, 161, 164, 167, 170, 173, 176, 179, 182, 185, 188, 191, 194, 197, 325, 327, 330, 333, 335, 337, 339, 342, 344, 347, or 349.

In some embodiments, a CAR of the invention comprises an extracellular ligand-binding domain having any one of partial light chain sequence as listed in Table 2 and/or any one of partial heavy chain sequence as listed in Table 2.

In Table 2, the underlined sequences are CDR sequences according to Kabat and in bold according to Chothia, except for the heavy chain CDR2 sequences of P4F6, P4C7, P3A1, P5A3, P9B5, P9F1, P1B4, P1B11, P7H3, P3E10, P1A5, P5F7, P4H11, P15F7, P12B6, P8B6, P14G2, and P7F9, in which the Chothia CDR sequence is underlined and the Kabat CDR sequence is in bold.

TABLE 2

| mAb | Light Chain | Heavy Chain |
|---|---|---|
| P4F6 | EIVLTQSPGTLSLSPGERATLSCRASHSVSSSYLAWYQQKPGQAPRLLIYGASSRATGIPDRFSGSGSGTDFTLTISRLEPEDFAVYYCQQYGSPPRTFGQGTKVEIK (SEQ ID NO: 1) | QVQLVQSGAEVKKPGSSVKVSCKASGGTFGSSYGISWVRQAPGQGLEWMGGIIPIFGTVTYAQKFQGRVTITADESTRTAYMELSSLRSEDTAVYYCARDSWSGATGASDTWGQGTLVTVSS (SEQ ID NO: 2) |
| P4C7 | EIVLTQSPGTLSLSPGERATLSCRASQYVSASLLAWYQQKPGQAPRLLIYGASTRATGIPDRFSGSGSGTDFTLTISRLEPEDFAVYYCQQYARSSTFGQGTKVEIK (SEQ ID NO: 3) | QVQLVQSGAEVKKPGSSVKVSCKASGGTFSSYTISWVRQAPGQGLEWMGGIIPAFGIANYAQKFQGRVTITADKSTSTAYMELSSLRSEDTAVYYCAKGGSYSLDYFDIWGQGTLVTVSS (SEQ ID NO: 4) |
| P3A1 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGQGTKVEIK (SEQ ID NO: 5) | QVQLVQSGAEVKKPGSSVKVSCKASGGTFSSYDISWVRQAPGQGLEWMGGIIPVSGRANYAQKFQGRVTITTDKSTSTAYMELSSLRSEDTAVYYCARVRPTYWPLDYWGQGTLVTVSS (SEQ ID NO: 6) |
| P5A3 | QSALTQPASVSGSPGQSITISCTGTSSDVGGYNYVSWYQQHPGKAPKLMIYEVSKRPSGVPDRFSGSKSGNTASLTVSGLQAEDEADYYCSSYAGSNTVVFGGGTKLTVL (SEQ ID NO: 7) | QVQLVQSGAEVKKPGSSVKVSCKASGGTFSSYYIGWVRQAPGQGLEWMGGIIPWFGTANYAQKFQGRVTITADKSTNTAYMELSSLRSEDTAVYYCAADHHDSPSGYTSGGFDVWGQGTLVTVSS (SEQ ID NO: 8) |
| P9B5 | QSVLTQPPSASGTPGQRVTISCSGSSSNIGSNYVYWYQQLPGTAPKLLIYRNNQRPSGVPDRFSGSKSGTSASLAISGLRSEDEADYYCAAWDDSLSGVVFGGGTKLTVL (SEQ ID NO: 9) | EVQLLESGGGLVQPGGSLRLSCAASGFIFASYAMSWVRQAPGKGLEWVSEISSSGGSTTYADSVKGRFTISRDNSKNTLYLQMNSLRAEDTAVYYCARDRVMAGLGYDPFDYWGQGTLVTVSS (SEQ ID NO: 10) |
| P9F1 | QSVLTQPPSASGTPGQRVTISCSGSGSNIGSNYVYWYQQLPGTAPKLLIYRNNQRPSGVPDRFSGSKSGTSASLAISGLRSEDEADYYCAAWDGSLSRPVFGTGTKLTVL (SEQ ID NO: 11) | EVQLLESGGGLVQPGGSLRLSCAASGFIFSSFAMSWVRQAPGKGLEWVSDISGSGASTYYADSVKGRFTISRDNSKNTLYLQMNSLRAEDTAVYYCASASGGSGSYWPYMDPWGQGTLVTVSS (SEQ ID NO: 12) |
| P1B4 | EIVLTQSPGTLSLSPGERATLSCRASQSVPNEQLAWYQQKPGQAPSRYLIYDASSRATGIPDRFSGSGSGTDFTLTISRLEPEDFAVYYCQQYGSPPLTFGQGTKVEIK (SEQ ID NO: 13) | QVQLVQSGAEVKKPGSSVKVSCKASGGVFSRYALSWVRQAPGQGLEWMGGIIPMLGFANYAQKFQGRVTITADESTSTAYMELSSLRSEDTAVYYCATLDFGALDYWGQGTLVTVSS (SEQ ID NO: 14) |
| P1B11 | EIVLTQSPGTLSLSPGERATLSCRASQSVSSSELAWYQQKPGQAPRLLIYDASSRATGIPDRFSGSGSGTDFTLTISRLEPEDFAVYYCQQYDSSPLTFGQGTKVEIK (SEQ ID NO: 15) | QVQLVQSGAEVKKPGSSVKVSCKASGGTFRSFDISWVRQAPGQGLEWMGRIIPILGYANYAQKFQGRVTITADESTSTAYMELSSLRSEDTAVYYCASDLGAPWAGYPFDPWGQGTLVTVSS (SEQ ID NO: 16) |
| P7H3 | QSVLTQPPSVSVAPGKTARITCGGNNIGSKSVHWYQQKPGQAPVLVIYYDSDRPSGIPERFSGSNSGNTATLTISRVEAGDEADYYCQVWDSSTAWVFGGGTKLTVL (SEQ ID NO: 17) | EVQLLESGGGLVQPGGSLRLSCAASGFTFSSYAMHWVRQAPGKGLEWVSAISGSGGSTYYADSVKGRFTISRDNSKNTLYLQMNSLRAEDTAVYYCARGTRWWWGDAFDHWGQGTLVTVSS (SEQ ID NO: 18) |
| P3E10 | EIVLTQSPGTLSLSPGERATLSCRASQSVPSSQLAWYQQKPGQAPRLLIYDASSRATGIPDRFSGSGSGTDFTLTISRLEPEDFAVYYCQQYGSSPLTFGQGTKVEIK (SEQ ID NO: 19) | QVQLVQSGAEVKKPGSSVKVSCKASGGTFSSYAIQWVRQAPGQGLEWMGGIVGSWGLANYAQKFQGRVTITTDKSTSTAYMELSSLRSEDTAVYYCATSAFGELASWGQGTLVTVSS (SEQ ID NO: 20) |
| P1A5 | EIVLTQSPGTLSLSPGERATLSCRASQAVDSSDLAWYQQKPGQAPRLLIYDAYTRPSGIPDRFSGSGSGTDFTLTISRLEPEDFAVYYCQQYGSSPLTFGGGTKLEIK (SEQ ID NO: 21) | QVQLVQSGAEVKKPGSSVKVSCKASGGVFSRYALSWVRQAPGQGLEWMGGIIPMLGFANYAQKFQGRVTITADESTSTAYMELSSLRSEDTAVYYCATLDFGALDYWGQGTLVTVSS (SEQ ID NO: 22) |

TABLE 2-continued

| mAb | Light Chain | Heavy Chain |
|---|---|---|
| P5F7 | EIVLTQSPATLSLSPGERATLSCRASQ SVSSNLAWYQQKPGQAPRLLIYDTF TRATGIPARFSGSGSGTDFTLTISRLE PEDFAVYYCQQYGSSPPTFGQGTRL EIK (SEQ ID NO: 23) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 24) |
| P4H11 | EIVLTQSPGTLSLSPGERATLSCRASQ SVSNTYLAWYQQKPGQAPRLLIYDT SSRATGIPDRFSGSGSGTDFTLTISRLE PEDFAVYYCQQYGSSLTFGQGTKVE IK (SEQ ID NO: 25) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 26) |
| P15F7 | DIQMTQSPSSLSASVGDRVTITCRAS QSISTYLNWYQQKPGKAPKLLIYAAS NLQSGVPSRFSGSGSGTDFTLTISSLQ PEDFATYYCQQSYSIPLTFGQGTKVE IK (SEQ ID NO: 27) | EVQLLESGGGLVQPGGSLRLSCAAS GFTFNNYAMNWVRQAPGKGLEWV SVISGSGGTTYYADSVKGRFTISRD NSKNTLYLQMNSLRAEDTAVYYCA SGIWDLRYWGQGTLVTVSS (SEQ ID NO: 28) |
| P12B6 | EIVLTQSPGTLSLSPGERATLSCRASQ IVSSSYLAWYQQKPGQAPRLLIYGAS SRASGIPDRFSGSGSGTDFTLTISRLEP EDFAVYYCQQYGGSPYTFGQGTKV EIK (SEQ ID NO: 29) | QVQLVQSGAEVKKPGSSVKVSCKAS GGTFMSYAISWVRQAPGQGLEWM GGIIPIFGIANYAQKFQGRVTITADK STSTAYMELSSLRSEDTAVYYCARE TLIYPIPFELWGQGTLVTVSS (SEQ ID NO: 30) |
| P8B6 | EIVLTQSPGTLSLSPGERATLSCRASQ SVSHSYLAWYQQKPGQAPRLLIYGA SFRAAGIPDRFSGSGSGTDFTLTISRL EPEDFAVYYCQQYGSDPYTFGQGTK VEIK (SEQ ID NO: 31) | QVQLVQSGAEVKKPGSSVKVSCKAS GGTFSSYAVSWVRQAPGQGLEWM GGIIPIFGIANYAQKFQGRVTITADT STSTAYMELSSLRSEDTAVYYCAIEG IGGDLRYDGYDAWGQGTLVTVSS (SEQ ID NO: 32) |
| P14G2 | DIQMTQSPSSLSASVGDRVTITCRAS QSISSYLNWYQQKPGKAPKLLIYDAS DLQRGVPSRFSGSGSGTDFTLTISSLQ PEDFATYYCQQSYNTPWTFGQGTKV EIK (SEQ ID NO: 33) | EVQLLESGGGLVQPGGSLRLSCAAS GFTFSNYVMNWVRQAPGKGLEWV SAISGSGATTYYADSVKGRFTISRD NSKNTLYLQMNSLRAEDTAVYYCV SGLWAGGIWGQGTLVTVSS (SEQ ID NO: 34) |
| P7F9 | NFMLTQPHSVSESPGKTVTISCTRSSG SIASNYVQWYQQKPGQAPVLVVYD DSDRPSGIPERFSGSNSGNTATLTISR VEAGDEADYYCQVWDSSSDHWVFG GGTKLTVL (SEQ ID NO: 35) | EVQLLESGGGLVQPGGSLRLSCAAS GFTFSSYAMSWVRQAPGKGLEWVS AIGGSGGSTYYADSVKGRFTISRDN SKNTLYLQMNSLRAEDTAMYYCAR DYYAFSDPAYGGMDVWGQGTLVT VSS (SEQ ID NO: 36) |
| PQ8BQ 6EE | EIVLTQSPGTLSLSPGERATLSCRASQ SVSHSYLAWYQQKPGQAPRLLIYGA SFRAAGIPDRFSGSGSGTDFTLTISRL EPEDFAVYYCQQYGSEPYTFGQGTK VEIK (SEQ ID NO: 264) | QVQLVQSGAEVKKPGSSVKVSCKAS GGTFSSYAVSWVRQAPGQGLEWM GGIIPIFGIANYAQKFQGRVTITADTS TSTAYMELSSLRSEDTAVYYCAIIEGI GGDLRYEGYDAWGQGTLVTVSS (SEQ ID NO: 265) |
| P04A0 4 | EIVLTQSPGTLSLSPGERATLSCRASQ SVTSSQLAWYQQKPGQAPRLLIYDA SSRATGIPDRFSGSGSGTDFTLTISRLE PEDFAVYYCQQYGSSLLITFGQGTK VEIK (SEQ ID NO: 266) | QVQLVQSGAEVKKPGSSVKVSCKAS GGTFSSYYITWVRQAPGQGLEWMG RIMPAFGWTNYAQKFQGRVTITTDK STSTAYMELSSLRSEDTAVYYCASD EFGAFDVWGQGTLVTVSS (SEQ ID NO: 267) |
| PQIAQ 5 | EIVLTQSPGTLSLSPGERATLSCRASQ AVDSSDLAWYQHKPGQAPRLLIYDA YTRPSGIPDRFSGSGSGTDFTLTISRLE PEDFAVYYCQQYGSSPLTFGGGTKL EIK (SEQ ID NO: 268) | QVQLVQSGAEVKKPGSSVKVSCKAS GGVFSRYALSWVRQAPGQGLEWM GGIIPMLGFANYAQKFQGRVTITAD ESTSTAYMELSSLRSEDTAVYYCAT LDFGALDYWGQGTLVTVSS (SEQ ID NO: 269) |
| PQ8BQ 3 | DIVMTQSPGTLSLSPGERATLSCRAS QSVSSNLAWYQQKPGQAPRLLIYDA YTRATGIPARFSGSGSGTDFTLTISRL EPEDFAVYYCQQYGSPYTFGQGTKV EIK (SEQ ID NO: 270) | QVQLVQSGAEVKKPGSSVKVSCKAS GGTFSSYDISWVRQAPGQGLEWMG RIIPSFGAANYAQKFQGRVTITADKS TSTAYMELSSLRSEDTAVYYCATDD GEGWTPPFGYWGQGTLVTVSS (SEQ ID NO: 271) |

TABLE 2-continued

| mAb | Light Chain | Heavy Chain |
|---|---|---|
| P5F7 | DIVMTQSPATLSLSPGERATLSCRAS QSVSSNLAWYQQKPGQAPRLLIYDT FTRATGIPARFSGSGSGTDFTLTISRL EPEDFAVYYCQQYGSSPPTFGQGTR LEIK (SEQ ID NO: 272) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 273) |
| P5F7g | EIVLTQSPATLSLSPGERATLSCRASQ SVSSNLAWYQQKPGQAPRLLIYDTF TRATGIPARFSGSGSGTDFTLTISSLEP EDFAVYYCQQYGSSPPTFGQGTRLEI K (SEQ ID NO: 274) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 275) |
| P10A0 2g | EIVLTQSPATLSLSPGERATLSCRASQ DVSDLLAWYQQKPGQAPRLLIYDAY TRATGIPARFSGSGSGTDFTLTISSLEP EDFAVYYCQQYASSPITFGQGTRLEI K (SEQ ID NO: 276) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 277) |
| P10A0 4g | EIVLTQSPATLSLSPGERATLSCRASQ KVSDLLAWYQQKPGQAPRLLIYDAY TRATGIPARFSGSGSGTDFTLTISSLEP EDFAVYYCQQYTGSPITFGQGTRLEI K (SEQ ID NO: 278) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 279) |
| P10A0 5g | EIVLTQSPATLSLSPGERATLSCRASL SVSDLLAWYQQKPGQAPRLLIYDAY SRATGIPARFSGSGSGTDFTLTISSLEP EDFAVYYCQQYSSNPITFGQGTRLEI K (SEQ ID NO: 280) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 281) |
| P10A0 7g | EIVLTQSPATLSLSPGERATLSCRASG SVSDLLAWYQQKPGQAPRLLIYDAY SRATGIPARFSGSGSGTDFTLTISSLEP EDFAVYYCQQYASYPITFGQGTRLEI K (SEQ ID NO: 282) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 283) |
| P1QBQ 3g | EIVLTQSPATLSLSPGERATLSCRASQ SVSDLLAWYQQKPGQAPRLLIYDAF SRATGIPARFSGSGSGTDFTLTISSLEP EDFAVYYCQQYGTPPITFGQGTRLEI K (SEQ ID NO: 284) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 285) |
| P1QBQ 6g | EIVLTQSPATLSLSPGERATLSCRASE SVSDLLAWYQQKPGQAPRLLIYDAY SRATGIPARFSGSGSGTDFTLTISSLEP EDFAVYYCQQYSASPITFGQGTRLEI K (SEQ ID NO: 286) | EVQLLESGGGLVQPGGSLRLSCAAS GFTFSSYAMNWVRQAPGKGLEWVS SISGGGRSTYYADSVKGRFTISRDNS KNTLYLQMNSLRAEDTAVYYCARD LSPSDVGWGYGFDIWGQGTLVTVS S (SEQ ID NO: 287) |
| P5F7g 2 | EIVLTQSPATLSLSPGERATLSCRASQ SVSSNLAWYQQKPGQAPRLLIYDTF TRATGIPARFSGSGSGTDFTLTISSLEP EDFAVYYCQQYGSSPPTFGQGTRLEI K (SEQ ID NO: 288) | EVQLLESGGGLVQPGGSLRLSCAAS GFTFSSYAMNWVRQAPGKGLEWVS AISGGGRSTYYADSVKGRFTISRDNS KNTLYLQMNSLRAEDTAVYYCARD LSPSDVGWGYGFDIWGQGTLVTVS S (SEQ ID NO: 289) |
| P5F7g 3 | EIVLTQSPATLSLSPGERATLSCRASQ SVSSLLAWYQQKPGQAPRLLIYDAY TRATGIPARFSGSGSGTDFTLTISSLEP EDFAVYYCQQYTGSPITFGQGTRLEI K (SEQ ID NO: 290) | EVQLLESGGGLVQPGGSLRLSCAAS GFTFSSYAMNWVRQAPGKGLEWVS AISGGGRSTYYADSVKGRFTISRDNS KNTLYLQMNSLRAEDTAVYYCARD LSPSDVGWGYGFDIWGQGTLVTVS S (SEQ ID NO: 291) |
| P5F7g 4 | EIVLTQSPATLSLSPGERATLSCRASQ SVSSLLAWYQQKPGQAPRLLIYDAY TRATGIPARFSGSGSGTDFTLTISSLEP EDFAVYYCQQYTGSPITFGQGTRLEI K (SEQ ID NO: 292) | EVQLLESGGGLVQPGGSLRLSCAAS GFTFSSYAMSWVRQAPGKGLEWVS AISGGGRSTYYADSVKGRFTISRDNS KNTLYLQMNSLRAEDTAVYYCARD LSPSDVGWGYGFDIWGQGTLVTVS S (SEQ ID NO: 293) |

Also provided herein are CDR portions of antigen binding domains of antibodies to FLT3 or CDR portions of extracellular ligand-binding domains of CARs to FLT3 (including Chothia, Kabat CDRs, and CDR contact regions). Determination of CDR regions is well within the skill of the art. It is understood that in some embodiments, CDRs can be a combination of the Kabat and Chothia CDR (also termed "combined CRs" or "extended CDRs"). In some embodiments, the CDRs are the Kabat CDRs. In other embodiments, the CDRs are the Chothia CDRs. In other words, in embodiments with more than one CDR, the CDRs may be any of Kabat, Chothia, combination CDRs, or combinations thereof. Table 3 provides examples of CDR sequences provided herein.

TABLE 3

| | Heavy Chain | | |
|---|---|---|---|
| mAb | CDRH1 | CDRH2 | CDRH3 |
| P4F6 | SYGIS (SEQ ID NO: 37) (Kabat); GGTFGSY (SEQ ID NO: 38) (Chothia); GGTFGSYGIS (SEQ ID NO: 39) (Extended) | GIIPIFGTVTYAQK FQG (SEQ ID NO: 40) (Kabat); IPIFGT (SEQ ID NO: 41) (Chothia) | DSWSGATGASD T (SEQ ID NO: 42) |
| P4C7 | SYTIS (SEQ ID NO: 43) (Kabat); GGTFSSY (SEQ ID NO: 44) (Chothia) GGTFSSYTIS (Extended) (SEQ ID NO: 45) | GIIPAFGIANYAQK FQG (SEQ ID NO: 46) (Kabat); IPAFGI (SEQ ID NO: 47) (Chothia) | GGSYSLDYFDI (SEQ ID NO: 48) |
| P3A1 | SYDIS (SEQ ID NO: 49) (Kabat); GGTFSSY (SEQ ID NO: 44) (Chothia); GGTFSSYDIS (SEQ ID NO: 50) (Extended) | GIIPVSGRANYAQ KFQG (SEQ ID NO: 51) (Kabat); IPVSGR (SEQ ID NO: 52) (Chothia) | VRPTYWPLDY (SEQ ID NO: 53) |
| P5A3 | SYYIG (SEQ ID NO: 54) (Kabat); GGTFSSY (SEQ ID NO: 55) (Chothia); GGTFSSYYIG (SEQ ID NO: 56) (Extended) | GIIPWFGTANYAQ KFQG (SEQ ID NO: 57) (Kabat); IPWFGT (SEQ ID NO: 58) (Chothia) | DHHDSPSGYTSG GFDV (SEQ ID NO: 59) |
| P9B5 | SYAMS (SEQ ID NO: 60) (Kabat); GFIFASY (SEQ ID NO: 61) (Chothia); GFIFASYAMS (SEQ ID NO: 62) (Extended) | EISSSGGSTTYADS VKG (SEQ ID NO: 63) (Kabat); SSSGGS (SEQ ID NO: 64) (Chothia) | DRVMAGLGYDP FDY (SEQ ID NO: 65) |
| P9F1 | SFAMS (SEQ ID NO: 66) (Kabat); GFIFSSF (SEQ ID NO: 67) (Chothia); GFIFSSFAMS (SEQ ID NO: 68) (Extended) | DISGSGASTYYAD SVKG (SEQ ID NO: 69) (Kabat); SGSGAS (SEQ ID NO: 70) (Chothia) | ASGGSGSYWPY MDP (SEQ ID NO: 71) |
| P1B4 | RYALS (SEQ ID NO: 72) (Kabat); GGVFSRY (SEQ ID NO: 73) (Chothia); GGVFSRYALS (SEQ ID NO: 74) (Extended) | GIIPMLGFANYAQ KFQG (SEQ ID NO: 75) (Kabat); IPMLGF (SEQ ID NO: 76) (Chothia) | LDFGALDY (SEQ ID NO: 77) |
| P1B11 | SFDIS (SEQ ID NO: 78) (Kabat); GGTFRSF (SEQ ID NO: 79) (Chothia); GGTFRSFDIS (SEQ ID NO: 80) (Extended) | RIIPILGYANYAQK FQG (SEQ ID NO: 81) (Kabat); IPILGY (SEQ ID NO: 82) (Chothia) | DLGAPWAGYPF DP (SEQ ID NO: 83) |
| P7H3 | SYAMH (SEQ ID NO: 84) (Kabat); GFTFSSY (SEQ ID NO: 85) (Chothia); GFTFSSYAMH (SEQ ID NO: 86) (Extended) | AISGSGGSTYYAD SVKG (SEQ ID NO: 87) (Kabat); SGSGGS (SEQ ID NO: 88) (Chothia) | GTRWWWGDAF DH (SEQ ID NO: 89) |
| P3E10 | SYAIQ (SEQ ID NO: 90) (Kabat); GGTFSSY (SEQ ID NO: 91) | GIVGSWGLANYA QKFQG (SEQ ID NO: 93) (Kabat); | SAFGELAS (SEQ ID NO: 95) |

TABLE 3-continued

| | | | |
|---|---|---|---|
| | (Chothia); GGTFSSYAIQ (SEQ ID NO: 92) (Extended) | VGSWGL (SEQ ID NO: 94) (Chothia) | |
| P1A5 | RYALS (SEQ ID NO: 96) (Kabat); GGVFSRY (SEQ ID NO: 97) (Chothia); GGVFSRYALS (SEQ ID NO: 98) (Extended) | GIIPMLGFANYAQ KFQG (SEQ ID NO: 99) (Kabat); IPMLGF (SEQ ID NO: 100) (Chothia) | LDFGALDY (SEQ ID NO: 101) |
| P5F7 | SYAMN (SEQ ID NO: 102) (Kabat); GFTFSSY (SEQ ID NO: 103) (Chothia); GFTFSSYAMN (SEQ ID NO: 104) (Extended) | SISGGGRSTYYAD SVKG (SEQ ID NO: 105) (Kabat); SGGGRS (SEQ ID NO: 106) (Chothia) | DLSPSDVGWGY GFDI (SEQ ID NO: 107) |
| P4H11 | SYAMN (SEQ ID NO: 108) (Kabat); GFTFSSY (SEQ ID NO: 109) (Chothia); GFTFSSYAMN (SEQ ID NO: 110) (Extended) | SISGGGRSTYYAD SVKG (SEQ ID NO: 111) (Kabat); SGGGRS (SEQ ID NO: 112) (Chothia) | DLSPSDVGWGY GFDI (SEQ ID NO: 113) |
| P15F7 | NYAMN (SEQ ID NO: 114) (Kabat); GFTFNNY (SEQ ID NO: 115) (Chothia); GFTFNNYAMN (SEQ ID NO: 116) (Extended) | VISGSGGTTYYAD SVKG (SEQ ID NO: 117) (Kabat); SGSGGT (SEQ ID NO: 118) (Chothia) | GIWDLRY (SEQ ID NO: 119) |
| P12B6 | SYAIS (SEQ ID NO: 120) (Kabat); GGTFMSY (SEQ ID NO: 121) (Chothia); GGTFMSYAIS (SEQ ID NO: 122) (Extended) | GIIPIFGIANYAQKF QG (SEQ ID NO: 123) (Kabat); IPIFGI (SEQ ID NO: 124) (Chothia) | ETLIYPIPFEL (SEQ ID NO: 125) |
| P8B6 | SYAVS (SEQ ID NO: 126) (Kabat); GGTFSSY (SEQ ID NO: 127) (Chothia); GGTFSSYAVS (SEQ ID NO: 128) (Extended) | GIIPIFGIANYAQKF QG (SEQ ID NO: 129) (Kabat); IPIFGI (SEQ ID NO: 130) (Chothia) | EGIGGDLRYDGY DA (SEQ ID NO: 131) |
| P14G2 | NYVMN (SEQ ID NO: 132) (Kabat); GFTFSNY (SEQ ID NO: 133) (Chothia); GFTFSNYVMN (SEQ ID NO: 134) (Extended) | AISGSGATTYYAD SVKG (SEQ ID NO: 135) (Kabat); SGSGAT (SEQ ID NO: 136) (Chothia) | GLWAGGI (SEQ ID NO: 137) |
| P7F9 | SYAMS (SEQ ID NO: 138) (Kabat); GFTFSSY (SEQ ID NO: 139) (Chothia); GFTFSSYAMS (SEQ ID NO: 140) (Extended) | AIGGSGGSTYYAD SVKG (SEQ ID NO: 141) (Kabat); GGSGGS (SEQ ID NO: 142) (Chothia) | DYYAFSDPAYG GMDV (SEQ ID NO: 143) |
| P08B06EE | SYAVS (SEQ ID NO: 294) (Kabat); GGTFSSY (SEQ ID NO: 295) (Chothia); GGTFSSYAVS (SEQ ID NO: 296) (Extended) | GIIPIFGIANYAQKF QG (SEQ ID NO: 297) (Kabat); IPIFGI (SEQ ID NO: 298) (Chothia) | EGIGGDLRYEGY DA (SEQ ID NO: 299) |
| P04A04 | SYYIT (SEQ ID NO: 300) GGTFSSY (SEQ ID NO: 295) (Chothia) GGTFSSYYIT (SEQ ID NO: 301) (Extended) | RIMPAFGWTNYA QKFQG (SEQ ID NO: 302) (Kabat); MPAFGW (SEQ ID NO: 303) (Chothia) | DEFGAFDV (SEQ ID NO: 304) |
| P01A05 | RYALS (SEQ ID NO: 305) (Kabat); GGVFSRY (SEQ ID NO: 306) (Chothia); GGVFSRYALS (SEQ ID NO: 307) (Extended) | IPMLGF (SEQ ID NO: 308) (Chothia) GGIIPMLGFANYA QKFQG (SEQ ID NO: 309) (Kabat) | LDFGALDY (SEQ ID NO: 3110) |

TABLE 3-continued

| | | | |
|---|---|---|---|
| P08B03 | SYDIS (SEQ ID NO: 311) (Kabat); GGTFSSY (SEQ ID NO: 295) (Chothia); GGTFSSYDIS (SEQ ID NO: 312) (Extended) | RIIPSFGAANYAQK FQG (SEQ ID NO: 313) (Kabat) IPSFGA (SEQ ID NO: 314) (Chothia) | DDGEGWTPPFG Y (SEQ ID NO: 315) |
| P5F7g; P10A02g; P10A04g; P10A05g; P10A07g; P10B03g; P10B06g | SYAMN (SEQ ID NO: 316) (Kabat); GFTFSSY (SEQ ID NO: 317) (Chothia); GFTFSSYAMN (SEQ ID NO: 318) (Extended) | SISGGGRSTYYAD SVKG (SEQ ID NO: 319) (Kabat); SGGGRS (SEQ ID NO: 320) (Chothia) | DLSPSDVGWGY GFDI (SEQ ID NO: 321) |
| P5F7g2; P5F7g3 | SYAMN (SEQ ID NO: 316) (Kabat); GFTFSSY (SEQ ID NO: 317) (Chothia); GFTFSSYAMN (SEQ ID NO: 318) (Extended) | AISGGGRSTYYAD SVKG (SEQ ID NO: 322) (Kabat); SGGGRS (SEQ ID NO: 320) (Chothia) | DLSPSDVGWGY GFDI (SEQ ID NO: 321) |
| P5F7g4 | SYAMS (SEQ ID NO: 138) (Kabat); GFTFSSY (SEQ ID NO: 317) (Chothia); GFTFSSYAMS (SEQ ID NO: 140) (Extended) | AISGGGRSTYYAD SVKG (SEQ ID NO: 322) (Kabat); SGGGRS (SEQ ID NO: 320) (Chothia) | DLSPSDVGWGY GFDI (SEQ ID NO: 321) |

| Light Chain | | | |
|---|---|---|---|
| mAb | CDRL1 | CDRL2 | CDRL3 |
| P4F6 | RASHSVSSSYLA (SEQ ID NO: 144) | GASSRAT (SEQ ID NO: 145) | QQYGSPPRT (SEQ ID NO: 146) |
| P4C7 | RASQYVSASLLA (SEQ ID NO: 147) | GASTRAT (SEQ ID NO: 148) | QQYARSST (SEQ ID NO: 149) |
| P3A1 | RASQSISSYLN (SEQ ID NO: 150) | AASSLQS (SEQ ID NO: 151) | QQSYSTPLT (SEQ ID NO: 152) |
| P5A3 | TGTSSDVGGYNYVS (SEQ ID NO: 153) | EVSKRPS (SEQ ID NO: 154) | SSYAGSNTVV (SEQ ID NO: 155) |
| P9B5 | SGSSSNIGSNYVY (SEQ ID NO: 156) | RNNQRPS (SEQ ID NO: 157) | AAWDDSLSGVV (SEQ ID NO: 158) |
| P9F1 | SGSGSNIGSNYVY (SEQ ID NO: 159) | RNNQRPS (SEQ ID NO: 160) | AAWDGSLSRPV (SEQ ID NO: 161) |
| P1B4 | RASQSVPNEQLA (SEQ ID NO: 162) | DASSRAT (SEQ ID NO: 163) | QQYGSPPLT (SEQ ID NO: 164) |
| P1B11 | RASQSVSSSELA (SEQ ID NO: 165) | DASSRAT (SEQ ID NO: 166) | QQYDSSPLT (SEQ ID NO: 167) |
| P7H3 | GGNNIGSKSVH (SEQ ID NO: 168) | YDSDRPS (SEQ ID NO: 169) | QVWDSSTAWV (SEQ ID NO: 170) |
| P3E10 | RASQSVPSSQLA (SEQ ID NO: 171) | DASSRAT (SEQ ID NO: 172) | QQYGSSPLT (SEQ ID NO: 173) |
| P1A5 | RASQAVDSSDLA (SEQ ID NO: 174) | DAYTRPS (SEQ ID NO: 175) | QQYGSSPLT (SEQ ID NO: 176) |
| P5F7 | RASQSVSSNLA (SEQ ID NO: 177) | DTFTRAT (SEQ ID NO: 178) | QQYGSSPPT (SEQ ID NO: 179) |
| P4H11 | RASQSVSNTYLA (SEQ ID NO: 180) | DTSSRAT (SEQ ID NO: 181) | QQYGSSLT (SEQ ID NO: 182) |
| P15F7 | RASQSISTYLN (SEQ ID NO: 183) | AASNLQS (SEQ ID NO: 184) | QQSYSIPLT (SEQ ID NO: 185) |
| P12B6 | RASQIVSSSYLA (SEQ ID NO: 186) | GASSRAS (SEQ ID NO: 187) | QQYGGSPYT (SEQ ID NO: 188) |
| P8B6 | RASQSVSHSYLA (SEQ ID NO: 189) | GASFRAA (SEQ ID NO: 190) | QQYGSDPYT (SEQ ID NO: 191) |

TABLE 3-continued

| | | | |
|---|---|---|---|
| P14G2 | RASQSISSYLN (SEQ ID NO: 192) | DASDLQR (SEQ ID NO: 193) | QQSYNTPWT (SEQ ID NO: 194) |
| P7F9 | TRSSGSIASNYVQ (SEQ ID NO: 195) | DDSDRPS (SEQ ID NO: 196) | QVWDSSSDHWV (SEQ ID NO: 197) |
| P08B06EE | RASQSVSHSYLA (SEQ ID NO: 323) | GASFRAA (SEQ ID NO: 324) | QQYGSEPYT (SEQ ID NO: 325) |
| P04A04 | RASQSVTSSQLA (SEQ ID NO: 326) | GASFRAA (SEQ ID NO: 324) | QQYGSSLLIT (SEQ ID NO: 327) |
| P01A05 | RASQAVDSSDLA (SEQ ID NO: 328) | DAYTRPS (SEQ ID NO: 329) | QQYGSSPLT (SEQ ID NO: 330) |
| P08B03 | RASQSVSSNLA (SEQ ID NO: 331) | DAYTRAT (SEQ ID NO: 332) | QQYGSPYT (SEQ ID NO: 333) |
| P5F7g | RASQSVSSNLA (SEQ ID NO: 331) | DTFTRAT (SEQ ID NO: 334) | QQYGSSPPT (SEQ ID NO: 335) |
| P10A02g | RASQDVSDLLA (SEQ ID NO: 336) | DAYTRAT (SEQ ID NO: 332) | QQYASSPIT (SEQ ID NO: 337) |
| P10A04g | RASQKVSDLLA (SEQ ID NO: 338) | DAYTRAT (SEQ ID NO: 332) | QQYTGSPIT (SEQ ID NO: 339) |
| P10A05g | RASLSVSDLLA (SEQ ID NO: 340) | DAYSRAT (SEQ ID NO: 341) | QQYSSNPIT (SEQ ID NO: 342) |
| P10A07g | RASGSVSDLLA (SEQ ID NO: 343) | DAYSRAT (SEQ ID NO: 341) | QQYASYPIT (SEQ ID NO: 344) |
| P10B03g | RASQSVSDLLA (SEQ ID NO: 345) | DAFSRAT (SEQ ID NO: 346) | QQYGTPPIT (SEQ ID NO: 347) |
| P10B06g | RASESVSDLLA (SEQ ID NO: 348) | DAYSRAT (SEQ ID NO: 341) | QQYSASPIT (SEQ ID NO: 349) |
| P5F7g2 | RASQSVSSNLA (SEQ ID NO: 331) | DTFTRAT (SEQ ID NO: 334) | QQYGSSPPT (SEQ ID NO: 335) |
| P5F7g3; P5F7g4 | RASQSVSSLLA (SEQ ID NO: 350) | DAYTRAT (SEQ ID NO: 332) | QQYTGSPIT (SEQ ID NO: 339) |

The invention encompasses modifications to the CARs and polypeptides of the invention shown in Table 2, including functionally equivalent CARs having modifications which do not significantly affect their properties and variants which have enhanced or decreased activity and/or affinity. For example, the amino acid sequence may be mutated to obtain an antibody with the desired binding affinity to FLT3. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or which mature (enhance) the affinity of the polypeptide for its ligand, or use of chemical analogs.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the half-life of the antibody in the blood circulation.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 4 under the heading of "conservative substitutions." If such substitutions result in a change in biological activity, then more substantial changes, denominated "exemplary substitutions" in Table 4, or as further described below in reference to amino acid classes, may be introduced and the products screened.

TABLE 4

Amino Acid Substitutions

| Original Residue (naturally occurring amino acid) | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |

TABLE 4-continued

Amino Acid Substitutions

| Original Residue (naturally occurring amino acid) | Conservative Substitutions | Exemplary Substitutions |
|---|---|---|
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

In some embodiments, provided herein is a CAR comprising an extracellular ligand-binding domain that binds to FLT3 and competes for binding to FLT3 with a CAR described herein, including CAR comprising an extracellular domain comprising P4F6, P4C7, P3A1, P5A3, P9B5, P9F1, P1B4, P1B11, P7H3, P3E10, P1A5, P5F7, P4H11, P15F7, P12B6, P8B6, P14G2, P7F9, P08B06EE, P04A04, P01A05, P08B03, P5F7g, P10A02g, P10A04g, P10A05g, P10A07g, P10B03g, P10B06g, P5F7g2, P5F7g3, and P5F7g4.

In some embodiments, provided herein is a CAR, which specifically binds to FLT3, wherein the CAR comprises a VH region comprising a sequence shown in SEQ ID NO: 4; and/or a VL region comprising a sequence shown in SEQ ID NO: 3. In some embodiments, provided herein is a CAR, which specifically binds to FLT3, wherein the CAR comprises a VH region comprising a sequence shown in SEQ ID NO: 6; and/or a VL region comprising a sequence shown in SEQ ID NO: 5. In some embodiments, the invention provides a CAR, which specifically binds to FLT3, wherein the CAR comprises a VH region comprising a sequence shown in SEQ ID NO: 10; and/or a VL region comprising a sequence shown in SEQ ID NO: 9. In some embodiments, provided herein is a CAR, which specifically binds to FLT3, wherein the CAR comprises a VH region comprising a sequence shown in SEQ ID NO: 20; and/or a VL region comprising a sequence shown in SEQ ID NO: 19.

In some embodiments, the invention also provides CARs comprising CDR portions of antibodies to FLT3 antibodies based on CDR contact regions. CDR contact regions are regions of an antibody that imbue specificity to the antibody for an antigen. In general, CDR contact regions include the residue positions in the CDRs and Vernier zones which are constrained in order to maintain proper loop structure for the antibody to bind a specific antigen. See, e.g., Makabe et al., J. Biol. Chem., 283:1156-1166, 2007. Determination of CDR contact regions is well within the skill of the art.

The binding affinity ($K_D$) of the ligand binding domain of the FLT3 specific CAR as described herein to FLT3 (such as human FLT3 (e.g., (SEQ ID NO: 198)) can be for example about 0.1 to about 1000 nM, for example between about 0.5 nM to about 500 nM, or for example between about 1 nM to about 250 nM. In some embodiments, the binding affinity is about any of 1000 nm, 750 nm, 500 nM, 400 nm, 300 nm, 250 nm, 200 nM, 100 nM, 90 nM, 80 nM, 70 nM, 60 nM, 50 nM, 45 nM, 40 nM, 35 nM, 30 nM, 25 nM, 20 nM, 19 nm, 18 nm, 17 nm, 16 nm, 15 nM, 10 nM, 8 nM, 7.5 nM, 7 nM, 6.5 nM, 6 nM, 5.5 nM, 5 nM, 4 nM, 3 nM, 2 nM, 1 nM, 0.5 nM, 0.3 nM or 0.1 nM.

In some embodiments, the binding affinity ($K_D$) of the scFv of the ligand binding domain of the FLT3 specific CAR as described herein to FLT3 is about 10 nM to about 100 nM, about 10 nM to about 90 nM, about 10 nM to about 80 nM, about 20 nM to about 70 nM, about 25 nM to about 75 nM, or about 40 nM to about 110 nM. In one embodiment, the binding affinities of the scFv described in this paragraph are for human FLT3.

In some embodiments, the binding affinity ($K_D$) of the scFv of the ligand binding domain of the FLT3 specific CAR as described herein to domain 4 of the extracellular domain of human FLT3 is about 1 nM to about 100 nM, about 10 nM to about 100 nM, about 20 nM to about 100 nM, about 25 nM to about 105 nM, about 40 nM to about 80 nM, about 40 nM to about 100 nM, or about 50 nM to about 100 nM.

In some embodiments, the binding affinity ($K_D$) of the scFv of the ligand binding domain of the FLT3 specific CAR as described herein to domain 2-3 of the extracellular domain of human FLT3 is about 5 nM to about 30 nM, about 5 nM to about 25 nM, about 10 nM to about 30 nM, about 10 nM to about 40 nM, or about 10 nM to about 25 nM.

In an exemplary embodiment, the $K_D$ of the ScFv is measured as disclosed in Example 1.

In some embodiments, the binding affinity is less than about any of 1000 nm, 900 nm, 800 nm, 250 nM, 200 nM, 100 nM, 50 nM, 30 nM, 20 nM, 10 nM, 7.5 nM, 7 nM, 6.5 nM, 6 nM, 5 nM.

Monoclonal Antibody-Specific Epitopes

In some embodiments, the extracellular domain of any one of the FLT3 specific CARs disclosed herein may comprise one or more epitopes specific for (i.e., specifically recognized by) a monoclonal antibody. These epitopes are also referred to herein as mAb-specific epitopes. In these embodiments, the extracellular domain comprises the VH and VL polypeptides that specifically bind to FLT3 and one or more epitopes that bind to one or more monoclonal antibodies (mAbs). CARs comprising the mAb-specific epitopes can be single-chain or multi-chain.

The inclusion of epitopes specific for monoclonal antibodies in the extracellular domain of the CARs described herein allows sorting and depletion of engineered immune cells expressing the CARs. In some embodiments, this feature also promotes recovery of endogenous FLT3 expressing cells that were depleted by administration of engineered immune cells expressing the CARs.

Accordingly, in some embodiments, the present invention relates to a method for sorting and/or depleting the engineered immune cells endowed with the CARs comprising mAb-specific epitopes and a method for promoting recovery of endogenous FLT3 expressing cells, such as bone marrow progenitor cells.

Several epitope-monoclonal antibody couples can be used to generate CARs comprising monoclonal antibody specific epitopes; in particular, those already approved for medical use, such as CD20 epitope/rituximab as a non-limiting example.

In some embodiments, the monoclonal antibody specific for the epitope may be conjugated with a cytotoxic drug. It is also possible to promote CDC cytotoxicity by using engineered antibodies on which are grafted component(s) of the complement system. In some embodiments, activation of the CAR-T cells can be modulated by depleting the cells using an antibody which recognizes the epitope.

The invention also encompasses methods for sorting the engineered immune cells endowed with the FLT3 specific CARs expressing the mAb-specific epitope(s) and therapeutic methods where the activation of the engineered immune cells endowed with these CARs is modulated by depleting the cells using an antibody that targets the external ligand binding domain of said CARs.

CARs comprising one or more epitopes specifically recognized by a monoclonal antibody are disclosed in WO2016/120216, which is hereby incorporated by reference in its entirety. The epitope can be selected from any number of epitopes known in the art. In some embodiments, the epitope can be a target of a monoclonal antibody approved for medical use, such as, for example without limitation, the CD20 epitope recognized by rituximab. In some embodiments, the epitope comprises the amino acid sequence shown in SEQ ID NO: 229. CPYSNPSLC (SEQ ID NO: 229)

In some embodiments, the epitope can be located between the scFv and the hinge of a CAR. In some embodiments, two instances of the same epitope, separated by linkers, may be used in the CAR. For example, a polypeptide comprising 2 copies of the epitope shown in SEQ ID NO: 229, separated by linkers, as shown in GSGGGGSCPYSNPSLCSGGGGSCPYSNPSLCSGGGGS (SEQ ID NO: 230), can be used within a CAR, located between the light chain variable region and the hinge.

In some embodiments, the extracellular binding domain of the CAR comprising the VH and VL polypeptides and the mAb-specific epitope(s) may have different structures depending on the position of insertion of the epitope and the use of linkers. For example, the extracellular binding domain of the FLT3 specific CAR comprising mAb-specific epitopes may have one of the following structures:

$V_1$-$L_1$-$V_2$-$(L)_x$-Epitope1-$(L)_x$-;
$V_1$-$L_1$-$V_2$-$(L)_x$-Epitope1-$(L)_x$-Epitope2-$(L)_x$-;
$V_1$-$L_1$-$V_2$-$(L)_x$-Epitope1-$(L)_x$-Epitope2-$(L)_x$-Epitope3-$(L)_x$-;
$(L)_x$-Epitope1-$(L)_x$-$V_1$-$L_1$-$V_2$;
$(L)_x$-Epitope1-$(L)_x$-Epitope2-$(L)_x$-$V_1$-$L_1$-$V_2$;
Epitope1-$(L)_x$-Epitope2-$(L)_x$-Epitope3-$(L)_x$-$V_1$-$L_1$-$V_2$;
$(L)_x$-Epitope1-$(L)_x$-$V_1$-$L_1$-$V_2$-$(L)_x$-Epitope2-$(L)_x$;
$(L)_x$-Epitope1-$(L)_x$-$V_1$-$L_1$-$V_2$-$(L)_x$-Epitope2-$(L)_x$-Epitope3-$(L)_x$-;
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-;
$(L)_x$-Epitope1-$(L)_x$-Epitope2-$(L)_x$-$V_1$-$L_1$-$V_2$-$(L)_x$-Epitope3-$(L)_x$-;
$(L)_x$-Epitope1-$(L)_x$-Epitope2-$(L)_x$-$V_1$-$L_1$-$V_2$-$(L)_x$-Epitope3-$(L)_x$-Epitope4-$(L)_x$-;
$V_1$-$(L)_x$-Epitope1-$(L)_x$-$V_2$;
$V_1$-$(L)_x$-Epitope1-$(L)_x$-$V_2$-$(L)_x$-Epitope2-$(L)_x$;
$V_1$-$(L)_x$-Epitope1-$(L)_x$-$V_2$-$(L)_x$-Epitope2-$(L)_x$-Epitope3-$(L)_x$;
$V_1$-$(L)_x$-Epitope1-$(L)_x$-$V_2$-$(L)_x$-Epitope2-$(L)_x$-Epitope3-$(L)_x$-Epitope4-$(L)_x$;
$(L)_x$-Epitope1-$(L)_x$-$V_1$-$(L)_x$-Epitope2-$(L)_x$-$V_2$; or,
$(L)_x$-Epitope1-$(L)_x$-$V_1$-$(L)_x$-Epitope2-$(L)_x$-$V_2$-$(L)_x$-Epitope3-$(L)_x$;

wherein,
$V_1$ is $V_L$ and $V_2$ is $V_H$ or $V_1$ is $V_H$ and $V_2$ is $V_L$;
$L_1$ is a linker suitable to link the $V_H$ chain to the $V_L$ chain;
L is a linker comprising glycine and serine residues, and each occurrence of L in the extracellular binding domain can be identical or different to other occurrence of L in the same extracellular binding domain, for example SGGGG, GGGGS or SGGGGS, and,
x is 0 or 1 and each occurrence of x is selected independently from the others; and, Epitope 1, Epitope 2, Epitope 3 and Epitope 4 are mAb-specific epitopes and can be identical or different. In some embodiments, Epitope 1, Epitope 2 and Epitope 4 are a mAb-specific epitope having an amino acid sequence of SEQ ID NO: 229 and Epitope 3 is a mAb-specific epitope having an amino acid sequence of SEQ ID NO: 231.

In some embodiments, the extracellular binding domain of the CAR comprises the following sequence $V_1$-$L_1$-$V_2$-$(L)_x$-Epitope1-$(L)_x$-Epitope2-$(L)_x$-; or,
$(L)_x$-Epitope1-$(L)_x$-$V_1$-$L_1$-$V_2$-$(L)_x$-Epitope2-$(L)_x$-Epitope3-$(L)_x$-Epitope4-$(L)_x$-. wherein $V_1$, $V_2$, $L_1$, L, x and Epitope 1, Epitope 2, Epitope 3 and Epitope 4 are as defined above.

In some embodiments, any one of the FLT3 specific CARs disclosed herein may comprise one or more mAb-specific epitopes selected from a CD52 epitope, a CD20 epitope, a CD3 epitope, a CD41 epitope, a CD25 epitope, a CD30 epitope, an EGFR epitope, a TNFα epitope, a VEGF epitope, a complement protein C5 epitope, a CD11a epitope, a CD33 epitope, an alpha-4 integrin epitope, an IgE Fc region epitope, an RSV protein F epitope, an IL-6 receptor epitope, a HER2 receptor epitope, an integrin $α_4β_7$ epitope, a BAFF (B-cell activating factor) epitope, an IL-1β epitope, a RANKL epitope, a CTLA4 epitope, a CD34 epitope, an IL-12 epitope, and/or an IL-23 epitope.

In some embodiments, the FLT3 specific CARs disclosed herein may comprise one or more mAb-specific epitopes selected from epitopes specifically recognized by alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab.

In some embodiments, the FLT3 specific CARs comprise one or more mAb-specific epitopes selected from the epitopes disclosed in Table 5:

TABLE 5

Examples of mAb-specific epitopes that can be used in the extracellular binding domain of the FLT3 specific CARs of the invention such as for example mimotopes and epitope with their corresponding mAh

| Rituximab | | | |
|---|---|---|---|
| Mimotope | SEQ ID NO: 229 | CPYSNPSLC | |

| Palivizumab | | | |
|---|---|---|---|
| Epitope | SEQ ID NO: 255 | NSELLSLINDMPIT NDQKKLMSNN | |

| Cetuximab | | | |
|---|---|---|---|
| Mimotope 1 | SEQ ID NO: 256 | CQFDLSTRRLKC | |
| Mimotope 2 | SEQ ID NO: 257 | CQYNLSSRALKC | |

TABLE 5-continued

Examples of mAb-specific epitopes that can be used in the extracellular binding domain of the FLT3 specific CARs of the invention such as for example mimotopes and epitope with their corresponding mAh

| Mimotope 3 | SEQ ID NO: 258 | CVWQRWQKSYVC |
| Mimotope 4 | SEQ ID NO: 259 | CMWDRFSRWYKC |

Nivolumab

| Epitope 1 | SEQ ID NO: 260 | SFVLNWYRMSPSNQ TDKLAAFPEDR |
| Epitope 2 | SEQ ID NO:261 | SGTYLCGAISLAPKAQIKE |

QBEND-10

| Epitope | SEQ ID NO: 262 | ELPTQGTFSNVSTNVSP AKPTTTA |

Alemtuzumab

| Epitope | SEQ ID NO: 263 | GQNDTSQTSSPS |

The intracellular signaling domain of a CAR according to the invention is responsible for intracellular signaling following the binding of extracellular ligand-binding domain to the target resulting in the activation of the immune cell and immune response. The intracellular signaling domain has the ability to activate of at least one of the normal effector functions of the immune cell in which the CAR is expressed. For example, the effector function of a T cell can be a cytolytic activity or helper activity including the secretion of cytokines.

In some embodiments, an intracellular signaling domain for use in a CAR can be the cytoplasmic sequences of, for example without limitation, the T cell receptor and co-receptors that act in concert to initiate signal transduction following antigen receptor engagement, as well as any derivative or variant of these sequences and any synthetic sequence that has the same functional capability. Intracellular signaling domains comprise two distinct classes of cytoplasmic signaling sequences: those that initiate antigen-dependent primary activation, and those that act in an antigen-independent manner to provide a secondary or co-stimulatory signal. Primary cytoplasmic signaling sequences can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRζ, FcRγ, FcRβ, FcRε, CD3γ, CD3ζ, CD3ε, CD5, CD22, CD79a, CD79b and CD66d. In some embodiments, the intracellular signaling domain of the CAR can comprise the CD3ζ signaling domain which has amino acid sequence with at least about 70%, for example at least 80%, or at least 90%, 95%, 97%, or 99% sequence identity with an amino acid sequence shown in SEQ. ID NO: 210. In some embodiments the intracellular signaling domain of the CAR of the invention comprises a domain of a co-stimulatory molecule.

In some embodiments, the intracellular signaling domain of a CAR of the invention comprises a part of co-stimulatory molecule selected from the group consisting of fragment of 41BB (GenBank: AAA53133.) and CD28 (NP_006130.1). In some embodiments, the intracellular signaling domain of the CAR of the invention comprises amino acid sequence which comprises at least 70%, for example at least 80%, or at least 90%, 95%, 97%, or 99% sequence identity with an amino acid sequence shown in SEQ. ID NO: 209 and SEQ. ID NO: 213. In some embodiments, the intracellular signaling domain of the CAR of the invention comprises amino acid sequence which comprises at least 70%, for example at least 80%, or at least 90%, 95%, 97%, or 99% sequence identity with an amino acid sequence shown in SEQ. ID NO: 209 and SEQ. ID NO: 214.

CARs are expressed on the surface membrane of the cell. Thus, the CAR can comprise a transmembrane domain. Suitable transmembrane domains for a CAR disclosed herein have the ability to (a) be expressed at the surface of a cell, e.g. an immune cell such as, for example without limitation, lymphocyte cells or Natural killer (NK) cells, and (b) interact with the ligand-binding domain and intracellular signaling domain for directing cellular response of immune cell against a predefined target cell. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or δ, polypeptide constituting CD3 complex, IL-2 receptor p55 (a chain), p75 (β chain) or γ chain, subunit chain of Fc receptors, in particular Fcγ receptor III, or CD proteins. Alternatively, the transmembrane domain can be synthetic and can comprise predominantly hydrophobic residues such as leucine and valine. In some embodiments said transmembrane domain is derived from the human CD8α chain (e.g., NP_001139345.1).

The transmembrane domain is linked to the extracellular ligand-binding domain by a stalk domain (also called hinge domain). A stalk domain may comprise up to 300 amino acids, e.g. 10 to 100 amino acids or 25 to 50 amino acids. Stalk region may be derived from all or part of naturally occurring molecules, such as from all or part of the extracellular region of CD8, CD4, or CD28, or from all or part of an antibody constant region. Alternatively the stalk domain may be a synthetic sequence that corresponds to a naturally occurring stalk sequence, or may be an entirely synthetic stalk sequence. In some embodiments said stalk domain is a part of human CD8α chain (e.g., NP_001139345.1). In another particular embodiment, said transmembrane and hinge domains comprise a part of human CD8α chain, e.g. which comprises at least 70%, or at least 80%, or at least 90%, 95% 97%, or 99% sequence identity with amino acid sequence selected from the group consisting of SEQ ID NO: 206 and 208. In some embodiments, the stalk domain of FLT3 specific CARs described herein comprises a CD8α hinge, an IgG1 hinge, or an FcγRIIIα hinge. In some embodiments, the stalk domain comprises a human CD8α hinge, a human IgG1 hinge, or a human FcγRIIIα hinge. In some embodiments, CARs disclosed herein can comprise an extracellular ligand-binding domain that specifically binds FLT3, CD8α human hinge and transmembrane domains, the CD3ζ signaling domain, and 4-1BB signaling domain.

Table 6 provides exemplary sequences of domains which can be used in the CARs disclosed herein.

TABLE 6

Exemplary sequences of CAR Components

| Domain | Amino Acid Sequence | SEQ ID NO: |
|---|---|---|
| CD8α signal peptide | MALPVTALLLPLALLLHAARP | 204 |
| FcγRIIIα hinge | GLAVSTISSFFPPGYQ | 205 |
| CD8α hinge | TTTPAPRPPTPAPTIASQPLSLRPEACRPAAGGAVHTRGLDFACD | 206 |
| IgG1 hinge | EPKSPDKTHTCPPCPAPPVAGPSVFLFPPKPKDTLMIARTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | 207 |
| CD8α transmembrane (TM) domain | IYIWAPLAGTCGVLLLSLVITLYC | 208 |
| 41BB intracellular signaling domain (ISD) | KRGRKKLLYIFKQPFMRPVQTTQEEDGCSCRFPEEEEGGCEL | 209 |
| CD3ζ intracellular signaling domain (ISD) | RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 210 |
| FcεRI α-TM-IC (FcεRI α chain transmembrane and intracellular domain) | FFIPLLVVILFAVDTGLFISTQQQVTFLLKIKRTRKGFRLLNPHPKPNPKNN | 211 |
| FcεRIβ-AITAM (FcεRI β chain without ITAM) | MDTESNRRANLALPQEPSSVPAFEVLEISPQEVSSGRLLKSASSPPLHTWLTVLKKEQEFLGVTQILTAMICLCFGTVVCSVLDISHIEGDIFSSFKAGYPFWGAIFFSISGMLSIISERRNATYLVRGSLGANTASSIAGGTGITILIINLKKSLAYIHIHSCQKFFETKCFMASFSTEIVVMMLFLTILGLGSAVSLTICGAGEELKGNKVPE | 212 |
| 41BB-IC (41BB co-stimulatory domain) | KRGRKKLLYIFKQPFMRPVQTTQEEDGCSCRFPEEEEGGCEL | 213 |
| CD28-IC (CD28 co-stimulatory domain) | RSKRSRGGHSDYMNMTPRRPGPTRKHYQPYAPPRDFAAYRS | 214 |
| FcεRIγ-SP (signal peptide) | MIPAVVLLLLLLVEQAAA | 215 |
| FcεRI γ-AITAM (FcεRI γ chain without ITAM) | LGEPQLCYILDAILFLYGIVLTLLYCRLKIQVRKAAITSYEKS | 216 |
| GSG-P2A (GSG-P2A ribosomal skip polypeptide) | GSGATNFSLLKQAGDVEENPGP | 217 |
| GSG-T2A (GSG-T2A ribosomal skip polypeptide) | GSGEGRGSLLTCGDVEENPGP | 218 |

Downregulation or mutation of target antigens is commonly observed in cancer cells, creating antigen-loss escape variants. Thus, to offset tumor escape and render immune cell more specific to target, the FLT3 specific CAR can comprise one or more additional extracellular ligand-binding domains, to simultaneously bind different elements in target thereby augmenting immune cell activation and function. In some embodiments, the extracellular ligand-binding domains can be placed in tandem on the same transmembrane polypeptide, and optionally can be separated by a linker. In some embodiments, said different extracellular ligand-binding domains can be placed on different transmembrane polypeptides composing the CAR. In some embodiments, the invention relates to a population of CARs, each CAR comprising a different extracellular ligand-binding domain. In particular, the invention relates to a method of engineering immune cells comprising providing an immune cell and expressing at the surface of the cell a population of CARs, each CAR comprising different extracellular ligand-binding domains. In another particular embodiment, the invention relates to a method of engineering an immune cell comprising providing an immune cell and introducing into the cell polynucleotides encoding polypeptides composing a population of CAR each one comprising different extracellular ligand-binding domains. By population of CARs, it is meant at least two, three, four, five, six or more CARs each one comprising different extracellular ligand-binding domains. The different extracellular ligand-binding domains according to the invention can for example simultaneously bind different elements in target thereby augmenting immune cell activation and function. The invention also relates to an isolated immune cell which comprises a population of CARs each one comprising different extracellular ligand-binding domains.

In another aspect, provided herein are polynucleotides encoding any of the CARs and polypeptides described herein. Polynucleotides can be made and expressed by procedures known in the art.

In another aspect, provided herein are compositions (such as a pharmaceutical compositions) comprising any of the cells of the invention. In some embodiments, the composition comprises a cell comprising a polynucleotide encoding any of the CARs described herein. In still other embodiments, the composition comprises either or both of the polynucleotides shown in SEQ ID NO: 245 and SEQ ID NO:246 below:

```
P3E10 heavy chain variable region
                                (SEQ ID NO: 245)
CAGGTGCAGCTGGTGCAGAGCGGAGCAGAGGTGAA

GAAGCCAGGCAGCTCCGTGAAGGTGTCCTGCAAGG

CCTCTGGCGGCACATTCTCTAGCTACGCCATCCAG

TGGGTGCGGCAGGCACCAGGACAGGGCCTGGAGTG

GATGGGAGGAATCGTGGGAAGCTGGGCCTGGCAA

ACTACGCCCAGAAGTTTCAGGGCAGAGTGACCATC

ACCACCGATAAGTCTACAAGCACCGCCTATATGGA

GCTGTCCTCTCTGAGGTCCGAGGACACAGCCGTGT

ACTATTGCGCCACCTCCGCCTTCGGCGAGCTGGCA

TCTTGGGGACAGGGCACACTGGTGACCGTGAGCTC

C

P3E10 light chain variable region
                                (SEQ ID NO: 246)
GAGATCGTGCTGACACAGAGCCCAGGCACCCTGTC

CCTGTCTCCAGGAGAGAGGGCCACACTGTCCTGTA

GGGCCAGCCAGTCCGTGCCTTCTAGCCAGCTGGCC

TGGTACCAGCAGAAGCCAGGCCAGGCCCCCAGACT

GCTGATCTATGACGCCTCCTCTAGAGCCACAGGCA

TCCCAGATAGGTTCTCTGGCAGCGGCTCCGGCACC

GACTTTACACTGACCATCTCCAGGCTGGAGCCCGA

GGATTTCGCCGTGTACTATTGCCAGCAGTACGGCA

GCTCCCCTCTGACATTTGGCCAGGGCACCAAGGTG

GAGATCAAGG
```

In still other embodiments, the composition comprises either or both of the polynucleotides shown in SEQ ID NO: 247 and SEQ ID NO:248 below:

```
P3A1 heavy chain variable region
                                (SEQ ID NO: 247)
CAGGTGCAGCTGGTGCAGAGCGGAGCAGAGGTGAA

GAAGCCCGGCAGCTCCGTGAAGGTGTCTTGCAAGG

CCAGCGGCGGCACATTCTCTAGCTACGATATCTCT

TGGGTGAGGCAGGCCCCAGGCCAGGGACTGGAGTG

GATGGGAGGAATCATCCCCGTGAGCGGAAGGGCAA

ACTACGCACAGAAGTTTCAGGGCCGGGTGACCATC

ACCACAGACAAGTCCACATCTACCGCCTATATGGA

GCTGTCCTCTCTGAGAAGCGAGGATACAGCCGTGT

ACTATTGCGCCAGAGTGAGGCCTACCTACTGGCCA

CTGGACTATTGGGGCCAGGGCACACTGGTGACCGT

GAGCTCC

P3A1 light chain variable region
                                (SEQ ID NO: 248)
GACATCCAGATGACCCAGTCCCCATCTAGCCTGAG

CGCCTCCGTGGGCGATAGAGTGACAATCACCTGTA

GGGCCTCTCAGAGCATCTCCTCTTACCTGAATTGG

TATCAGCAGAAGCCCGGCAAGGCCCCTAAGCTGCT

GATCTACGCAGCAAGCTCCCTGCAGTCCGGAGTGC

CATCTCGGTTCTCCGGCTCTGGCAGCGGCACAGAC

TTTACACTGACCATCTCTAGCCTGCAGCCTGAGGA

TTTCGCCACCTACTATTGCCAGCAGTCCTATTCTA

CACCACTGACCTTTGGCCAGGGCACAAAGGTGGAG

ATCAAG.
```

In still other embodiments, the composition comprises either or both of the polynucleotides shown in SEQ ID NO: 249 and SEQ ID NO:250 below:

```
P9B5 heavy chain variable region
                                (SEQ ID NO: 249)
GAGGTGCAGCTGCTGGAGAGCGGCGGCGGCCTGGT

GCAGCCTGGCGGCTCTCTGAGACTGAGCTGCGCAG

CATCCGGCTTCATCTTTGCCTCTTACGCAATGAGC

TGGGTGAGGCAGGCCCCTGGCAAGGGACTGGAGTG

GGTGAGCGAGATCAGCTCCTCTGGCGGCAGCACCA

CATATGCCGACTCCGTGAAGGGCCGCTTCACAATC

AGCCGGGACAACTCTAAGAATACCCTGTACCTGCA

GATGAACTCCCTGAGAGCCGAGGACACAGCCGTGT

ACTATTGCGCCAGAGATAGAGTGATGGCCGGCCTG

GGCTATGACCCATTTGATTACTGGGGCCAGGGCAC

ACTGGTGACCGTGAGCTCC.
```

-continued

P9B5 light chain variable region
(SEQ ID NO 250)
CAGAGCGTGCTGACCCAGCCACCTTCCGCCTCTGG

AACACCCGGCCAGAGGGTGACCATCAGCTGTTCCG

GCTCTAGCTCCAACATCGGCTCCAATTACGTGTAT

TGGTACCAGCAGCTGCCCGGCACAGCCCCTAAGCT

GCTGATCTACAGAAACAATCAGAGGCCATCTGGCG

TGCCCGACCGCTTCTCTGGCAGCAAGTCCGGCACC

TCTGCCAGCCTGGCAATCAGCGGACTGCGGTCCGA

GGACGAGGCCGATTACTATTGCGCAGCATGGGACG

ATTCCCTGTCTGGAGTGGTGTTTGGCGGCGGCACA

AAGCTGACCGTGCTG.

In still other embodiments, the composition comprises either or both of the polynucleotides shown in SEQ ID NO: 251 and SEQ ID NO:252 below:

P4C7 heavy chain variable region
(SEQ ID NO: 251)
CAGGTGCAGCTGGTGCAGAGCGGAGCAGAGGTGAA

GAAGCCTGGCAGCTCCGTGAAGGTGTCTTGCAAGG

CCAGCGGCGGCACATTCTCTAGCTACACCATCTCC

TGGGTGCGGCAGGCCCCAGGCCAGGGACTGGAGTG

GATGGGAGGAATCATCCCAGCCTTCGGCATCGCCA

ACTACGCCCAGAAGTTTCAGGGCCGCGTGACAATC

ACCGCCGACAAGTCCACATCTACCGCCTATATGGA

GCTGTCCTCTCTGCGGAGCGAGGATACCGCCGTGT

ACTATTGCGCCAAGGGCGGCAGCTACTCCCTGGAC

TATTTTGATATCTGGGGCCAGGGCACACTGGTGAC

CGTGAGCTCC

P4C7 light chain variable region
(SEQ ID NO: 252)
GAGATCGTGCTGACACAGTCCCCTGGCACCCTGTC

TCTGAGCCCAGGCGAGAGGGCCACACTGTCCTGTA

GGGCATCTCAGTACGTGTCCGCCTCTCTGCTGGCC

TGGTATCAGCAGAAGCCTGGCCAGGCCCCAAGACT

GCTGATCTACGGAGCATCCACAAGAGCCACCGGCA

TCCCCGACAGGTTCAGCGGCTCCGGCTCTGGAACC

GACTTCACCCTGACCATCTCTAGACTGGAGCCTGA

GGACTTCGCCGTGTACTATTGCCAGCAGTATGCCA

GGTCTAGCACATTTGGCCAGGGCACCAAGGTGGAG

ATCAAG

Expression vectors, and administration of polynucleotide compositions are further described herein.

In another aspect, provided herein is a method of making any of the polynucleotides described herein.

Polynucleotides complementary to any such sequences are also encompassed by the invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity of the encoded polypeptide is not diminished, relative to a native immunoreactive molecule. The effect on the immunoreactivity of the encoded polypeptide may generally be assessed as described herein. Variants generally exhibit at least about 70% identity, or at least about 80% identity, or even at least about 90% or 95% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O., 1978, A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J., 1990, Unified Approach to Alignment and Phylogenes pp. 626-645 Methods in Enzymology vol. 183, Academic Press, Inc., San Diego, CA; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mol. Biol. Evol. 4:406-425; Sneath, P. H. A. and Sokal, R. R., 1973, Numerical Taxonomy the Principles and Practice of Numerical Taxonomy, Freeman Press, San Francisco, CA; Wilbur, W. J. and Lipman, D. J., 1983, Proc. Natl. Acad. Sci. USA 80:726-730.

Generally, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/ 0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the invention. Further, alleles of the genes comprising the polynucleotide sequences provided herein are within the scope of the invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

Alternatively, PCR allows reproduction of DNA sequences. PCR technology is well known in the art and is described in U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

A polynucleotide encoding a FLT3 specific CAR disclosed herein may exist in an expression cassette or expression vector (e.g., a plasmid for introduction into a bacterial host cell, or a viral vector such as a baculovirus vector for transfection of an insect host cell, or a plasmid or viral vector such as a lentivirus for transfection of a mammalian host cell). In some embodiments, a polynucleotide or vector can include a nucleic acid sequence encoding ribosomal skip sequences such as, for example without limitation, a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see (Donnelly and Elliott 2001; Atkins, Wills et al. 2007; Doronina, Wu et al. 2008)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct transmembrane polypeptides into the secretory pathway of a host cell, in some embodiments, a secretory signal sequence (also known as a leader sequence, prepro sequence or pre sequence) is provided in a polynucleotide sequence or vector sequence. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In some embodiments the signal peptide comprises the amino acid sequence shown in SEQ ID NO: 204 or 215. Those skilled in the art will recognize that, in view of the degeneracy of the genetic code, considerable sequence variation is possible among these polynucleotide molecules. In some embodiments, nucleic acid sequences of the invention are codon-optimized for expression in mammalian cells, e.g. for expression in primate (e.g. human or monkey) cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Methods of Engineering an Immune Cell

Methods of preparing immune cells for use in immunotherapy are provided herein. In some embodiments, the methods comprise obtaining immune cells, introducing a CAR according to the invention into immune cells, and expanding the cells. In some embodiments, the invention relates to a method of engineering an immune cell comprising: providing a cell and expressing at the surface of the cell at least one CAR as described above. Methods for engineering immune cells are described in, for example, PCT Patent Application Publication Nos. WO/2014/039523, WO/2014/184741, WO/2014/191128, WO/2014/184744, and WO/2014/184143, each of which is incorporated herein by reference in its entirety. In some embodiments, the method comprises: transfecting the cell with at least one polynucleotide encoding CAR as described above, and expressing the polynucleotides in the cell.

Prior to engineering of cells, a source of cells can be obtained from a subject through a variety of non-limiting methods. Cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available and known to those skilled in the art, may be used. In some embodiments, cells can be derived from a healthy donor or from a donor suffering from a disease or disorder, for example, an individual diagnosed with cancer or from an individual diagnosed with an infection. In some embodiments, cells can be part of a mixed population of cells which present different phenotypic characteristics.

In some embodiments, the polynucleotides are present in lentiviral vectors for stable expression in the cells.

In some embodiments, the method can further comprise a step of genetically modifying a cell by disrupting or inactivating at least one gene expressing, for example without limitation, a component of the TCR, a target for an immunosuppressive agent, an HLA gene, and/or an immune checkpoint protein such as, for example, PDCD1 or CTLA-4. By disruption or inactivating a gene it is intended that the gene of interest is not expressed in a functional protein form. In some embodiments, the gene to be disrupted or inactivated is selected from the group consisting of, for example without limitation, TCRα, TCRβ, CD52, glucocorticoid receptor (GR), deoxycytidine kinase (DCK), PD-1, and CTLA-4. In some embodiments, the method comprises inactivating one or more genes by introducing into the cells a rare-cutting endonuclease able to selectively inactivate a gene by selective DNA cleavage. In some embodiments the rare-cutting endonuclease can be, for example, a transcription activator-like effector nuclease (TALE-nuclease) or Cas9 endonuclease.

In some embodiments, an additional catalytic domain is used with a rare-cutting endonuclease to enhance its capacity to inactivate targeted genes. For example, an additional catalytic domain can be a DNA end-processing enzyme. Non-limiting examples of DNA end-processing enzymes include 5-3' exonucleases, 3-5' exonucleases, 5-3' alkaline exonucleases, 5' flap endonucleases, helicases, phosphatase, hydrolases and template-independent DNA polymerases. Non-limiting examples of such catalytic domain comprise of a protein domain or catalytically active derivate of the protein domain selected from the group consisting of hExoI (EXO1_HUMAN), Yeast ExoI (EXO1_YEAST), E. coli ExoI, Human TREX2, Mouse TREX1, Human TREX1, Bovine TREX1, Rat TREX1, TdT (terminal deoxynucleotidyl transferase) Human DNA2, Yeast DNA2 (DNA2 YEAST). In some embodiments, an additional catalytic domain can have a 3'-5'-exonuclease activity, and In some embodiments, said additional catalytic domain is TREX, e.g. a TREX2 catalytic domain (WO2012/058458). In some embodiments, said catalytic domain is encoded by a single chain TREX polypeptide. The additional catalytic domain may be fused to a nuclease fusion protein or chimeric protein. In some embodiments, the additional catalytic domain is fused using, for example, a peptide linker.

In some embodiments, the method further comprises a step of introducing into cells an exogenous nucleic acid comprising at least a sequence homologous to a portion of the target nucleic acid sequence, such that homologous recombination occurs between the target nucleic acid sequence and the exogenous nucleic acid. In some embodiments, said exogenous nucleic acid comprises first and second portions which are homologous to region 5' and 3' of the target nucleic acid sequence, respectively. The exogenous nucleic acid may also comprise a third portion positioned between the first and the second portion which comprises no homology with the regions 5' and 3' of the target nucleic acid sequence. Following cleavage of the target nucleic acid sequence, a homologous recombination event is stimulated between the target nucleic acid sequence and the exogenous nucleic acid. In some embodiments, homologous sequences of at least about 50 bp, greater than about 100 bp, or greater than about 200 bp can be used within the donor matrix. The exogenous nucleic acid can be, for example without limitation, from about 200 bp to about 6000 bp, e.g. from about 1000 bp to about 2000 bp. Shared nucleic acid homologies are located in regions flanking upstream and downstream the site of the break, and the nucleic acid sequence to be introduced is located between the two arms.

In some embodiments, a nucleic acid successively comprises a first region of homology to sequences upstream of said cleavage; a sequence to inactivate a targeted gene selected from the group consisting of TCRα, TCRβ, CD52, glucocorticoid receptor (GR), deoxycytidine kinase (DCK), and an immune checkpoint protein such as for example programmed death-1 (PD-1); and a second region of homology to sequences downstream of the cleavage. The polynucleotide introduction step can be simultaneous, before or after the introduction or expression of the rare-cutting endonuclease. Depending on the location of the target nucleic acid sequence wherein break event has occurred, such exogenous nucleic acid can be used to knock-out a gene, e.g. when exogenous nucleic acid is located within the open reading frame of the gene, or to introduce new sequences or genes of interest. Sequence insertions by using such exogenous nucleic acid can be used to modify a targeted existing gene, by correction or replacement of the gene (allele swap as a non-limiting example), or to up- or down-regulate the expression of the targeted gene (promoter swap as non-limiting example), the targeted gene correction or replacement. In some embodiments, inactivation of a gene selected from the group consisting of TCRα, TCRβ, CD52, GR, DCK, and immune checkpoint proteins, can be done at a precise genomic location targeted by a specific TALE-nuclease, wherein said specific TALE-nuclease catalyzes a cleavage and wherein the exogenous nucleic acid successively comprising at least a region of homology and a sequence to inactivate one targeted gene selected from the group consisting of TCRα, TCRβ, CD52, GR, DCK, immune checkpoint proteins which is integrated by homologous recombination. In some embodiments, several genes can be, successively or at the same time, inactivated by using several TALE-nucleases respectively and specifically targeting one defined gene and several specific polynucleotides for specific gene inactivation.

In some embodiments, the method comprises inactivation of one or more additional genes selected from the group consisting of TCRα, TCRβ, CD52, GR, DCK, and immune checkpoint proteins. In some embodiments, inactivation of a gene can be accomplished by introducing into the cells at least one rare-cutting endonuclease such that the rare-cutting endonuclease specifically catalyzes cleavage in a targeted sequence of the cell genome; and optionally, introducing into the cells an exogenous nucleic acid successively comprising a first region of homology to sequences upstream of the cleavage, a sequence to be inserted in the genome of the cell, and a second region of homology to sequences downstream of the cleavage; wherein the introduced exogenous nucleic acid inactivates a gene and integrates at least one exogenous polynucleotide sequence encoding at least one recombinant protein of interest. In some embodiments, the exogenous polynucleotide sequence is integrated within a gene encoding a protein selected from the group consisting of TCRα, TCRβ, CD52, GR, DCK, and immune checkpoint protein.

In another aspect, a step of genetically modifying cells can comprise: modifying T cells by inactivating at least one gene expressing a target for an immunosuppressive agent, and; expanding the cells, optionally in presence of the immunosuppressive agent. An immunosuppressive agent is an agent that suppresses immune function by one of several mechanisms of action. An immunosuppressive agent can diminish the extent and/or voracity of an immune response. Non-limiting examples of immunosuppressive agents include calcineurin inhibitors, targets of rapamycin, interleukin-2 α-chain blockers, inhibitors of inosine monophosphate dehydrogenase, inhibitors of dihydrofolic acid reductase, corticosteroids, and immunosuppressive antimetabolites. Some cytotoxic immunosuppressants act by inhibiting DNA synthesis. Others may act through activation of T cells or by inhibiting the activation of helper cells. The methods according to the invention allow conferring immunosuppressive resistance to T cells for immunotherapy by inactivating the target of the immunosuppressive agent in T cells. As non-limiting examples, targets for immunosuppressive agent can be a receptor for an immunosuppressive agent such as for example without limitation CD52, glucocorticoid receptor (GR), FKBP family gene members, and cyclophilin family gene members.

In some embodiments, the genetic modification of the method involves expression, in provided cells to engineer, of one rare-cutting endonuclease such that the one rare-cutting endonuclease specifically catalyzes cleavage in one targeted gene, thereby inactivating the targeted gene. In some embodiments, a method of engineering cells comprises at least one of the following steps: providing a T cell, such as from a cell culture or from a blood sample; selecting a gene in the T cell expressing a target for an immunosuppressive agent; introducing into the T cell a rare-cutting endonuclease able to selectively inactivate by DNA cleavage, e.g. by double-strand break the gene encoding a target for the immunosuppressive agent, and expanding the cells, optionally in presence of the immunosuppressive agent.

In some embodiments, the method comprises: providing a T cell, such as from a cell culture or from a blood sample; selecting a gene in the T cell wherein the gene expresses a target for an immunosuppressive agent; transfecting the T cell with nucleic acid encoding a rare-cutting endonuclease able to selectively inactivate by DNA cleavage, for example by double-strand break the gene encoding a target for the immunosuppressive agent, and expressing the rare-cutting endonucleases into the T cells; and expanding the cells, optionally in presence of the immunosuppressive agent.

In some embodiments, the rare-cutting endonuclease specifically targets CD52 or GR. In some embodiments, the gene selected for inactivation encodes CD52, and the immunosuppressive treatment comprises a humanized antibody targeting CD52 antigen. In some embodiments, the gene selected for inactivation encodes GR, and the immunosuppressive treatment comprises a corticosteroid such as dexamethasone. In some embodiments, the gene selected for inactivation is a FKBP family gene member or a variant thereof and the immunosuppressive treatment comprises FK506, also known as Tacrolimus or fujimycin. In some embodiments, the FKBP family gene member is FKBP12 or a variant thereof. In some embodiments, gene selected for inactivation is a cyclophilin family gene member or a variant thereof and the immunosuppressive treatment comprises cyclosporine.

In some embodiments, the rare-cutting endonuclease can be, for example, a meganuclease, a zinc finger nuclease, or a TALE-nuclease (TALEN). In some embodiments, the rare-cutting endonuclease is a TALE-nuclease.

Also provided herein are methods of engineering T cells, suitable for immunotherapy, wherein the methods comprise:

genetically modifying T cells by inactivating at least immune checkpoint protein. In some embodiments the immune checkpoint protein is, for example, PD-1 and/or CTLA-4. In some embodiments, methods of genetically modifying a cell comprises: modifying T cells by inactivating at least one immune checkpoint protein; and expanding the cells. Immune checkpoint proteins include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), B7H5 (also known as C10orf54, homolog of mouse vista gene, accession number: NM_022153.1), LAIR1 (also known as CD305, GenBank accession number: CR542051.1), SIGLEC10 (GeneBank accession number: AY358337.1), 2B4 (also known as CD244, accession number: NM_001166664.1), which directly inhibit immune cells. For example, CTLA-4 is a cell-surface protein expressed on certain CD4 and CD8 T cells; when engaged by its ligands (B7-1 and B7-2) on antigen presenting cells, T cell activation and effector function are inhibited.

In some embodiments, said method to engineer cells comprises at least one of the following steps: providing a T cell, such as from a cell culture or from a blood sample; introducing into the T cell a rare-cutting endonuclease able to selectively inactivate by DNA cleavage, for example by double-strand break one gene encoding a immune checkpoint protein; and expanding the cells. In some embodiments, the method comprises: providing a T cell, such as from a cell culture or from a blood sample; transfecting said T cell with nucleic acid encoding a rare-cutting endonuclease able to selectively inactivate by DNA cleavage, for example by double-strand break a gene encoding a immune checkpoint protein; expressing the rare-cutting endonucleases into the T cells; expanding the cells. In some embodiments, the rare-cutting endonuclease specifically targets a gene selected from the group consisting of: PD-1, CTLA-4, LAG3, Tim3, BTLA, BY55, TIGIT, B7H5, LAIR1, SIGLEC10, 2B4, TCRα, and TCRβ. In some embodiments, the rare-cutting endonuclease can be a meganuclease, a zinc finger nuclease or a TALE-nuclease. In some embodiments, the rare-cutting endonuclease is a TALE-nuclease.

In some embodiments, the present invention can be particularly suitable for allogeneic immunotherapy. In such embodiments, cells may be modified by a method comprising: inactivating at least one gene encoding a component of the T cell receptor (TCR) in T cells; and expanding the T cells. In some embodiments, the genetic modification of the method relies on the expression, in provided cells to engineer, of one rare-cutting endonuclease such that the rare-cutting endonuclease specifically catalyzes cleavage in one targeted gene thereby inactivating the targeted gene. In some embodiments, said method to engineer cells comprises at least one of the following steps: providing a T cell, such as from a cell culture or from a blood sample; introducing into the T cell a rare-cutting endonuclease able to selectively inactivate by DNA cleavage, for example by double-strand break at least one gene encoding a component of the T cell receptor (TCR), and expanding the cells.

In some embodiments, the method comprises: providing a T cell, such as from a cell culture or from a blood sample; transfecting said T cell with nucleic acid encoding a rare-cutting endonuclease able to selectively inactivate by DNA cleavage, for example by double-strand break at least one gene encoding a component of the T cell receptor (TCR); expressing the rare-cutting endonucleases into the T cells; sorting the transformed T cells, which do not express TCR on their cell surface; and expanding the cells.

In some embodiments, the rare-cutting endonuclease can be a meganuclease, a zinc finger nuclease or a TALE-nuclease. In some embodiments, the rare-cutting endonuclease is a TALE-nuclease. In some embodiments, the TALE-nucleases recognize and cleave a sequence encoding TCRα or TCRβ. In some embodiments, a TALE-nuclease comprises a polypeptide sequence selected from the amino acid sequence shown in SEQ ID NO: 219, 220, 221, 222, 223, 224, 225, or 226.

```
TALE-nuclease polypeptide sequences:
Repeat TRAC_T01-L
                               (SEQ ID NO: 219)
LTPQQVVAIASNGGGKQALETVQRLLPVLCQAHGL

TPQQVVAIASNNGGKQALETVQRLLPVLCQAHGLT

PQQVVAIASNGGGKQALETVQRLLPVLCQAHGLTP

EQVVAIASHDGGKQALETVQRLLPVLCQAHGLTPE

QVVAIASHDGGKQALETVQRLLPVLCQAHGLTPEQ

VVAIASHDGGKQALETVQRLLPVLCQAHGLTPEQV

VAIASNIGGKQALETVQALLPVLCQAHGLTPEQVV

AIASHDGGKQALETVQRLLPVLCQAHGLTPEQVVA

IASNIGGKQALETVQALLPVLCQAHGLTPQQVVAI

ASNNGGKQALETVQRLLPVLCQAHGLTPEQVVAIA

SNIGGKQALETVQALLPVLCQAHGLTPQQVVAIAS

NGGGKQALETVQRLLPVLCQAHGLTPEQVVAIASN

IGGKQALETVQALLPVLCQAHGLTPQQVVAIASNG

GGKQALETVQRLLPVLCQAHGLTPEQVVAIASHDG

GKQALETVQRLLPVLCQAHGLTPQQVVAIASNGGG

RPALE.

Repeat TRAC_T01-R
                               (SEQ ID NO: 220)
LTPEQVVAIASHDGGKQALETVQRLLPVLCQAHGL

TPQQVVAIASNGGGKQALETVQRLLPVLCQAHGLT

PEQVVAIASHDGGKQALETVQRLLPVLCQAHGLTP

EQVVAIASNIGGKQALETVQALLPVLCQAHGLTPQ

QVVAIASNNGGKQALETVQRLLPVLCQAHGLTPEQ

VVAIASHDGGKQALETVQRLLPVLCQAHGLTPQQV

VAIASNGGGKQALETVQRLLPVLCQAHGLTPQQVV

AIASNNGGKQALETVQRLLPVLCQAHGLTPQQVVA

IASNNGGKQALETVQRLLPVLCQAHGLTPQQVVAI

ASNGGGKQALETVQRLLPVLCQAHGLTPEQVVAIA
```

-continued

SNIGGKQALETVQALLPVLCQAHGLTPEQVVAIAS

HDGGKQALETVQRLLPVLCQAHGLTPEQVVAIASN

IGGKQALETVQALLPVLCQAHGLTPEQVVAIASHD

GGKQALETVQRLLPVLCQAHGLTPQQVVAIASNNG

GKQALETVQRLLPVLCQAHGLTPQQVVAIASNGGG

RPALE.

Repeat TRBC_T01-L
(SEQ ID NO: 221)
LTPQQVVAIASNNGGKQALETVQRLLPVLCQAHGL

TPQQVVAIASNGGGKQALETVQRLLPVLCQAHGLT

PQQVVAIASNNGGKQALETVQRLLPVLCQAHGLTP

QQVVAIASNGGGKQALETVQRLLPVLCQAHGLTPQ

QVVAIASNGGGKQALETVQRLLPVLCQAHGLTPQQ

VVAIASNGGGKQALETVQRLLPVLCQAHGLTPQQV

VAIASNNGGKQALETVQRLLPVLCQAHGLTPEQVV

AIASNIGGKQALETVQALLPVLCQAHGLTPQQVVA

IASNNGGKQALETVQRLLPVLCQAHGLTPEQVVAI

ASHDGGKQALETVQRLLPVLCQAHGLTPEQVVAIA

SHDGGKQALETVQRLLPVLCQAHGLTPEQVVAIAS

NIGGKQALETVQALLPVLCQAHGLTPQQVVAIASN

GGGKQALETVQRLLPVLCQAHGLTPEQVVAIASHD

GGKQALETVQRLLPVLCQAHGLTPEQVVAIASNIG

GKQALETVQALLPVLCQAHGLTPQQVVAIASNGGG

RPALE.

Repeat TRBC_T01-R
(SEQ ID NO: 222)
NPQRSTVWYLTPQQVVAIASNNGGKQALETVQRLL

PVLCQAHGLTPQQVVAIASNGGGKQALETVQRLLP

VLCQAHGLTPQQVVAIASNNGGKQALETVQRLLPV

LCQAHGLTPQQVVAIASNNGGKQALETVQRLLPVL

CQAHGLTPEQVVAIASHDGGKQALETVQRLLPVLC

QAHGLTPEQVVAIASHDGGKQALETVQRLLPVLCQ

AHGLTPQQVVAIASNGGGKQALETVQRLLPVLCQA

HGLTPQQVVAIASNGGGKQALETVQRLLPVLCQAH

GLTPQQVVAIASNGGGKQALETVQRLLPVLCQAHG

LTPQQVVAIASNGGGKQALETVQRLLPVLCQAHGL

TPQQVVAIASNNGGKQALETVQRLLPVLCQAHGLT

PQQVVAIASNNGGKQALETVQRLLPVLCQAHGLTP

QQVVAIASNNGGKQALETVQRLLPVLCQAHGLTPQ

QVVAIASNGGGKQALETVQRLLPVLCQAHGLTPQQ

VVAIASNNGGKQALETVQRLLPVLCQAHGLTPQQV

VAIASNGGGRPALE.

-continued

Repeat TRBC_T02-L
(SEQ ID NO: 223)
LTPEQVVAIASHDGGKQALETVQRLLPVLCQAHGL

TPEQVVAIASHDGGKQALETVQRLLPVLCQAHGLT

PEQVVAIASHDGGKQALETVQRLLPVLCQAHGLTP

EQVVAIASNIGGKQALETVQALLPVLCQAHGLTPE

QVVAIASHDGGKQALETVQRLLPVLCQAHGLTPEQ

VVAIASHDGGKQALETVQRLLPVLCQAHGLTPEQV

VAIASHDGGKQALETVQRLLPVLCQAHGLTPQQVV

AIASNNGGKQALETVQRLLPVLCQAHGLTPEQVVA

IASNIGGKQALETVQALLPVLCQAHGLTPQQVVAI

ASNNGGKQALETVQRLLPVLCQAHGLTPQQVVAIA

SNNGGKQALETVQRLLPVLCQAHGLTPQQVVAIAS

NGGGKQALETVQRLLPVLCQAHGLTPEQVVAIASH

DGGKQALETVQRLLPVLCQAHGLTPQQVVAIASNN

GGKQALETVQRLLPVLCQAHGLTPEQVVAIASHDG

GKQALETVQRLLPVLCQAHGLTPQQVVAIASNGGG

RPALE.

Repeat TRBC_T02-R
(SEQ ID NO: 224)
LTPQQVVAIASNNGGKQALETVQRLLPVLCQAHGL

TPQQVVAIASNNGGKQALETVQRLLPVLCQAHGLT

PQQVVAIASNNGGKQALETVQRLLPVLCQAHGLTP

EQVVAIASNIGGKQALETVQALLPVLCQAHGLTPQ

QVVAIASNNGGKQALETVQRLLPVLCQAHGLTPEQ

VVAIASNIGGKQALETVQALLPVLCQAHGLTPQQV

VAIASNGGGKQALETVQRLLPVLCQAHGLTPEQVV

AIASHDGGKQALETVQRLLPVLCQAHGLTPQQVVA

IASNGGGKQALETVQRLLPVLCQAHGLTPEQVVAI

ASHDGGKQALETVQRLLPVLCQAHGLTPQQVVAIA

SNGGGKQALETVQRLLPVLCQAHGLTPQQVVAIAS

NNGGKQALETVQRLLPVLCQAHGLTPEQVVAIASH

DGGKQALETVQRLLPVLCQAHGLTPQQVVAIASNG

GGKQALETVQRLLPVLCQAHGLTPQQVVAIASNGG

GKQALETVQRLLPVLCQAHGLTPQQVVAIASNGGG

RPALE.

Repeat CD52_T02-L
(SEQ ID NO: 225)
LTPQQVVAIASNGGGKQALETVQRLLPVLCQAHGL

TPEQVVAIASHDGGKQALETVQRLLPVLCQAHGLT

PEQVVAIASHDGGKQALETVQRLLPVLCQAHGLTP

QQVVAIASNGGGKQALETVQRLLPVLCQAHGLTPE

QVVAIASHDGGKQALETVQRLLPVLCQAHGLTPEQ

```
VVAIASHDGGKQALETVQRLLPVLCQAHGLTPQQV

VAIASNGGGKQALETVQRLLPVLCQAHGLTPEQVV

AIASNIGGKQALETVQALLPVLCQAHGLTPEQVVA

IASHDGGKQALETVQRLLPVLCQAHGLTPQQVVAI

ASNGGGKQALETVQRLLPVLCQAHGLTPEQVVAIA

SHDGGKQALETVQRLLPVLCQAHGLTPEQVVAIAS

NIGGKQALETVQALLPVLCQAHGLTPEQVVAIASH

DGGKQALETVQRLLPVLCQAHGLTPEQVVAIASHD

GGKQALETVQRLLPVLCQAHGLTPEQVVAIASNIG

GKQALETVQALLPVLCQAHGLTPQQVVAIASNGGG

RPALE.

Repeat CD52_T02-R
                              (SEQ ID NO: 226)
LTPQQVVAIASNGGGKQALETVQRLLPVLCQAHGL

TPQQVVAIASNNGGKQALETVQRLLPVLCQAHGLT

PEQVVAIASHDGGKQALETVQRLLPVLCQAHGLTP

QQVVAIASNGGGKQALETVQRLLPVLCQAHGLTPE

QVVAIASHDGGKQALETVQRLLPVLCQAHGLTPQQ

VVAIASNGGGKQALETVQRLLPVLCQAHGLTPQQV

VAIASNGGGKQALETVQRLLPVLCQAHGLTPEQVV

AIASNIGGKQALETVQALLPVLCQAHGLTPEQVVA

IASHDGGKQALETVQRLLPVLCQAHGLTPEQVVAI

ASHDGGKQALETVQRLLPVLCQAHGLTPQQVVAIA

SNGGGKQALETVQRLLPVLCQAHGLTPQQVVAIAS

NNGGKQALETVQRLLPVLCQAHGLTPQQVVAIASN

GGGKQALETVQRLLPVLCQAHGLTPEQVVAIASNI

GGKQALETVQALLPVLCQAHGLTPEQVVAIASHDG

GKQALETVQRLLPVLCQAHGLTPQQVVAIASNGGG

RPALE.
```

In another aspect, one another step of genetically modifying cell can be a method of expanding TCRα deficient T cells comprising introducing into the T cell pTα (also known as preTCRα) or a functional variant thereof and expanding the cells, optionally through stimulation of the CD3 complex. In some embodiments, the method comprises: a) transfecting the cells with nucleic acid encoding at least a fragment of pTα to support CD3 surface expression; b) expressing said pTα into the cells; and c) expanding the cells, optionally through stimulation of the CD3 complex.

Also provided are methods of preparing T cells for immunotherapy comprising steps of the method for expansion for T cell. In some embodiments, the pTα polynucleotide sequence can be introduced randomly or by homologous recombination. In some embodiments, the insertion can be associated with the inactivation of the TCRα gene.

Different functional variants of pTα can be used. A "functional variant" of the peptide refers to a molecule substantially similar to either the entire peptide or a fragment thereof. A "fragment" of the pTα or functional variant thereof refers to any subset of the molecule, that is, a shorter peptide than the full-length pTα. In some embodiments, pTα or functional variants can be, for example, full-length pTα or a C-terminal truncated pTα version. C-terminal truncated pTα lacks in C-terminal end one or more residues. As non limiting examples, C-terminal truncated pTα version lacks 18, 48, 62, 78, 92, 110 or 114 residues from the C-terminus of the protein. Amino acid sequence variants of the peptide can be prepared by mutations in the DNA which encodes the peptide. Such functional variants include, for example, deletions from, or insertions or substitutions of, residues within the amino acid sequence. Any combination of deletion, insertion, and substitution may also be made to arrive at the final construct, provided that the final construct possesses the desired activity, in particular the restoration of a functional CD3 complex. In an exemplary embodiment, at least one mutation is introduced in the different pTα versions as described above to affect dimerization. As non limiting example, mutated residue can be at least W46R, D22A, K24A, R102A or R117A of the human pTα protein or aligned positions using CLUSTALW method on pTα family or homologue member. For example pTα or variant thereof as described above comprise the mutated residue W46R or the mutated residues D22A, K24A, R102A and R117A. In some embodiments, said pTα or variants are also fused to a signal-transducing domain such as CD28, OX40, ICOS, CD27, CD137 (4-1BB) and CD8 as non limiting examples. The extracellular domain of pTα or variants as described above can be fused to a fragment of the TCRα protein, particularly the transmembrane and intracellular domain of TCRα. pTα variants can also be fused to the intracellular domain of TCRα.

In some embodiments, pTα versions can be fused to an extracellular ligand-binding domain. In some embodiments, pTα or functional variant thereof is fused to a single chain antibody fragment (scFv) comprising the light and the heavy variable fragment of a target antigen specific monoclonal antibody joined by a flexible linker.

The term "TCRα deficient T cell" refers to an isolated T cell that lacks expression of a functional TCRα chain. This may be accomplished by different means, as non limiting examples, by engineering a T cell such that it does not express any functional TCRα on its cell surface or by engineering a T cell such that it produces very little functional TCRα chain on its surface or by engineering a T cell to express mutated or truncated form of TCRα chain. TCRα deficient cells can no longer be expanded through CD3 complex. Thus, to overcome this problem and to allow proliferation of TCRα deficient cells, pTα or functional variant thereof is introduced into the cells, thus restoring a functional CD3 complex. In some embodiments, the method further comprises introducing into said T cells rare-cutting endonucleases able to selectively inactivate by DNA cleavage one gene encoding one component of the T cell receptor (TCR). In some embodiments, the rare-cutting endonuclease is a TALE-nuclease.

In some embodiments, polynucleotides encoding polypeptides according to the present invention can be mRNA which is introduced directly into the cells, for example by electroporation. In some embodiments, cytoPulse technology can be used to transiently permeabilize living cells for delivery of material into the cells. Parameters can be modified in order to determine conditions for high transfection efficiency with minimal mortality.

Also provided herein are methods of transfecting T cell. In some embodiments, the method comprises: contacting a T cell with RNA and applying to T cell an agile pulse sequence consisting of: (a) an electrical pulse with a voltage range from about 2250 to 3000 V per centimeter; (b) a pulse width of 0.1 ms; (c) a pulse interval of about 0.2 to 10 ms between the electrical pulses of step (a) and (b); (d) an electrical pulse with a voltage range from about 2250 to 3000 V with a pulse width of about 100 ms and a pulse interval of about 100 ms between the electrical pulse of step (b) and the first electrical pulse of step (c); and (e) four electrical pulses with a voltage of about 325 V with a pulse width of about 0.2 ms and a pulse interval of 2 ms between each of 4 electrical pulses. In some embodiments, a method of transfecting T cell comprising contacting said T cell with RNA and applying to T cell an agile pulse sequence comprising: (a) an electrical pulse with a voltage of about 2250, 2300, 2350, 2400, 2450, 2500, 2550, 2400, 2450, 2500, 2600, 2700, 2800, 2900 or 3000V per centimeter; (b) a pulse width of 0.1 ms; (c) and a pulse interval of about 0.2, 0.5, 1, 2, 3, 4, 5, 6, 7, 8, 9 or 10 ms between the electrical pulses of step (a) and (b); (d) one electrical pulse with a voltage range from about 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (e) 4 electrical pulses with a voltage of about 325 V with a pulse width of about 0.2 ms and a pulse interval of about 2 ms between each of 4 electrical pulses. Any values included in the value range described above are disclosed in the present application. Electroporation medium can be any suitable medium known in the art. In some embodiments, the electroporation medium has conductivity in a range spanning about 0.01 to about 1.0 milliSiemens.

In some embodiments, as non limiting examples, an RNA encodes a rare-cutting endonuclease, one monomer of the rare-cutting endonuclease such as half-TALE-nuclease, a CAR, at least one component of the multi-chain chimeric antigen receptor, a pTα or functional variant thereof, an exogenous nucleic acid, and/or one additional catalytic domain.

Engineered Immune Cells

The invention also provides engineered immune cells comprising any of the CAR polynucleotides described herein. In some embodiments, a CAR can be introduced into an immune cell as a transgene via a plasmid vector. In some embodiments, the plasmid vector can also contain, for example, a selection marker which provides for identification and/or selection of cells which received the vector.

CAR polypeptides may be synthesized in situ in the cell after introduction of polynucleotides encoding the CAR polypeptides into the cell. Alternatively, CAR polypeptides may be be produced outside of cells, and then introduced into cells. Methods for introducing a polynucleotide construct into cells are known in the art. In some embodiments, stable transformation methods can be used to integrate the polynucleotide construct into the genome of the cell. In other embodiments, transient transformation methods can be used to transiently express the polynucleotide construct, and the polynucleotide construct not integrated into the genome of the cell. In other embodiments, virus-mediated methods can be used. The polynucleotides may be introduced into a cell by any suitable means such as for example, recombinant viral vectors (e.g. retroviruses, adenoviruses), liposomes, and the like. Transient transformation methods include, for example without limitation, microinjection, electroporation or particle bombardment. Polynucleotides may be included in vectors, such as for example plasmid vectors or viral vectors.

Also provided herein are isolated cells and cell lines obtained by the above-described methods of engineering cells provided herein. In some embodiments, an isolated cell comprises at least one CAR as described above. In some embodiments, an isolated cell comprises a population of CARs, each CAR comprising different extracellular ligand-binding domains.

Also provided herein are isolated immune cells obtained according to any one of the methods described above. Any immune cell capable of expressing heterologous DNAs can be used for the purpose of expressing the CAR of interest. In some embodiments, the immune cell used for expressing any one of the CARs described herein is a T cell. In some embodiments, an immune cell used for expressing CARs can be derived from, for example without limitation, a stem cell. The stem cells can be adult stem cells, non-human embryonic stem cells, more particularly non-human stem cells, cord blood stem cells, progenitor cells, bone marrow stem cells, induced pluripotent stem cells, totipotent stem cells or hematopoietic stem cells. Representative human stem cells are CD34+ cells.

In some embodiments, the engineered immune cells expressing at their cell surface membrane a FLT3 specific CAR of the invention comprise a percentage of stem cell memory and central memory cells greater than 10%, 20%, 30%, 40%, 50%, or 60%. In some embodiments, the engineered immune cells expressing at their cell surface membrane a FLT3 specific CAR of the invention comprise a percentage of stem cell memory and central memory cells of about 10% to about 60%, about 10% to about 50%, about 10% to about 40%, about 15% to about 50%, about 15% to about 40%, about 20% to about 60%, or about 20% to about 70%.

In some embodiments, the percentage of stem cell memory and central memory cells is measured as disclosed in Example 2d.

The immune cell used for expressing any one of the CARs described herein can also be a dendritic cell, killer dendritic cell, a mast cell, a NK-cell, a B-cell or a T cell selected from the group consisting of inflammatory T-lymphocytes, cytotoxic T-lymphocytes, regulatory T-lymphocytes or helper T-lymphocytes. In some embodiments, the cell can be derived from the group consisting of CD4+ T-lymphocytes and CD8+ T-lymphocytes.

In one embodiment, the immune cell is an inflammatory T-lymphocyte that expresses any one of the CARs described herein. In one embodiment, the immune cell is a cytotoxic T-lymphocyte that expresses any one of the CARs described herein. In one embodiment, the immune cell is a regulatory T-lymphocyte that expresses any one of the CARs described herein. In one embodiment, the immune cell is a helper T-lymphocyte that expresses any one of the CARs described herein.

Also provided herein are cell lines obtained from a transformed T cell according to any of the above-described methods. Also provided herein are modified cells resistant to an immunosuppressive treatment. In some embodiments, an isolated cell according to the invention comprises a polynucleotide encoding a CAR.

The immune cells of the invention can be activated and expanded, either prior to or after genetic modification of the T cells, using methods as generally described, for example without limitation, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T cells can be expanded in vitro or in vivo. Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-2, IL-15, TGFp, and TNF, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics In some embodiments, the cells of the invention can be expanded by co-culturing with tissue or cells. The cells can also be expanded in vivo, for example in the subject's blood after administrating the cell into the subject.

In some embodiments, an isolated cell according to the present invention comprises one inactivated gene selected from the group consisting of CD52, GR, PD-1, CTLA-4, LAG3, Tim3, BTLA, BY55, TIGIT, B7H5, LAIR1, SIGLEC10, 2B4, HLA, TCRα and TCRβ and/or expresses a CAR, a multi-chain CAR and/or a pTα transgene. In some embodiments, an isolated cell comprises polynucleotides encoding polypeptides comprising a multi-chain CAR. In some embodiments, the isolated cell according to the present invention comprises two inactivated genes selected from the group consisting of: CD52 and GR, CD52 and TCRα, CDR52 and TCRβ, GR and TCRα, GR and TCRβ, TCRα and TCRβ, PD-1 and TCRα, PD-1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ and/or expresses a CAR, a multi-chain CAR and a pTα transgene.

In some embodiments, TCR is rendered not functional in the cells according to the invention by inactivating TCRα gene and/or TCRβ gene(s). In some embodiments, a method to obtain modified cells derived from an individual is provided, wherein the cells can proliferate independently of the major histocompatibility complex (MHC) signaling pathway. Modified cells, which can proliferate independently of the MHC signaling pathway, susceptible to be obtained by this method are encompassed in the scope of the present invention. Modified cells disclosed herein can be used in for treating individuals in need thereof against Host versus Graft (HvG) rejection and Graft versus Host Disease (GvHD); therefore in the scope of the present invention is a method of treating individuals in need thereof against Host versus Graft (HvG) rejection and Graft versus Host Disease (GvHD) comprising treating said individual by administering to said individual an effective amount of modified cells comprising inactivated TCRα and/or TCRβ genes.

In some embodiments, the immune cells are engineered to be resistant to one or more chemotherapy drugs. The chemotherapy drug can be, for example, a purine nucleotide analogue (PNA), thus making the immune cell suitable for cancer treatment combining adoptive immunotherapy and chemotherapy. Exemplary PNAs include, for example, clofarabine, fludarabine, and cytarabine, alone or in combination. PNAs are metabolized by deoxycytidine kinase (dCK) into mono-, di-, and tri-phosphate PNA. Their tri-phosphate forms compete with ATP for DNA synthesis, act as pro-apoptotic agents, and are potent inhibitors of ribonucleotide reductase (RNR), which is involved in trinucleotide production. Provided herein are FLT3 specific CAR-T cells comprising an inactivated dCK gene. In some embodiments, the dCK knockout cells are made by transfection of T cells using polynucleotides encoding specific TAL-nuclease directed against dCK genes by, for example, electroporation of mRNA. The dCK knockout FLT3 specific CAR-T cells are resistant to PNAs, including for example clorofarabine and/or fludarabine, and maintain T cell cytotoxic activity toward FLT3-expressing cells.

In some embodiments, isolated cells or cell lines of the invention can comprise a pTα or a functional variant thereof. In some embodiments, an isolated cell or cell line can be further genetically modified by inactivating the TCRα gene.

In some embodiments, the CAR-T cell comprises a polynucleotide encoding a suicide polypeptide, such as for example RQR8. See, e.g., WO2013153391A, which is hereby incorporated by reference in its entirety. In CAR-T cells comprising the polynucleotide, the suicide polypeptide is expressed at the surface of a CAR-T cell. In some embodiments, the suicide polypeptide comprises the amino acid sequence shown in SEQ ID NO: 227.

```
                                              (SEQ ID NO: 227)
            CPYSNPSLCSGGGGSELPTQGTFSNVSTNVSPAKP

TTTACPYSNPSLCSGGGGSPAPRPPTPAPTIASQP

LSLRPEACRPAAGGAVHTRGLDFACDIYIWAPLAG

TCGVLLLSLVITLYCNHRNRRRVCKCPRPVV.
```

The suicide polypeptide may also comprise a signal peptide at the amino terminus. In some embodiments, the suicide polypeptide comprises the amino acid sequence shown in SEQ ID NO: 228.

(SEQ ID NO: 228)
MGTSLLCWMALCLLGADHADACPYSNPSLCSGGGG

SELPTQGTFSNVSTNVSPAKPTTTACPYSNPSLCS

GGGGSPAPRPPTPAPTIASQPLSLRPEACRPAAGG

AVHTRGLDFACDIYIWAPLAGTCGVLLLSLVITLY

CNHRNRRRVCKCPRPVV.

When the suicide polypeptide is expressed at the surface of a CAR-T cell, binding of rituximab to the rituximab epitopes of the polypeptide causes lysis of the cell. More than one molecule of rituximab may bind per polypeptide expressed at the cell surface. Each rituximab epitope of the polypeptide may bind a separate molecule of rituximab. Deletion of FLT3 specific CAR-T cells may occur in vivo, for example by administering rituximab to a subject. The decision to delete the transferred cells may arise from undesirable effects being detected in the subject which are attributable to the transferred cells, such as for example, when unacceptable levels of toxicity are detected.

In some embodiments, upon administration to a patient, engineered immune cells expressing at their cell surface any one of the FLT3 specific CARs described herein may reduce, kill or lyse endogenous FLT3 expressing cells of the patient. In one embodiment, a percentage reduction or lysis of FLT3 expressing endogenous cells or cells of a cell line expressing FLT3 by engineered immune cells expressing any one of the FLT3 specific CARs described herein is at least about or greater than 10%, 15%, 20%, 25%, 30%, 35%, 40%, 45%, 50%, 55%, 60%, 65%, 70%, 75%, 80%, 85%, 90%, or 95%. In one embodiment, a percentage reduction or lysis of FLT3 expressing endogenous cells or cells of a cell line expressing FLT3 by engineered immune cells expressing any one of the FLT3 specific CARs described herein is about 5% to about 95%, about 10% to about 95%, about 10% to about 90%, about 10% to about 80%, about 10% to about 70%, about 10% to about 60%, about 10% to about 50%, about 10% to about 40%, about 20% to about 90%, about 20% to about 80%, about 20% to about 70%, about 20% to about 60%, about 20% to about 50%, about 25% to about 75%, or about 25% to about 60%. In one embodiment, the endogenous FLT3 expressing cells are endogenous FLT3 expressing bone marrow cells.

In one embodiment, the percent reduction or lysis of target cells, e.g., a cell line expressing FLT3, by engineered immune cells expressing at their cell surface membrane a FLT3 specific CAR of the invention can be measured using the assay disclosed in Example 2e.

Method for Sorting CAR-Positive Immune Cells

In one aspect, provided are methods for in vitro sorting of a population of immune cells, wherein a subset of the population of immune cells comprises engineered immune cells expressing any one of the FLT3 specific CARs comprising epitopes specific for monoclonal antibodies described herein. The method comprises contacting the population of immune cells with a monoclonal antibody specific for the epitopes and selecting the immune cells that bind to the monoclonal antibody to obtain a population of cells enriched in engineered immune cells expressing FLT3 specific CAR.

In some embodiments, said monoclonal antibody specific for said epitope is optionally conjugated to a fluorophore. In this embodiment, the step of selecting the cells that bind to the monoclonal antibody can be done by Fluorescence Activated Cell Sorting (FACS). In some embodiments, said monoclonal antibody specific for said epitope is optionally conjugated to a magnetic particle. In this embodiment, the step of selecting the cells that bind to the monoclonal antibody can be done by Magnetic Activated Cell Sorting (MACS).

In some embodiments, the extracellular binding domain of the CAR comprises a mAb-specific epitope of SEQ ID NO: 262. In some embodiments, the extracellular binding domain of the CAR comprises a mAb-specific epitope of SEQ ID NO: 262 and the antibody used to contact the population of immune cells is QBEND-10.

In some embodiments, the extracellular binding domain of the CAR comprises a mAb-specific epitope of SEQ ID NO: 229. In some embodiments, the extracellular binding domain of the CAR comprises a mAb-specific epitope of SEQ ID NO: 229 and the antibody used to contact the population of immune cells is Rituximab.

In some embodiments, the population of FLT3 CAR-expressing immune cells obtained when using the method for in vitro sorting of immune cells described above, comprises at least 60%, 65%, 70%, 75%, 80%, 85%, 90%, or 95% of FLT3 CAR-expressing immune cells. In some embodiments, the population of FLT3 CAR-expressing immune cells obtained when using the method for in vitro sorting of CAR-expressing immune cells described above, comprises at least 85% of FLT3 CAR-expressing immune cells.

In some embodiments, the mAbs used in the in vitro sorting method are previously bound onto a support such as a column or on beads such as routinely realized by the skilled in the art. In some embodiments, immune cells expressing CARs are T-cells.

According to the invention, cells to be administered to the recipient may be enriched in vitro from the source population. Methods of expanding source populations are well known in the art, and may include selecting cells that express an antigen such as CD34 antigen, using combinations of density centrifugation, immuno-magnetic bead purification, affinity chromatography, and fluorescent activated cell sorting, known to those skilled in the art.

Flow cytometry is widely used in the art and is a method well known to one of ordinary skill to sort and quantify specific cell types within a population of cells. In general, flow cytometry is a method for quantitating components or structural features of cells primarily by optical means. Since different cell types can be distinguished by quantitating structural features, flow cytometry and cell sorting can be used to count and sort cells of different phenotypes in a mixture.

A flow cytometric analysis involves two basic steps: 1) labeling selected cell types with one or more labeled markers, and 2) determining the number of labeled cells relative to the total number of cells in the population.

The primary method of labeling cell types is by binding labeled antibodies to markers expressed by the specific cell type. The antibodies are either directly labeled with a fluorescent compound or indirectly labeled using, for example, a fluorescent-labeled second antibody which recognizes the first antibody.

In some embodiments, the method used for sorting immune cells expressing a CAR is the Magnetic-Activated Cell Sorting (MACS).

Magnetic-activated cell sorting (MACS) is a method for separation of various cell populations depending on their surface antigens (CD molecules) by using superparamagnetic nanoparticles and columns. It takes a few simple steps to get pure cell populations. Cells in a single-cell suspension are magnetically labeled with microbeads. The sample is applied to a column composed of ferromagnetic spheres, which are covered with a cell-friendly coating allowing fast and gentle separation of cells. The unlabeled cells pass through while the magnetically labeled cells are retained within the column. The flow-through can be collected as the unlabeled cell fraction. After a short washing step, the column is removed from the separator, and the magnetically labeled cells are eluted from the column.

In some embodiments, the mAb used in the method for sorting immune cells expressing the CAR is chosen from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10 and/or ustekinumab. In some embodiments, said mAb is rituximab. In another embodiment, said mAb is QBEND-10.

Therapeutic Applications

Isolated cells obtained by the methods described above, or cell lines derived from such isolated cells, expressing FLT3 specific CARs can be used as a medicament. Similarly, FLT3 specific antibodies disclosed herein can be used as a medicament. In some embodiments, such a medicament can be used for treating a FLT3-associated disease or a condition. In some embodiments, the FLT3-associated disease or a condition comprises malignant cells expressing FLT3, for example, cancer. In some embodiments, the cancer is a cancer of hematopoietic origin, such as a lymphoma or leukemia. In some embodiments, the cancer is multiple myeloma malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulinemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmacytic lymphoma, Waldenström macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBV positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHV8-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, or other hematopoietic cells related cancers.

In an exemplary embodiment the cancer is AML. In an exemplary embodiment the cancer is ALL.

In some embodiments, an isolated cell according to the invention, or cell line derived from the isolated cells, or an antibody can be used in the manufacture of a medicament for treatment of a cancer in a subject in need thereof.

Also provided herein are methods for treating subjects. In some embodiments, the method comprises providing an immune cell of the invention to a subject in need thereof. In some embodiments, the method comprises a step of administering transformed immune cells of the invention to a subject in need thereof. In some embodiments, the method comprises administering an antibody of the invention to a subject in need thereof.

In some embodiments, T cells of the invention can undergo robust in vivo T cell expansion and can persist for an extended amount of time.

Methods of treatment of the invention can be ameliorating, curative or prophylactic. The method of the invention may be either part of an autologous immunotherapy or part of an allogeneic immunotherapy treatment. The invention is particularly suitable for allogeneic immunotherapy. T cells from donors can be transformed into non-alloreactive cells using standard protocols and reproduced as needed, thereby producing CAR-T cells which may be administered to one or several subjects. Such CAR-T cell therapy can be made available as an "off the shelf" therapeutic product.

Cells that can be used with the disclosed methods are described in the previous section. Treatment can be used to treat subjects diagnosed with, for example, cancer. Cancers that may be treated include, for example without limitation, cancers that involve B lymphocytes, including any of the above-listed cancers. Types of cancers to be treated with the CARs and CAR-T cells of the invention include, but are not limited to certain leukemia or lymphoid malignancies. Adult tumors/cancers and pediatric tumors/cancers are also included. In some embodiments, the treatment can be in combination with one or more therapies against cancer selected from the group of antibodies therapy, chemotherapy, cytokines therapy, dendritic cell therapy, gene therapy, hormone therapy, laser light therapy and radiation therapy.

In some embodiments, treatment can be administered into subjects undergoing an immunosuppressive treatment. Indeed, the invention generally relies on cells or a population of cells, which have been made resistant to at least one immunosuppressive agent due to the inactivation of a gene encoding a receptor for such immunosuppressive agent. In this aspect, the immunosuppressive treatment should help the selection and expansion of the T cells according to the invention within the subject. The administration of the cells or population of cells according to the invention may be carried out in any convenient manner, including by aerosol inhalation, injection, ingestion, transfusion, implantation or transplantation. The compositions described herein may be administered to a subject subcutaneously, intradermally, intratumorally, intranodally, intramedullary, intramuscularly, by intravenous or intralymphatic injection, or intraperitoneally. In some embodiments, the cell compositions of the invention are administered by intravenous injection.

In some embodiments, the administration of the cells or population of cells can comprise administration of, for example, about $10^4$ to about $10^9$ cells per kg body weight including all integer values of cell numbers within those ranges. In some embodiments the administration of the cells or population of cells can comprise administration of about $10^5$ to $10^6$ cells per kg body weight including all integer values of cell numbers within those ranges. The cells or population of cells can be administered in one or more doses. In some embodiments, said effective amount of cells can be administered as a single dose. In some embodiments, said effective amount of cells can be administered as more than one dose over a period time. Timing of administration is within the judgment of managing physician and depends on the clinical condition of the subject. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administered will be dependent upon the age, health and weight of the recipient, kind of concurrent treatment, if any, frequency of treatment and the nature of the effect desired. In some embodiments, an effective amount of cells or composition comprising those cells are administered parenterally. In some embodiments, administration can be an intravenous administration. In some embodiments, administration can be directly done by injection within a tumor.

In some embodiments of the invention, cells are administered to a subject in conjunction with (e.g., before, simultaneously or following) any number of relevant treatment modalities, including but not limited to treatment with agents such as monoclonal antibody therapy, CCR2 antagonist (e.g., INC-8761), antiviral therapy, cidofovir and interleukin-2, Cytarabine (also known as ARA-C) or natalizumab treatment for MS patients or efalizumab treatment for psoriasis patients or other treatments for PML patients. In some embodiments, FLT3 specific CAR-T cells are administered to a subject in conjunction with one or more of the following: an anti-PD-1 antibody (e.g., nivolumab, pembrolizumab, or PF-06801591), an anti-PD-L1 antibody (e.g., avelumab, atezolizumab, or durvalumab), an anti-OX40 antibody (e.g., PF-04518600), an anti-4-1BB antibody (e.g., PF-05082566), an anti-MCSF antibody (e.g., PD-0360324), an anti-GITR antibody, and/or an anti-TIGIT antibody. In some embodiments, a FLT3 specific CAR comprising the amino acid sequence shown in SEQ ID NO: 236 is administered to a subject in conjunction with anti-PD-L1 antibody avelumab. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and/or irradiation. These drugs inhibit either the calcium dependent phosphatase calcineurin (cyclosporine and FK506) or inhibit the p70S6 kinase that is important for growth factor induced signaling (rapamycin) (Henderson, Naya et al. 1991; Liu, Albers et al. 1992; Bierer, Hollander et al. 1993). In further embodiments, the T cells of the invention may be used in combination with Receptor Tyrosine Kinase inhibitors such as Midostaurin and Sunitinib, mTOR inhibitors such as Rapamacyn and Everolimus, epigenetic modulators such as Vormostat, proteasome inhibitors such as Bortezomib, immunomodulatory agents such as lenalidomide, Hedgehog inhibitors such as Erismodegib and PF-04449913 or Isocitrate Dehydrogenase (IDH) inhibitors such as AG-120 and AG-221. In a further embodiment, the cell compositions of the invention are administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In some embodiments, the cell compositions of the invention are administered following B-cell ablative therapy such as agents that react with CD20, e.g., Rituxan. For example, In some embodiments, subjects may undergo standard treatment with high dose chemotherapy followed by peripheral blood stem cell transplantation. In certain embodiments, following the transplant, subjects receive an infusion of the expanded immune cells of the invention. In some embodiments, expanded cells are administered before or following surgery.

In some embodiments, provided are methods for depleting FLT3 specific CAR-expressing engineered immune cells from a subject administered with said cells. Depletion can be by inhibition or elimination.

In one aspect, a method for depleting engineered immune cells expressing a FLT3 specific CAR comprising an epitope specific for a monoclonal antibody comprises contacting said engineered immune cell with a monoclonal antibody specific for the epitope.

In some embodiments, a method for depleting from a subject administered with engineered immune cells expressing a FLT3 specific CAR comprising an epitope specific for a monoclonal antibody comprises administering to the subject a monoclonal antibody specific for the epitope. In these embodiments, administration of the monoclonal antibody specific for the epitope present in the extracellular domain of the CAR to the subject eliminates or inhibits the activity of engineered CAR-expressing immune cells from the subject. In one aspect, depletion of engineered CAR expressing immune cells allows for recovery of an endogenous population of FLT3 expressing cells.

In one aspect, the invention relates to a method for promoting recovery of endogenous FLT3-expressing cells in a subject administered with engineered immune cells expressing at cell surface a FLT3 specific CAR comprising an epitope specific for a monoclonal antibody, the method comprising administering a monoclonal antibody specific for the epitope to the subject. In some embodiments, endogenous FLT3 expressing cells are endogenous FLT3 expressing bone marrow cells. In one aspect, the term "recovery" refers to increasing the number of endogenous FLT3 expressing cells. The number of endogenous FLT3 expressing cells may increase due to increase in proliferation of endogenous FLT3 expressing cells and/or due to reduction in elimination of endogenous FLT3 expressing cells by FLT3 CAR expressing engineered immune cells. In some embodiments, administration of the monoclonal antibody to the subject depletes the FLT3 CAR expressing engineered immune cells and increases the number of endogenous FLT3-expressing cells, e.g., endogenous FLT3-expressing bone marrow progenitor cells, in the subject. In one embodiment, administration of the monoclonal antibody to the subject increases the number of endogenous FLT3 expressing cells by at least about 10%, 15%, 20%, 25%, 30%, 35%, 40%, 45%, 50%, 55%, 60%, 65%, 70%, 75%, 80%, 85%, 90%, or 95%, compared to the number of endogenous FLT3 expressing cells prior to administration of the monoclonal antibody.

In one aspect, provided is a method for treating a FLT3-mediated condition in a subject, the method comprising: (a) administering to the subject engineered immune cells expressing at cell surface FLT3 specific CARs comprising one or more epitopes specific for one or more monoclonal antibodies; and (b) subsequently depleting the engineered immune cells from the subject by administering one or more monoclonal antibodies specific for the epitope to the subject.

In some embodiments, the mAbs used in the method for depleting CAR-expressing engineered immune cells are selected from alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10, ustekinumab, and combinations thereof.

In some embodiments, said epitope specific for a monoclonal antibody (mAb-specific epitope) is a CD20 epitope or mimotope, e.g. SEQ ID NO. 229 and the mAb specific for the epitope is rituximab.

In some embodiments, the step of administering a monoclonal antibody to the subject comprises infusing the subject with the monoclonal antibody. In some embodiments, the amount of epitope-specific mAb administered to the subject is sufficient to eliminate at least 20%, 30%, 40%, 50%, 60%, 70%, 80% or 90% of the CAR-expressing immune cell in the subject.

In some embodiments, the step of administering a monoclonal antibody to the subject comprises infusing the subject with 375 mg/m$^2$ of rituximab, once or several times weekly.

In some embodiments, when immune cells expressing a CAR comprising an mAb-specific epitope (CAR-expressing immune cells) are depleted in a CDC assay using epitope-specific mAb, the amount of viable CAR-expressing immune cells decreases, e.g. by at least 10%, 20%, 30%, 40%, 50%, 60%, 70%, 80% or 90%.

In some embodiments, a cytotoxic drug is coupled to the epitope-specific mAbs which are used to deplete CAR-expressing immune cells. By combining targeting capabilities of monoclonal antibodies with the cell-killing ability of cytotoxic drugs, antibody-drug conjugate (ADC) allows a sensitive discrimination between healthy and diseased tissue when compared to the use of the drug alone. Market approvals were received for several ADCs; the technology for making them—particularly on linkers—is abundantly presented in the following prior art (Payne, G. (2003) Cancer Cell 3:207-212; Trail et al (2003) Cancer Immunol. Immunother. 52:328-337; Syrigos and Epenetos (1999) Anticancer Research 19:605-614; Niculescu-Duvaz and Springer (1997) Adv. Drug Del. Rev. 26:151-172; U.S. Pat. No. 4,975,278).

In some embodiments, the epitope-specific mAb to be infused is conjugated beforehand with a molecule able to promote complement dependent cytotoxicity (CDC). Therefore, the complement system helps or complements the ability of antibodies to clear pathogens from the organism. When stimulated by one of several, is triggered an activation cascade as a massive amplification of the response and activation of the cell-killing membrane attack complex. Different molecule may be used to conjugate the mAb, such as glycans [Courtois, A, Gac-Breton, S., Berthou, C, Guezennec, J., Bordron, A. and Boisset, C. (2012), Complement dependent cytotoxicity activity of therapeutic antibody fragments is acquired by immunogenic glycan coupling, Electronic Journal of Biotechnology ISSN: 0717-3458; http://www.ejbiotechnology.info DOI: 10.2225/vol15-issue5).

Kits

The invention also provides kits for use in the instant methods. Kits of the invention include one or more containers comprising a polynucleotide encoding a FLT3 specific CAR, an engineered immune cell comprising a polynucleotide encoding a FLT3 specific CAR, or a FLT specific antibody, as described herein, and instructions for use in accordance with any of the methods of the invention described herein. Generally, these instructions comprise a description of administration of the engineered immune cell for the above described therapeutic treatments.

The instructions relating to the use of the engineered immune cells or antibodies as described herein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a FLT3 specific CAR or a FLT3 specific antibody. The container may further comprise a second pharmaceutically active agent.

Kits may optionally provide additional components such as buffers and interpretive information. Normally, the kit comprises a container and a label or package insert(s) on or associated with the container.

The following examples are offered for illustrative purposes only, and are not intended to limit the scope of the invention in any way. Indeed, various modifications of the invention in addition to those shown and described herein will become apparent to those skilled in the art from the foregoing description and fall within the scope of the appended claims.

Representative materials of the present invention were deposited in the American Type Culture Collection, 10801 University Boulevard, Manassas, Va. 20110-2209, USA, on Jun. 1, 2017. Vector P3E10-VL having ATCC Accession No. PTA-124228 is a polynucleotide encoding the P3E10 light chain variable region, and vector P3E10-VH having ATCC Accession No. PTA-124227 is a polynucleotide encoding the P3E10 heavy chain variable region. The deposit was made under the provisions of the Budapest Treaty on the International Recognition of the Deposit of Microorganisms for the Purpose of Patent Procedure and Regulations thereunder (Budapest Treaty). This assures maintenance of a viable culture of the deposit for 30 years from the date of deposit. The deposit will be made available by ATCC under the terms of the Budapest Treaty, and subject to an agreement between Pfizer, Inc. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. Section 122 and the Commissioner's rules pursuant thereto (including 37 C.F.R. Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

EXAMPLES

Example 1

Determination of Kinetics and Affinity of Human FLT3/FLT3 Antibodies Interactions at 37° C.

This example determines the kinetics and affinity of various anti-FLT3 antibodies at 37° C. All experiments were performed on a Biacore T200 surface Plasmon resonance biosensor (GE Lifesciences, Piscataway NJ).

The sensor chip preparation was performed at 25° C. with a running buffer of 10 mM HEPES, 150 mM NaCl, 0.05% (v/v) Tween-20, pH 7.4. An anti-human Fc sensor chip was made by activating all flow cells of a Biacore CM4 sensor chip with a 1:1 (v/v) mixture of 400 mM EDC and 100 mM NHS for 7 minutes, at a flow rate of 10 µL/min. An anti-human Fc reagent (Goat Anti-Human IgG Fc, SouthernBiotech Catalog #2081-01) was diluted to 30 µg/mL in 10 mM Sodium Acetate pH 4.5 and injected on all flow cells for 7 minutes at 20 µL/min. All flow cells were blocked with 100 mM ethylenediamine in 150 mM Borate buffer pH 8.5 for 7 minutes at 10 µL/min.

The experiments were performed at 37° C. using a running buffer of 10 mM HEPES, 150 mM NaCl, 0.05% (v/v) Tween-20, pH 7.4, 1 mg/mL BSA. FLT3 antibodies were captured from undiluted supernatants onto downstream flow cells (flow cells 2, 3 and 4) at a flow rate of 10 µL/min for 1 minute. Different antibodies were captured on each flow cell. Flow cell 1 was used as a reference surface. Following capture of FLT3 antibodies, analyte (buffer, hFLT3) was injected at 30 µL/min on all flow cells for two minutes. After the analyte injection, dissociation was monitored for 10 minutes followed by regeneration of all flow cells with three 1-minute injections of 75 mM Phosphoric Acid. For each captured FLT3 antibody, the following analyte injections were performed: buffer, 11 nM hFLT3, 33 nM hFLT3, 100 nM hFLT3 and 300 nM hFLT3. Buffer cycles were collected for each captured FLT3 antibody for double-referencing purposes (double-referencing as described in Myszka, D.G. Improving biosensor analysis. *J. Mol. Recognit.* 12, 279-284 (1999)). The double-referenced sensorgrams were fit globally to a simple 1:1 Langmuir with mass transport binding model.

The kinetics and affinity parameters for tested anti-FLT3 antibodies are shown in Table 7. The antibodies shown in Table 7 share the same VH and VL regions as the CARs shown in Table 8 having the same name.

TABLE 7

| | | IgG format | | | | | scFv format | | | |
|---|---|---|---|---|---|---|---|---|---|---|
| | | | | | huFlt3 | mFlt3 | | | | |
| | domain | $k_a$ (1/Ms) | $k_d$ (1/s) | $t_{1/2}$ (min) | $K_D$ (nM) | Kd (nM) | $k_a$ (1/Ms) | $k_d$ (1/s) | $t_{1/2}$ (min) | $K_D$ (nM) |
| P4F6 | 1 | 1.40E+05 | 3.50E-03 | 3.3 | 25 | 36.1 | 1.32E+05 | 1.99E-03 | 5.8 | 15.1 |
| P4C7 | 1 | 1.60E+05 | 1.20E-03 | 9.3 | 7.7 | 402.4 | 1.21E+05 | 1.64E-03 | 7 | 13.6 |
| P3A1 | 2-3 | 9.50E+04 | 6.00E-03 | 1.9 | 64 | — | 1.07E+05 | 1.67E-03 | 6.9 | 15.67 |
| P5A3 | 2-3 | 9.80E+04 | 1.00E-02 | 1.2 | 102 | 19.3 | 8.10E+04 | 1.75E-02 | 0.7 | 216 |
| P9B5 | 2-3 | 4.20E+04 | 4.70E-04 | 24.4 | 11 | 1.5 | 3.80E+04 | 6.87E-04 | 16.8 | 18.1 |
| P9F1 | 2-3 | 1.80E+05 | 2.30E-02 | 0.5 | 127 | — | 2.26E+05 | 2.86E-02 | 0.4 | 126.5 |
| P1B4 | 4 | 1.80E+05 | 5.80E-03 | 2 | 32 | — | 1.20E+05 | 3.27E-03 | 3.5 | 27.3 |
| P1B11 | 4 | 1.20E+05 | 5.50E-03 | 2.1 | 45 | — | 8.47E+04 | 2.57E-03 | 4.5 | 30.3 |
| P7H3 | 4 | 9.90E+05 | 1.80E-03 | 6.6 | 2 | 0.9 | 2.05E+05 | 1.87E-03 | 6.2 | 9.1 |
| P3E10 | 4 | 1.80E+05 | 1.90E-02 | 0.6 | 106 | — | 1.72E+05 | 1.12E-02 | 1 | 65.1 |
| P1A5 | 4 | 1.78E+06 | 3.47E-04 | 33 | 0.19 | — | 2.59E+05 | 2.92E-04 | 40 | 1.1 |
| P4A4 | 4 | 1.16E+06 | 4.69E-04 | 25 | 0.4 | — | | | | |
| P1G12 | 4 | 6.17E+05 | 2.92E-04 | 40 | 0.47 | 6.5 | | | | |
| P4E5 | 4 | 1.20E+06 | 1.51E-04 | 77 | 0.13 | 18.9 | | | | |
| P5A4 | 4 | 5.53E+05 | 1.01E-04 | 114 | 0.18 | — | | | | |
| P5F7 | 4 | 6.36E+05 | 1.52E-04 | 76 | 0.24 | — | 1.89E+05 | 1.97E-04 | 59 | 1 |
| P4H11 | 4 | 6.18E+14 | 1.44E-02 | 1 | 233 | — | 1.60E+05 | 9.33E-03 | 1 | 58.3 |
| P15F7 | 5 | 1.40E+05 | 5.50E-03 | 2.1 | 38 | — | | | | |
| P12B6 | 5 | 1.10E+05 | 9.00E-03 | 1.3 | 84 | — | | | | |
| P7D3 | 5 | 7.10E+04 | 5.20E-03 | 2.2 | 72 | — | | | | |
| P7A6 | 5 | 3.40E+04 | 3.70E-04 | 31 | 11 | — | | | | |
| P8B6 | 5 | 9.30E+04 | 2.30E-04 | 51 | 2.5 | — | | | | |
| P14G2 | 5 | 1.40E+05 | 1.10E-03 | 10.7 | 8 | — | 9.35E+04 | 3.05E-04 | 37.9 | 3.3 |
| P7F9 | 4 | 1.10E+05 | 1.30E-03 | 8.9 | 12 | 13.8 | 8.70E+04 | 2.41E-03 | 4.8 | 27.7 |

Example 2

Generation of FLT3 Specific CAR-T Cells a) Plasmids

The following codon-optimized FLT3 CAR sequences listed in Table 8 below were, synthesized and subcloned into a lentiviral vector such as pLVX-EF1a-IRES-Puro (Clontech) using the EcoRI (5') and MluI (3') restriction sites (thus removing the IRES-Puro cassette).

TABLE 8

Exemplary FLT3 specific CARs

| CAR | CAR Amino Acid Sequence | Components |
| --- | --- | --- |
| P1A5 | MALPVTALLLPLALLLHAARPQVQLVQSGAEVKKP GSSVKVSCKASGGVFSRYALSWVRQAPGQGLEWM GGIIPMLGFANYAQKFQGRVTITADESTSTAYMELS SLRSEDTAVYYCATLDFGALDYWGQGTLVTVSSG GGGSGGGGSGGGGSEIVLTQSPGTLSLSPGERATLS CRASQAVDSSDLAWYQQKPGQAPRLLIYDAYTRPS GIPDRFSGSGSGTDFTLTISRLEPEDFAVYYCQQYGS SPLTFGGGTKLEIKTTTPAPRPPTPAPTIASQPLSLR PEACRPAAGGAVHTRGLDFACDIYIWAPLAGTCGVL LLSLVITLYCKRGRKKLLYIFKQPFMRPVQTTQEED GCSCRFPEEEGGCELRVKFSRSADAPAYQQGQNQ LYNELNLGRREEYDVLDKRRGRDPEMGGKPRRKN PQEGLYNELQKDKMAEAYSEIGMKGERRRGKGHD GLYQGLSTATKDTYDALHMQALPPR (SEQ ID NO: 233) | CD8α signal peptide; P1A5_VHVL VH; GS linker; P1A5_VHVL VL; CD8α hinge; CD8α TM domain; 41BB ISD; CD3ζ ISD |
| P1B4 | MALPVTALLLPLALLLHAARPQVQLVQSGAEVKKP GSSVKVSCKASGGVFSRYALSWVRQAPGQGLEWM GGIIPMLGFANYAQKFQGRVTITADESTSTAYMELS SLRSEDTAVYYCATLDFGALDYWGQGTLVTVSSG GGGSGGGGSGGGGSEIVLTQSPGTLSLSPGERATLS CRASQSVPNEQLAWYQQKPGQAPRLLIYDASSRAT GIPDRFSGSGSGTDFTLTISRLEPEDFAVYYCQQYGS PPLTFGQGTKVEIKTTTPAPRPPTPAPTIASQPLSL RPEACRPAAGGAVHTRGLDFACDIYIWAPLAGTCGVL LLSLVITLYCKRGRKKLLYIFKQPFMRPVQTTQEED GCSCRFPEEEGGCELRVKFSRSADAPAYQQGQNQ LYNELNLGRREEYDVLDKRRGRDPEMGGKPRRKN PQEGLYNELQKDKMAEAYSEIGMKGERRRGKGHD GLYQGLSTATKDTYDALHMQALPPR (SEQ ID NO: 234) | CD8α signal peptide; P1B4_VHVL VH; GS linker; P1B4_VHVL VL; CD8α hinge; CD8α TM domain; 41BB ISD; CD3ζ ISD |
| P3A1 | MALPVTALLLPLALLLHAARPQVQLVQSGAEVKKP GSSVKVSCKASGGTFSSYDISWVRQAPGQGLEWM GGIIPVSGRANYAQKFQGRVTITTDKSTSTAYMELS SLRSEDTAVYYCARVRPTYWPLDYWGQGTLVTVS SGGGGSGGGGSGGGGSDIQMTQSPSSLSASVGDRV TITCRASQSISSYLNWYQQKPGKAPKLLIYAASSLQ SGVPSRFSGSGSGTDFTLTISSLQPEDFATYYCQQSY STPLTFGQGTKVEIKTTTPAPRPPTPAPTIASQPLS LRPEACRPAAGGAVHTRGLDFACDIYIWAPLAGTCG VLLLSLVITLYCKRGRKKLLYIFKQPFMRPVQTTQEE DGCSCRFPEEEGGCELRVKFSRSADAPAYQQGQN QLYNELNLGRREEYDVLDKRRGRDPEMGGKPRRK NPQEGLYNELQKDKMAEAYSEIGMKGERRRGKGH DGLYQGLSTATKDTYDALHMQALPPR (SEQ ID NO: 235) | CD8α signal peptide; P3A1_VHVL VH; GS linker; P3A1_VHVL VL; CD8α hinge; CD8α TM domain; 41BB ISD; CD3ζ ISD |
| P3E10 | MALPVTALLLPLALLLHAARPQVQLVQSGAEVKKP GSSVKVSCKASGGTFSSYAIQWVRQAPGQGLEWM GGIVGSWGLANYAQKFQGRVTITTDKSTSTAYMEL SSLRSEDTAVYYCATSAFGELASWGQGTLVTVSSG GGGSGGGGSGGGGSEIVLTQSPGTLSLSPGERATLS CRASQSVPSSQLAWYQQKPGQAPRLLIYD ASSRAT GIPDRFSGSGSGTDFTLTISRLEPEDFAVYYCQQYGS SPLTFGQGTKVEIKTTTPAPRPPTPAPTIASQPLSLRP EACRPAAGGAVHTRGLDFACDIYIWAPLAGTCGVL LLSLVITLYCKRGRKKLLYIFKQPFMRPVQTTQEED GCSCRFPEEEGGCELRVKFSRSADAPAYQQGQNQ LYNELNLGRREEYDVLDKRRGRDPEMGGKPRRKN PQEGLYNELQKDKMAEAYSEIGMKGERRRGKGHD GLYQGLSTATKDTYDALHMQALPPR (SEQ ID NO: 236) | CD8α signal peptide; P3E10_VHVL VH; GS linker; P3E10_VHVL VL; CD8α hinge; CD8α TM domain; 41BB ISD; CD3ζ ISD |

TABLE 8-continued

Exemplary FLT3 specific CARs

| CAR | CAR Amino Acid Sequence | Components |
|---|---|---|
| P4C7 | MALPVTALLLPLALLLHAARPQVQLVQSGAEVKKP GSSVKVSCKASGGTFSSYTISWVRQAPGQGLEWMG GIIPAFGIANYAQKFQGRVTITADKSTSTAYMELSSL RSEDTAVYYCAKGGSYSLDYFDIWGQGTLVTVSSG GGGSGGGGSGGGGSEIVLTQSPGTLSLSPGERATLS CRASQYVSASLLAWYQQKPGQAPRLLIYGASTRAT GIPDRFSGSGSGTDFTLTISRLEPEDFAVYYCQQYAR SSTFGQGTKVEIKTTTPAPRPPTPAPTIASQPLSLRPE ACRPAAGGAVHTRGLDFACDIYIWAPLAGTCGVLL LSLVITLYCKRGRKKLLYIFKQPFMRPVQTTQEEDG CSCRFPEEEEGGCELRVKFSRSADAPAYQQGQNQL YNELNLGRREEYDVLDKRRGRDPEMGGKPRRKNP QEGLYNELQKDKMAEAYSEIGMKGERRRGKGHDG LYQGLSTATKDTYDALHMQALPPR (SEQ ID NO: 237) | CD8α signal peptide; P4C7_VHVL VH; GS linker; P4C7_VHVL VL; CD8α hinge; CD8α TM domain; 41BB ISD; CD3ζ ISD |
| P4H11 | MALPVTALLLPLALLLHAARPEVQLLESGGGLVQP GGSLRLSCAASGFTFSSYAMNWVRQAPGKGLEWV SSISGGGRSTYYADSVKGRFTISRDNSKNTLYLQMN SLRAEDTAVYYCARDLSPSDVGWGYGFDIWGQGT LVTVSSGGGGSGGGGSGGGGSEIVLTQSPGTLSLSP GERATLSCRASQSVSNTYLAWYQQKPGQAPRLLIY DTSSRATGIPDRFSGSGSGTDFTLTISRLEPEDFAVY YCQQYGSSLTFGQGTKVEIKTTTPAPRPPTPAPTIAS QPLSLRPEACRPAAGGAVHTRGLDFACDIYIWAPL AGTCGVLLLSLVITLYCKRGRKKLLYIFKQPFMRPV QTTQEEDGCSCRFPEEEEGGCELRVKFSRSADAPAY QQGQNQLYNELNLGRREEYDVLDKRRGRDPEMGG KPRRKNPQEGLYNELQKDKMAEAYSEIGMKGERR RGKGHDGLYQGLSTATKDTYDALHMQALPPR (SEQ ID NO: 238) | CD8α signal peptide; P4H11_VHVL VH; GS linker; P4H11_VHVL VL; CD8α hinge; CD8α TM domain; 41BB ISD; CD3ζ ISD |
| P5F7 | MALPVTALLLPLALLLHAARPEVQLLESGGGLVQP GGSLRLSCAASGFTFSSYAMNWVRQAPGKGLEWV SSISGGGRSTYYADSVKGRFTISRDNSKNTLYLQMN SLRAEDTAVYYCARDLSPSDVGWGYGFDIWGQGT LVTVSSGGGGSGGGGSGGGGSEIVLTQSPATLSLSP GERATLSCRASQSVSSNLAWYQQKPGQAPRLLIYD TFTRATGIPARFSGSGSGTDFTLTISRLEPEDFAVYY CQQYGSSPPTFGQGTRLEIKTTTPAPRPPTPAPTIAS QPLSLRPEACRPAAGGAVHTRGLDFACDIYIWAPL AGTCGVLLLSLVITLYCKRGRKKLLYIFKQPFMRPV QTTQEEDGCSCRFPEEEEGGCELRVKFSRSADAPAY QQGQNQLYNELNLGRREEYDVLDKRRGRDPEMGG KPRRKNPQEGLYNELQKDKMAEAYSEIGMKGERR RGKGHDGLYQGLSTATKDTYDALHMQALPPR (SEQ ID NO: 239) | CD8α signal peptide; P5F7_VHVL VH; GS linker; P5F7_VHVL VL; CD8α hinge; CD8α TM domain; 41BB ISD; CD3ζ ISD |
| P7H3 | MALPVTALLLPLALLLHAARPEVQLLESGGGLVQP GGSLRLSCAASGFTFSSYAMHWVRQAPGKGLEWV SAISGSGGSTYYADSVKGRFTISRDNSKNTLYLQMN SLRAEDTAVYYCARGTRWWWGDAFDHWGQGTL VTVSSGGGGSGGGGSGGGGSQSVLTQPPSVSVAPG KTARITCGGNNIGSKSVHWYQQKPGQAPVLVIYYD SDRPSGIPERFSGSNSGNTATLTISRVEAGDEADYYC QVWDSSTAWVFGGGTKLTVLTTTPAPRPPTPAPTIA SQPLSLRPEACRPAAGGAVHTRGLDFACDIYIWAPL AGTCGVLLLSLVITLYCKRGRKKLLYIFKQPFMRPV QTTQEEDGCSCRFPEEEEGGCELRVKFSRSADAPAY QQGQNQLYNELNLGRREEYDVLDKRRGRDPEMGG KPRRKNPQEGLYNELQKDKMAEAYSEIGMKGERR RGKGHDGLYQGLSTATKDTYDALHMQALPPR (SEQ ID NO: 240) | CD8α signal peptide; P7H3_VHVL VH; GS linker; P7H3_VHVL VL; CD8α hinge; CD8α TM domain; 41BB ISD; CD3ζ ISD |
| P8B6 | MALPVTALLLPLALLLHAARPQVQLVQSGAEVKKP GSSVKVSCKASGGTFSSYAVSWVRQAPGQGLEWM GGIIPIFGIANYAQKFQGRVTITADTSTSTAYMELSS LRSEDTAVYYCAIEGIGGDLRYDGYDAWGQGTLV TVSSGGGGSGGGGSGGGGSEIVLTQSPGTLSLSPGE RATLSCRASQSVSHSYLAWYQQKPGQAPRLLIYGA SFRAAGIPDRFSGSGSGTDFTLTISRLEPEDFAVYYC QQYGSDPYTFGQGTKVEIKTTTPAPRPPTPAPTIASQ PLSLRPEACRPAAGGAVHTRGLDFACDIYIWAPLA GTCGVLLLSLVITLYCKRGRKKLLYIFKQPFMRPVQ TTQEEDGCSCRFPEEEEGGCELRVKFSRSADAPAYQ QGQNQLYNELNLGRREEYDVLDKRRGRDPEMGGK | CD8α signal peptide; P8B6_VHVL VH; GS linker; P8B6 VHVL VL; CD8α hinge; CD8α TM domain; 41BB ISD; CD3ζ ISD |

TABLE 8-continued

Exemplary FLT3 specific CARs

| CAR | CAR Amino Acid Sequence | Components |
|-----|------------------------|------------|
|  | PRRKNPQEGLYNELQKDKMAEAYSEIGMKGERRR GKGHDGLYQGLSTATKDTYDALHMQALPPR (SEQ ID NO: 241) |  |
| P9B5 | MALPVTALLLPLALLLHAARPEVQLLESGGGLVQP GGSLRLSCAASGFIFASYAMSWVRQAPGKGLEWVS EISSSGGSTTYADSVKGRFTISRDNSKNTLYLQMNS LRAEDTAVYYCARDRVMAGLGYDPFDYWGQGTL VTVSSGGGGSGGGGSGGGGSQSVLTQPPSASGTPG QRVTISCSGSSSNIGSNYVYWYQQLPGTAPKLLIYR NNQRPSGVPDRFSGSKSGTSASLAISGLRSEDEADY YCAAWDDSLSGWFGGGTKLTVLTTTPAPRPPTP A PTIASQPLSLRPEACRPAAGGAVHTRGLDFACDIYI WAPLAGTCGVLLLSLVITLYCKRGRKKLLYIFKQPF MRPVQTTQEEDGCSCRFPEEEEGGCELRVKFSRSA DAPAYQQGQNQLYNELNLGRREEYDVLDKRRGRD PEMGGKPRRKNPQEGLYNELQKDKMAEAYSEIGM KGERRGKGHDGLYQGLSTATKDTYDALHMQALP PR (SEQ ID NO: 242) | CD8α signal peptide; P9B5_VHVL VH; GS linker; P9B5_VHVL VL; CD8α hinge; CD8α TM domain; 41BB ISD; CD3ζ ISD |
| P12B6 | MALPVTALLLPLALLLHAARPQVQLVQSGAEVKKP GSSVKVSCKASGGTFMSYAISWVRQAPGQGLEWM GGIIPIFGIANYAQKFQGRVTITADKSTSTAYMELSS LRSEDTAVYYCARETLIYPIPFELWGQGTLVTVSSG GGGSGGGGSGGGGSEIVLTQSPGTLSLSPGERATLS CRASQIVSSSYLAWYQQKPGQAPRLLIYGASSRASG IPDRFSGSGSGTDFTLTISRLEPEDFAVYYCQQYGGS PYTFGQGTKVEIKTTTPAPRPPTPAPTIASQPLSLRPE ACRPAAGGAVHTRGLDFACDIYIWAPLAGTCGVLL LSLVITLYCKRGRKKLLYIFKQPFMRPVQTTQEEDG CSCRFPEEEEGGCELRVKFSRSADAPAYQQGQNQL YNELNLGRREEYDVLDKRRGRDPEMGGKPRRKNP QEGLYNELQKDKMAEAYSEIGMKGERRRGKGHDG LYQGLSTATKDTYDALHMQALPPR (SEQ ID NO: 243) | CD8α signal peptide; P12B6_VHVL VH; GS linker; P12B6_VHVL VL; CD8α hinge; CD8α TM domain; 41BB ISD; CD3ζ ISD |
| P14G2 | MALPVTALLLPLALLLHAARPEVQLLESGGGLVQP GGSLRLSCAASGFTFSNYVMNWVRQAPGKGLEWV SAISGSGATTYYADSVKGRFTISRDNSKNTLYLQMN SLRAEDTAVYYCVSGLWAGGIWQGTLVTVSSGG GGSGGGGSGGGGSDIQMTQSPSSLSASVGDRVTITC RASQSISSYLNWYQQKPGKAPKLLIYDASDLQRGV PSRFSGSGSGTDFTLTISSLQPEDFATYYCQQSYNTP WTFGQGTKVEIKTTTPAPRPPTPAPTIASQPLSLRPE ACRPAAGGAVHTRGLDFACDIYIWAPLAGTCGVLL LSLVITLYCKRGRKKLLYIFKQPFMRPVQTTQEEDG CSCRFPEEEEGGCELRVKFSRSADAPAYQQGQNQL YNELNLGRREEYDVLDKRRGRDPEMGGKPRRKNP QEGLYNELQKDKMAEAYSEIGMKGERRRGKGHDG LYQGLSTATKDTYDALHMQALPPR (SEQ ID NO: 244) | CD8α signal peptide; P14G2_VHVL VH; GS linker; P14G2_VHVL VL; CD8α hinge; CD8α TM domain; 41BB ISD; CD3ζ ISD |

In some experiments, the sequence encoding the CAR is preceded by a sequence encoding a fluorescent protein such as BFP (Blue Fluorescent Protein) and separated from such sequence by a sequence encoding a self-cleaving 2A peptide. Lentiviruses were produced using psPAX2, an HIV-1 gag-pol packaging plasmid, and pMD2.G, a VSV-G expression plasmid.

b) T Cell Activation and Lentiviral Transduction

Untouched T cells were isolated from human peripheral blood mononuclear cells (PBMCs) using the Pan T Cell isolation kit (Miltenyi Biotec) and activated for three days with antibodies against human CD2, CD3, and CD28 (T Cell activation/expansion kit—Miltenyi Biotec). Lentiviral vectors (LV) were produced by transient transfection of subconfluent HEK-293T/17 (American Type Culture Collection (ATCC)) cells in 6-well plates. Briefly, pLVX, psPAX2, and pMD2.G plasmids were transfected at a 4:3:1 ratio, respectively, using Lipofectamine 2000 (Invitrogen) following the manufacturer's instructions. The following day, the media was replaced with T cell culture medium (5% human AB serum in X-vivo-15 medium (Lonza)), and 48 h after transfection the LV supernatant was harvested and filtered through a 0.45 μm syringe filter (Millipore). Activated T cells were seeded at $0.25 \times 10^6$ cells/mL in T cell culture medium containing 40 ng/ml IL-2 and transduced by adding an equal volume of fresh LV supernatant. LVs comprising the following CAR constructs were used in these experiments: P1A5, P1B4, P3A1, P3E10, P4C7, P4H11, P7H3, P9B5, P12B6, and P14G2. Cells were cultured at 37° C. and 5% $CO_2$ for three days and used for flow cytometry analysis or expanded in fresh T cell medium containing 20 ng/ml IL-2.

c) Measurement of the Transduction Efficiency by Flow Cytometry

Figure 2:
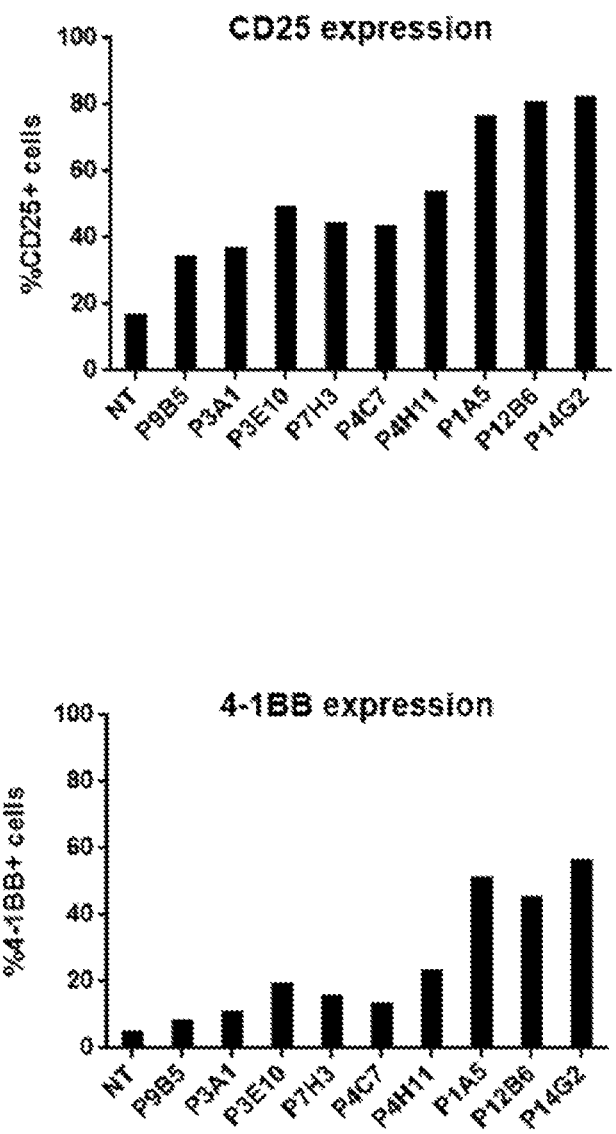
FIG. 2 shows the expression of activation markers CD25 and 4-1BB in T cells transduced with the various CAR constructs assessed by flow cytometry.
Figure 2:
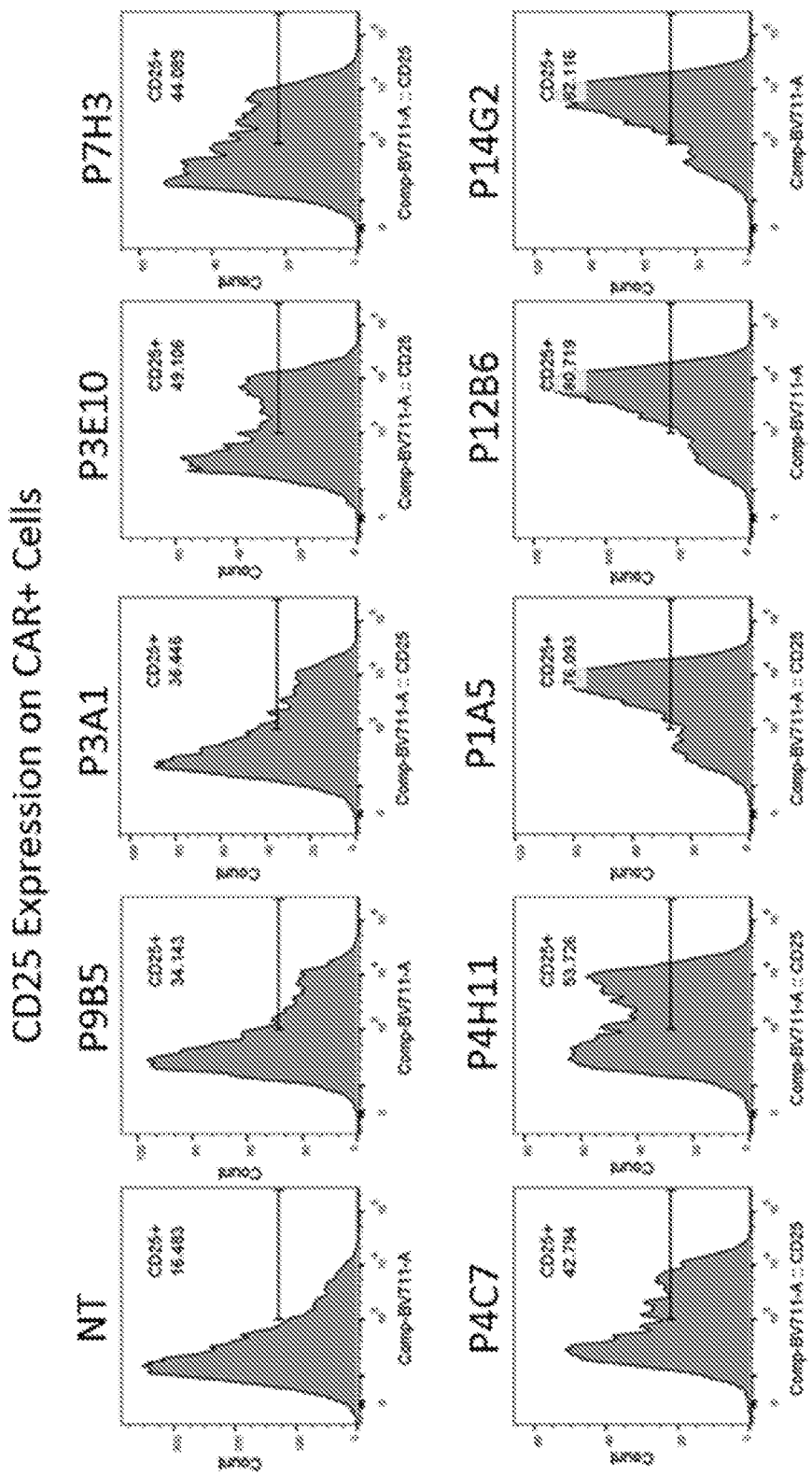
Figure 2:
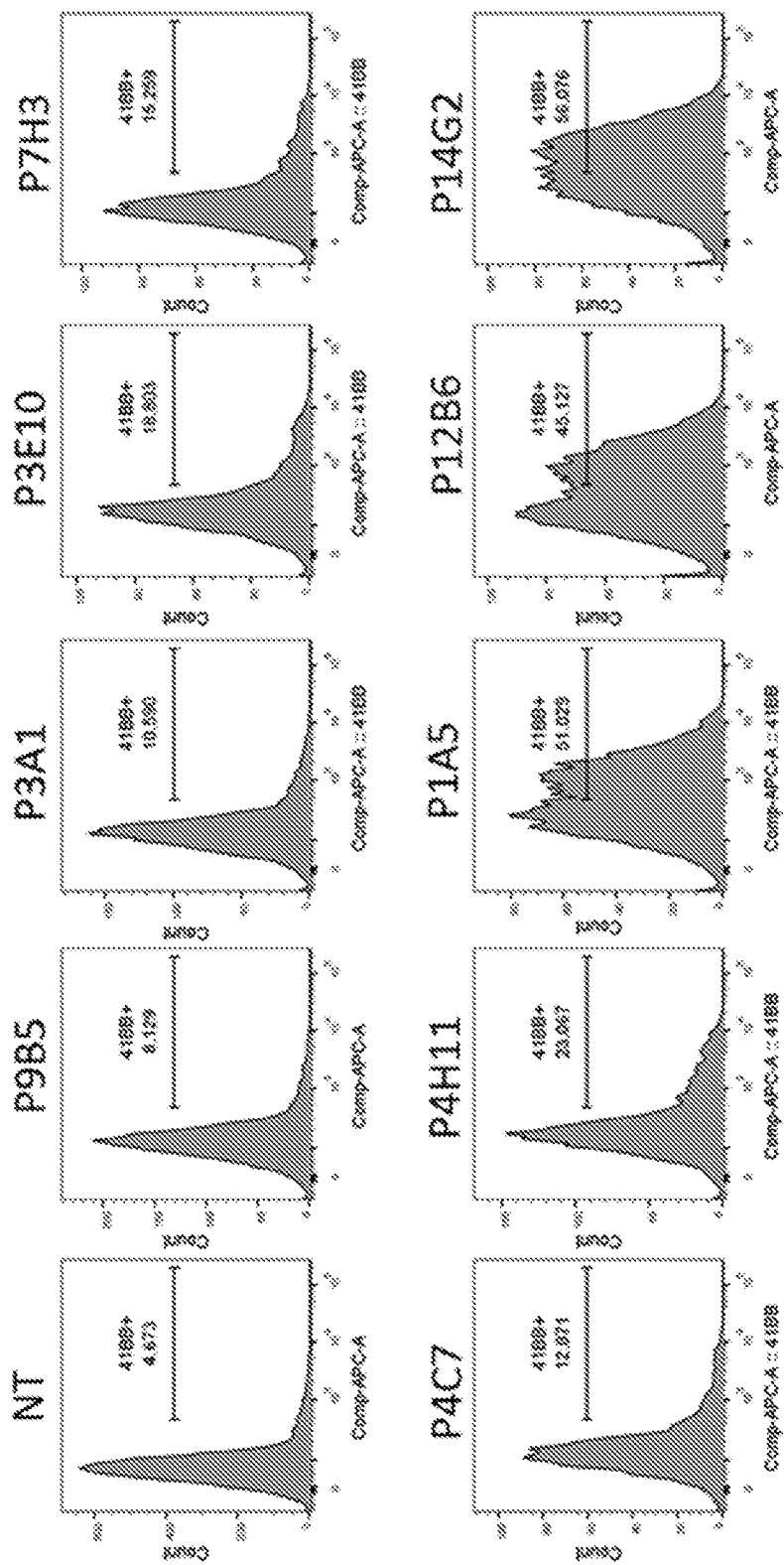
Figure 3:
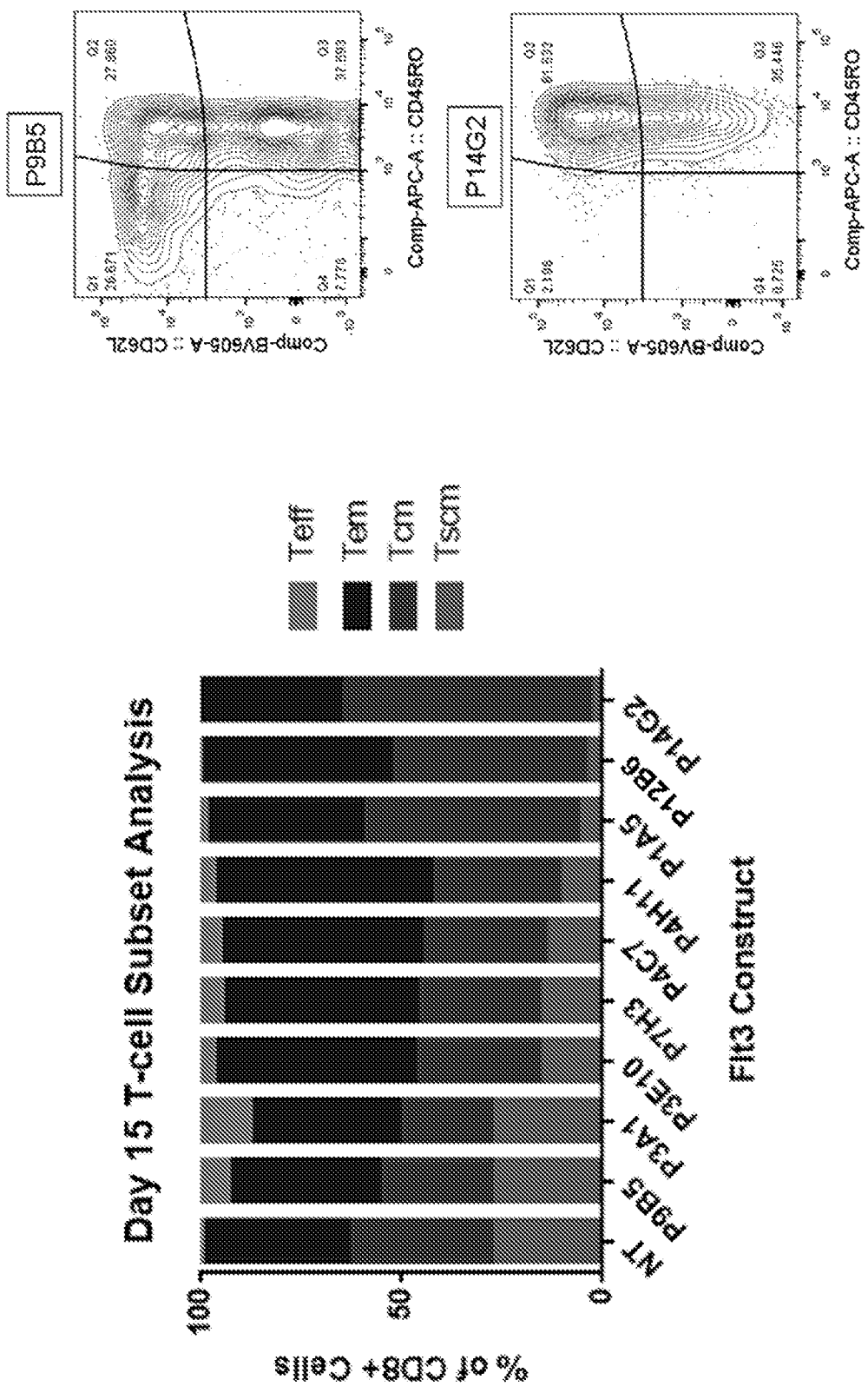
FIG. 3 shows the phenotype of CAR-T cells at the end of the culture as determined by flow cytometry analysis of the expression of the CD62L and/or CD45RO markers.

To determine the transduction efficiency of the different FLT3 CAR lentiviral constructs, flow cytometry analysis was performed on T cells 72 h after transduction. Briefly, single cells were gated using forward scatter and side scatter parameters and the transduction efficiency calculated as the percentage of BFP positive cells. In other instances, CAR-expressing cells were detected by staining with anti-CD20 antibody rituximab, which binds the CD20 epitopes in the CAR molecule, followed by FITC-conjugated anti-human IgG. FIG. 1 shows that activated T cells were effectively transduced with the different FLT3 CAR constructs at varying efficiencies (30% to 70%).

d) FLT3FLT3 CAR-T Cells Differentiate During Culture but Maintain a High Percentage of Memory T Cell Subsets Expression of the activation markers CD25 and 4-1BB (CD137) on CAR-T cells during culture has been associated with T cell exhaustion and increased differentiation towards effector memory phenotype (Long et al., 2015). In this experiment, T cells transduced with the P1A5, P1B4, P3A1, P3E10, P4C7, P4H11, P7H3, P9B5, P12B6, and P14G2 CARs were stained with CD25 and CD137 antibodies ten days post-stimulation and analyzed by flow cytometry. The degree of T cell activation was determined by the percentage of CAR-T cells positive for CD25 and 4-1BB. A non-transduced (NT) T cell population was included for comparison (FIG. 2). Expression of some FLT3FLT3 CARs (P1A5, P12B6 and P14G2) was associated with an "activated" state (FIG. 2) whereas expression of other FLT3FLT3 CARs including P9B5, P3E10, P4C7, and P3A1 resulted in levels of activation markers that were comparable with non-transduced cells (FIG. 2). Higher levels of activation marker expression translate into increased differentiation of CAR-T cells, which can be assessed by day 15 post-stimulation by measuring the expression of CD62L and CD45RO on their cell surface. In this experiment, CAR-T cells were stained with such markers using specific antibodies and classified into four different categories or subsets with increasing degree of differentiation: 1) $CD62L^{HIGH} CD45RO^{LOW}$ stem cell memory (Tscm) cells; 2) $CD62L^{HIGH} CD45RO^{HIGH}$ central memory (Tcm) cells; $CD62L^{LOW} CD45RO^{HIGH}$ effector memory (Tem) cells; and $CD62L^{LOW} CD45RO^{LOW}$ effector (Teff) cells. FIG. 3 shows representative FACS plots for P9B5 CAR-T cells (low differentiation) and P14G2 CAR-T cells (high differentiation) and the T cell subset composition of all the different FLT3FLT3 CAR-T cells on day 15 post-stimulation. CAR-T cells exhibiting an "activated" phenotype also showed a more differentiated phenotype (i.e. higher percentage of Tem cells and lower percentage of Tscm cells) by the end of the culture (FIG. 3). In particular, expression of P9B5, P3A1, P7H3, and P3E10 FLT3 CARs was associated with a high percentage of stem cell memory and central memory cells, which have been correlated with increased persistence and antitumor efficacy in ALL and CLL subjects (Xu et al., *Blood.* 2014; 123(24): 3750-3759).

e) In Vitro Proliferation and Long-Term Killing Activity Assay

Figure 4:
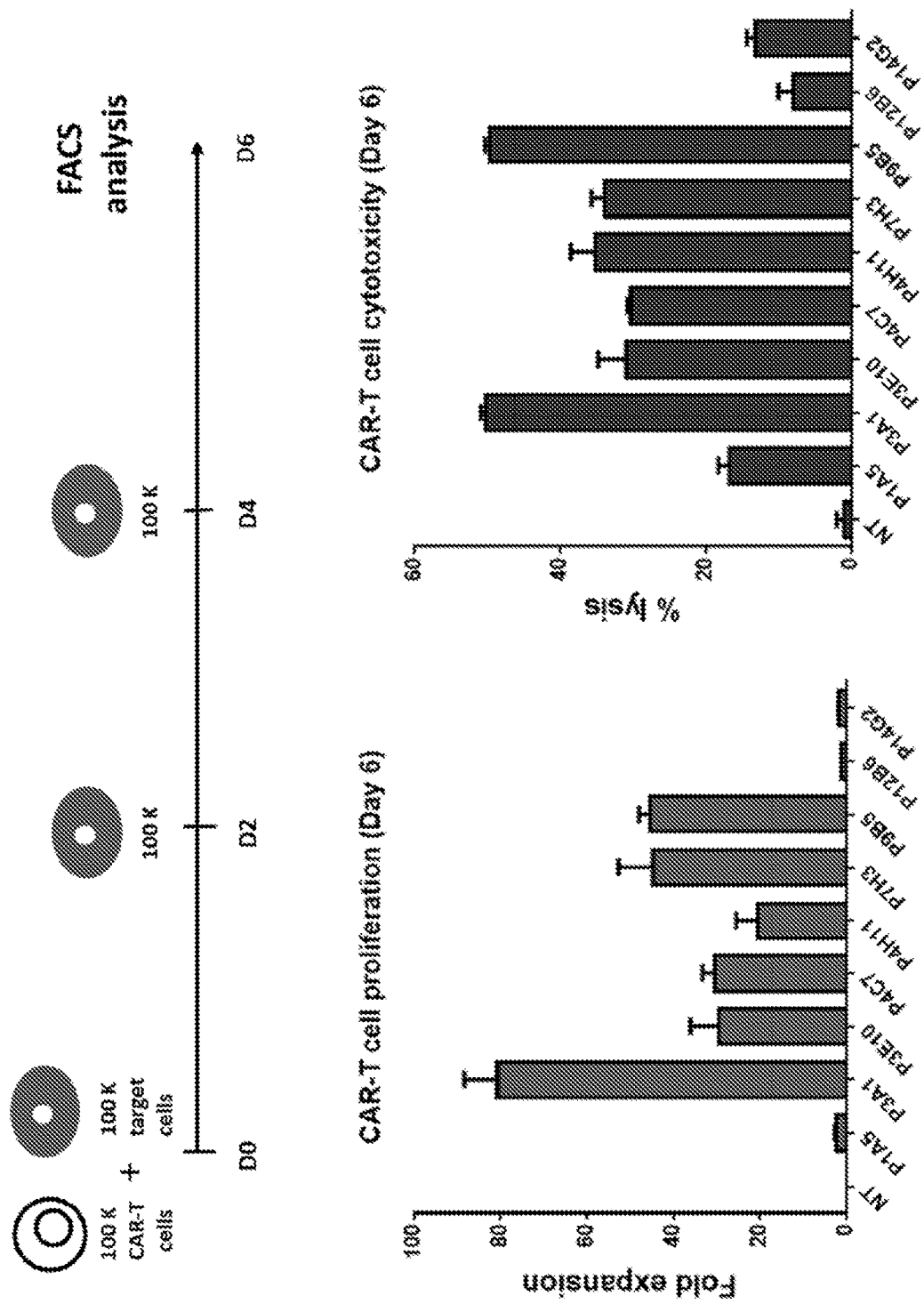
FIG. 4 shows the overall experimental design of the long-term killing assay and the response of the different CAR-T cells to repeated exposure to target cells measured as fold-expansion and cytotoxic activity (percentage of lysis) on day 6.

The capacity of CAR-T cells to proliferate and lyse target cells expressing the cognate antigen is an effective way to assess their activity in vitro. To monitor target cell viability by luminescence, FLT3-expressing Molm13 cells were stably transduced to express the luciferase gene. These Luc+ target cells were then incubated with FLT3 CAR-T cells and the killing activity as well as the proliferation of CAR-T cells was measured by luminescence and viable cell counting, respectively. For a more stringent assay designed to stress the effector cells (CAR-T cells), new target cells were added periodically to the initial culture and the long-term killing activity of CAR-T cells determined by luminescence at the end of the culture (FIG. 4). Consistent with the higher proliferative capacity of stem cell memory and central memory T cells, P9B5, P3A1, P7H3, and P3E10 CAR-T cell populations showed higher target-dependent expansion and long-term cytotoxic activity in vitro whereas CAR-T cells with a higher degree of differentiation such as P12B6 and P14G2 expanded poorly in the presence of target cells and had reduced killing activity.

f) Activity of FLT3 Specific CAR-T Cells in an Orthotopic Mouse Assay

This example illustrates treatment of AML with FLT3 CAR-T cells using the Eol1 orthotopic model. In vivo efficacy study of FLT3 CAR-T cells was performed with Eol1 cells, expressing luciferase and GFP, in an orthotopic model. Three hundred thousand Eol1 Luc2AGFP cells were injected intravenously through the tail vein into 6-8 weeks old female CB17/SCID animals. Intraperitoneal injection of D-luciferin (Regis Technologies, Morton Grove, IL) (200 uL per animal at 15 mg/mL), followed by anesthesia with isofluorane and subsequent whole body bioluminescence imaging (BLI) enable monitoring of tumor burden. Bioluminescent signals emitted by the interaction between luciferase expressed by the tumor cells and luciferin were captured by imaging using an IVIS Spectrum CT (Perkin Elmer, MA) and quantified as total flux (photons/sec) using Living Image 4.4 (Caliper Life Sciences, Alameda, CA).

When the total flux reached an average of 30E6 for all animals (day 10 post tumor implant), the animals were randomized into three groups. Each group was administered one of the following cells: 1) non-transduced T cells used as a control, 2) FLT3 CAR-T cells expressing P3E10 ("P3E10 V1"), or 3) FLT3 CAR-T cells expressing P3A1 ("P3A1 v1") All of cells 1-3 possess TCRα. The FLT3 CAR-T cells were prepared as described in example above. FLT3 CAR constructs P3E10 and P3A1 are shown in Table 8 above. A single dose of 2.5 or 5 million control (NT) or FLT3 CAR-T (P3E10 or P3A1) cells were administered through bolus tail vein injection. Animals were terminated when they lose more than 15% of total body weight, an endpoint for Eol1 orthotopic models.

Figure 5:
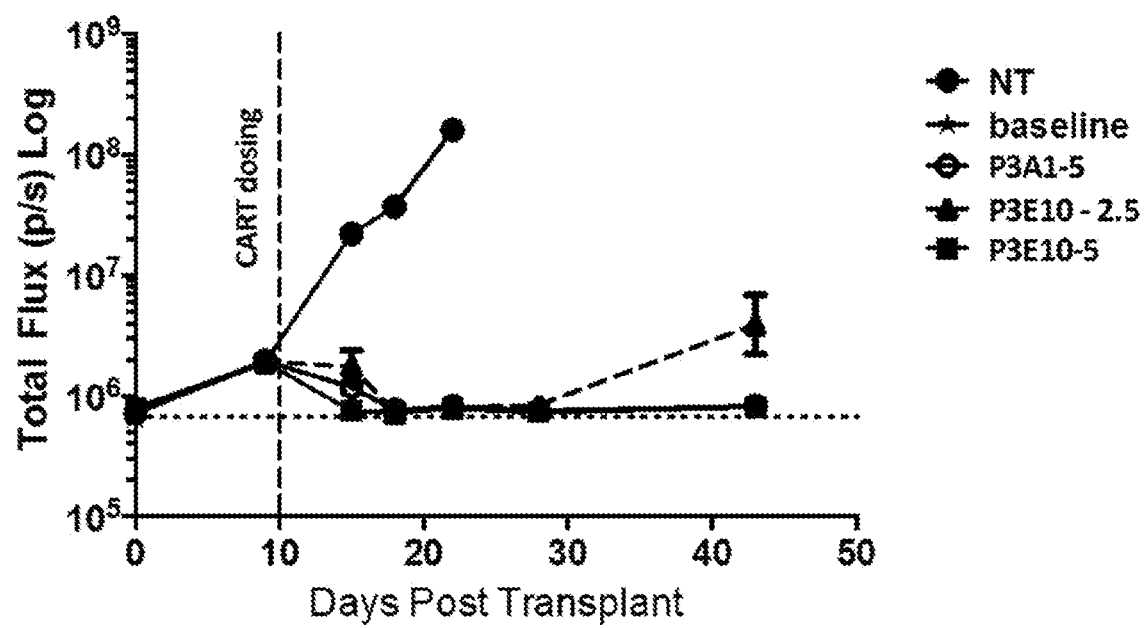
FIG. 5 shows the antitumor activity of CAR-T cells expressing the P3A1 or P3E10 construct at two doses using an orthotopic mouse model of human AML. Bioluminescent signals quantified as total flux (photon/sec) are shown at different time points.

Results from the study are summarized in FIG. 5. A single dose of 5 million P3E10 or P3A1 FLT3 CAR-T cells or 2.5 million P3E10 FLT3 CAR-T cells resulted in lower total flux from days 13-43 post tumor implant as compared to the negative control. Thus, treatment with FLT3 CAR-T cells inhibited tumor progression as compared to the negative control.

These results demonstrate FLT3 CAR-T cells are effective to inhibit tumor progression.

Example 3

Figure 6:
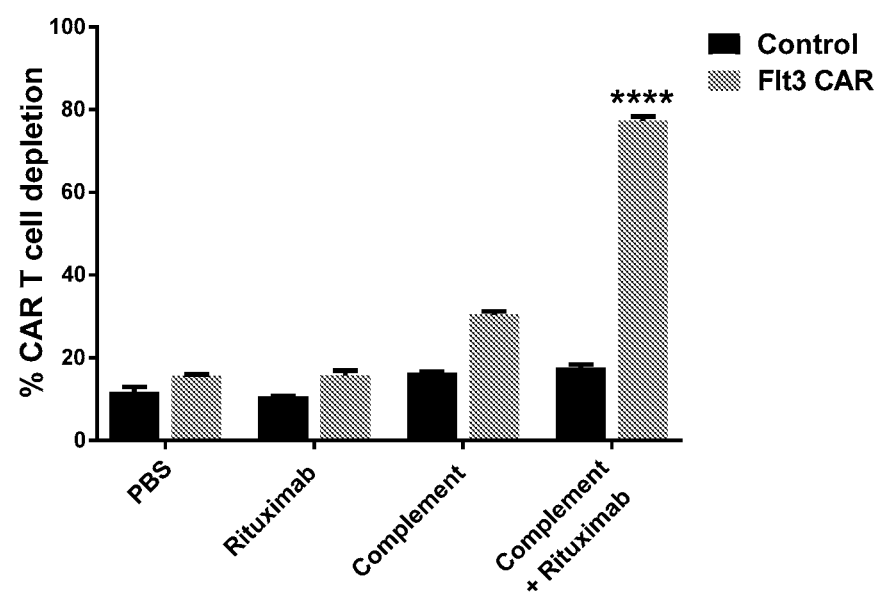
FIG. 6 shows the sensitivity of T cells expressing at cell surface FLT3 specific CAR comprising CD20 epitopes to complement-dependent-cytotoxicity (CDC) induced by the anti-CD20 antibody rituximab.

Depletion of FLT3 Specific CAR T Cells Expressing CD20 Epitopes a) FLT3 Specific CAR T Cells Expressing CD20 Epitopes are Sensitive to Complement-Dependent Cytotoxicity (CDC) in the Presence of Rituximab The sensitivity of FLT3 specific CAR T cells to complement in the presence of an anti-CD20 antibody was evaluated in vitro using a CDC assay. For this experiment, T cells transduced with a lentiviral construct for the expression of a FLT3 CAR containing CD20 epitopes in the extracellular domain were mixed or in the presence or absence of rituximab (100 μg/mL) and incubated at 37° C. and 5% $CO_2$ for 4 hours. Depletion of FLT3 CAR-T cells was determined by flow cytometry analysis using biotinylated FLT3 protein. FIG. 6 shows that the cells expressing the FLT3 CAR and the CD20 epitopes were efficiently depleted in the presence of the antibody and complement, while control FLT3 specific CAR T cells that do not express the CD20 epitopes were minimally affected.

Figure 7:
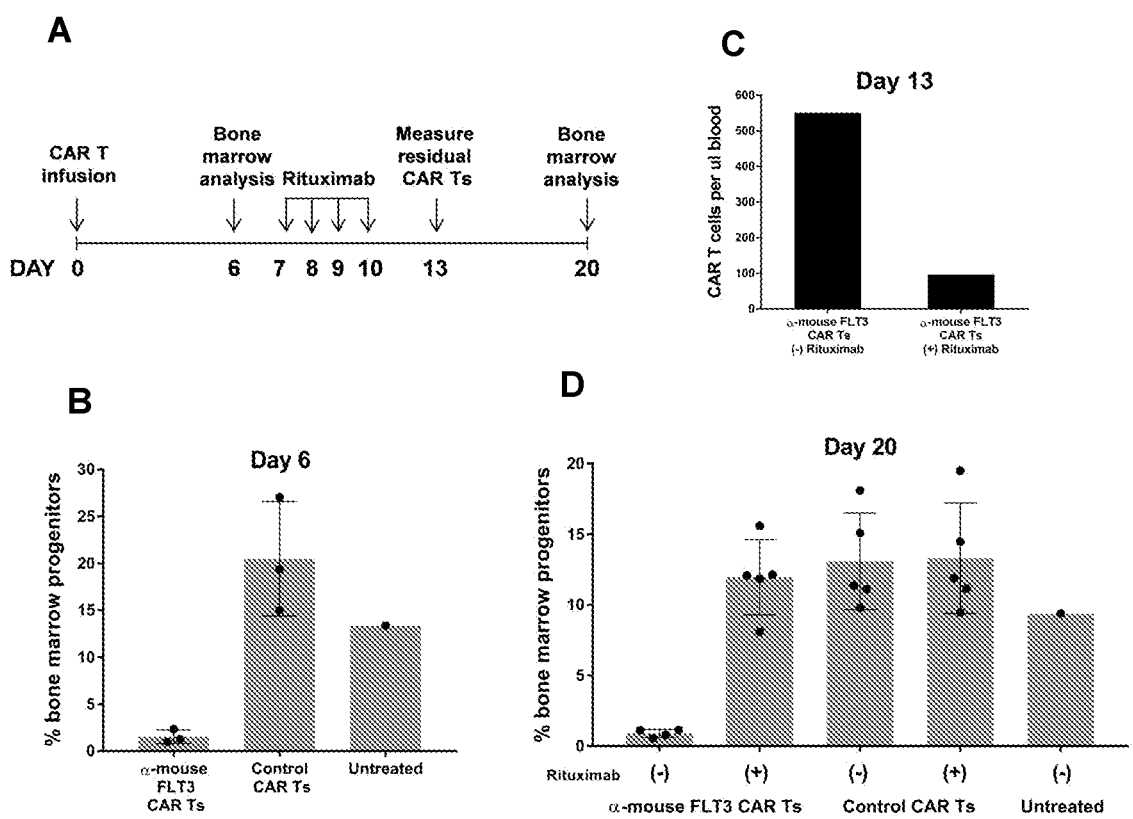
FIG. 7 shows the recovery of endogenous bone marrow progenitor cells in mice treated with anti-mouse FLT3 CAR T cells expressing CD20 epitopes and subsequently administered with rituximab.

These results demonstrate that FLT3 specific CAR-T cells expressing CD20 epitopes can be depleted in vitro in the presence of rituximab and complement.

b) Depletion of FLT3 CAR T Cells Following Rituximab Administration Allows Recovery of FLT3-Expressing Bone Marrow Progenitors in NSG Mice The ability of the anti-CD20 antibody rituximab to mediate depletion of FLT3 specific CAR T cells expressing CD20 epitopes and facilitate bone marrow recovery was tested in mice. In this experiment, mice were treated with T cells expressing either a FLT3 CAR that can bind to mouse FLT3 protein on the surface of bone marrow progenitors (α-mouse FLT3 CAR Ts) and comprising a CD20 epitope recognized by rituximab or a control CAR, with negligible binding to mouse FLT3 protein. Flow cytometry analysis of bone marrow cells was used to demonstrate CAR T cell cytotoxic activity against FLT3-expressing hematopoietic progenitors, seen as a reduction of progenitors compared to mice that received control CAR T cells or to untreated mice (FIG. 7, Panel B). After confirmation of CAR T cell killing activity, mice were given rituximab for four consecutive days and circulating residual CAR T cells were enumerated by flow cytometry at day 13. FIG. 7, Panel C shows that the FLT3 CAR T cells in the blood of these mice is were depleted compared to the control group, which did not receive rituximab. Finally, flow cytometry analysis of bone marrow cells demonstrated that only the mice that received rituximab (day 20) showed bone marrow recovery (FIG. 7, Panel D).

This experiment demonstrates that rituximab-dependent depletion of FLT3 CAR T cells that express CD20 epitopes mitigates damage to FLT3-expressing tissues such as bone marrow, allowing for rapid bone marrow recovery from residual progenitor cells.

Although the disclosed teachings have been described with reference to various applications, methods, kits, and compositions, it will be appreciated that various changes and modifications can be made without departing from the teachings herein and the claimed invention below. The foregoing examples are provided to better illustrate the disclosed teachings and are not intended to limit the scope of the teachings presented herein. While the present teachings have been described in terms of these exemplary embodiments, the skilled artisan will readily understand that numerous variations and modifications of these exemplary embodiments are possible without undue experimentation. All such variations and modifications are within the scope of the current teachings.

All references cited herein, including patents, patent applications, papers, text books, and the like, and the references cited therein, to the extent that they are not already, are hereby incorporated by reference in their entirety. In the event that one or more of the incorporated literature and similar materials differs from or contradicts this application, including but not limited to defined terms, term usage, described techniques, or the like, application controls.

The foregoing description and Examples detail certain specific embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

The invention claimed is:

1. A Fms-like tyrosine kinase 3 (FLT3) specific chimeric antigen receptor (CAR) comprising an extracellular ligand-binding domain, a first transmembrane domain, and an intracellular signaling domain, wherein the extracellular ligand-binding domain comprises a single chain variable fragment (scFv) comprising a heavy chain variable (VH) region and a light chain variable (VL) region, wherein:

(a) the VH region comprises (i) a VH complementarity determining region one (CDR1) having the amino acid sequence shown in SEQ ID NO: 90, 91, or 92, (ii) a VH complementarity determining region two (CDR2) having the amino acid sequence shown in SEQ ID NO: 93 or 94, and (iii) a VH complementarity determining region three (CDR3) having the amino acid sequence shown in SEQ ID NO: 95; and the VL region comprises (i) a VL complementarity determining region one (CDR1) having the amino acid sequence shown in SEQ ID NO: 171; (ii) a VL complementarity determining region two (CDR2) having the amino acid sequence shown in SEQ ID NO: 172; and (iii) a VL complementarity determining region three (CDR3) having the amino acid sequence shown in SEQ ID NO: 173;

(b) the VH region comprises a VH CDR1 comprising the amino acid sequence shown in SEQ ID NO: 49, 44, or 50; a VH CDR2 comprising the amino acid sequence shown in SEQ ID NO: 51 or 52; and a VH CDR3 comprising the amino acid sequence shown in SEQ ID NO: 53; and the VL region comprises a VL CDR1 comprising the amino acid sequence shown in SEQ ID NO: 150; a VL CDR2 comprising the amino acid sequence shown in SEQ ID NO: 151; and a VL CDR3 comprising the amino acid sequence shown in SEQ ID NO: 152;

(c) the VH region comprises a VH CDR1 comprising the amino acid sequence shown in SEQ ID NO: 60, 61, or 62; a VH CDR2 comprising the amino acid sequence shown in SEQ ID NO: 63 or 64; and a VH CDR3 comprising the amino acid sequence shown in SEQ ID NO: 65; and the VL region comprises a VL CDRI comprising the amino acid sequence shown in SEQ ID NO: 156; a VL CDR2 comprising the amino acid sequence shown in SEQ ID NO: 157; and a VL CDR3 comprising the amino acid sequence shown in SEQ ID NO: 158;

(d) the VH region comprises a VH CDR1 comprising the amino acid sequence shown in SEQ ID NO: 84, 85, or 86; a VH CDR2 comprising the amino acid sequence shown in SEQ ID NO: 87 or 88; and a VH CDR3 comprising the amino acid sequence shown in SEQ ID NO: 89; and the VL region comprises a VL CDR1 comprising the amino acid sequence shown in SEQ ID NO: 168; a VL CDR2 comprising the amino acid sequence shown in SEQ ID NO: 169; and a VL CDR3 comprising the amino acid sequence shown in SEQ ID NO: 170; or (e) the VH region comprises a VH CDR1 comprising the amino acid sequence shown in SEQ ID NO: 108, 109, or 110; a VH CDR2 comprising the amino acid sequence shown in SEQ ID NO: 111 or 112; and a VH CDR3 comprising the amino acid sequence shown in SEQ ID NO: 113; and the VL region comprises a VL CDR1 comprising the amino acid sequence shown in SEQ ID NO: 180; a VL CDR2 comprising the amino acid sequence shown in SEQ ID NO: 181; and a VL CDR3 comprising the amino acid sequence shown in SEQ ID NO: 182.

2. The Fms-like tyrosine kinase 3 (FLT3) specific chimeric antigen receptor (CAR) of claim 1, comprising an extracellular ligand-binding domain, a first transmembrane domain, and an intracellular signaling domain, wherein the extracellular ligand-binding domain comprises a single chain variable fragment (scFv) comprising a heavy chain variable (VH) region having the sequence shown in SEQ ID NO: 20, and a light chain variable (VL) region having the sequence shown in SEQ ID NO: 19.

3. The Fms-like tyrosine kinase 3 (FLT3) specific chimeric antigen receptor (CAR) of claim 1, wherein
the VH region comprises a VH CDR1 comprising the amino acid sequence shown in SEQ ID NO: 90, 91, or 92; a VH CDR2 comprising the amino acid sequence shown in SEQ ID NO: 93 or 94; and a VH CDR3 comprising the amino acid sequence shown in SEQ ID NO: 95; and the VL region comprises a VL CDR1 comprising the amino acid sequence shown in SEQ ID NO: 171; a VL CDR2 comprising the amino acid sequence shown in SEQ ID NO: 172; and a VL CDR3 comprising the amino acid sequence shown in SEQ ID NO: 173.

4. The FLT3 specific CAR of claim 1, wherein:
the VH region comprises a VH CDR1 comprising the amino acid sequence shown in SEQ ID NO: 49, 44, or 50; a VH CDR2 comprising the amino acid sequence shown in SEQ ID NO: 51 or 52; and a VH CDR3 comprising the amino acid sequence shown in SEQ ID NO: 53; and the VL region comprises a VL CDR1 comprising the amino acid sequence shown in SEQ ID NO: 150; a VL CDR2 comprising the amino acid sequence shown in SEQ ID NO: 151; and a VL CDR3 comprising the amino acid sequence shown in SEQ ID NO: 152.

5. The FLT3 specific CAR of claim 1, wherein the CAR is characterized by one or more of the following:
(i) the intracellular signaling domain comprises a CD3ζ signaling domain or a 4-1BB domain;
(ii) the first transmembrane domain comprises a CD8a chain transmembrane domain;
(iii) the FLT3 specific CAR comprises a second intracellular signaling domain;
(iv) the FLT3 specific CAR comprises a stalk domain between the extracellular ligand-binding domain and the first transmembrane domain; and
(v) the FLT3 specific CAR comprises a second extracellular ligand-binding domain that is not specific for FLT3.

6. The FLT3 specific CAR of claim 1, comprising one or more epitopes specific for a monoclonal antibody (iii).

7. The FLT3 specific CAR of claim 1, wherein the FLT3 specific CAR comprises the amino acid sequence shown in SEQ ID NO: 235, 236, 237, 238, 240, or 242.

8. The FLT3 specific CAR of claim 1, wherein: (i) the extracellular ligand-binding domain(s), the first transmembrane domain, and intracellular signaling domain(s) are on a single polypeptide; and/or (ii) the FLT3 specific CAR comprises a second transmembrane domain, wherein the first transmembrane domain and the extracellular ligand-binding domain(s) are on a first polypeptide, and wherein the second transmembrane domain and the intracellular signaling domain(s) are on a second polypeptide, wherein the first transmembrane domain comprises a transmembrane domain from the α chain of the high-affinity IgE receptor (FcεRI) and the second transmembrane domain comprises a transmembrane domain from the γ or β chain of FcεRI.

9. A polynucleotide comprising a nucleic acid sequence encoding a FLT3 specific CAR, wherein the polynucleotide comprises the nucleic acid sequence shown in SEQ ID NO: 249, 250, 253, 248, 247, 246, or 245, or comprises a nucleic acid sequence encoding a FLT3 specific CAR according to claim 1.

10. An engineered immune cell expressing a FLT3 specific CAR of claim 1.

11. The engineered immune cell of claim 10, comprising any of (i) another CAR which is not specific for FLT3, (ii) a polynucleotide encoding a suicide polypeptide; and (iii) a disruption of one or more endogenous genes, wherein the endogenous gene encodes TCRα, TCRβ, CD52, glucocorticoid receptor (GR), deoxycytidine kinase (dCK), or an immune checkpoint protein; wherein the engineered immune cell is (iv) derived from an inflammatory T-lymphocyte, a cytotoxic T-lymphocyte, a regulatory T-lymphocyte, or a helper T-lymphocyte; or (v) is obtained from a healthy donor or from a donor suffering from a disease or disorder, or (iv) and (v).

12. The engineered immune cell of claim 10, wherein the FLT3 specific CAR comprises an extracellular domain comprising an ScFv,
wherein the scFv binds to the extracellular domain of human FLT3 with a $K_D$ comprised between 10 nM and 80 nM, or
wherein the scFv binds to domain 4 of the extracellular domain of human FLT3 with a $K_D$ comprised between 1 nM and 100 nM, or
wherein the scFv binds to domain 2-3 of the extracellular domain of human FLT3 with a $K_D$ comprised between 5 nM and 30 nM.

13. A method of engineering an immune cell expressing a FLT3 specific CAR, comprising:
 a. providing an immune cell; and
 b. introducing into the cell at least one polynucleotide encoding a FLT3 specific CAR of claim 1
whereby the immune cell expresses the FLT3 specific CAR.

14. The FLT3 specific CAR of claim 1, wherein:
 (i) the intracellular signaling domain comprises a CD3ζ signaling domain which has an amino acid sequence comprising at least 90% or 100% sequence identity with the amino acid sequence of SEQ ID NO: 210, and
 (ii) the intracellular signaling domain further comprises one or more of a 4-1BB domain which has an amino acid sequence comprising at least 90% or 100% sequence identity with the amino acid sequence of SEQ ID NO: 209 and a CD28 co-stimulatory domain which has an amino acid sequence comprising at least 90% or 100% sequence identity with the amino acid sequence of SEQ ID NO: 214.

15. The FLT3 specific CAR of claim 14, wherein
 (iii) the first transmembrane domain comprises a CD8α chain transmembrane domain which has an amino acid sequence comprising at least 90% or 100% sequence identity with the amino acid sequence of SEQ ID NO:208; and/or
 (iv) the FLT3 specific CAR comprises a stalk domain between the extracellular ligand-binding domain and the first transmembrane domain, wherein the stalk domain is selected from the group consisting of: a CD8α hinge which has an amino acid sequence comprising at least 90% or 100% sequence identity with the amino acid sequence of SEQ ID NO: 206, an IgG1 hinge which has an amino acid sequence comprising at least 90% or 100% sequence identity with the amino acid sequence of SEQ ID NO: 207, and an FcγRIIIα hinge which has an amino acid sequence comprising at least 90% or 100% sequence identity with the amino acid sequence of SEQ ID NO: 205.

16. The FLT3 specific CAR of claim 1, wherein:
 (a) the VH region comprises the amino acid sequence shown in SEQ ID NO: 10 and the VL region comprises the amino acid sequence shown in SEQ ID NO: 9;
 (b) the VH region comprises the amino acid sequence shown in SEQ ID NO: 18 and the VL region comprises the amino acid sequence shown in SEQ ID NO: 17; or
 (c) the VH region comprises the amino acid sequence shown in SEQ ID NO: 26 and the VL region comprises the amino acid sequence shown in SEQ ID NO: 25.

17. The FLT3 specific CAR of claim 4, wherein the VH region comprises the amino acid sequence shown in SEQ ID NO: 6 and the VL region comprises the amino acid sequence shown in SEQ ID NO: 5.

18. The FLT3 specific CAR of claim 5, wherein the the FLT3 specific CAR comprises one or more of the following:
 (i) the second intracellular signaling domain comprises a 4-1BB domain; and
 (ii) the stalk domain is selected from the group consisting of: a CD8α hinge, an IgG1 hinge, and an FcγRIIIα hinge.

19. The FLT3 specific CAR of claim 6, wherein the one or more epitopes is or are selected from the group consisting of:
 (i) a CD52 epitope, a CD20 epitope, a CD3 epitope, a CD41 epitope, a CD25 epitope, a CD30 epitope, an EGFR epitope, a TNFα epitope, a VEGF epitope, a complement protein C5 epitope, a CD11a epitope, a CD33 epitope, an alpha-4 integrin epitope, an IgE Fc region epitope, an RSV protein F epitope, an IL-6 receptor epitope, a HER2 receptor epitope, an integrin α4β7epitope, a BAFF (B-cell activating factor) epitope, an IL-1β epitope, a RANKL epitope, a CTLA4 epitope, a CD34 epitope, an IL-12 epitope, an IL-23 epitope, and combinations thereof;
 (ii) an epitope specifically recognized by alemtuzumab, ibritumomab tiuxetan, muromonab-CD3, tositumomab, abciximab, basiliximab, brentuximab vedotin, cetuximab, infliximab, rituximab, bevacizumab, certolizumab pegol, daclizumab, eculizumab, efalizumab, gemtuzumab, natalizumab, omalizumab, palivizumab, ranibizumab, tocilizumab, trastuzumab, vedolizumab, adalimumab, belimumab, canakinumab, denosumab, golimumab, ipilimumab, ofatumumab, panitumumab, QBEND-10, or ustekinumab; and
 (iii) a CD20 epitope.

20. The FLT3 specific CAR of claim 19, wherein the FLT3 specific CAR comprises a CD20 epitope comprising the amino acid sequence shown in SEQ ID NO: 229.

21. The FLT3 specific CAR of claim 7, wherein the FLT3 specific CAR comprises the amino acid sequence shown in SEQ ID NO: 235.

22. The FLT3 specific CAR of claim 7, wherein the FLT3 specific CAR comprises the amino acid sequence shown in SEQ ID NO: 236.

23. The FLT3 specific CAR of claim 8, wherein the FLT3 specific CAR comprises a third polypeptide comprising a third transmembrane domain fused to an intracellular signaling domain from a co-stimulatory molecule, wherein the third transmembrane domain comprises a transmembrane domain from the γ or β chain of FcεRI.

24. The engineered immune cell of claim 11, wherein (i) the suicide polypeptide is RQR8, or (ii) the immune checkpoint protein is programmed death-1 (PD-1), or (iii) the suicide polypeptide is RQR8 and the immune checkpoint protein is programmed death-1 (PD-1).

* * * * *

SEQUENCE LISTING

```
<160> NUMBER OF SEQ ID NOS: 353

<210> SEQ ID NO 1
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Pro
                85                  90                  95

Arg Thr Phe Gly Gln Gly Thr Lys Val Glu Ile Lys
            100                 105

<210> SEQ ID NO 2
<211> LENGTH: 121
```

```
<212> TYPE: PRT
<213> ORGANISM: Artificial Sequence
<220> FEATURE:
<223> OTHER INFORMATION: artificial amino acid sequence

<400> SEQUENCE: 2

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Gly Ile Ser Trp Val Arg Gln Ala Pro Gly Gln Gly Leu Glu Trp Met
        35                  40                  45

Gly Gly Ile Ile Pro Ile Phe Gly Thr Val Thr Tyr Ala Gln Lys Phe
    50                  55                  60

Gln Gly Arg Val Thr Ile Thr Ala Asp Glu Ser Thr Arg Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Trp Ser Gly Ala Thr Gly Ala Ser Asp Thr Trp Gly
            100                 105                 110

Gln Gly Thr Leu Val Thr Val Ser Ser
        115                 120

<210> SEQ ID NO 3
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Tyr Val Ser Ala Ser
            20                  25                  30

Leu Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Arg Ser Ser
                85                  90                  95

Thr Phe Gly Gln Gly Thr Lys Val Glu Ile Lys
            100                 105

<210> SEQ ID NO 4
<211> LENGTH: 120
<212> TYPE: PRT
<213> ORGANISM: Artificial Sequence
<220> FEATURE:
<223> OTHER INFORMATION: artificial amino acid sequence

<400> SEQUENCE: 4

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Thr Ile Ser Trp Val Arg Gln Ala Pro Gly Gln Gly Leu Glu Trp Met
```

```
            35                  40                  45
Gly Gly Ile Ile Pro Ala Phe Gly Ile Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Lys Gly Gly Ser Tyr Ser Leu Asp Tyr Phe Asp Ile Trp Gly Gln
            100                 105                 110

Gly Thr Leu Val Thr Val Ser Ser
            115                 120

<210> SEQ ID NO 5
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 5

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gln Gly Thr Lys Val Glu Ile Lys
            100                 105

<210> SEQ ID NO 6
<211> LENGTH: 119
<212> TYPE: PRT
<213> ORGANISM: Artificial Sequence
<220> FEATURE:
<223> OTHER INFORMATION: artificial amino acid sequence

<400> SEQUENCE: 6

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Asp Ile Ser Trp Val Arg Gln Ala Pro Gly Gln Gly Leu Glu Trp Met
         35                  40                  45

Gly Gly Ile Ile Pro Val Ser Gly Arg Ala Asn Tyr Ala Gln Lys Phe
     50                  55                  60

Gln Gly Arg Val Thr Ile Thr Thr Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Val Arg Pro Thr Tyr Trp Pro Leu Asp Tyr Trp Gly Gln Gly
            100                 105                 110
```

```
Thr Leu Val Thr Val Ser Ser
            115

<210> SEQ ID NO 7
<211> LENGTH: 110
<212> TYPE: PRT
<213> ORGANISM: Artificial Sequence
<220> FEATURE:
<223> OTHER INFORMATION: artificial amino acid sequence

<400> SEQUENCE: 7

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Asp Tyr Tyr Cys Ser Ser Tyr Ala Gly Ser
                85                  90                  95

Asn Thr Val Val Phe Gly Gly Gly Thr Lys Leu Thr Val Leu
            100                 105                 110

<210> SEQ ID NO 8
<211> LENGTH: 125
<212> TYPE: PRT
<213> ORGANISM: Artificial Sequence
<220> FEATURE:
<223> OTHER INFORMATION: artificial amino acid sequence

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Gly Trp Val Arg Gln Ala Pro Gly Gln Gly Leu Glu Trp Met
        35                  40                  45

Gly Gly Ile Ile Pro Trp Phe Gly Thr Ala Asn Tyr Ala Gln Lys Phe
    50                  55                  60

Gln Gly Arg Val Thr Ile Thr Ala Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Ala Asp His His Asp Ser Pro Ser Gly Tyr Thr Ser Gly Gly Phe
            100                 105                 110

Asp Val Trp Gly Gln Gly Thr Leu Val Thr Val Ser Ser
        115                 120                 125

<210> SEQ ID NO 9
<211> LENGTH: 110
<212> TYPE: PRT
<213> ORGANISM: Artificial Sequence
<220> FEATURE:
<223> OTHER INFORMATION: artificial amino acid sequence

<400> SEQUENCE: 9

Gln Ser Val Leu Thr Gln Pro Pro Ser Ala Ser Gly Thr Pro Gly Gln
```

```
1               5                   10                  15
Arg Val Thr Ile Ser Cys Ser Gly Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly Val Val Phe Gly Gly Gly Thr Lys Leu Thr Val Leu
            100                 105                 110
```

<210> SEQ ID NO 10
<211> LENGTH: 123
<212> TYPE: PRT
<213> ORGANISM: Artificial Sequence
<220> FEATURE:
<223> OTHER INFORMATION: artificial amino acid sequence

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ala Ser Tyr
                20                  25                  30

Ala Met Ser Trp Val Arg Gln Ala Pro Gly Lys Gly Leu Glu Trp Val
            35                  40                  45

Ser Glu Ile Ser Ser Ser Gly Gly Ser Thr Thr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Met Ala Gly Leu Gly Tyr Asp Pro Phe Asp Tyr
            100                 105                 110

Trp Gly Gln Gly Thr Leu Val Thr Val Ser Ser
        115                 120
```

<210> SEQ ID NO 11
<211> LENGTH: 110
<212> TYPE: PRT
<213> ORGANISM: Artificial Sequence
<220> FEATURE:
<223> OTHER INFORMATION: artificial amino acid sequence

<400> SEQUENCE: 11

```
Gln Ser Val Leu Thr Gln Pro Pro Ser Ala Ser Gly Thr Pro Gly Gln
1               5                   10                  15

Arg Val Thr Ile Ser Cys Ser Gly Ser Gly Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80
```

Ser Glu Asp Glu Ala Asp Tyr Tyr Cys Ala Ala Trp Asp Gly Ser Leu
                85                  90                  95

Ser Arg Pro Val Phe Gly Thr Gly Thr Lys Leu Thr Val Leu
            100                 105                 110

<210> SEQ ID NO 12
<211> LENGTH: 123
<212> TYPE: PRT
<213> ORGANISM: Artificial Sequence
<220> FEATURE:
<223> OTHER INFORMATION: artificial amino acid sequence

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Ser Phe
            20                  25                  30

Ala Met Ser Trp Val Arg Gln Ala Pro Gly Lys Gly Leu Glu Trp Val
        35                  40                  45

Ser Asp Ile Ser Gly Ser Gly Ala Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ala Ser Gly Gly Ser Gly Ser Tyr Trp Pro Tyr Met Asp Pro
            100                 105                 110

Trp Gly Gln Gly Thr Leu Val Thr Val Ser Ser
        115                 120

<210> SEQ ID NO 13
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 13

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Asn Glu
            20                  25                  30

Gln Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Pro Pro
                85                  90                  95

Leu Thr Phe Gly Gln Gly Thr Lys Val Glu Ile Lys
            100                 105

<210> SEQ ID NO 14
<211> LENGTH: 117
<212> TYPE: PRT
<213> ORGANISM: Artificial Sequence
<220> FEATURE:
<223> OTHER INFORMATION: artificial amino acid sequence

```
<400> SEQUENCE: 14

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Arg Tyr
            20                  25                  30

Ala Leu Ser Trp Val Arg Gln Ala Pro Gly Gln Gly Leu Glu Trp Met
        35                  40                  45

Gly Gly Ile Ile Pro Met Leu Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asp Phe Gly Ala Leu Asp Tyr Trp Gly Gln Gly Thr Leu
            100                 105                 110

Val Thr Val Ser Ser
            115

<210> SEQ ID NO 15
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Glu Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Leu Thr Phe Gly Gln Gly Thr Lys Val Glu Ile Lys
            100                 105

<210> SEQ ID NO 16
<211> LENGTH: 122
<212> TYPE: PRT
<213> ORGANISM: Artificial Sequence
<220> FEATURE:
<223> OTHER INFORMATION: artificial amino acid sequence

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Arg Ser Phe
            20                  25                  30

Asp Ile Ser Trp Val Arg Gln Ala Pro Gly Gln Gly Leu Glu Trp Met
        35                  40                  45

Gly Arg Ile Ile Pro Ile Leu Gly Tyr Ala Asn Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Asp Leu Gly Ala Pro Trp Ala Gly Tyr Pro Phe Asp Pro Trp
            100                 105                 110

Gly Gln Gly Thr Leu Val Thr Val Ser Ser
            115                 120

<210> SEQ ID NO 17
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 17

Gln Ser Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Thr Ala Trp
                85                  90                  95

Val Phe Gly Gly Gly Thr Lys Leu Thr Val Leu
            100                 105

<210> SEQ ID NO 18
<211> LENGTH: 121
<212> TYPE: PRT
<213> ORGANISM: Artificial Sequence
<220> FEATURE:
<223> OTHER INFORMATION: artificial amino acid sequence

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Arg Trp Trp Trp Gly Asp Ala Phe Asp His Trp Gly
            100                 105                 110

Gln Gly Thr Leu Val Thr Val Ser Ser
            115                 120

<210> SEQ ID NO 19

-continued

```
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 19

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Pro Ser Ser
            20                  25                  30

Gln Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 20
<211> LENGTH: 117
<212> TYPE: PRT
<213> ORGANISM: Artificial Sequence
<220> FEATURE:
<223> OTHER INFORMATION: artificial amino acid sequence

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Gln Trp Val Arg Gln Ala Pro Gly Gln Gly Leu Glu Trp Met
        35                  40                  45

Gly Gly Ile Val Gly Ser Trp Gly Leu Ala Asn Tyr Ala Gln Lys Phe
    50                  55                  60

Gln Gly Arg Val Thr Ile Thr Thr Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Ala Phe Gly Glu Leu Ala Ser Trp Gly Gln Gly Thr Leu
            100                 105                 110

Val Thr Val Ser Ser
        115

<210> SEQ ID NO 21
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 21

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ala Val Asp Ser Ser
            20                  25                  30
```

Asp Leu Ala Trp Tyr Gln Gln Lys Pro Gly Gln Ala Pro Arg Leu Leu
            35                  40                  45

Ile Tyr Asp Ala Tyr Thr Arg Pro Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Leu Glu Ile Lys
            100                 105

<210> SEQ ID NO 22
<211> LENGTH: 117
<212> TYPE: PRT
<213> ORGANISM: Artificial Sequence
<220> FEATURE:
<223> OTHER INFORMATION: artificial amino acid sequence

<400> SEQUENCE: 22

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Arg Tyr
            20                  25                  30

Ala Leu Ser Trp Val Arg Gln Ala Pro Gly Gln Gly Leu Glu Trp Met
        35                  40                  45

Gly Gly Ile Ile Pro Met Leu Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asp Phe Gly Ala Leu Asp Tyr Trp Gly Gln Gly Thr Leu
            100                 105                 110

Val Thr Val Ser Ser
        115

<210> SEQ ID NO 23
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Phe Thr Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105

```
<210> SEQ ID NO 24
<211> LENGTH: 124
<212> TYPE: PRT
<213> ORGANISM: Artificial Sequence
<220> FEATURE:
<223> OTHER INFORMATION: artificial amino acid sequence

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 25
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Thr
            20                  25                  30

Tyr Leu Ala Trp Tyr Gln Gln Lys Pro Gly Gln Ala Pro Arg Leu Leu
        35                  40                  45

Ile Tyr Asp Thr Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gln Gly Thr Lys Val Glu Ile Lys
            100                 105

<210> SEQ ID NO 26
<211> LENGTH: 124
<212> TYPE: PRT
<213> ORGANISM: Artificial Sequence
<220> FEATURE:
<223> OTHER INFORMATION: artificial amino acid sequence

<400> SEQUENCE: 26

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120
```

```
<210> SEQ ID NO 27
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ile Pro Leu
                85                  90                  95

Thr Phe Gly Gln Gly Thr Lys Val Glu Ile Lys
            100                 105
```

```
<210> SEQ ID NO 28
<211> LENGTH: 116
<212> TYPE: PRT
<213> ORGANISM: Artificial Sequence
<220> FEATURE:
<223> OTHER INFORMATION: artificial amino acid sequence

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr
            20                  25                  30

Ala Met Asn Trp Val Arg Gln Ala Pro Gly Lys Gly Leu Glu Trp Val
        35                  40                  45

Ser Val Ile Ser Gly Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Ser Gly Ile Trp Asp Leu Arg Tyr Trp Gly Gln Gly Thr Leu Val
            100                 105                 110

Thr Val Ser Ser
        115

<210> SEQ ID NO 29
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 29

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ile Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Gly Ser Pro
                85                  90                  95

Tyr Thr Phe Gly Gln Gly Thr Lys Val Glu Ile Lys
            100                 105

<210> SEQ ID NO 30
<211> LENGTH: 120
<212> TYPE: PRT
<213> ORGANISM: Artificial Sequence
<220> FEATURE:
<223> OTHER INFORMATION: artificial amino acid sequence

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Met Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Thr Leu Ile Tyr Pro Ile Pro Phe Glu Leu Trp Gly Gln
            100                 105                 110

Gly Thr Leu Val Thr Val Ser Ser
        115                 120

<210> SEQ ID NO 31
<211> LENGTH: 108
<212> TYPE: PRT
<213> ORGANISM: Artificial Sequence
<220> FEATURE:
<223> OTHER INFORMATION: artificial amino acid sequence

<400> SEQUENCE: 31

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser His Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Phe Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Asp Pro
                85                  90                  95

Tyr Thr Phe Gly Gln Gly Thr Lys Val Glu Ile Lys
            100                 105

<210> SEQ ID NO 32
<211> LENGTH: 123
<212> TYPE: PRT
<213> ORGANISM: Artificial Sequence
<220> FEATURE:
<223> OTHER INFORMATION: artificial amino acid sequence

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Val Ser Trp Val Arg Gln Ala Pro Gly Gln Gly Leu Glu Trp Met
        35                  40                  45

Gly Gly Ile Ile Pro Ile Phe Gly Ile Ala Asn Tyr Ala Gln Lys Phe
    50                  55                  60

Gln Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ile Glu Gly Ile Gly Gly Asp Leu Arg Tyr Asp Gly Tyr Asp Ala
            100                 105                 110

Trp Gly Gln Gly Thr Leu Val Thr Val Ser Ser
        115                 120

<210> SEQ ID NO 33
<211> LENGTH: 107
<212> TYPE: PRT
<213> ORGANISM: Artificial Sequence
<220> FEATURE:
<223> OTHER INFORMATION: artificial amino acid sequence

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Asp Ala Ser Asp Leu Gln Arg Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Asn Thr Pro Trp
                 85                  90                  95

Thr Phe Gly Gln Gly Thr Lys Val Glu Ile Lys
            100                 105

<210> SEQ ID NO 34
<211> LENGTH: 116
<212> TYPE: PRT
<213> ORGANISM: Artificial Sequence
<220> FEATURE:
<223> OTHER INFORMATION: artificial amino acid sequence

<400> SEQUENCE: 34

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Val Met Asn Trp Val Arg Gln Ala Pro Gly Lys Gly Leu Glu Trp Val
        35                  40                  45

Ser Ala Ile Ser Gly Ser Gly Ala Thr Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Val Ser Gly Leu Trp Ala Gly Gly Ile Trp Gly Gln Gly Thr Leu Val
            100                 105                 110

Thr Val Ser Ser
            115

<210> SEQ ID NO 35
<211> LENGTH: 110
<212> TYPE: PRT
<213> ORGANISM: Artificial Sequence
<220> FEATURE:
<223> OTHER INFORMATION: artificial amino acid sequence

<400> SEQUENCE: 35

Asn Phe Met Leu Thr Gln Pro His Ser Val Ser Glu Ser Pro Gly Lys
 1               5                  10                  15

Thr Val Thr Ile Ser Cys Thr Arg Ser Ser Gly Ser Ile Ala Ser Asn
            20                  25                  30

Tyr Val Gln Trp Tyr Gln Gln Lys Pro Gly Gln Ala Pro Val Leu Val
        35                  40                  45

Val Tyr Asp Asp Ser Asp Arg Pro Ser Gly Ile Pro Glu Arg Phe Ser
 50                  55                  60

Gly Ser Asn Ser Gly Asn Thr Ala Thr Leu Thr Ile Ser Arg Val Glu
 65                  70                  75                  80

Ala Gly Asp Glu Ala Asp Tyr Tyr Cys Gln Val Trp Asp Ser Ser
             85                  90                  95

Asp His Trp Val Phe Gly Gly Gly Thr Lys Leu Thr Val Leu
            100                 105                 110

<210> SEQ ID NO 36
<211> LENGTH: 124
<212> TYPE: PRT
```

<213> ORGANISM: Artificial Sequence
<220> FEATURE:
<223> OTHER INFORMATION: artificial amino acid sequence

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Gly Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Met Tyr Tyr Cys
                85                  90                  95

Ala Arg Asp Tyr Tyr Ala Phe Ser Asp Pro Ala Tyr Gly Gly Met Asp
            100                 105                 110

Val Trp Gly Gln Gly Thr Leu Val Thr Val Ser Ser
        115                 120
```

<210> SEQ ID NO 37
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 37

```
Ser Tyr Gly Ile Ser
1               5
```

<210> SEQ ID NO 38
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 38

```
Gly Gly Thr Phe Gly Ser Tyr
1               5
```

<210> SEQ ID NO 39
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 39

```
Gly Gly Thr Phe Gly Ser Tyr Gly Ile Ser
1               5                   10
```

<210> SEQ ID NO 40
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 40
```

```
Gly Ile Ile Pro Ile Phe Gly Thr Val Thr Tyr Ala Gln Lys Phe Gln
1               5                   10                  15

Gly

<210> SEQ ID NO 41
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 41

Ile Pro Ile Phe Gly Thr
1               5

<210> SEQ ID NO 42
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 42

Asp Ser Trp Ser Gly Ala Thr Gly Ala Ser Asp Thr
1               5                   10

<210> SEQ ID NO 43
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 43

Ser Tyr Thr Ile Ser
1               5

<210> SEQ ID NO 44
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 44

Gly Gly Thr Phe Ser Ser Tyr
1               5

<210> SEQ ID NO 45
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 45

Gly Gly Thr Phe Ser Ser Tyr Thr Ile Ser
1               5                   10

<210> SEQ ID NO 46
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 46
```

```
Gly Ile Ile Pro Ala Phe Gly Ile Ala Asn Tyr Ala Gln Lys Phe Gln
1               5                   10                  15

Gly

<210> SEQ ID NO 47
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 47

Ile Pro Ala Phe Gly Ile
1               5

<210> SEQ ID NO 48
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 48

Gly Gly Ser Tyr Ser Leu Asp Tyr Phe Asp Ile
1               5                   10

<210> SEQ ID NO 49
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 49

Ser Tyr Asp Ile Ser
1               5

<210> SEQ ID NO 50
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 50

Gly Gly Thr Phe Ser Ser Tyr Asp Ile Ser
1               5                   10

<210> SEQ ID NO 51
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 51

Gly Ile Ile Pro Val Ser Gly Arg Ala Asn Tyr Ala Gln Lys Phe Gln
1               5                   10                  15

Gly

<210> SEQ ID NO 52
<211> LENGTH: 6
<212> TYPE: PRT
<213> ORGANISM: Artificial Sequence
<220> FEATURE:
```

```
<223> OTHER INFORMATION: artificial amino acid sequence

<400> SEQUENCE: 52

Ile Pro Val Ser Gly Arg
1               5

<210> SEQ ID NO 53
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 53

Val Arg Pro Thr Tyr Trp Pro Leu Asp Tyr
1               5                   10

<210> SEQ ID NO 54
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 54

Ser Tyr Tyr Ile Gly
1               5

<210> SEQ ID NO 55
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 55

Gly Gly Thr Phe Ser Ser Tyr
1               5

<210> SEQ ID NO 56
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 56

Gly Gly Thr Phe Ser Ser Tyr Tyr Ile Gly
1               5                   10

<210> SEQ ID NO 57
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 57

Gly Ile Ile Pro Trp Phe Gly Thr Ala Asn Tyr Ala Gln Lys Phe Gln
1               5                   10                  15

Gly

<210> SEQ ID NO 58
<211> LENGTH: 6
<212> TYPE: PRT
<213> ORGANISM: Artificial Sequence
```

```
<220> FEATURE:
<223> OTHER INFORMATION: artificial amino acid sequence

<400> SEQUENCE: 58

Ile Pro Trp Phe Gly Thr
1               5

<210> SEQ ID NO 59
<211> LENGTH: 16
<212> TYPE: PRT
<213> ORGANISM: Artificial Sequence
<220> FEATURE:
<223> OTHER INFORMATION: artificial amino acid sequence

<400> SEQUENCE: 59

Asp His His Asp Ser Pro Ser Gly Tyr Thr Ser Gly Gly Phe Asp Val
1               5                   10                  15

<210> SEQ ID NO 60
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 60

Ser Tyr Ala Met Ser
1               5

<210> SEQ ID NO 61
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 61

Gly Phe Ile Phe Ser Ser Phe
1               5

<210> SEQ ID NO 62
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 62

Gly Phe Ile Phe Ala Ser Tyr Ala Met Ser
1               5                   10

<210> SEQ ID NO 63
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 63

Glu Ile Ser Ser Ser Gly Gly Ser Thr Thr Tyr Ala Asp Ser Val Lys
1               5                   10                  15

Gly

<210> SEQ ID NO 64
<211> LENGTH: 6
<212> TYPE: PRT
```

```
<213> ORGANISM: Artificial Sequence
<220> FEATURE:
<223> OTHER INFORMATION: artificial amino acid sequence

<400> SEQUENCE: 64

Ser Ser Ser Gly Gly Ser
1               5

<210> SEQ ID NO 65
<211> LENGTH: 14
<212> TYPE: PRT
<213> ORGANISM: Artificial Sequence
<220> FEATURE:
<223> OTHER INFORMATION: artificial amino acid sequence

<400> SEQUENCE: 65

Asp Arg Val Met Ala Gly Leu Gly Tyr Asp Pro Phe Asp Tyr
1               5                   10

<210> SEQ ID NO 66
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 66

Ser Phe Ala Met Ser
1               5

<210> SEQ ID NO 67
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 67

Gly Phe Ile Phe Ser Ser Phe
1               5

<210> SEQ ID NO 68
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 68

Gly Phe Ile Phe Ser Ser Phe Ala Met Ser
1               5                   10

<210> SEQ ID NO 69
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 69

Asp Ile Ser Gly Ser Gly Ala Ser Thr Tyr Tyr Ala Asp Ser Val Lys
1               5                   10                  15

Gly

<210> SEQ ID NO 70
<211> LENGTH: 6
```

```
<212> TYPE: PRT
<213> ORGANISM: Artificial Sequence
<220> FEATURE:
<223> OTHER INFORMATION: artificial amino acid sequence

<400> SEQUENCE: 70

Ser Gly Ser Gly Ala Ser
1               5

<210> SEQ ID NO 71
<211> LENGTH: 14
<212> TYPE: PRT
<213> ORGANISM: Artificial Sequence
<220> FEATURE:
<223> OTHER INFORMATION: artificial amino acid sequence

<400> SEQUENCE: 71

Ala Ser Gly Gly Ser Gly Ser Tyr Trp Pro Tyr Met Asp Pro
1               5                   10

<210> SEQ ID NO 72
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 72

Arg Tyr Ala Leu Ser
1               5

<210> SEQ ID NO 73
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 73

Gly Gly Val Phe Ser Arg Tyr
1               5

<210> SEQ ID NO 74
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 74

Gly Gly Val Phe Ser Arg Tyr Ala Leu Ser
1               5                   10

<210> SEQ ID NO 75
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 75

Gly Ile Ile Pro Met Leu Gly Phe Ala Asn Tyr Ala Gln Lys Phe Gln
1               5                   10                  15

Gly

<210> SEQ ID NO 76
```

```
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 76

Ile Pro Met Leu Gly Phe
1               5

<210> SEQ ID NO 77
<211> LENGTH: 8
<212> TYPE: PRT
<213> ORGANISM: Artificial Sequence
<220> FEATURE:
<223> OTHER INFORMATION: artificial amino acid sequence

<400> SEQUENCE: 77

Leu Asp Phe Gly Ala Leu Asp Tyr
1               5

<210> SEQ ID NO 78
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 78

Ser Phe Asp Ile Ser
1               5

<210> SEQ ID NO 79
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 79

Gly Gly Thr Phe Arg Ser Phe
1               5

<210> SEQ ID NO 80
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 80

Gly Gly Thr Phe Arg Ser Phe Asp Ile Ser
1               5                   10

<210> SEQ ID NO 81
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 81

Arg Ile Ile Pro Ile Leu Gly Tyr Ala Asn Tyr Ala Gln Lys Phe Gln
1               5                   10                  15

Gly
```

```
<210> SEQ ID NO 82
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 82

Ile Pro Ile Leu Gly Tyr
1               5

<210> SEQ ID NO 83
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 83

Asp Leu Gly Ala Pro Trp Ala Gly Tyr Pro Phe Asp Pro
1               5                   10

<210> SEQ ID NO 84
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 84

Ser Tyr Ala Met His
1               5

<210> SEQ ID NO 85
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 85

Gly Phe Thr Phe Ser Ser Tyr
1               5

<210> SEQ ID NO 86
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 86

Gly Phe Thr Phe Ser Ser Tyr Ala Met His
1               5                   10

<210> SEQ ID NO 87
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 87

Ala Ile Ser Gly Ser Gly Gly Ser Thr Tyr Tyr Ala Asp Ser Val Lys
1               5                   10                  15

Gly
```

<210> SEQ ID NO 88
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 88

Ser Gly Ser Gly Gly Ser
1               5

<210> SEQ ID NO 89
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 89

Gly Thr Arg Trp Trp Trp Gly Asp Ala Phe Asp His
1               5                   10

<210> SEQ ID NO 90
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 90

Ser Tyr Ala Ile Gln
1               5

<210> SEQ ID NO 91
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 91

Gly Gly Thr Phe Ser Ser Tyr
1               5

<210> SEQ ID NO 92
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 92

Gly Gly Thr Phe Ser Ser Tyr Ala Ile Gln
1               5                   10

<210> SEQ ID NO 93
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 93

Gly Ile Val Gly Ser Trp Gly Leu Ala Asn Tyr Ala Gln Lys Phe Gln
1               5                   10                  15

Gly

```
<210> SEQ ID NO 94
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 94

Val Gly Ser Trp Gly Leu
1               5

<210> SEQ ID NO 95
<211> LENGTH: 8
<212> TYPE: PRT
<213> ORGANISM: Artificial Sequence
<220> FEATURE:
<223> OTHER INFORMATION: artificial amino acid sequence

<400> SEQUENCE: 95

Ser Ala Phe Gly Glu Leu Ala Ser
1               5

<210> SEQ ID NO 96
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 96

Arg Tyr Ala Leu Ser
1               5

<210> SEQ ID NO 97
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 97

Gly Gly Val Phe Ser Arg Tyr
1               5

<210> SEQ ID NO 98
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 98

Gly Gly Val Phe Ser Arg Tyr Ala Leu Ser
1               5                   10

<210> SEQ ID NO 99
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 99

Gly Ile Ile Pro Met Leu Gly Phe Ala Asn Tyr Ala Gln Lys Phe Gln
1               5                   10                  15
```

Gly

<210> SEQ ID NO 100
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 100

Ile Pro Met Leu Gly Phe
1               5

<210> SEQ ID NO 101
<211> LENGTH: 8
<212> TYPE: PRT
<213> ORGANISM: Artificial Sequence
<220> FEATURE:
<223> OTHER INFORMATION: artificial amino acid sequence

<400> SEQUENCE: 101

Leu Asp Phe Gly Ala Leu Asp Tyr
1               5

<210> SEQ ID NO 102
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 102

Ser Tyr Ala Met Asn
1               5

<210> SEQ ID NO 103
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 103

Gly Phe Thr Phe Ser Ser Tyr
1               5

<210> SEQ ID NO 104
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 104

Gly Phe Thr Phe Ser Ser Tyr Ala Met Asn
1               5                   10

<210> SEQ ID NO 105
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 105

Ser Ile Ser Gly Gly Gly Arg Ser Thr Tyr Tyr Ala Asp Ser Val Lys
1               5                   10                  15

Gly

<210> SEQ ID NO 106
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 106

Ser Gly Gly Gly Arg Ser
1               5

<210> SEQ ID NO 107
<211> LENGTH: 15
<212> TYPE: PRT
<213> ORGANISM: Artificial Sequence
<220> FEATURE:
<223> OTHER INFORMATION: artificial amino acid sequence

<400> SEQUENCE: 107

Asp Leu Ser Pro Ser Asp Val Gly Trp Gly Tyr Gly Phe Asp Ile
1               5                   10                  15

<210> SEQ ID NO 108
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 108

Ser Tyr Ala Met Asn
1               5

<210> SEQ ID NO 109
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 109

Gly Phe Thr Phe Ser Ser Tyr
1               5

<210> SEQ ID NO 110
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 110

Gly Phe Thr Phe Ser Ser Tyr Ala Met Asn
1               5                   10

<210> SEQ ID NO 111
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 111

Ser Ile Ser Gly Gly Gly Arg Ser Thr Tyr Tyr Ala Asp Ser Val Lys

Gly

<210> SEQ ID NO 112
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 112

Ser Gly Gly Gly Arg Ser
1               5

<210> SEQ ID NO 113
<211> LENGTH: 15
<212> TYPE: PRT
<213> ORGANISM: Artificial Sequence
<220> FEATURE:
<223> OTHER INFORMATION: artificial amino acid sequence

<400> SEQUENCE: 113

Asp Leu Ser Pro Ser Asp Val Gly Trp Gly Tyr Gly Phe Asp Ile
1               5                   10                  15

<210> SEQ ID NO 114
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 114

Asn Tyr Ala Met Asn
1               5

<210> SEQ ID NO 115
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 115

Gly Phe Thr Phe Asn Asn Tyr
1               5

<210> SEQ ID NO 116
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 116

Gly Phe Thr Phe Asn Asn Tyr Ala Met Asn
1               5                   10

<210> SEQ ID NO 117
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 117

Val Ile Ser Gly Ser Gly Gly Thr Thr Tyr Tyr Ala Asp Ser Val Lys
1               5                   10                  15
Gly

<210> SEQ ID NO 118
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 118

Ser Gly Ser Gly Gly Thr
1               5

<210> SEQ ID NO 119
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 119

Gly Ile Trp Asp Leu Arg Tyr
1               5

<210> SEQ ID NO 120
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 120

Ser Tyr Ala Ile Ser
1               5

<210> SEQ ID NO 121
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 121

Gly Gly Thr Phe Met Ser Tyr
1               5

<210> SEQ ID NO 122
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 122

Gly Gly Thr Phe Met Ser Tyr Ala Ile Ser
1               5                   10

<210> SEQ ID NO 123
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 123

```
Gly Ile Ile Pro Ile Phe Gly Ile Ala Asn Tyr Ala Gln Lys Phe Gln
1               5                   10                  15
Gly

<210> SEQ ID NO 124
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 124

Ile Pro Ile Phe Gly Ile
1               5

<210> SEQ ID NO 125
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 125

Glu Thr Leu Ile Tyr Pro Ile Pro Phe Glu Leu
1               5                   10

<210> SEQ ID NO 126
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 126

Ser Tyr Ala Val Ser
1               5

<210> SEQ ID NO 127
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 127

Gly Gly Thr Phe Ser Ser Tyr
1               5

<210> SEQ ID NO 128
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 128

Gly Gly Thr Phe Ser Ser Tyr Ala Val Ser
1               5                   10

<210> SEQ ID NO 129
<211> LENGTH: 17
<212> TYPE: PRT
<213> ORGANISM: Artificial Sequence
<220> FEATURE:
<223> OTHER INFORMATION: artificial amino acid sequence
```

<400> SEQUENCE: 129

Gly Ile Ile Pro Ile Phe Gly Ile Ala Asn Tyr Ala Gln Lys Phe Gln
1               5                   10                  15
Gly

<210> SEQ ID NO 130
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 130

Ile Pro Ile Phe Gly Ile
1               5

<210> SEQ ID NO 131
<211> LENGTH: 14
<212> TYPE: PRT
<213> ORGANISM: Artificial Sequence
<220> FEATURE:
<223> OTHER INFORMATION: artificial amino acid sequence

<400> SEQUENCE: 131

Glu Gly Ile Gly Gly Asp Leu Arg Tyr Asp Gly Tyr Asp Ala
1               5                   10

<210> SEQ ID NO 132
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 132

Asn Tyr Val Met Asn
1               5

<210> SEQ ID NO 133
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 133

Gly Phe Thr Phe Ser Asn Tyr
1               5

<210> SEQ ID NO 134
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 134

Gly Phe Thr Phe Ser Asn Tyr Val Met Asn
1               5                   10

<210> SEQ ID NO 135
<211> LENGTH: 17
<212> TYPE: PRT
<213> ORGANISM: Artificial Sequence
<220> FEATURE:
<223> OTHER INFORMATION: artificial amino acid sequence

<400> SEQUENCE: 135

Ala Ile Ser Gly Ser Gly Ala Thr Thr Tyr Tyr Ala Asp Ser Val Lys
1               5                   10                  15
Gly

<210> SEQ ID NO 136
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 136

Ser Gly Ser Gly Ala Thr
1               5

<210> SEQ ID NO 137
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 137

Gly Leu Trp Ala Gly Gly Ile
1               5

<210> SEQ ID NO 138
<211> LENGTH: 5
<212> TYPE: PRT
<213> ORGANISM: Artificial Sequence
<220> FEATURE:
<223> OTHER INFORMATION: artificial amino acid sequence

<400> SEQUENCE: 138

Ser Tyr Ala Met Ser
1               5

<210> SEQ ID NO 139
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 139

Gly Phe Thr Phe Ser Ser Tyr
1               5

<210> SEQ ID NO 140
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 140

Gly Phe Thr Phe Ser Ser Tyr Ala Met Ser
1               5                   10

<210> SEQ ID NO 141
<211> LENGTH: 17
<212> TYPE: PRT
<213> ORGANISM: Artificial Sequence
<220> FEATURE:

<223> OTHER INFORMATION: artificial amino acid sequence

<400> SEQUENCE: 141

Ala Ile Gly Gly Ser Gly Gly Ser Thr Tyr Tyr Ala Asp Ser Val Lys
1               5                   10                  15
Gly

<210> SEQ ID NO 142
<211> LENGTH: 6
<212> TYPE: PRT
<213> ORGANISM: Artificial Sequence
<220> FEATURE:
<223> OTHER INFORMATION: artificial amino acid sequence

<400> SEQUENCE: 142

Gly Gly Ser Gly Gly Ser
1               5

<210> SEQ ID NO 143
<211> LENGTH: 15
<212> TYPE: PRT
<213> ORGANISM: Artificial Sequence
<220> FEATURE:
<223> OTHER INFORMATION: artificial amino acid sequence

<400> SEQUENCE: 143

Asp Tyr Tyr Ala Phe Ser Asp Pro Ala Tyr Gly Gly Met Asp Val
1               5                   10                  15

<210> SEQ ID NO 144
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 144

Arg Ala Ser His Ser Val Ser Ser Ser Tyr Leu Ala
1               5                   10

<210> SEQ ID NO 145
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 145

Gly Ala Ser Ser Arg Ala Thr
1               5

<210> SEQ ID NO 146
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 146

Gln Gln Tyr Gly Ser Pro Pro Arg Thr
1               5

<210> SEQ ID NO 147
<211> LENGTH: 12
<212> TYPE: PRT
<213> ORGANISM: Artificial Sequence

```
<220> FEATURE:
<223> OTHER INFORMATION: artificial amino acid sequence

<400> SEQUENCE: 147

Arg Ala Ser Gln Tyr Val Ser Ala Ser Leu Leu Ala
1               5                   10

<210> SEQ ID NO 148
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 148

Gly Ala Ser Thr Arg Ala Thr
1               5

<210> SEQ ID NO 149
<211> LENGTH: 8
<212> TYPE: PRT
<213> ORGANISM: Artificial Sequence
<220> FEATURE:
<223> OTHER INFORMATION: artificial amino acid sequence

<400> SEQUENCE: 149

Gln Gln Tyr Ala Arg Ser Ser Thr
1               5

<210> SEQ ID NO 150
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 150

Arg Ala Ser Gln Ser Ile Ser Ser Tyr Leu Asn
1               5                   10

<210> SEQ ID NO 151
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 151

Ala Ala Ser Ser Leu Gln Ser
1               5

<210> SEQ ID NO 152
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 152

Gln Gln Ser Tyr Ser Thr Pro Leu Thr
1               5

<210> SEQ ID NO 153
<211> LENGTH: 14
<212> TYPE: PRT
<213> ORGANISM: Artificial Sequence
<220> FEATURE:
```

<223> OTHER INFORMATION: artificial amino acid sequence

<400> SEQUENCE: 153

Thr Gly Thr Ser Ser Asp Val Gly Gly Tyr Asn Tyr Val Ser
1               5                   10

<210> SEQ ID NO 154
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 154

Glu Val Ser Lys Arg Pro Ser
1               5

<210> SEQ ID NO 155
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 155

Ser Ser Tyr Ala Gly Ser Asn Thr Val Val
1               5                   10

<210> SEQ ID NO 156
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 156

Ser Gly Ser Ser Ser Asn Ile Gly Ser Asn Tyr Val Tyr
1               5                   10

<210> SEQ ID NO 157
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 157

Arg Asn Asn Gln Arg Pro Ser
1               5

<210> SEQ ID NO 158
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 158

Ala Ala Trp Asp Asp Ser Leu Ser Gly Val Val
1               5                   10

<210> SEQ ID NO 159
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 159

Ser Gly Ser Gly Ser Asn Ile Gly Ser Asn Tyr Val Tyr
1               5                   10

<210> SEQ ID NO 160
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 160

Arg Asn Asn Gln Arg Pro Ser
1               5

<210> SEQ ID NO 161
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 161

Ala Ala Trp Asp Gly Ser Leu Ser Arg Pro Val
1               5                   10

<210> SEQ ID NO 162
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 162

Arg Ala Ser Gln Ser Val Pro Asn Glu Gln Leu Ala
1               5                   10

<210> SEQ ID NO 163
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 163

Asp Ala Ser Ser Arg Ala Thr
1               5

<210> SEQ ID NO 164
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 164

Gln Gln Tyr Gly Ser Pro Pro Leu Thr
1               5

<210> SEQ ID NO 165
<211> LENGTH: 12
<212> TYPE: PRT
<213> ORGANISM: Artificial Sequence
<220> FEATURE:
<223> OTHER INFORMATION: artificial amino acid sequence

```
<400> SEQUENCE: 165

Arg Ala Ser Gln Ser Val Ser Ser Ser Glu Leu Ala
1               5                   10

<210> SEQ ID NO 166
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 166

Asp Ala Ser Ser Arg Ala Thr
1               5

<210> SEQ ID NO 167
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 167

Gln Gln Tyr Asp Ser Ser Pro Leu Thr
1               5

<210> SEQ ID NO 168
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 168

Gly Gly Asn Asn Ile Gly Ser Lys Ser Val His
1               5                   10

<210> SEQ ID NO 169
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 169

Tyr Asp Ser Asp Arg Pro Ser
1               5

<210> SEQ ID NO 170
<211> LENGTH: 10
<212> TYPE: PRT
<213> ORGANISM: Artificial Sequence
<220> FEATURE:
<223> OTHER INFORMATION: artificial amino acid sequence

<400> SEQUENCE: 170

Gln Val Trp Asp Ser Ser Thr Ala Trp Val
1               5                   10

<210> SEQ ID NO 171
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 171
```

```
Arg Ala Ser Gln Ser Val Pro Ser Ser Gln Leu Ala
1               5                   10

<210> SEQ ID NO 172
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 172

Asp Ala Ser Ser Arg Ala Thr
1               5

<210> SEQ ID NO 173
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 173

Gln Gln Tyr Gly Ser Ser Pro Leu Thr
1               5

<210> SEQ ID NO 174
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 174

Arg Ala Ser Gln Ala Val Asp Ser Ser Asp Leu Ala
1               5                   10

<210> SEQ ID NO 175
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 175

Asp Ala Tyr Thr Arg Pro Ser
1               5

<210> SEQ ID NO 176
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 176

Gln Gln Tyr Gly Ser Ser Pro Leu Thr
1               5

<210> SEQ ID NO 177
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 177
```

Arg Ala Ser Gln Ser Val Ser Ser Asn Leu Ala
1               5                   10

<210> SEQ ID NO 178
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 178

Asp Thr Phe Thr Arg Ala Thr
1               5

<210> SEQ ID NO 179
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 179

Gln Gln Tyr Gly Ser Ser Pro Pro Thr
1               5

<210> SEQ ID NO 180
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 180

Arg Ala Ser Gln Ser Val Ser Asn Thr Tyr Leu Ala
1               5                   10

<210> SEQ ID NO 181
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 181

Asp Thr Ser Ser Arg Ala Thr
1               5

<210> SEQ ID NO 182
<211> LENGTH: 8
<212> TYPE: PRT
<213> ORGANISM: Artificial Sequence
<220> FEATURE:
<223> OTHER INFORMATION: artificial amino acid sequence

<400> SEQUENCE: 182

Gln Gln Tyr Gly Ser Ser Leu Thr
1               5

<210> SEQ ID NO 183
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 183

Arg Ala Ser Gln Ser Ile Ser Thr Tyr Leu Asn

```
1               5              10
```

<210> SEQ ID NO 184
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 184

```
Ala Ala Ser Asn Leu Gln Ser
1               5
```

<210> SEQ ID NO 185
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 185

```
Gln Gln Ser Tyr Ser Ile Pro Leu Thr
1               5
```

<210> SEQ ID NO 186
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 186

```
Arg Ala Ser Gln Ile Val Ser Ser Ser Tyr Leu Ala
1               5                  10
```

<210> SEQ ID NO 187
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 187

```
Gly Ala Ser Ser Arg Ala Ser
1               5
```

<210> SEQ ID NO 188
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 188

```
Gln Gln Tyr Gly Gly Ser Pro Tyr Thr
1               5
```

<210> SEQ ID NO 189
<211> LENGTH: 12
<212> TYPE: PRT
<213> ORGANISM: Artificial Sequence
<220> FEATURE:
<223> OTHER INFORMATION: artificial amino acid sequence

<400> SEQUENCE: 189

```
Arg Ala Ser Gln Ser Val Ser His Ser Tyr Leu Ala
1               5                  10
```

<210> SEQ ID NO 190
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 190

Gly Ala Ser Phe Arg Ala Ala
1               5

<210> SEQ ID NO 191
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 191

Gln Gln Tyr Gly Ser Asp Pro Tyr Thr
1               5

<210> SEQ ID NO 192
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 192

Arg Ala Ser Gln Ser Ile Ser Ser Tyr Leu Asn
1               5                   10

<210> SEQ ID NO 193
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 193

Asp Ala Ser Asp Leu Gln Arg
1               5

<210> SEQ ID NO 194
<211> LENGTH: 9
<212> TYPE: PRT
<213> ORGANISM: Artificial Sequence
<220> FEATURE:
<223> OTHER INFORMATION: artificial amino acid sequence

<400> SEQUENCE: 194

Gln Gln Ser Tyr Asn Thr Pro Trp Thr
1               5

<210> SEQ ID NO 195
<211> LENGTH: 13
<212> TYPE: PRT
<213> ORGANISM: Artificial Sequence
<220> FEATURE:
<223> OTHER INFORMATION: artificial amino acid sequence

<400> SEQUENCE: 195

Thr Arg Ser Ser Gly Ser Ile Ala Ser Asn Tyr Val Gln
1               5                   10

```
<210> SEQ ID NO 196
<211> LENGTH: 7
<212> TYPE: PRT
<213> ORGANISM: Artificial Sequence
<220> FEATURE:
<223> OTHER INFORMATION: artificial amino acid sequence

<400> SEQUENCE: 196

Asp Asp Ser Asp Arg Pro Ser
1               5

<210> SEQ ID NO 197
<211> LENGTH: 11
<212> TYPE: PRT
<213> ORGANISM: Artificial Sequence
<220> FEATURE:
<223> OTHER INFORMATION: artificial amino acid sequence

<400> SEQUENCE: 197

Gln Val Trp Asp Ser Ser Ser Asp His Trp Val
1               5                   10

<210> SEQ ID NO 198
<211> LENGTH: 993
<212> TYPE: PRT
<213> ORGANISM: Homo sapiens

<400> SEQUENCE: 198

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
                20                  25                  30

Ile Lys Cys Val Leu Ile Asn His Lys Asn Asn Asp Ser Ser Val Gly
            35                  40                  45

Lys Ser Ser Ser Tyr Pro Met Val Ser Glu Ser Pro Glu Asp Leu Gly
        50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125

Val Ile Leu Lys Met Thr Glu Thr Gln Ala Gly Glu Tyr Leu Leu Phe
    130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
        195                 200                 205

Glu Ser Pro Ala Val Val Lys Lys Glu Glu Lys Val Leu His Glu Leu
    210                 215                 220

Phe Gly Thr Asp Ile Arg Cys Cys Ala Arg Asn Glu Leu Gly Arg Glu
225                 230                 235                 240
```

-continued

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
        275                 280                 285

Asn Lys Ala Leu Glu Glu Gly Asn Tyr Phe Glu Met Ser Thr Tyr Ser
    290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
        355                 360                 365

Phe Ser Val Arg Phe Lys Ala Tyr Pro Gln Ile Arg Cys Thr Trp Thr
    370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
        435                 440                 445

Gln Ala Ser Cys Phe Ser Asp Gly Tyr Pro Leu Pro Ser Trp Thr Trp
    450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
        515                 520                 525

Leu Asn Ser Pro Gly Pro Phe Pro Phe Ile Gln Asp Asn Ile Ser Phe
    530                 535                 540

Tyr Ala Thr Ile Gly Val Cys Leu Leu Phe Ile Val Val Leu Thr Leu
545                 550                 555                 560

Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
            580                 585                 590

Asp Phe Arg Glu Tyr Glu Tyr Asp Leu Lys Trp Glu Phe Pro Arg Glu
    595                 600                 605

Asn Leu Glu Phe Gly Lys Val Leu Gly Ser Gly Ala Phe Gly Lys Val
    610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu

```
                    660                 665                 670
Asn Ile Val Asn Leu Leu Gly Ala Cys Thr Leu Ser Gly Pro Ile Tyr
                675                 680                 685
Leu Ile Phe Glu Tyr Cys Cys Tyr Gly Asp Leu Leu Asn Tyr Leu Arg
            690                 695                 700
Ser Lys Arg Glu Lys Phe His Arg Thr Trp Thr Glu Ile Phe Lys Glu
705                 710                 715                 720
His Asn Phe Ser Phe Tyr Pro Thr Phe Gln Ser His Pro Asn Ser Ser
                725                 730                 735
Met Pro Gly Ser Arg Glu Val Gln Ile His Pro Asp Ser Asp Gln Ile
            740                 745                 750
Ser Gly Leu His Gly Asn Ser Phe His Ser Glu Asp Glu Ile Glu Tyr
            755                 760                 765
Glu Asn Gln Lys Arg Leu Glu Glu Glu Asp Leu Asn Val Leu Thr
            770                 775                 780
Phe Glu Asp Leu Leu Cys Phe Ala Tyr Gln Val Ala Lys Gly Met Glu
785                 790                 795                 800
Phe Leu Glu Phe Lys Ser Cys Val His Arg Asp Leu Ala Ala Arg Asn
                805                 810                 815
Val Leu Val Thr His Gly Lys Val Val Lys Ile Cys Asp Phe Gly Leu
            820                 825                 830
Ala Arg Asp Ile Met Ser Asp Ser Asn Tyr Val Val Arg Gly Asn Ala
            835                 840                 845
Arg Leu Pro Val Lys Trp Met Ala Pro Glu Ser Leu Phe Glu Gly Ile
            850                 855                 860
Tyr Thr Ile Lys Ser Asp Val Trp Ser Tyr Gly Ile Leu Leu Trp Glu
865                 870                 875                 880
Ile Phe Ser Leu Gly Val Asn Pro Tyr Pro Gly Ile Pro Val Asp Ala
                885                 890                 895
Asn Phe Tyr Lys Leu Ile Gln Asn Gly Phe Lys Met Asp Gln Pro Phe
            900                 905                 910
Tyr Ala Thr Glu Glu Ile Tyr Ile Ile Met Gln Ser Cys Trp Ala Phe
            915                 920                 925
Asp Ser Arg Lys Arg Pro Ser Phe Pro Asn Leu Thr Ser Phe Leu Gly
            930                 935                 940
Cys Gln Leu Ala Asp Ala Glu Glu Ala Met Tyr Gln Asn Val Asp Gly
945                 950                 955                 960
Arg Val Ser Glu Cys Pro His Thr Tyr Gln Asn Arg Arg Pro Phe Ser
                965                 970                 975
Arg Glu Met Asp Leu Gly Leu Leu Ser Pro Gln Ala Gln Val Glu Asp
            980                 985                 990
Ser

<210> SEQ ID NO 199
<211> LENGTH: 135
<212> TYPE: PRT
<213> ORGANISM: Homo sapiens

<400> SEQUENCE: 199

Asn Gln Asp Leu Pro Val Ile Lys Cys Val Leu Ile Asn His Lys Asn
1               5                   10                  15
Asn Asp Ser Ser Val Gly Lys Ser Ser Ser Tyr Pro Met Val Ser Glu
            20                  25                  30
Ser Pro Glu Asp Leu Gly Cys Ala Leu Arg Pro Gln Ser Ser Gly Thr
```

```
                35                  40                  45
Val Tyr Glu Ala Ala Val Glu Val Asp Val Ser Ala Ser Ile Thr
 50                  55                  60

Leu Gln Val Leu Val Asp Ala Pro Gly Asn Ile Ser Cys Leu Trp Val
 65                  70                  75                  80

Phe Lys His Ser Ser Leu Asn Cys Gln Pro His Phe Asp Leu Gln Asn
                 85                  90                  95

Arg Gly Val Val Ser Met Val Ile Leu Lys Met Thr Glu Thr Gln Ala
            100                 105                 110

Gly Glu Tyr Leu Leu Phe Ile Gln Ser Glu Ala Thr Asn Tyr Thr Ile
        115                 120                 125

Leu Phe Thr Val Ser Ile Arg
130                 135

<210> SEQ ID NO 200
<211> LENGTH: 82
<212> TYPE: PRT
<213> ORGANISM: Homo sapiens

<400> SEQUENCE: 200

Asn Thr Leu Leu Tyr Leu Arg Arg Pro Tyr Phe Arg Lys Met Glu Asn
  1               5                  10                  15

Gln Asp Ala Leu Val Cys Ile Ser Glu Ser Val Pro Glu Pro Ile Val
             20                  25                  30

Glu Trp Val Leu Cys Asp Ser Gln Gly Glu Ser Cys Lys Glu Glu Ser
         35                  40                  45

Pro Ala Val Val Lys Lys Glu Lys Val Leu His Glu Leu Phe Gly
 50                  55                  60

Thr Asp Ile Arg Cys Cys Ala Arg Asn Glu Leu Gly Arg Glu Cys Thr
 65                  70                  75                  80

Arg Leu

<210> SEQ ID NO 201
<211> LENGTH: 102
<212> TYPE: PRT
<213> ORGANISM: Homo sapiens

<400> SEQUENCE: 201

Phe Thr Ile Asp Leu Asn Gln Thr Pro Gln Thr Thr Leu Pro Gln Leu
  1               5                  10                  15

Phe Leu Lys Val Gly Glu Pro Leu Trp Ile Arg Cys Lys Ala Val His
             20                  25                  30

Val Asn His Gly Phe Gly Leu Thr Trp Glu Leu Glu Asn Lys Ala Leu
         35                  40                  45

Glu Glu Gly Asn Tyr Phe Glu Met Ser Thr Tyr Ser Thr Asn Arg Thr
 50                  55                  60

Met Ile Arg Ile Leu Phe Ala Phe Val Ser Ser Val Ala Arg Asn Asp
 65                  70                  75                  80

Thr Gly Tyr Tyr Thr Cys Ser Ser Ser Lys His Pro Ser Gln Ser Ala
             85                  90                  95

Leu Val Thr Ile Val Glu
            100

<210> SEQ ID NO 202
<211> LENGTH: 88
<212> TYPE: PRT
<213> ORGANISM: Homo sapiens
```

<400> SEQUENCE: 202

Lys Gly Phe Ile Asn Ala Thr Asn Ser Ser Glu Asp Tyr Glu Ile Asp
1               5                   10                  15

Gln Tyr Glu Glu Phe Cys Phe Ser Val Arg Phe Lys Ala Tyr Pro Gln
            20                  25                  30

Ile Arg Cys Thr Trp Thr Phe Ser Arg Lys Ser Phe Pro Cys Glu Gln
        35                  40                  45

Lys Gly Leu Asp Asn Gly Tyr Ser Ile Ser Lys Phe Cys Asn His Lys
    50                  55                  60

His Gln Pro Gly Glu Tyr Ile Phe His Ala Glu Asn Asp Asp Ala Gln
65                  70                  75                  80

Phe Thr Lys Met Phe Thr Leu Asn
                85

<210> SEQ ID NO 203
<211> LENGTH: 107
<212> TYPE: PRT
<213> ORGANISM: Homo sapiens

<400> SEQUENCE: 203

Ile Arg Arg Lys Pro Gln Val Leu Ala Glu Ala Ser Ala Ser Gln Ala
1               5                   10                  15

Ser Cys Phe Ser Asp Gly Tyr Pro Leu Pro Ser Trp Thr Trp Lys Lys
            20                  25                  30

Cys Ser Asp Lys Ser Pro Asn Cys Thr Glu Glu Ile Thr Glu Gly Val
        35                  40                  45

Trp Asn Arg Lys Ala Asn Arg Lys Val Phe Gly Gln Trp Val Ser Ser
    50                  55                  60

Ser Thr Leu Asn Met Ser Glu Ala Ile Lys Gly Phe Leu Val Lys Cys
65                  70                  75                  80

Cys Ala Tyr Asn Ser Leu Gly Thr Ser Cys Glu Thr Ile Leu Leu Asn
                85                  90                  95

Ser Pro Gly Pro Phe Pro Phe Ile Gln Asp Asn
            100                 105

<210> SEQ ID NO 204
<211> LENGTH: 21
<212> TYPE: PRT
<213> ORGANISM: Homo sapiens

<400> SEQUENCE: 204

Met Ala Leu Pro Val Thr Ala Leu Leu Leu Pro Leu Ala Leu Leu Leu
1               5                   10                  15

His Ala Ala Arg Pro
            20

<210> SEQ ID NO 205
<211> LENGTH: 16
<212> TYPE: PRT
<213> ORGANISM: Homo sapiens

<400> SEQUENCE: 205

Gly Leu Ala Val Ser Thr Ile Ser Ser Phe Phe Pro Pro Gly Tyr Gln
1               5                   10                  15

<210> SEQ ID NO 206
<211> LENGTH: 45
<212> TYPE: PRT

<213> ORGANISM: Homo sapiens

<400> SEQUENCE: 206

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 207
<211> LENGTH: 231
<212> TYPE: PRT
<213> ORGANISM: Homo sapiens

<400> SEQUENCE: 207

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 208
<211> LENGTH: 24
<212> TYPE: PRT
<213> ORGANISM: Homo sapiens

<400> SEQUENCE: 208

Ile Tyr Ile Trp Ala Pro Leu Ala Gly Thr Cys Gly Val Leu Leu Leu
1               5                   10                  15

Ser Leu Val Ile Thr Leu Tyr Cys
            20

```
<210> SEQ ID NO 209
<211> LENGTH: 42
<212> TYPE: PRT
<213> ORGANISM: Homo sapiens

<400> SEQUENCE: 209

Lys Arg Gly Arg Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
        35                  40

<210> SEQ ID NO 210
<211> LENGTH: 112
<212> TYPE: PRT
<213> ORGANISM: Homo sapiens

<400> SEQUENCE: 210

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Gly Arg Asp Pro Glu Met Gly Gly Lys
        35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 211
<211> LENGTH: 52
<212> TYPE: PRT
<213> ORGANISM: Homo sapiens

<400> SEQUENCE: 211

Phe Phe Ile Pro Leu Leu Val Val Ile Leu Phe Ala Val Asp Thr Gly
1               5                   10                  15

Leu Phe Ile Ser Thr Gln Gln Gln Val Thr Phe Leu Leu Lys Ile Lys
                20                  25                  30

Arg Thr Arg Lys Gly Phe Arg Leu Leu Asn Pro His Pro Lys Pro Asn
        35                  40                  45

Pro Lys Asn Asn
    50

<210> SEQ ID NO 212
<211> LENGTH: 215
<212> TYPE: PRT
<213> ORGANISM: Homo sapiens

<400> SEQUENCE: 212

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
```

```
                20                  25                  30
Val Ser Ser Gly Arg Leu Leu Lys Ser Ala Ser Pro Pro Leu His
             35                  40                  45

Thr Trp Leu Thr Val Leu Lys Lys Glu Gln Glu Phe Leu Gly Val Thr
 50                  55                  60

Gln Ile Leu Thr Ala Met Ile Cys Leu Cys Phe Gly Thr Val Val Cys
 65                  70                  75                  80

Ser Val Leu Asp Ile Ser His Ile Glu Gly Asp Ile Phe Ser Ser Phe
                 85                  90                  95

Lys Ala Gly Tyr Pro Phe Trp Gly Ala Ile Phe Ser Ile Ser Gly
                100                 105                 110

Met Leu Ser Ile Ile Ser Glu Arg Arg Asn Ala Thr Tyr Leu Val Arg
                115                 120                 125

Gly Ser Leu Gly Ala Asn Thr Ala Ser Ser Ile Ala Gly Gly Thr Gly
                130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
                165                 170                 175

Phe Ser Thr Glu Ile Val Val Met Met Leu Phe Leu Thr Ile Leu Gly
                180                 185                 190

Leu Gly Ser Ala Val Ser Leu Thr Ile Cys Gly Ala Gly Glu Leu
                195                 200                 205

Lys Gly Asn Lys Val Pro Glu
    210                 215

<210> SEQ ID NO 213
<211> LENGTH: 42
<212> TYPE: PRT
<213> ORGANISM: Homo sapiens

<400> SEQUENCE: 213

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
                35                  40

<210> SEQ ID NO 214
<211> LENGTH: 41
<212> TYPE: PRT
<213> ORGANISM: Homo sapiens

<400> SEQUENCE: 214

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
                20                  25                  30

Pro Arg Asp Phe Ala Ala Tyr Arg Ser
                35                  40

<210> SEQ ID NO 215
<211> LENGTH: 18
<212> TYPE: PRT
<213> ORGANISM: Homo sapiens

<400> SEQUENCE: 215
```

```
Met Ile Pro Ala Val Val Leu Leu Leu Leu Val Glu Gln Ala
1               5                   10                  15

Ala Ala
```

<210> SEQ ID NO 216
<211> LENGTH: 43
<212> TYPE: PRT
<213> ORGANISM: Homo sapiens

<400> SEQUENCE: 216

```
Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
                20                  25                  30

Arg Lys Ala Ala Ile Thr Ser Tyr Glu Lys Ser
            35                  40
```

<210> SEQ ID NO 217
<211> LENGTH: 22
<212> TYPE: PRT
<213> ORGANISM: Homo sapiens

<400> SEQUENCE: 217

```
Gly Ser Gly Ala Thr Asn Phe Ser Leu Leu Lys Gln Ala Gly Asp Val
1               5                   10                  15

Glu Glu Asn Pro Gly Pro
                20
```

<210> SEQ ID NO 218
<211> LENGTH: 21
<212> TYPE: PRT
<213> ORGANISM: Homo sapiens

<400> SEQUENCE: 218

```
Gly Ser Gly Glu Gly Arg Gly Ser Leu Leu Thr Cys Gly Asp Val Glu
1               5                   10                  15

Glu Asn Pro Gly Pro
                20
```

<210> SEQ ID NO 219
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 219

```
Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
                20                  25                  30

His Gly Leu Thr Pro Gln Gln Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Gln Gln Val Val Ala Ile Ala Ser Asn
65                  70                  75                  80

Gly Gly Gly Lys Gln Ala Leu Glu Thr Val Gln Arg Leu Leu Pro Val
                85                  90                  95
```

```
Leu Cys Gln Ala His Gly Leu Thr Pro Glu Gln Val Val Ala Ile Ala
            100                 105                 110

Ser His Asp Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
        195                 200                 205

Gln Val Val Ala Ile Ala Ser Asn Ile Gly Gly Lys Gln Ala Leu Glu
    210                 215                 220

Thr Val Gln Ala Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
            340                 345                 350

Ile Gly Gly Lys Gln Ala Leu Glu Thr Val Gln Ala Leu Leu Pro Val
        355                 360                 365

Leu Cys Gln Ala His Gly Leu Thr Pro Gln Gln Val Val Ala Ile Ala
    370                 375                 380

Ser Asn Gly Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser Asn Ile Gly Gly Lys Gln Ala Leu Glu Thr Val Gln Ala
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
```

-continued

```
                515                 520                 525
Leu Glu
    530

<210> SEQ ID NO 220
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 220

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Ala Ile Ala Ser Asn Gly Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Asn Gly Gly Lys
        275                 280                 285

Gln Ala Leu Glu Thr Val Gln Arg Leu Leu Pro Val Leu Cys Gln Ala
    290                 295                 300

His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser Asn
```

```
              340             345             350
Ile Gly Gly Lys Gln Ala Leu Glu Thr Val Gln Ala Leu Leu Pro Val
            355             360             365
Leu Cys Gln Ala His Gly Leu Thr Pro Glu Gln Val Val Ala Ile Ala
            370             375             380
Ser His Asp Gly Gly Lys Gln Ala Leu Glu Thr Val Gln Arg Leu Leu
385             390             395             400
Pro Val Leu Cys Gln Ala His Gly Leu Thr Pro Glu Gln Val Val Ala
                405             410             415
Ile Ala Ser Asn Ile Gly Gly Lys Gln Ala Leu Glu Thr Val Gln Ala
                420             425             430
Leu Leu Pro Val Leu Cys Gln Ala His Gly Leu Thr Pro Glu Gln Val
            435             440             445
Val Ala Ile Ala Ser His Asp Gly Gly Lys Gln Ala Leu Glu Thr Val
            450             455             460
Gln Arg Leu Leu Pro Val Leu Cys Gln Ala His Gly Leu Thr Pro Gln
465             470             475             480
Gln Val Val Ala Ile Ala Ser Asn Asn Gly Gly Lys Gln Ala Leu Glu
                485             490             495
Thr Val Gln Arg Leu Leu Pro Val Leu Cys Gln Ala His Gly Leu Thr
            500             505             510
Pro Gln Gln Val Val Ala Ile Ala Ser Asn Gly Gly Gly Arg Pro Ala
            515             520             525
Leu Glu
    530

<210> SEQ ID NO 221
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 221

Leu Thr Pro Gln Gln Val Val Ala Ile Ala Ser Asn Asn Gly Gly Lys
1               5                   10                  15
Gln Ala Leu Glu Thr Val Gln Arg Leu Leu Pro Val Leu Cys Gln Ala
            20                  25                  30
His Gly Leu Thr Pro Gln Gln Val Val Ala Ile Ala Ser Asn Gly Gly
        35                  40                  45
Gly Lys Gln Ala Leu Glu Thr Val Gln Arg Leu Leu Pro Val Leu Cys
    50                  55                  60
Gln Ala His Gly Leu Thr Pro Gln Gln Val Val Ala Ile Ala Ser Asn
65                  70                  75                  80
Asn Gly Gly Lys Gln Ala Leu Glu Thr Val Gln Arg Leu Leu Pro Val
                85                  90                  95
Leu Cys Gln Ala His Gly Leu Thr Pro Gln Gln Val Val Ala Ile Ala
            100                 105                 110
Ser Asn Gly Gly Gly Lys Gln Ala Leu Glu Thr Val Gln Arg Leu Leu
        115                 120                 125
Pro Val Leu Cys Gln Ala His Gly Leu Thr Pro Gln Gln Val Val Ala
    130                 135                 140
Ile Ala Ser Asn Gly Gly Gly Lys Gln Ala Leu Glu Thr Val Gln Arg
145                 150                 155                 160
Leu Leu Pro Val Leu Cys Gln Ala His Gly Leu Thr Pro Gln Gln Val
```

```
            165                 170                 175
Val Ala Ile Ala Ser Asn Gly Gly Lys Gln Ala Leu Glu Thr Val
            180                 185                 190

Gln Arg Leu Leu Pro Val Leu Cys Gln Ala His Gly Leu Thr Pro Gln
            195                 200                 205

Gln Val Val Ala Ile Ala Ser Asn Asn Gly Gly Lys Gln Ala Leu Glu
        210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Gln Gln Val Val Ala Ile Ala Ser Asn Asn Gly Gly Lys
            275                 280                 285

Gln Ala Leu Glu Thr Val Gln Arg Leu Leu Pro Val Leu Cys Gln Ala
        290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
        370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Gly Lys Gln Ala Leu Glu Thr Val Gln Arg
            420                 425                 430

Leu Leu Pro Val Leu Cys Gln Ala His Gly Leu Thr Pro Glu Gln Val
            435                 440                 445

Val Ala Ile Ala Ser His Asp Gly Gly Lys Gln Ala Leu Glu Thr Val
        450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 222
<211> LENGTH: 539
<212> TYPE: PRT
<213> ORGANISM: Artificial Sequence
<220> FEATURE:
<223> OTHER INFORMATION: artificial amino acid sequence
```

<400> SEQUENCE: 222

```
Asn Pro Gln Arg Ser Thr Val Trp Tyr Leu Thr Pro Gln Gln Val Val
1               5                   10                  15

Ala Ile Ala Ser Asn Asn Gly Gly Lys Gln Ala Leu Glu Thr Val Gln
            20                  25                  30

Arg Leu Leu Pro Val Leu Cys Gln Ala His Gly Leu Thr Pro Gln Gln
        35                  40                  45

Val Val Ala Ile Ala Ser Asn Gly Gly Lys Gln Ala Leu Glu Thr
    50                  55                  60

Val Gln Arg Leu Leu Pro Val Leu Cys Gln Ala His Gly Leu Thr Pro
65                  70                  75                  80

Gln Gln Val Val Ala Ile Ala Ser Asn Asn Gly Gly Lys Gln Ala Leu
                85                  90                  95

Glu Thr Val Gln Arg Leu Leu Pro Val Leu Cys Gln Ala His Gly Leu
            100                 105                 110

Thr Pro Gln Gln Val Val Ala Ile Ala Ser Asn Asn Gly Gly Lys Gln
        115                 120                 125

Ala Leu Glu Thr Val Gln Arg Leu Leu Pro Val Leu Cys Gln Ala His
    130                 135                 140

Gly Leu Thr Pro Glu Gln Val Val Ala Ile Ala Ser His Asp Gly Gly
145                 150                 155                 160

Lys Gln Ala Leu Glu Thr Val Gln Arg Leu Leu Pro Val Leu Cys Gln
                165                 170                 175

Ala His Gly Leu Thr Pro Glu Gln Val Val Ala Ile Ala Ser His Asp
            180                 185                 190

Gly Gly Lys Gln Ala Leu Glu Thr Val Gln Arg Leu Leu Pro Val Leu
        195                 200                 205

Cys Gln Ala His Gly Leu Thr Pro Gln Gln Val Val Ala Ile Ala Ser
    210                 215                 220

Asn Gly Gly Gly Lys Gln Ala Leu Glu Thr Val Gln Arg Leu Leu Pro
225                 230                 235                 240

Val Leu Cys Gln Ala His Gly Leu Thr Pro Gln Gln Val Val Ala Ile
                245                 250                 255

Ala Ser Asn Gly Gly Gly Lys Gln Ala Leu Glu Thr Val Gln Arg Leu
            260                 265                 270

Leu Pro Val Leu Cys Gln Ala His Gly Leu Thr Pro Gln Gln Val Val
        275                 280                 285

Ala Ile Ala Ser Asn Gly Gly Gly Lys Gln Ala Leu Glu Thr Val Gln
    290                 295                 300

Arg Leu Leu Pro Val Leu Cys Gln Ala His Gly Leu Thr Pro Gln Gln
305                 310                 315                 320

Val Val Ala Ile Ala Ser Asn Gly Gly Gly Lys Gln Ala Leu Glu Thr
                325                 330                 335

Val Gln Arg Leu Leu Pro Val Leu Cys Gln Ala His Gly Leu Thr Pro
            340                 345                 350

Gln Gln Val Val Ala Ile Ala Ser Asn Asn Gly Gly Lys Gln Ala Leu
        355                 360                 365

Glu Thr Val Gln Arg Leu Leu Pro Val Leu Cys Gln Ala His Gly Leu
    370                 375                 380

Thr Pro Gln Gln Val Val Ala Ile Ala Ser Asn Asn Gly Gly Lys Gln
385                 390                 395                 400

Ala Leu Glu Thr Val Gln Arg Leu Leu Pro Val Leu Cys Gln Ala His
                405                 410                 415
```

```
Gly Leu Thr Pro Gln Gln Val Ala Ile Ala Ser Asn Asn Gly Gly
            420                 425                 430

Lys Gln Ala Leu Glu Thr Val Gln Arg Leu Leu Pro Val Leu Cys Gln
            435                 440                 445

Ala His Gly Leu Thr Pro Gln Gln Val Ala Ile Ala Ser Asn Gly
            450                 455                 460

Gly Gly Lys Gln Ala Leu Glu Thr Val Gln Arg Leu Leu Pro Val Leu
465                 470                 475                 480

Cys Gln Ala His Gly Leu Thr Pro Gln Gln Val Val Ala Ile Ala Ser
                485                 490                 495

Asn Asn Gly Gly Lys Gln Ala Leu Glu Thr Val Gln Arg Leu Leu Pro
            500                 505                 510

Val Leu Cys Gln Ala His Gly Leu Thr Pro Gln Gln Val Val Ala Ile
            515                 520                 525

Ala Ser Asn Gly Gly Gly Arg Pro Ala Leu Glu
            530                 535

<210> SEQ ID NO 223
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 223

Leu Thr Pro Glu Gln Val Val Ala Ile Ala Ser His Asp Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
            35                  40                  45

Gly Lys Gln Ala Leu Glu Thr Val Gln Arg Leu Leu Pro Val Leu Cys
50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
            115                 120                 125

Pro Val Leu Cys Gln Ala His Gly Leu Thr Pro Glu Gln Val Val Ala
130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Glu
            195                 200                 205

Gln Val Val Ala Ile Ala Ser His Asp Gly Gly Lys Gln Ala Leu Glu
            210                 215                 220

Thr Val Gln Arg Leu Leu Pro Val Leu Cys Gln Ala His Gly Leu Thr
225                 230                 235                 240
```

Pro Gln Gln Val Val Ala Ile Ala Ser Asn Asn Gly Gly Lys Gln Ala
                245                 250                 255

Leu Glu Thr Val Gln Arg Leu Leu Pro Val Leu Cys Gln Ala His Gly
            260                 265                 270

Leu Thr Pro Glu Gln Val Val Ala Ile Ala Ser Asn Ile Gly Gly Lys
        275                 280                 285

Gln Ala Leu Glu Thr Val Gln Ala Leu Leu Pro Val Leu Cys Gln Ala
    290                 295                 300

His Gly Leu Thr Pro Gln Gln Val Val Ala Ile Ala Ser Asn Asn Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Asn Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Asn Gly Gly Lys Gln Ala Leu Glu Thr Val
    450                 455                 460

Gln Arg Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 224
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 224

Leu Thr Pro Gln Gln Val Val Ala Ile Ala Ser Asn Asn Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
        35                  40                  45

Gly Lys Gln Ala Leu Glu Thr Val Gln Arg Leu Leu Pro Val Leu Cys
    50                  55                  60

```
Gln Ala His Gly Leu Thr Pro Gln Gln Val Val Ala Ile Ala Ser Asn
 65                  70                  75                  80

Asn Gly Gly Lys Gln Ala Leu Glu Thr Val Gln Arg Leu Leu Pro Val
             85                  90                  95

Leu Cys Gln Ala His Gly Leu Thr Pro Glu Gln Val Val Ala Ile Ala
            100                 105                 110

Ser Asn Ile Gly Gly Lys Gln Ala Leu Glu Thr Val Gln Ala Leu Leu
        115                 120                 125

Pro Val Leu Cys Gln Ala His Gly Leu Thr Pro Gln Gln Val Val Ala
    130                 135                 140

Ile Ala Ser Asn Asn Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser Asn Ile Gly Gly Lys Gln Ala Leu Glu Thr Val
            180                 185                 190

Gln Ala Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser His Asp Gly Gly Lys Gln Ala
                245                 250                 255

Leu Glu Thr Val Gln Arg Leu Leu Pro Val Leu Cys Gln Ala His Gly
            260                 265                 270

Leu Thr Pro Gln Gln Val Val Ala Ile Ala Ser Asn Gly Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
            340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
            420                 425                 430

Leu Leu Pro Val Leu Cys Gln Ala His Gly Leu Thr Pro Gln Gln Val
        435                 440                 445

Val Ala Ile Ala Ser Asn Gly Gly Gly Lys Gln Ala Leu Glu Thr Val
    450                 455                 460

Gln Arg Leu Leu Pro Val Leu Cys Gln Ala His Gly Leu Thr Pro Gln
465                 470                 475                 480
```

```
Gln Val Val Ala Ile Ala Ser Asn Gly Gly Gly Lys Gln Ala Leu Glu
                485                 490                 495

Thr Val Gln Arg Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
        515                 520                 525

Leu Glu
    530

<210> SEQ ID NO 225
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 225

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Glu Gln Val Val Ala Ile Ala Ser His Asp Gly
        35                  40                  45

Gly Lys Gln Ala Leu Glu Thr Val Gln Arg Leu Leu Pro Val Leu Cys
    50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
            100                 105                 110

Ser Asn Gly Gly Gly Lys Gln Ala Leu Glu Thr Val Gln Arg Leu Leu
        115                 120                 125

Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Glu Gln Val
                165                 170                 175

Val Ala Ile Ala Ser His Asp Gly Gly Lys Gln Ala Leu Glu Thr Val
            180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
            260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300
```

```
His Gly Leu Thr Pro Gln Gln Val Val Ala Ile Ala Ser Asn Gly Gly
305                 310                 315                 320

Gly Lys Gln Ala Leu Glu Thr Val Gln Arg Leu Leu Pro Val Leu Cys
            325                 330                 335

Gln Ala His Gly Leu Thr Pro Glu Gln Val Val Ala Ile Ala Ser His
            340                 345                 350

Asp Gly Gly Lys Gln Ala Leu Glu Thr Val Gln Arg Leu Leu Pro Val
            355                 360                 365

Leu Cys Gln Ala His Gly Leu Thr Pro Glu Gln Val Val Ala Ile Ala
        370                 375                 380

Ser Asn Ile Gly Gly Lys Gln Ala Leu Glu Thr Val Gln Ala Leu Leu
385                 390                 395                 400

Pro Val Leu Cys Gln Ala His Gly Leu Thr Pro Glu Gln Val Val Ala
                405                 410                 415

Ile Ala Ser His Asp Gly Gly Lys Gln Ala Leu Glu Thr Val Gln Arg
                420                 425                 430

Leu Leu Pro Val Leu Cys Gln Ala His Gly Leu Thr Pro Glu Gln Val
            435                 440                 445

Val Ala Ile Ala Ser His Asp Gly Gly Lys Gln Ala Leu Glu Thr Val
450                 455                 460

Gln Arg Leu Leu Pro Val Leu Cys Gln Ala His Gly Leu Thr Pro Glu
465                 470                 475                 480

Gln Val Val Ala Ile Ala Ser Asn Ile Gly Gly Lys Gln Ala Leu Glu
                485                 490                 495

Thr Val Gln Ala Leu Leu Pro Val Leu Cys Gln Ala His Gly Leu Thr
            500                 505                 510

Pro Gln Gln Val Val Ala Ile Ala Ser Asn Gly Gly Gly Arg Pro Ala
            515                 520                 525

Leu Glu
    530

<210> SEQ ID NO 226
<211> LENGTH: 530
<212> TYPE: PRT
<213> ORGANISM: Artificial Sequence
<220> FEATURE:
<223> OTHER INFORMATION: artificial amino acid sequence

<400> SEQUENCE: 226

Leu Thr Pro Gln Gln Val Val Ala Ile Ala Ser Asn Gly Gly Gly Lys
1               5                   10                  15

Gln Ala Leu Glu Thr Val Gln Arg Leu Leu Pro Val Leu Cys Gln Ala
            20                  25                  30

His Gly Leu Thr Pro Gln Gln Val Val Ala Ile Ala Ser Asn Asn Gly
            35                  40                  45

Gly Lys Gln Ala Leu Glu Thr Val Gln Arg Leu Leu Pro Val Leu Cys
        50                  55                  60

Gln Ala His Gly Leu Thr Pro Glu Gln Val Val Ala Ile Ala Ser His
65                  70                  75                  80

Asp Gly Gly Lys Gln Ala Leu Glu Thr Val Gln Arg Leu Leu Pro Val
                85                  90                  95

Leu Cys Gln Ala His Gly Leu Thr Pro Gln Gln Val Val Ala Ile Ala
                100                 105                 110

Ser Asn Gly Gly Gly Lys Gln Ala Leu Glu Thr Val Gln Arg Leu Leu
            115                 120                 125
```

```
Pro Val Leu Cys Gln Ala His Gly Leu Thr Pro Glu Gln Val Val Ala
    130                 135                 140

Ile Ala Ser His Asp Gly Gly Lys Gln Ala Leu Glu Thr Val Gln Arg
145                 150                 155                 160

Leu Leu Pro Val Leu Cys Gln Ala His Gly Leu Thr Pro Gln Gln Val
                165                 170                 175

Val Ala Ile Ala Ser Asn Gly Gly Lys Gln Ala Leu Glu Thr Val
                180                 185                 190

Gln Arg Leu Leu Pro Val Leu Cys Gln Ala His Gly Leu Thr Pro Gln
        195                 200                 205

Gln Val Val Ala Ile Ala Ser Asn Gly Gly Lys Gln Ala Leu Glu
    210                 215                 220

Thr Val Gln Arg Leu Leu Pro Val Leu Cys Gln Ala His Gly Leu Thr
225                 230                 235                 240

Pro Glu Gln Val Val Ala Ile Ala Ser Asn Ile Gly Gly Lys Gln Ala
                245                 250                 255

Leu Glu Thr Val Gln Ala Leu Leu Pro Val Leu Cys Gln Ala His Gly
                260                 265                 270

Leu Thr Pro Glu Gln Val Val Ala Ile Ala Ser His Asp Gly Gly Lys
        275                 280                 285

Gln Ala Leu Glu Thr Val Gln Arg Leu Leu Pro Val Leu Cys Gln Ala
    290                 295                 300

His Gly Leu Thr Pro Glu Gln Val Val Ala Ile Ala Ser His Asp Gly
305                 310                 315                 320

Gly Lys Gln Ala Leu Glu Thr Val Gln Arg Leu Leu Pro Val Leu Cys
                325                 330                 335

Gln Ala His Gly Leu Thr Pro Gln Gln Val Val Ala Ile Ala Ser Asn
                340                 345                 350

Gly Gly Gly Lys Gln Ala Leu Glu Thr Val Gln Arg Leu Leu Pro Val
        355                 360                 365

Leu Cys Gln Ala His Gly Leu Thr Pro Gln Gln Val Val Ala Ile Ala
    370                 375                 380

Ser Asn Asn Gly Gly Lys Gln Ala Leu Glu Thr Val Gln Arg Leu Leu
385                 390                 395                 400

Pro Val Leu Cys Gln Ala His Gly Leu Thr Pro Gln Gln Val Val Ala
                405                 410                 415

Ile Ala Ser Asn Gly Gly Lys Gln Ala Leu Glu Thr Val Gln Arg
                420                 425                 430

Leu Leu Pro Val Leu Cys Gln Ala His Gly Leu Thr Pro Glu Gln Val
        435                 440                 445

Val Ala Ile Ala Ser Asn Ile Gly Gly Lys Gln Ala Leu Glu Thr Val
    450                 455                 460

Gln Ala Leu Leu Pro Val Leu Cys Gln Ala His Gly Leu Thr Pro Glu
465                 470                 475                 480

Gln Val Val Ala Ile Ala Ser His Asp Gly Gly Lys Gln Ala Leu Glu
                485                 490                 495

Thr Val Gln Arg Leu Leu Pro Val Leu Cys Gln Ala His Gly Leu Thr
                500                 505                 510

Pro Gln Gln Val Val Ala Ile Ala Ser Asn Gly Gly Arg Pro Ala
        515                 520                 525

Leu Glu
    530
```

-continued

```
<210> SEQ ID NO 227
<211> LENGTH: 136
<212> TYPE: PRT
<213> ORGANISM: Artificial Sequence
<220> FEATURE:
<223> OTHER INFORMATION: artificial amino acid sequence

<400> SEQUENCE: 227

Cys Pro Tyr Ser Asn Pro Ser Leu Cys Ser Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
        35                  40                  45

Ser Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65              70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Val Val
    130                 135

<210> SEQ ID NO 228
<211> LENGTH: 157
<212> TYPE: PRT
<213> ORGANISM: Artificial Sequence
<220> FEATURE:
<223> OTHER INFORMATION: artificial amino acid sequence

<400> SEQUENCE: 228

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65              70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val
145                 150                 155

<210> SEQ ID NO 229
<211> LENGTH: 9
```

```
<212> TYPE: PRT
<213> ORGANISM: Artificial Sequence
<220> FEATURE:
<223> OTHER INFORMATION: artificial amino acid sequence

<400> SEQUENCE: 229

Cys Pro Tyr Ser Asn Pro Ser Leu Cys
1               5

<210> SEQ ID NO 230
<211> LENGTH: 37
<212> TYPE: PRT
<213> ORGANISM: Artificial Sequence
<220> FEATURE:
<223> OTHER INFORMATION: artificial amino acid sequence

<400> SEQUENCE: 230

Gly Ser Gly Gly Gly Ser Cys Pro Tyr Ser Asn Pro Ser Leu Cys
1               5                   10                  15

Ser Gly Gly Gly Gly Ser Cys Pro Tyr Ser Asn Pro Ser Leu Cys Ser
            20                  25                  30

Gly Gly Gly Gly Ser
        35

<210> SEQ ID NO 231
<211> LENGTH: 24
<212> TYPE: PRT
<213> ORGANISM: Artificial Sequence
<220> FEATURE:
<223> OTHER INFORMATION: artificial amino acid sequence

<400> SEQUENCE: 231

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 232
<211> LENGTH: 15
<212> TYPE: PRT
<213> ORGANISM: Artificial Sequence
<220> FEATURE:
<223> OTHER INFORMATION: artificial amino acid sequence

<400> SEQUENCE: 232

Gly Gly Gly Gly Ser Gly Gly Gly Ser Gly Gly Gly Gly Ser
1               5                   10                  15

<210> SEQ ID NO 233
<211> LENGTH: 484
<212> TYPE: PRT
<213> ORGANISM: Artificial Sequence
<220> FEATURE:
<223> OTHER INFORMATION: artificial amino acid sequence

<400> SEQUENCE: 233

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Val Phe Ser Arg Tyr Ala Leu Ser Trp Val Arg Gln Ala Pro Gly Gln
    50                  55                  60
```

```
Gly Leu Glu Trp Met Gly Gly Ile Ile Pro Met Leu Gly Phe Ala Asn
 65                  70                  75                  80

Tyr Ala Gln Lys Phe Gln Gly Arg Val Thr Ile Thr Ala Asp Glu Ser
                 85                  90                  95

Thr Ser Thr Ala Tyr Met Glu Leu Ser Ser Leu Arg Ser Glu Asp Thr
            100                 105                 110

Ala Val Tyr Tyr Cys Ala Thr Leu Asp Phe Gly Ala Leu Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Ser Glu Ile Val Leu Thr Gln Ser
145                 150                 155                 160

Pro Gly Thr Leu Ser Leu Ser Pro Gly Glu Arg Ala Thr Leu Ser Cys
                165                 170                 175

Arg Ala Ser Gln Ala Val Asp Ser Ser Asp Leu Ala Trp Tyr Gln Gln
            180                 185                 190

Lys Pro Gly Gln Ala Pro Arg Leu Leu Ile Tyr Asp Ala Tyr Thr Arg
        195                 200                 205

Pro Ser Gly Ile Pro Asp Arg Phe Ser Gly Ser Gly Ser Gly Thr Asp
    210                 215                 220

Phe Thr Leu Thr Ile Ser Arg Leu Glu Pro Glu Asp Phe Ala Val Tyr
225                 230                 235                 240

Tyr Cys Gln Gln Tyr Gly Ser Ser Pro Leu Thr Phe Gly Gly Gly Thr
                245                 250                 255

Lys Leu Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
        355                 360                 365

Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480
```

Leu Pro Pro Arg

<210> SEQ ID NO 234
<211> LENGTH: 484
<212> TYPE: PRT
<213> ORGANISM: Artificial Sequence
<220> FEATURE:
<223> OTHER INFORMATION: artificial amino acid sequence

<400> SEQUENCE: 234

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Val Phe Ser Arg Tyr Ala Leu Ser Trp Val Arg Gln Ala Pro Gly Gln
    50                  55                  60

Gly Leu Glu Trp Met Gly Gly Ile Ile Pro Met Leu Gly Phe Ala Asn
65                  70                  75                  80

Tyr Ala Gln Lys Phe Gln Gly Arg Val Thr Ile Thr Ala Asp Glu Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Thr Leu Asp Phe Gly Ala Leu Asp Tyr Trp
        115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Glu Ile Val Leu Thr Gln Ser
145                 150                 155                 160

Pro Gly Thr Leu Ser Leu Ser Pro Gly Glu Arg Ala Thr Leu Ser Cys
                165                 170                 175

Arg Ala Ser Gln Ser Val Pro Asn Glu Gln Leu Ala Trp Tyr Gln Gln
            180                 185                 190

Lys Pro Gly Gln Ala Pro Arg Leu Leu Ile Tyr Asp Ala Ser Ser Arg
        195                 200                 205

Ala Thr Gly Ile Pro Asp Arg Phe Ser Gly Ser Gly Ser Gly Thr Asp
    210                 215                 220

Phe Thr Leu Thr Ile Ser Arg Leu Glu Pro Glu Asp Phe Ala Val Tyr
225                 230                 235                 240

Tyr Cys Gln Gln Tyr Gly Ser Pro Pro Leu Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly

```
                355                 360                 365
Gly Cys Glu Leu Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Gly Arg Asp Pro Glu
                    405                 410                 415

Met Gly Gly Lys Pro Arg Arg Lys Asn Pro Gln Glu Gly Leu Tyr Asn
                420                 425                 430

Glu Leu Gln Lys Asp Lys Met Ala Glu Ala Tyr Ser Glu Ile Gly Met
                435                 440                 445

Lys Gly Glu Arg Arg Arg Gly Lys Gly His Asp Gly Leu Tyr Gln Gly
                450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 235
<211> LENGTH: 485
<212> TYPE: PRT
<213> ORGANISM: Artificial Sequence
<220> FEATURE:
<223> OTHER INFORMATION: artificial amino acid sequence

<400> SEQUENCE: 235

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
            35                  40                  45

Thr Phe Ser Ser Tyr Asp Ile Ser Trp Val Arg Gln Ala Pro Gly Gln
        50                  55                  60

Gly Leu Glu Trp Met Gly Gly Ile Ile Pro Val Ser Gly Arg Ala Asn
65                  70                  75                  80

Tyr Ala Gln Lys Phe Gln Gly Arg Val Thr Ile Thr Thr Asp Lys Ser
                85                  90                  95

Thr Ser Thr Ala Tyr Met Glu Leu Ser Ser Leu Arg Ser Glu Asp Thr
                100                 105                 110

Ala Val Tyr Tyr Cys Ala Arg Val Arg Pro Thr Tyr Trp Pro Leu Asp
            115                 120                 125

Tyr Trp Gly Gln Gly Thr Leu Val Thr Val Ser Ser Gly Gly Gly Gly
        130                 135                 140

Ser Gly Gly Gly Gly Ser Gly Gly Gly Gly Ser Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Ile Ser Ser Tyr Leu Asn Trp Tyr Gln
                180                 185                 190

Gln Lys Pro Gly Lys Ala Pro Lys Leu Leu Ile Tyr Ala Ala Ser Ser
            195                 200                 205

Leu Gln Ser Gly Val Pro Ser Arg Phe Ser Gly Ser Gly Ser Gly Thr
        210                 215                 220

Asp Phe Thr Leu Thr Ile Ser Ser Leu Gln Pro Glu Asp Phe Ala Thr
225                 230                 235                 240
```

```
Tyr Tyr Cys Gln Gln Ser Tyr Ser Thr Pro Leu Thr Phe Gly Gln Gly
                245                 250                 255

Thr Lys Val Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
            275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
            355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
            435                 440                 445

Met Lys Gly Glu Arg Arg Arg Gly Lys Gly His Asp Gly Leu Tyr Gln
450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 236
<211> LENGTH: 484
<212> TYPE: PRT
<213> ORGANISM: Artificial Sequence
<220> FEATURE:
<223> OTHER INFORMATION: artificial amino acid sequence

<400> SEQUENCE: 236

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
            35                  40                  45

Thr Phe Ser Ser Tyr Ala Ile Gln Trp Val Arg Gln Ala Pro Gly Gln
    50                  55                  60

Gly Leu Glu Trp Met Gly Gly Ile Val Gly Ser Trp Gly Leu Ala Asn
65                  70                  75                  80

Tyr Ala Gln Lys Phe Gln Gly Arg Val Thr Ile Thr Thr Asp Lys Ser
                85                  90                  95

Thr Ser Thr Ala Tyr Met Glu Leu Ser Ser Leu Arg Ser Glu Asp Thr
            100                 105                 110
```

Ala Val Tyr Tyr Cys Ala Thr Ser Ala Phe Gly Glu Leu Ala Ser Trp
            115                 120                 125

Gly Gln Gly Thr Leu Val Thr Val Ser Ser Gly Gly Gly Ser Gly
    130                 135                 140

Gly Gly Gly Ser Gly Gly Gly Ser Glu Ile Val Leu Thr Gln Ser
145                 150                 155                 160

Pro Gly Thr Leu Ser Leu Ser Pro Gly Glu Arg Ala Thr Leu Ser Cys
                165                 170                 175

Arg Ala Ser Gln Ser Val Pro Ser Ser Gln Leu Ala Trp Tyr Gln Gln
                180                 185                 190

Lys Pro Gly Gln Ala Pro Arg Leu Leu Ile Tyr Asp Ala Ser Ser Arg
            195                 200                 205

Ala Thr Gly Ile Pro Asp Arg Phe Ser Gly Ser Gly Ser Gly Thr Asp
            210                 215                 220

Phe Thr Leu Thr Ile Ser Arg Leu Glu Pro Glu Asp Phe Ala Val Tyr
225                 230                 235                 240

Tyr Cys Gln Gln Tyr Gly Ser Ser Pro Leu Thr Phe Gly Gln Gly Thr
                245                 250                 255

Lys Val Glu Ile Lys Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
            275                 280                 285

Arg Pro Ala Ala Gly Gly Ala Val His Thr Arg Gly Leu Asp Phe Ala
            290                 295                 300

Cys Asp Ile Tyr Ile Trp Ala Pro Leu Ala Gly Thr Cys Gly Val Leu
305                 310                 315                 320

Leu Leu Ser Leu Val Ile Thr Leu Tyr Cys Lys Arg Gly Arg Lys Lys
                325                 330                 335

Leu Leu Tyr Ile Phe Lys Gln Pro Phe Met Arg Pro Val Gln Thr Thr
            340                 345                 350

Gln Glu Glu Asp Gly Cys Ser Cys Arg Phe Pro Glu Glu Glu Glu Gly
            355                 360                 365

Gly Cys Glu Leu Arg Val Lys Phe Ser Arg Ser Ala Asp Ala Pro Ala
370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
            435                 440                 445

Lys Gly Glu Arg Arg Arg Gly Lys Gly His Asp Gly Leu Tyr Gln Gly
            450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 237
<211> LENGTH: 486
<212> TYPE: PRT
<213> ORGANISM: Artificial Sequence
<220> FEATURE:
<223> OTHER INFORMATION: artificial amino acid sequence

<400> SEQUENCE: 237

Met Ala Leu Pro Val Thr Ala Leu Leu Pro Leu Ala Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
                35                  40                  45

Thr Phe Ser Ser Tyr Thr Ile Ser Trp Val Arg Gln Ala Pro Gly Gln
            50                  55                  60

Gly Leu Glu Trp Met Gly Gly Ile Ile Pro Ala Phe Gly Ile Ala Asn
65                  70                  75                  80

Tyr Ala Gln Lys Phe Gln Gly Arg Val Thr Ile Thr Ala Asp Lys Ser
                85                  90                  95

Thr Ser Thr Ala Tyr Met Glu Leu Ser Ser Leu Arg Ser Glu Asp Thr
                100                 105                 110

Ala Val Tyr Tyr Cys Ala Lys Gly Gly Ser Tyr Ser Leu Asp Tyr Phe
            115                 120                 125

Asp Ile Trp Gly Gln Gly Thr Leu Val Thr Val Ser Ser Gly Gly Gly
130                 135                 140

Gly Ser Gly Gly Gly Gly Ser Gly Gly Gly Gly Ser Glu Ile Val Leu
145                 150                 155                 160

Thr Gln Ser Pro Gly Thr Leu Ser Leu Ser Pro Gly Glu Arg Ala Thr
                165                 170                 175

Leu Ser Cys Arg Ala Ser Gln Tyr Val Ser Ala Ser Leu Leu Ala Trp
            180                 185                 190

Tyr Gln Gln Lys Pro Gly Gln Ala Pro Arg Leu Leu Ile Tyr Gly Ala
                195                 200                 205

Ser Thr Arg Ala Thr Gly Ile Pro Asp Arg Phe Ser Gly Ser Gly Ser
            210                 215                 220

Gly Thr Asp Phe Thr Leu Thr Ile Ser Arg Leu Glu Pro Glu Asp Phe
225                 230                 235                 240

Ala Val Tyr Tyr Cys Gln Gln Tyr Ala Arg Ser Ser Thr Phe Gly Gln
                245                 250                 255

Gly Thr Lys Val Glu Ile Lys Thr Thr Thr Pro Ala Pro Arg Pro Pro
                260                 265                 270

Thr Pro Ala Pro Thr Ile Ala Ser Gln Pro Leu Ser Leu Arg Pro Glu
            275                 280                 285

Ala Cys Arg Pro Ala Ala Gly Gly Ala Val His Thr Arg Gly Leu Asp
            290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
            370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp

Pro Glu Met Gly Gly Lys Pro Arg Arg Lys Asn Pro Gln Glu Gly Leu
             405                 410                 415
                      420                 425                 430

Tyr Asn Glu Leu Gln Lys Asp Lys Met Ala Glu Ala Tyr Ser Glu Ile
             435                 440                 445

Gly Met Lys Gly Glu Arg Arg Arg Gly Lys Gly His Asp Gly Leu Tyr
             450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 238
<211> LENGTH: 490
<212> TYPE: PRT
<213> ORGANISM: Artificial Sequence
<220> FEATURE:
<223> OTHER INFORMATION: artificial amino acid sequence

<400> SEQUENCE: 238

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
        50                  55                  60

Gly Leu Glu Trp Val Ser Ser Ile Ser Gly Gly Arg Ser Thr Tyr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Leu Ser Pro Ser Asp Val Gly Trp
        115                 120                 125

Gly Tyr Gly Phe Asp Ile Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Glu Ile Val Leu Thr Gln Ser Pro Gly Thr Leu Ser Leu Ser Pro Gly
                165                 170                 175

Glu Arg Ala Thr Leu Ser Cys Arg Ala Ser Gln Ser Val Ser Asn Thr
            180                 185                 190

Tyr Leu Ala Trp Tyr Gln Gln Lys Pro Gly Gln Ala Pro Arg Leu Leu
        195                 200                 205

Ile Tyr Asp Thr Ser Ser Arg Ala Thr Gly Ile Pro Asp Arg Phe Ser
    210                 215                 220

Gly Ser Gly Ser Gly Thr Asp Phe Thr Leu Thr Ile Ser Arg Leu Glu
225                 230                 235                 240

Pro Glu Asp Phe Ala Val Tyr Tyr Cys Gln Gln Tyr Gly Ser Ser Leu
                245                 250                 255

Thr Phe Gly Gln Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser

```
                  275                 280                 285
Leu Arg Pro Glu Ala Cys Arg Pro Ala Ala Gly Gly Ala Val His Thr
290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
                450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 239
<211> LENGTH: 490
<212> TYPE: PRT
<213> ORGANISM: Artificial Sequence
<220> FEATURE:
<223> OTHER INFORMATION: artificial amino acid sequence

<400> SEQUENCE: 239

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Thr Phe Ser Ser Tyr Ala Met Asn Trp Val Arg Gln Ala Pro Gly Lys
        50                  55                  60

Gly Leu Glu Trp Val Ser Ser Ile Ser Gly Gly Arg Ser Thr Tyr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
                100                 105                 110

Ala Val Tyr Tyr Cys Ala Arg Asp Leu Ser Pro Ser Asp Val Gly Trp
            115                 120                 125

Gly Tyr Gly Phe Asp Ile Trp Gly Gln Gly Thr Leu Val Thr Val Ser
        130                 135                 140

Ser Gly Gly Gly Gly Ser Gly Gly Gly Gly Ser Gly Gly Gly Gly Ser
```

```
            145                 150                 155                 160
        Glu Ile Val Leu Thr Gln Ser Pro Ala Thr Leu Ser Leu Ser Pro Gly
                        165                 170                 175
        Glu Arg Ala Thr Leu Ser Cys Arg Ala Ser Gln Ser Val Ser Ser Asn
                        180                 185                 190
        Leu Ala Trp Tyr Gln Gln Lys Pro Gly Gln Ala Pro Arg Leu Leu Ile
                    195                 200                 205
        Tyr Asp Thr Phe Thr Arg Ala Thr Gly Ile Pro Ala Arg Phe Ser Gly
            210                 215                 220
        Ser Gly Ser Gly Thr Asp Phe Thr Leu Thr Ile Ser Arg Leu Glu Pro
        225                 230                 235                 240
        Glu Asp Phe Ala Val Tyr Tyr Cys Gln Gln Tyr Gly Ser Ser Pro Pro
                        245                 250                 255
        Thr Phe Gly Gln Gly Thr Arg Leu Glu Ile Lys Thr Thr Thr Pro Ala
                        260                 265                 270
        Pro Arg Pro Pro Thr Pro Ala Pro Thr Ile Ala Ser Gln Pro Leu Ser
                    275                 280                 285
        Leu Arg Pro Glu Ala Cys Arg Pro Ala Ala Gly Gly Ala Val His Thr
            290                 295                 300
        Arg Gly Leu Asp Phe Ala Cys Asp Ile Tyr Ile Trp Ala Pro Leu Ala
        305                 310                 315                 320
        Gly Thr Cys Gly Val Leu Leu Leu Ser Leu Val Ile Thr Leu Tyr Cys
                        325                 330                 335
        Lys Arg Gly Arg Lys Lys Leu Leu Tyr Ile Phe Lys Gln Pro Phe Met
                        340                 345                 350
        Arg Pro Val Gln Thr Thr Gln Glu Glu Asp Gly Cys Ser Cys Arg Phe
                    355                 360                 365
        Pro Glu Glu Glu Glu Gly Gly Cys Glu Leu Arg Val Lys Phe Ser Arg
            370                 375                 380
        Ser Ala Asp Ala Pro Ala Tyr Gln Gln Gly Gln Asn Gln Leu Tyr Asn
        385                 390                 395                 400
        Glu Leu Asn Leu Gly Arg Arg Glu Glu Tyr Asp Val Leu Asp Lys Arg
                        405                 410                 415
        Arg Gly Arg Asp Pro Glu Met Gly Gly Lys Pro Arg Arg Lys Asn Pro
                        420                 425                 430
        Gln Glu Gly Leu Tyr Asn Glu Leu Gln Lys Asp Lys Met Ala Glu Ala
                    435                 440                 445
        Tyr Ser Glu Ile Gly Met Lys Gly Glu Arg Arg Arg Gly Lys Gly His
            450                 455                 460
        Asp Gly Leu Tyr Gln Gly Leu Ser Thr Ala Thr Lys Asp Thr Tyr Asp
        465                 470                 475                 480
        Ala Leu His Met Gln Ala Leu Pro Pro Arg
                        485                 490

<210> SEQ ID NO 240
<211> LENGTH: 487
<212> TYPE: PRT
<213> ORGANISM: Artificial Sequence
<220> FEATURE:
<223> OTHER INFORMATION: artificial amino acid sequence

<400> SEQUENCE: 240

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
```

```
                    20                  25                  30
            Val Gln Pro Gly Gly Ser Leu Arg Leu Ser Cys Ala Ala Ser Gly Phe
                        35                  40                  45

Thr Phe Ser Ser Tyr Ala Met His Trp Val Arg Gln Ala Pro Gly Lys
                50                  55                  60

Gly Leu Glu Trp Val Ser Ala Ile Ser Gly Ser Gly Gly Ser Thr Tyr
            65                  70                  75                  80

Tyr Ala Asp Ser Val Lys Gly Arg Phe Thr Ile Ser Arg Asp Asn Ser
                            85                  90                  95

Lys Asn Thr Leu Tyr Leu Gln Met Asn Ser Leu Arg Ala Glu Asp Thr
                        100                 105                 110

Ala Val Tyr Tyr Cys Ala Arg Gly Thr Arg Trp Trp Trp Gly Asp Ala
                    115                 120                 125

Phe Asp His Trp Gly Gln Gly Thr Leu Val Thr Val Ser Ser Gly Gly
                130                 135                 140

Gly Ser Gly Gly Gly Gly Ser Gly Gly Gly Gly Ser Gln Ser Val
            145                 150                 155                 160

Leu Thr Gln Pro Pro Ser Val Ser Val Ala Pro Gly Lys Thr Ala Arg
                            165                 170                 175

Ile Thr Cys Gly Gly Asn Asn Ile Gly Ser Lys Ser Val His Trp Tyr
                        180                 185                 190

Gln Gln Lys Pro Gly Gln Ala Pro Val Leu Val Ile Tyr Tyr Asp Ser
                    195                 200                 205

Asp Arg Pro Ser Gly Ile Pro Glu Arg Phe Ser Gly Ser Asn Ser Gly
                210                 215                 220

Asn Thr Ala Thr Leu Thr Ile Ser Arg Val Glu Ala Gly Asp Glu Ala
            225                 230                 235                 240

Asp Tyr Tyr Cys Gln Val Trp Asp Ser Ser Thr Ala Trp Val Phe Gly
                            245                 250                 255

Gly Gly Thr Lys Leu Thr Val Leu Thr Thr Thr Pro Ala Pro Arg Pro
                        260                 265                 270

Pro Thr Pro Ala Pro Thr Ile Ala Ser Gln Pro Leu Ser Leu Arg Pro
                    275                 280                 285

Glu Ala Cys Arg Pro Ala Ala Gly Gly Ala Val His Thr Arg Gly Leu
                290                 295                 300

Asp Phe Ala Cys Asp Ile Tyr Ile Trp Ala Pro Leu Ala Gly Thr Cys
            305                 310                 315                 320

Gly Val Leu Leu Leu Ser Leu Val Ile Thr Leu Tyr Cys Lys Arg Gly
                            325                 330                 335

Arg Lys Lys Leu Leu Tyr Ile Phe Lys Gln Pro Phe Met Arg Pro Val
                        340                 345                 350

Gln Thr Thr Gln Glu Glu Asp Gly Cys Ser Cys Arg Phe Pro Glu Glu
                    355                 360                 365

Glu Glu Gly Gly Cys Glu Leu Arg Val Lys Phe Ser Arg Ser Ala Asp
                370                 375                 380

Ala Pro Ala Tyr Gln Gln Gly Gln Asn Gln Leu Tyr Asn Glu Leu Asn
            385                 390                 395                 400

Leu Gly Arg Arg Glu Glu Tyr Asp Val Leu Asp Lys Arg Arg Gly Arg
                            405                 410                 415

Asp Pro Glu Met Gly Gly Lys Pro Arg Arg Lys Asn Pro Gln Glu Gly
                        420                 425                 430

Leu Tyr Asn Glu Leu Gln Lys Asp Lys Met Ala Glu Ala Tyr Ser Glu
                    435                 440                 445
```

```
Ile Gly Met Lys Gly Glu Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 241
<211> LENGTH: 490
<212> TYPE: PRT
<213> ORGANISM: Artificial Sequence
<220> FEATURE:
<223> OTHER INFORMATION: artificial amino acid sequence

<400> SEQUENCE: 241

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
            20                  25                  30

Lys Lys Pro Gly Ser Ser Val Lys Val Ser Cys Lys Ala Ser Gly Gly
        35                  40                  45

Thr Phe Ser Ser Tyr Ala Val Ser Trp Val Arg Gln Ala Pro Gly Gln
    50                  55                  60

Gly Leu Glu Trp Met Gly Gly Ile Ile Pro Ile Phe Gly Ile Ala Asn
65                  70                  75                  80

Tyr Ala Gln Lys Phe Gln Gly Arg Val Thr Ile Thr Ala Asp Thr Ser
                85                  90                  95

Thr Ser Thr Ala Tyr Met Glu Leu Ser Ser Leu Arg Ser Glu Asp Thr
            100                 105                 110

Ala Val Tyr Tyr Cys Ala Ile Glu Gly Ile Gly Gly Asp Leu Arg Tyr
        115                 120                 125

Asp Gly Tyr Asp Ala Trp Gly Gln Gly Thr Leu Val Thr Val Ser Ser
    130                 135                 140

Gly Gly Gly Gly Ser Gly Gly Gly Ser Gly Gly Gly Gly Ser Glu
145                 150                 155                 160

Ile Val Leu Thr Gln Ser Pro Gly Thr Leu Ser Leu Ser Pro Gly Glu
                165                 170                 175

Arg Ala Thr Leu Ser Cys Arg Ala Ser Gln Ser Val Ser His Ser Tyr
            180                 185                 190

Leu Ala Trp Tyr Gln Gln Lys Pro Gly Gln Ala Pro Arg Leu Leu Ile
        195                 200                 205

Tyr Gly Ala Ser Phe Arg Ala Ala Gly Ile Pro Asp Arg Phe Ser Gly
    210                 215                 220

Ser Gly Ser Gly Thr Asp Phe Thr Leu Thr Ile Ser Arg Leu Glu Pro
225                 230                 235                 240

Glu Asp Phe Ala Val Tyr Tyr Cys Gln Gln Tyr Gly Ser Asp Pro Tyr
                245                 250                 255

Thr Phe Gly Gln Gly Thr Lys Val Glu Ile Lys Thr Thr Thr Pro Ala
            260                 265                 270

Pro Arg Pro Pro Thr Pro Ala Pro Thr Ile Ala Ser Gln Pro Leu Ser
        275                 280                 285

Leu Arg Pro Glu Ala Cys Arg Pro Ala Ala Gly Gly Ala Val His Thr
    290                 295                 300

Arg Gly Leu Asp Phe Ala Cys Asp Ile Tyr Ile Trp Ala Pro Leu Ala
305                 310                 315                 320
```

```
Gly Thr Cys Gly Val Leu Leu Ser Leu Ile Thr Leu Tyr Cys
                325                 330                 335

Lys Arg Gly Arg Lys Lys Leu Leu Tyr Ile Phe Lys Gln Pro Phe Met
                340                 345                 350

Arg Pro Val Gln Thr Thr Gln Glu Glu Asp Gly Cys Ser Cys Arg Phe
                355                 360                 365

Pro Glu Glu Glu Glu Gly Gly Cys Glu Leu Arg Val Lys Phe Ser Arg
370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
                450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490

<210> SEQ ID NO 242
<211> LENGTH: 492
<212> TYPE: PRT
<213> ORGANISM: Artificial Sequence
<220> FEATURE:
<223> OTHER INFORMATION: artificial amino acid sequence

<400> SEQUENCE: 242

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
                20                  25                  30

Val Gln Pro Gly Gly Ser Leu Arg Leu Ser Cys Ala Ala Ser Gly Phe
            35                  40                  45

Ile Phe Ala Ser Tyr Ala Met Ser Trp Val Arg Gln Ala Pro Gly Lys
        50                  55                  60

Gly Leu Glu Trp Val Ser Glu Ile Ser Ser Gly Gly Ser Thr Thr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Arg Val Met Ala Gly Leu Gly Tyr
        115                 120                 125

Asp Pro Phe Asp Tyr Trp Gly Gln Gly Thr Leu Val Thr Val Ser Ser
    130                 135                 140

Gly Gly Gly Gly Ser Gly Gly Gly Gly Ser Gly Gly Gly Gly Ser Gln
145                 150                 155                 160

Ser Val Leu Thr Gln Pro Pro Ser Ala Ser Gly Thr Pro Gly Gln Arg
                165                 170                 175

Val Thr Ile Ser Cys Ser Gly Ser Ser Asn Ile Gly Ser Asn Tyr
            180                 185                 190
```

Val Tyr Trp Tyr Gln Gln Leu Pro Gly Thr Ala Pro Lys Leu Leu Ile
        195                 200                 205

Tyr Arg Asn Asn Gln Arg Pro Ser Gly Val Pro Asp Arg Phe Ser Gly
210                 215                 220

Ser Lys Ser Gly Thr Ser Ala Ser Leu Ala Ile Ser Gly Leu Arg Ser
225                 230                 235                 240

Glu Asp Glu Ala Asp Tyr Tyr Cys Ala Ala Trp Asp Asp Ser Leu Ser
                245                 250                 255

Gly Val Val Phe Gly Gly Gly Thr Lys Leu Thr Val Leu Thr Thr Thr
                260                 265                 270

Pro Ala Pro Arg Pro Pro Thr Pro Ala Pro Thr Ile Ala Ser Gln Pro
                275                 280                 285

Leu Ser Leu Arg Pro Glu Ala Cys Arg Pro Ala Ala Gly Gly Ala Val
                290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Gly Gly Cys Glu Leu Arg Val Lys Phe
                370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 243
<211> LENGTH: 487
<212> TYPE: PRT
<213> ORGANISM: Artificial Sequence
<220> FEATURE:
<223> OTHER INFORMATION: artificial amino acid sequence

<400> SEQUENCE: 243

Met Ala Leu Pro Val Thr Ala Leu Leu Leu Pro Leu Ala Leu Leu Leu
1               5                   10                  15

His Ala Ala Arg Pro Gln Val Gln Leu Val Gln Ser Gly Ala Glu Val
                20                  25                  30

Lys Lys Pro Gly Ser Ser Val Lys Val Ser Cys Lys Ala Ser Gly Gly
            35                  40                  45

Thr Phe Met Ser Tyr Ala Ile Ser Trp Val Arg Gln Ala Pro Gly Gln
        50                  55                  60

```
Gly Leu Glu Trp Met Gly Gly Ile Ile Pro Ile Phe Gly Ile Ala Asn
 65                  70                  75                  80

Tyr Ala Gln Lys Phe Gln Gly Arg Val Thr Ile Thr Ala Asp Lys Ser
                 85                  90                  95

Thr Ser Thr Ala Tyr Met Glu Leu Ser Ser Leu Arg Ser Glu Asp Thr
            100                 105                 110

Ala Val Tyr Tyr Cys Ala Arg Glu Thr Leu Ile Tyr Pro Ile Pro Phe
        115                 120                 125

Glu Leu Trp Gly Gln Gly Thr Leu Val Thr Val Ser Ser Gly Gly Gly
    130                 135                 140

Gly Ser Gly Gly Gly Gly Ser Gly Gly Gly Ser Glu Ile Val Leu
145                 150                 155                 160

Thr Gln Ser Pro Gly Thr Leu Ser Leu Ser Pro Gly Glu Arg Ala Thr
                165                 170                 175

Leu Ser Cys Arg Ala Ser Gln Ile Val Ser Ser Ser Tyr Leu Ala Trp
            180                 185                 190

Tyr Gln Gln Lys Pro Gly Gln Ala Pro Arg Leu Leu Ile Tyr Gly Ala
        195                 200                 205

Ser Ser Arg Ala Ser Gly Ile Pro Asp Arg Phe Ser Gly Ser Gly Ser
210                 215                 220

Gly Thr Asp Phe Thr Leu Thr Ile Ser Arg Leu Glu Pro Glu Asp Phe
225                 230                 235                 240

Ala Val Tyr Tyr Cys Gln Gln Tyr Gly Gly Ser Pro Tyr Thr Phe Gly
                245                 250                 255

Gln Gly Thr Lys Val Glu Ile Lys Thr Thr Pro Ala Pro Arg Pro
                260                 265                 270

Pro Thr Pro Ala Pro Thr Ile Ala Ser Gln Pro Leu Ser Leu Arg Pro
                275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480
```

Met Gln Ala Leu Pro Pro Arg
            485

<210> SEQ ID NO 244
<211> LENGTH: 482
<212> TYPE: PRT
<213> ORGANISM: Artificial Sequence
<220> FEATURE:
<223> OTHER INFORMATION: artificial amino acid sequence

<400> SEQUENCE: 244

Met Ala Leu Pro Val Thr Ala Leu Leu Leu Pro Leu Ala Leu Leu Leu
1               5                   10                  15

His Ala Ala Arg Pro Glu Val Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Val Met Asn Trp Val Arg Gln Ala Pro Gly Lys
    50                  55                  60

Gly Leu Glu Trp Val Ser Ala Ile Ser Gly Ser Gly Ala Thr Thr Tyr
65                  70                  75                  80

Tyr Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Val Ser Gly Leu Trp Ala Gly Gly Ile Trp Gly
        115                 120                 125

Gln Gly Thr Leu Val Thr Val Ser Ser Gly Gly Gly Ser Gly Gly
    130                 135                 140

Gly Gly Ser Gly Gly Gly Ser Asp Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Ser Ile Ser Ser Tyr Leu Asn Trp Tyr Gln Gln Lys Pro
            180                 185                 190

Gly Lys Ala Pro Lys Leu Leu Ile Tyr Asp Ala Ser Asp Leu Gln Arg
        195                 200                 205

Gly Val Pro Ser Arg Phe Ser Gly Ser Gly Ser Gly Thr Asp Phe Thr
    210                 215                 220

Leu Thr Ile Ser Ser Leu Gln Pro Glu Asp Phe Ala Thr Tyr Tyr Cys
225                 230                 235                 240

Gln Gln Ser Tyr Asn Thr Pro Trp Thr Phe Gly Gln Gly Thr Lys Val
                245                 250                 255

Glu Ile Lys Thr Thr Thr Pro Ala Pro Arg Pro Pro Thr Pro Ala Pro
            260                 265                 270

Thr Ile Ala Ser Gln Pro Leu Ser Leu Arg Pro Glu Ala Cys Arg Pro
        275                 280                 285

Ala Ala Gly Gly Ala Val His Thr Arg Gly Leu Asp Phe Ala Cys Asp
    290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

```
Glu Asp Gly Cys Ser Cys Arg Phe Pro Glu Glu Glu Gly Gly Cys
            355                 360                 365

Glu Leu Arg Val Lys Phe Ser Arg Ser Ala Asp Ala Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
                405                 410                 415

Gly Lys Pro Arg Lys Asn Pro Gln Glu Gly Leu Tyr Asn Glu Leu
                420                 425                 430

Gln Lys Asp Lys Met Ala Glu Ala Tyr Ser Glu Ile Gly Met Lys Gly
            435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg

<210> SEQ ID NO 245
<211> LENGTH: 351
<212> TYPE: DNA
<213> ORGANISM: Artificial Sequence
<220> FEATURE:
<223> OTHER INFORMATION: artificial nucleotide sequence

<400> SEQUENCE: 245
caggtgcagc tggtgcagag cggagcagag gtgaagaagc caggcagctc cgtgaaggtg      60
tcctgcaagg cctctggcgg cacattctct agctacgcca tccagtgggt gcggcaggca     120
ccaggacagg gcctggagtg gatgggagga atcgtgggaa gctggggcct ggcaaactac     180
gcccagaagt ttcagggcag agtgaccatc accaccgata gtctacaag caccgcctat     240 atggagctgt cctctctgag gtccgaggac acagccgtgt actattgcgc cacctccgcc     300
ttcggcgagc tggcatcttg gggacagggc acactggtga ccgtgagctc c              351

<210> SEQ ID NO 246
<211> LENGTH: 325
<212> TYPE: DNA
<213> ORGANISM: Artificial Sequence
<220> FEATURE:
<223> OTHER INFORMATION: artificial nucleotide sequence

<400> SEQUENCE: 246
gagatcgtgc tgacacagag cccaggcacc ctgtccctgt ctccaggaga gagggccaca      60
ctgtcctgta gggccagcca gtccgtgcct tctagccagc tggccctggta ccagcagaag    120 ccaggccagg cccccagact gctgatctat gacgcctcct ctagagccac aggcatccca    180
gataggttct ctggcagcgg ctccggcacc gactttacac tgaccatctc caggctggag    240
cccgaggatt tcgccgtgta ctattgccag cagtacggca gctcccctct gacatttggc    300
cagggcacca aggtggagat caagg                                           325

<210> SEQ ID NO 247
<211> LENGTH: 357
<212> TYPE: DNA
<213> ORGANISM: Artificial Sequence
<220> FEATURE:
<223> OTHER INFORMATION: artificial nucleotide sequence

<400> SEQUENCE: 247
```

```
caggtgcagc tggtgcagag cggagcagag gtgaagaagc ccggcagctc cgtgaaggtg      60
tcttgcaagg ccagcggcgg cacattctct agctacgata tctcttgggt gaggcaggcc     120
ccaggccagg gactggagtg gatgggagga atcatccccg tgagcggaag ggcaaactac     180
gcacagaagt ttcagggccg ggtgaccatc accacagaca agtccacatc taccgcctat     240
atggagctgt cctctctgag aagcgaggat acagccgtgt actattgcgc cagagtgagg     300
cctacctact ggccactgga ctattggggc cagggcacac tggtgaccgt gagctcc        357

<210> SEQ ID NO 248
<211> LENGTH: 321
<212> TYPE: DNA
<213> ORGANISM: Artificial Sequence
<220> FEATURE:
<223> OTHER INFORMATION: artificial nucleotide sequence

<400> SEQUENCE: 248
gacatccaga tgacccagtc cccatctagc ctgagcgcct ccgtgggcga tagagtgaca      60
atcacctgta gggcctctca gagcatctcc tcttacctga attggtatca gcagaagccc     120
ggcaaggccc ctaagctgct gatctacgca gcaagctccc tgcagtccgg agtgccatct     180
cggttctccg gctctggcag cggcacagac tttacactga ccatctctag cctgcagcct     240
gaggatttcg ccacctacta ttgccagcag tcctattcta caccactgac ctttggccag     300
ggcacaaagg tggagatcaa g                                               321

<210> SEQ ID NO 249
<211> LENGTH: 369
<212> TYPE: DNA
<213> ORGANISM: Artificial Sequence
<220> FEATURE:
<223> OTHER INFORMATION: artificial nucleotide sequence

<400> SEQUENCE: 249
gaggtgcagc tgctggagag cggcggcggc ctggtgcagc ctggcggctc tctgagactg      60
agctgcgcag catccggctt catctttgcc tcttacgcaa tgagctgggt gaggcaggcc     120
cctggcaagg gactggagtg ggtgagcgag atcagctcct ctggcggcag caccacatat     180
gccgactccg tgaagggccg cttcacaatc agccgggaca actctaagaa taccctgtac     240
ctgcagatga actccctgag agccgaggac acagccgtgt actattgcgc cagagataga     300
gtgatggccg cctgggcta tgacccattt gattactggg gccagggcac actggtgacc     360
gtgagctcc                                                             369

<210> SEQ ID NO 250
<211> LENGTH: 330
<212> TYPE: DNA
<213> ORGANISM: Artificial Sequence
<220> FEATURE:
<223> OTHER INFORMATION: artificial nucleotide sequence

<400> SEQUENCE: 250
cagagcgtgc tgacccagcc accttccgcc tctggaacac ccggccagag ggtgaccatc      60
agctgttccg gctctagctc caacatcggc tccaattacg tgtattggta ccagcagctg     120
cccggcacag cccctaagct gctgatctac agaaacaatc agaggccatc tggcgtgccc     180
gaccgcttct ctggcagcaa gtccggcacc tctgccagcc tggcaatcag cggactgcgg     240
tccgaggacg aggccgatta ctattgcgca gcatgggacg attccctgtc tggagtggtg     300
```

```
tttggcggcg gcacaaagct gaccgtgctg                                    330
```

<210> SEQ ID NO 251
<211> LENGTH: 360
<212> TYPE: DNA
<213> ORGANISM: Artificial Sequence
<220> FEATURE:
<223> OTHER INFORMATION: artificial nucleotide sequence

<400> SEQUENCE: 251

```
caggtgcagc tggtgcagag cggagcagag gtgaagaagc tggcagctc cgtgaaggtg    60
tcttgcaagg ccagcggcgg cacattctct agctacacca tctcctgggt gcggcaggcc   120
ccaggccagg gactggagtg gatgggagga atcatcccag ccttcggcat cgccaactac   180
gcccagaagt tcagggccg cgtgacaatc accgccgaca agtccacatc taccgcctat   240
atggagctgt cctctctgcg gagcgaggat accgccgtgt actattgcgc caagggcggc   300
agctactccc tggactattt tgatatctgg ggccagggca cactggtgac cgtgagctcc   360
```

<210> SEQ ID NO 252
<211> LENGTH: 321
<212> TYPE: DNA
<213> ORGANISM: Artificial Sequence
<220> FEATURE:
<223> OTHER INFORMATION: artificial nucleotide sequence

<400> SEQUENCE: 252

```
gagatcgtgc tgacacagtc ccctggcacc ctgtctctga gcccaggcga gagggccaca    60
ctgtcctgta gggcatctca gtacgtgtcc gcctctctgc tggcctggta tcagcagaag   120
cctggccagg ccccaagact gctgatctac ggagcatcca agagccac cggcatcccc     180
gacaggttca gcggctccgg ctctggaacc gacttcaccc tgaccatctc tagactggag   240
cctgaggact cgccgtgta ctattgccag cagtatgcca ggtctagcac atttggccag    300
ggcaccaagg tggagatcaa g                                              321
```

<210> SEQ ID NO 253
<211> LENGTH: 1455
<212> TYPE: DNA
<213> ORGANISM: Artificial Sequence
<220> FEATURE:
<223> OTHER INFORMATION: artificial nucleotide sequence

<400> SEQUENCE: 253

```
atggctctgc ccgtcaccgc tctgctgctg ccactggccc tgctgctgca cgccgctcgc    60
ccccaggtgc agctggtcca gagcggagcc gaggtgaaga accaggcag ctccgtgaag    120
gtcagctgca aggccagcgg cgggacattc tctagttacg ccatccagtg ggtgcggcag   180
gcccctggcc agggactgga atggatggga ggcattgtcg gctcttgggg gctggccaac   240
tacgctcaga gtttcagggg cagagtgacc atcaccacag ataaatcaac aagcactgca   300
tatatggagc tgtcaagcct gaggagcgaa gacaccgccg tctactattg cgcaacatct   360
gccttcggcg agctggctag ttggggacag gggacactgg tgactgtctc ctctggggga   420
ggaggatcag gaggaggagg aagcggagga ggaggctccg agattgtgct gactcagagc   480
cccggcaccc tgagcctgtc tcctggagaa cgggctacac tgagctgtag agcaagtcag   540
tcagtgccta gttcacagct ggcctggtac cagcagaagc ccggacaggc tcctagactg   600
ctgatctatg acgccagctc cagggctaca ggcattccag atcgcttcag cggatccggc   660
tctgggactg actttaccct gacaatctcc aggctggagc ctgaagattt cgccgtgtac   720
```

-continued

```
tattgccagc agtacggctc tagtccactg acatttggac agggcactaa ggtcgagatc    780
aaaactacca caccagcacc acgaccacct acccctgcac caacaattgc ctctcagcct    840
ctgagtctga gaccagaggc ctgcaggcca gcagcaggag gagcagtgca caccagaggc    900
ctggactttg cctgcgatat ctatatttgg gctcctctgg caggaacttg tggcgtgctg    960
ctgctgtccc tggtcatcac cctgtactgc aagcgaggcc ggaagaaact gctgtatatt   1020
ttcaaacagc ccttcatgcg acccgtgcag actacccagg aggaagatgg ctgcagctgt   1080
cggttccccg aggaagagga aggcgggtgt gagctgcgcg tcaagtttag tcgatcagct   1140
gacgcacctg cctaccagca gggccagaat cagctgtata cgagctgaa tctgggcgg     1200 agagaggaat acgacgtgct ggataaaagg cgaggaaggg acccagaaat gggaggcaag   1260
cctcgacgga aaaacccaca ggagggcctg tacaatgaac tgcagaagga taaaatggct   1320
gaggcatata gcgaaatcgg gatgaaggga gagagaaggc gcgggaaagg acatgacggc   1380
ctgtaccagg ggctgtccac tgcaaccaag gacacctatg atgccctgca tatgcaggca   1440
ctgcctccaa ggtga                                                    1455
```

<210> SEQ ID NO 254
<211> LENGTH: 185
<212> TYPE: PRT
<213> ORGANISM: Artificial Sequence
<220> FEATURE:
<223> OTHER INFORMATION: artificial amino acid sequence

<400> SEQUENCE: 254

```
Asn Thr Leu Leu Tyr Thr Leu Arg Arg Pro Tyr Phe Arg Lys Met Glu
 1               5                  10                  15

Asn Gln Asp Ala Leu Val Cys Ile Ser Glu Ser Val Pro Glu Pro Ile
            20                  25                  30

Val Glu Trp Val Leu Cys Asp Ser Gln Gly Glu Ser Cys Lys Glu Glu
        35                  40                  45

Ser Pro Ala Val Val Lys Lys Glu Glu Lys Val Leu His Glu Leu Phe
    50                  55                  60

Gly Thr Asp Ile Arg Cys Cys Ala Arg Asn Glu Leu Gly Arg Glu Cys
65                  70                  75                  80

Thr Arg Leu Phe Thr Ile Asp Leu Asn Gln Thr Pro Gln Thr Thr Leu
                85                  90                  95

Pro Gln Leu Phe Leu Lys Val Gly Glu Pro Leu Trp Ile Arg Cys Lys
           100                 105                 110

Ala Val His Val Asn His Gly Phe Gly Leu Thr Trp Glu Leu Glu Asn
       115                 120                 125

Lys Ala Leu Glu Glu Gly Asn Tyr Phe Glu Met Ser Thr Tyr Ser Thr
   130                 135                 140

Asn Arg Thr Met Ile Arg Ile Leu Phe Ala Phe Val Ser Ser Val Ala
145                 150                 155                 160

Arg Asn Asp Thr Gly Tyr Tyr Thr Cys Ser Ser Ser Lys His Pro Ser
                165                 170                 175

Gln Ser Ala Leu Val Thr Ile Val Glu
            180                 185
```

<210> SEQ ID NO 255
<211> LENGTH: 24
<212> TYPE: PRT
<213> ORGANISM: Homo sapiens

```
<400> SEQUENCE: 255

Asn Ser Glu Leu Leu Ser Leu Ile Asn Asp Met Pro Ile Thr Asn Asp
1               5                   10                  15

Gln Lys Lys Leu Met Ser Asn Asn
            20

<210> SEQ ID NO 256
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 256

Cys Gln Phe Asp Leu Ser Thr Arg Arg Leu Lys Cys
1               5                   10

<210> SEQ ID NO 257
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 257

Cys Gln Tyr Asn Leu Ser Ser Arg Ala Leu Lys Cys
1               5                   10

<210> SEQ ID NO 258
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 258

Cys Val Trp Gln Arg Trp Gln Lys Ser Tyr Val Cys
1               5                   10

<210> SEQ ID NO 259
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 259

Cys Met Trp Asp Arg Phe Ser Arg Trp Tyr Lys Cys
1               5                   10

<210> SEQ ID NO 260
<211> LENGTH: 25
<212> TYPE: PRT
<213> ORGANISM: Homo sapiens

<400> SEQUENCE: 260

Ser Phe Val Leu Asn Trp Tyr Arg Met Ser Pro Ser Asn Gln Thr Asp
1               5                   10                  15

Lys Leu Ala Ala Phe Pro Glu Asp Arg
            20                  25

<210> SEQ ID NO 261
<211> LENGTH: 19
<212> TYPE: PRT
<213> ORGANISM: Homo sapiens
```

-continued

<400> SEQUENCE: 261

Ser Gly Thr Tyr Leu Cys Gly Ala Ile Ser Leu Ala Pro Lys Ala Gln
1               5                   10                  15

Ile Lys Glu

<210> SEQ ID NO 262
<211> LENGTH: 24
<212> TYPE: PRT
<213> ORGANISM: Artificial Sequence
<220> FEATURE:
<223> OTHER INFORMATION: mAb-specific epitope

<400> SEQUENCE: 262

Glu Leu Pro Thr Gln Gly Thr Phe Ser Asn Val Ser Thr Asn Val Ser
1               5                   10                  15

Pro Ala Lys Pro Thr Thr Thr Ala
            20

<210> SEQ ID NO 263
<211> LENGTH: 12
<212> TYPE: PRT
<213> ORGANISM: Artificial Sequence
<220> FEATURE:
<223> OTHER INFORMATION: mAb-specific epitope

<400> SEQUENCE: 263

Gly Gln Asn Asp Thr Ser Gln Thr Ser Ser Pro Ser
1               5                   10

<210> SEQ ID NO 264
<211> LENGTH: 108
<212> TYPE: PRT
<213> ORGANISM: Artificial Sequence
<220> FEATURE:
<223> OTHER INFORMATION: mAb P08B06EE heavy chain

<400> SEQUENCE: 264

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser His Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Phe Arg Ala Ala Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Glu Pro
                85                  90                  95

Tyr Thr Phe Gly Gln Gly Thr Lys Val Glu Ile Lys
            100                 105

<210> SEQ ID NO 265
<211> LENGTH: 123
<212> TYPE: PRT
<213> ORGANISM: Artificial Sequence
<220> FEATURE:
<223> OTHER INFORMATION: mAb P08B06EE light chain

<400> SEQUENCE: 265

Gln Val Gln Leu Val Gln Ser Gly Ala Glu Val Lys Lys Pro Gly Ser

```
1               5                   10                  15
Ser Val Lys Val Ser Cys Lys Ala Ser Gly Gly Thr Phe Ser Ser Tyr
            20                  25                  30

Ala Val Ser Trp Val Arg Gln Ala Pro Gly Gln Gly Leu Glu Trp Met
            35                  40                  45

Gly Gly Ile Ile Pro Ile Phe Gly Ile Ala Asn Tyr Ala Gln Lys Phe
            50                  55                  60

Gln Gly Arg Val Thr Ile Thr Ala Asp Thr Ser Thr Ser Thr Ala Tyr
65                      70                  75                  80

Met Glu Leu Ser Ser Leu Arg Ser Glu Asp Thr Ala Val Tyr Tyr Cys
                    85                  90                  95

Ala Ile Glu Gly Ile Gly Gly Asp Leu Arg Tyr Glu Gly Tyr Asp Ala
                    100                 105                 110

Trp Gly Gln Gly Thr Leu Val Thr Val Ser Ser
            115                 120
```

<210> SEQ ID NO 266
<211> LENGTH: 109
<212> TYPE: PRT
<213> ORGANISM: Artificial Sequence
<220> FEATURE:
<223> OTHER INFORMATION: mAb P04A04 heavy chain

<400> SEQUENCE: 266

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Ser
            20                  25                  30

Gln Leu Ala Trp Tyr Gln Gln Lys Pro Gly Gln Ala Pro Arg Leu Leu
            35                  40                  45

Ile Tyr Asp Ala Ser Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
65                      70                  75                  80

Pro Glu Asp Phe Ala Val Tyr Tyr Cys Gln Gln Tyr Gly Ser Ser Leu
                    85                  90                  95

Leu Ile Thr Phe Gly Gln Gly Thr Lys Val Glu Ile Lys
                    100                 105
```

<210> SEQ ID NO 267
<211> LENGTH: 117
<212> TYPE: PRT
<213> ORGANISM: Artificial Sequence
<220> FEATURE:
<223> OTHER INFORMATION: mAb P04A04 light chain

<400> SEQUENCE: 267

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Tyr Ile Thr Trp Val Arg Gln Ala Pro Gly Gln Gly Leu Glu Trp Met
            35                  40                  45

Gly Arg Ile Met Pro Ala Phe Gly Trp Thr Asn Tyr Ala Gln Lys Phe
            50                  55                  60

Gln Gly Arg Val Thr Ile Thr Asp Lys Ser Thr Ser Thr Ala Tyr
65                      70                  75                  80
```

```
Met Glu Leu Ser Ser Leu Arg Ser Glu Asp Thr Ala Val Tyr Tyr Cys
                85                  90                  95

Ala Ser Asp Glu Phe Gly Ala Phe Asp Val Trp Gly Gln Gly Thr Leu
            100                 105                 110

Val Thr Val Ser Ser
            115

<210> SEQ ID NO 268
<211> LENGTH: 108
<212> TYPE: PRT
<213> ORGANISM: Artificial Sequence
<220> FEATURE:
<223> OTHER INFORMATION: mAb P01A05 heavy chain

<400> SEQUENCE: 268

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ala Val Asp Ser Ser
            20                  25                  30

Asp Leu Ala Trp Tyr Gln His Lys Pro Gly Gln Ala Pro Arg Leu Leu
            35                  40                  45

Ile Tyr Asp Ala Tyr Thr Arg Pro Ser Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Leu Glu Ile Lys
            100                 105

<210> SEQ ID NO 269
<211> LENGTH: 117
<212> TYPE: PRT
<213> ORGANISM: Artificial Sequence
<220> FEATURE:
<223> OTHER INFORMATION: mAb P01A05 light chain

<400> SEQUENCE: 269

Gln Val Gln Leu Val Gln Ser Gly Ala Glu Val Lys Lys Pro Gly Ser
1               5                   10                  15

Ser Val Lys Val Ser Cys Lys Ala Ser Gly Gly Val Phe Ser Arg Tyr
            20                  25                  30

Ala Leu Ser Trp Val Arg Gln Ala Pro Gly Gln Gly Leu Glu Trp Met
            35                  40                  45

Gly Gly Ile Ile Pro Met Leu Gly Phe Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Leu Asp Phe Gly Ala Leu Asp Tyr Trp Gly Gln Gly Thr Leu
            100                 105                 110

Val Thr Val Ser Ser
            115

<210> SEQ ID NO 270
<211> LENGTH: 106
<212> TYPE: PRT
<213> ORGANISM: Artificial Sequence
```

```
<220> FEATURE:
<223> OTHER INFORMATION: mAb P08B03 heavy chain

<400> SEQUENCE: 270

Asp Ile Val Met Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Pro Tyr Thr
                85                  90                  95

Phe Gly Gln Gly Thr Lys Val Glu Ile Lys
            100                 105

<210> SEQ ID NO 271
<211> LENGTH: 121
<212> TYPE: PRT
<213> ORGANISM: Artificial Sequence
<220> FEATURE:
<223> OTHER INFORMATION: mAb P08B03 light chain

<400> SEQUENCE: 271

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Asp Ile Ser Trp Val Arg Gln Ala Pro Gly Gln Gly Leu Glu Trp Met
        35                  40                  45

Gly Arg Ile Ile Pro Ser Phe Gly Ala Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Asp Asp Gly Glu Gly Trp Thr Pro Pro Phe Gly Tyr Trp Gly
            100                 105                 110

Gln Gly Thr Leu Val Thr Val Ser Ser
        115                 120

<210> SEQ ID NO 272
<211> LENGTH: 107
<212> TYPE: PRT
<213> ORGANISM: Artificial Sequence
<220> FEATURE:
<223> OTHER INFORMATION: mAb P5F7 heavy chain

<400> SEQUENCE: 272

Asp Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45
```

```
Tyr Asp Thr Phe Thr Arg Ala Thr Gly Ile Pro Ala Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro Pro
                 85                  90                  95

Thr Phe Gly Gln Gly Thr Arg Leu Glu Ile Lys
            100                 105

<210> SEQ ID NO 273
<211> LENGTH: 124
<212> TYPE: PRT
<213> ORGANISM: Artificial Sequence
<220> FEATURE:
<223> OTHER INFORMATION: mAb P5F7 light chain

<400> SEQUENCE: 273

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 274
<211> LENGTH: 107
<212> TYPE: PRT
<213> ORGANISM: Artificial Sequence
<220> FEATURE:
<223> OTHER INFORMATION: mAb P5F7g heavy chain

<400> SEQUENCE: 274

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Phe Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Gly Ser Ser Pro Pro
                 85                  90                  95

Thr Phe Gly Gln Gly Thr Arg Leu Glu Ile Lys
            100                 105

<210> SEQ ID NO 275
```

```
<211> LENGTH: 124
<212> TYPE: PRT
<213> ORGANISM: Artificial Sequence
<220> FEATURE:
<223> OTHER INFORMATION: mAb P5F7g light chain

<400> SEQUENCE: 275
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

```
<210> SEQ ID NO 276
<211> LENGTH: 107
<212> TYPE: PRT
<213> ORGANISM: Artificial Sequence
<220> FEATURE:
<223> OTHER INFORMATION: mAb P10A02g heavy chain

<400> SEQUENCE: 276
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Asp Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ala Ser Ser Pro Ile
                85                  90                  95

Thr Phe Gly Gln Gly Thr Arg Leu Glu Ile Lys
            100                 105

```
<210> SEQ ID NO 277
<211> LENGTH: 124
<212> TYPE: PRT
<213> ORGANISM: Artificial Sequence
<220> FEATURE:
<223> OTHER INFORMATION: mAb P10A02g light chain

<400> SEQUENCE: 277
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
            35                  40                  45

Ser Ser Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
            115                 120

<210> SEQ ID NO 278
<211> LENGTH: 107
<212> TYPE: PRT
<213> ORGANISM: Artificial Sequence
<220> FEATURE:
<223> OTHER INFORMATION: mAb P10A04g heavy chain

<400> SEQUENCE: 278

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Lys Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Thr Gly Ser Pro Ile
                85                  90                  95

Thr Phe Gly Gln Gly Thr Arg Leu Glu Ile Lys
            100                 105

<210> SEQ ID NO 279
<211> LENGTH: 124
<212> TYPE: PRT
<213> ORGANISM: Artificial Sequence
<220> FEATURE:
<223> OTHER INFORMATION: mAb P10A04g light chain

<400> SEQUENCE: 279

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

```
Ile Trp Gly Gln Gly Thr Leu Val Thr Val Ser Ser
        115                 120
```

<210> SEQ ID NO 280
<211> LENGTH: 107
<212> TYPE: PRT
<213> ORGANISM: Artificial Sequence
<220> FEATURE:
<223> OTHER INFORMATION: mAb P10A05g heavy chain

<400> SEQUENCE: 280

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Leu Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Ser Asn Pro Ile
                85                  90                  95

Thr Phe Gly Gln Gly Thr Arg Leu Glu Ile Lys
            100                 105
```

<210> SEQ ID NO 281
<211> LENGTH: 124
<212> TYPE: PRT
<213> ORGANISM: Artificial Sequence
<220> FEATURE:
<223> OTHER INFORMATION: mAb P10A05g light chain

<400> SEQUENCE: 281

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120
```

<210> SEQ ID NO 282
<211> LENGTH: 107
<212> TYPE: PRT
<213> ORGANISM: Artificial Sequence
<220> FEATURE:
<223> OTHER INFORMATION: mAb P10A07g heavy chain

<400> SEQUENCE: 282

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gly Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Ser Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ala Ser Tyr Pro Ile
                85                  90                  95

Thr Phe Gly Gln Gly Thr Arg Leu Glu Ile Lys
            100                 105
```

<210> SEQ ID NO 283
<211> LENGTH: 124
<212> TYPE: PRT
<213> ORGANISM: Artificial Sequence
<220> FEATURE:
<223> OTHER INFORMATION: mAb P10A07g light chain

<400> SEQUENCE: 283

```
Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Val Gly Trp Gly Tyr Gly Phe Asp
            100                 105                 110

Ile Trp Gly Gln Gly Thr Leu Val Thr Val Ser Ser
        115                 120
```

<210> SEQ ID NO 284
<211> LENGTH: 107
<212> TYPE: PRT
<213> ORGANISM: Artificial Sequence
<220> FEATURE:
<223> OTHER INFORMATION: mAb P10B03g heavy chain

<400> SEQUENCE: 284

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Phe Ser Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80
```

-continued

Glu Asp Phe Ala Val Tyr Tyr Cys Gln Gln Tyr Gly Thr Pro Pro Ile
                85                  90                  95

Thr Phe Gly Gln Gly Thr Arg Leu Glu Ile Lys
            100                 105

<210> SEQ ID NO 285
<211> LENGTH: 124
<212> TYPE: PRT
<213> ORGANISM: Artificial Sequence
<220> FEATURE:
<223> OTHER INFORMATION: mAb P10B03g light chain

<400> SEQUENCE: 285

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 286
<211> LENGTH: 107
<212> TYPE: PRT
<213> ORGANISM: Artificial Sequence
<220> FEATURE:
<223> OTHER INFORMATION: mAb P10B06g heavy chain

<400> SEQUENCE: 286

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Glu Ser Val Ser Asp Leu
            20                  25                  30

Leu Ala Trp Tyr Gln Gln Lys Pro Gly Gln Ala Pro Arg Leu Leu Ile
        35                  40                  45

Tyr Asp Ala Tyr Ser Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Ser Ala Ser Pro Ile
                85                  90                  95

Thr Phe Gly Gln Gly Thr Arg Leu Glu Ile Lys
            100                 105

<210> SEQ ID NO 287
<211> LENGTH: 124
<212> TYPE: PRT
<213> ORGANISM: Artificial Sequence
<220> FEATURE:
<223> OTHER INFORMATION: mAb P10B06g light chain

<400> SEQUENCE: 287

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ser Ile Ser Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
            115                 120

<210> SEQ ID NO 288
<211> LENGTH: 107
<212> TYPE: PRT
<213> ORGANISM: Artificial Sequence
<220> FEATURE:
<223> OTHER INFORMATION: mAb P5F7g2 heavy chain

<400> SEQUENCE: 288

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Thr Phe Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Gly Ser Ser Pro Pro
                85                  90                  95

Thr Phe Gly Gln Gly Thr Arg Leu Glu Ile Lys
            100                 105

<210> SEQ ID NO 289
<211> LENGTH: 124
<212> TYPE: PRT
<213> ORGANISM: Artificial Sequence
<220> FEATURE:
<223> OTHER INFORMATION: mAb P5F7g2 light chain

<400> SEQUENCE: 289

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Gly Arg Ser Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120
```

<210> SEQ ID NO 290
<211> LENGTH: 107
<212> TYPE: PRT
<213> ORGANISM: Artificial Sequence
<220> FEATURE:
<223> OTHER INFORMATION: mAb P5F7g3 heavy chain

<400> SEQUENCE: 290

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Leu
                 20                  25                  30

Leu Ala Trp Tyr Gln Gln Lys Pro Gly Gln Ala Pro Arg Leu Leu Ile
             35                  40                  45

Tyr Asp Ala Tyr Thr Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Tyr Thr Gly Ser Pro Ile
                 85                  90                  95

Thr Phe Gly Gln Gly Thr Arg Leu Glu Ile Lys
            100                 105
```

<210> SEQ ID NO 291
<211> LENGTH: 124
<212> TYPE: PRT
<213> ORGANISM: Artificial Sequence
<220> FEATURE:
<223> OTHER INFORMATION: mAb P5F7g3 light chain

<400> SEQUENCE: 291

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Ala Met Asn Trp Val Arg Gln Ala Pro Gly Lys Gly Leu Glu Trp Val
             35                  40                  45

Ser Ala Ile Ser Gly Gly Gly Arg Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120
```

```
<210> SEQ ID NO 292
<211> LENGTH: 107
<212> TYPE: PRT
<213> ORGANISM: Artificial Sequence
<220> FEATURE:
<223> OTHER INFORMATION: mAb P5F7g4 heavy chain

<400> SEQUENCE: 292

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Leu
            20                  25                  30

Leu Ala Trp Tyr Gln Gln Lys Pro Gly Gln Ala Pro Arg Leu Leu Ile
        35                  40                  45

Tyr Asp Ala Tyr Thr Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Thr Gly Ser Pro Ile
                85                  90                  95

Thr Phe Gly Gln Gly Thr Arg Leu Glu Ile Lys
            100                 105

<210> SEQ ID NO 293
<211> LENGTH: 124
<212> TYPE: PRT
<213> ORGANISM: Artificial Sequence
<220> FEATURE:
<223> OTHER INFORMATION: mAb P5F7g4 light chain

<400> SEQUENCE: 293

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Gly Gly Arg Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Pro Ser Asp Val Gly Trp Gly Tyr Gly Phe Asp
            100                 105                 110

Ile Trp Gly Gln Gly Thr Leu Val Thr Val Ser Ser
        115                 120

<210> SEQ ID NO 294
<211> LENGTH: 5
<212> TYPE: PRT
<213> ORGANISM: Artificial Sequence
<220> FEATURE:
<223> OTHER INFORMATION: mAb CDRH1

<400> SEQUENCE: 294

Ser Tyr Ala Val Ser
1               5

<210> SEQ ID NO 295
```

```
<211> LENGTH: 7
<212> TYPE: PRT
<213> ORGANISM: Artificial Sequence
<220> FEATURE:
<223> OTHER INFORMATION: mAb CDRH1

<400> SEQUENCE: 295

Gly Gly Thr Phe Ser Ser Tyr
1               5

<210> SEQ ID NO 296
<211> LENGTH: 10
<212> TYPE: PRT
<213> ORGANISM: Artificial Sequence
<220> FEATURE:
<223> OTHER INFORMATION: mAb CDRH1

<400> SEQUENCE: 296

Gly Gly Thr Phe Ser Ser Tyr Ala Val Ser
1               5                   10

<210> SEQ ID NO 297
<211> LENGTH: 17
<212> TYPE: PRT
<213> ORGANISM: Artificial Sequence
<220> FEATURE:
<223> OTHER INFORMATION: mAb CDRH2

<400> SEQUENCE: 297

Gly Ile Ile Pro Ile Phe Gly Ile Ala Asn Tyr Ala Gln Lys Phe Gln
1               5                   10                  15

Gly

<210> SEQ ID NO 298
<211> LENGTH: 6
<212> TYPE: PRT
<213> ORGANISM: Artificial Sequence
<220> FEATURE:
<223> OTHER INFORMATION: mAb CDRH2

<400> SEQUENCE: 298

Ile Pro Ile Phe Gly Ile
1               5

<210> SEQ ID NO 299
<211> LENGTH: 14
<212> TYPE: PRT
<213> ORGANISM: Artificial Sequence
<220> FEATURE:
<223> OTHER INFORMATION: mAb CDRH3

<400> SEQUENCE: 299

Glu Gly Ile Gly Gly Asp Leu Arg Tyr Glu Gly Tyr Asp Ala
1               5                   10

<210> SEQ ID NO 300
<211> LENGTH: 5
<212> TYPE: PRT
<213> ORGANISM: Artificial Sequence
<220> FEATURE:
<223> OTHER INFORMATION: mAb CDRH1

<400> SEQUENCE: 300

Ser Tyr Tyr Ile Thr
1               5
```

```
<210> SEQ ID NO 301
<211> LENGTH: 10
<212> TYPE: PRT
<213> ORGANISM: Artificial Sequence
<220> FEATURE:
<223> OTHER INFORMATION: mAb CDRH1

<400> SEQUENCE: 301

Gly Gly Thr Phe Ser Ser Tyr Tyr Ile Thr
1               5                   10

<210> SEQ ID NO 302
<211> LENGTH: 17
<212> TYPE: PRT
<213> ORGANISM: Artificial Sequence
<220> FEATURE:
<223> OTHER INFORMATION: mAb CDRH2

<400> SEQUENCE: 302

Arg Ile Met Pro Ala Phe Gly Trp Thr Asn Tyr Ala Gln Lys Phe Gln
1               5                   10                  15

Gly

<210> SEQ ID NO 303
<211> LENGTH: 6
<212> TYPE: PRT
<213> ORGANISM: Artificial Sequence
<220> FEATURE:
<223> OTHER INFORMATION: mAb CDRH2

<400> SEQUENCE: 303

Met Pro Ala Phe Gly Trp
1               5

<210> SEQ ID NO 304
<211> LENGTH: 8
<212> TYPE: PRT
<213> ORGANISM: Artificial Sequence
<220> FEATURE:
<223> OTHER INFORMATION: mAb CDRH3

<400> SEQUENCE: 304

Asp Glu Phe Gly Ala Phe Asp Val
1               5

<210> SEQ ID NO 305
<211> LENGTH: 5
<212> TYPE: PRT
<213> ORGANISM: Artificial Sequence
<220> FEATURE:
<223> OTHER INFORMATION: mAb CDRH1

<400> SEQUENCE: 305

Arg Tyr Ala Leu Ser
1               5

<210> SEQ ID NO 306
<211> LENGTH: 7
<212> TYPE: PRT
<213> ORGANISM: Artificial Sequence
<220> FEATURE:
<223> OTHER INFORMATION: mAb CDRH1

<400> SEQUENCE: 306

Gly Gly Val Phe Ser Arg Tyr
1               5
```

<210> SEQ ID NO 307
<211> LENGTH: 10
<212> TYPE: PRT
<213> ORGANISM: Artificial Sequence
<220> FEATURE:
<223> OTHER INFORMATION: mAb CDRH1

<400> SEQUENCE: 307

Gly Gly Val Phe Ser Arg Tyr Ala Leu Ser
1               5                   10

<210> SEQ ID NO 308
<211> LENGTH: 6
<212> TYPE: PRT
<213> ORGANISM: Artificial Sequence
<220> FEATURE:
<223> OTHER INFORMATION: mAb CDRH2

<400> SEQUENCE: 308

Ile Pro Met Leu Gly Phe
1               5

<210> SEQ ID NO 309
<211> LENGTH: 18
<212> TYPE: PRT
<213> ORGANISM: Artificial Sequence
<220> FEATURE:
<223> OTHER INFORMATION: mAb CDRH2

<400> SEQUENCE: 309

Gly Gly Ile Ile Pro Met Leu Gly Phe Ala Asn Tyr Ala Gln Lys Phe
1               5                   10                  15

Gln Gly

<210> SEQ ID NO 310
<211> LENGTH: 8
<212> TYPE: PRT
<213> ORGANISM: Artificial Sequence
<220> FEATURE:
<223> OTHER INFORMATION: mAb CDRH3

<400> SEQUENCE: 310

Leu Asp Phe Gly Ala Leu Asp Tyr
1               5

<210> SEQ ID NO 311
<211> LENGTH: 5
<212> TYPE: PRT
<213> ORGANISM: Artificial Sequence
<220> FEATURE:
<223> OTHER INFORMATION: mAb CDRH1

<400> SEQUENCE: 311

Ser Tyr Asp Ile Ser
1               5

<210> SEQ ID NO 312
<211> LENGTH: 10
<212> TYPE: PRT
<213> ORGANISM: Artificial Sequence
<220> FEATURE:
<223> OTHER INFORMATION: mAb CDRH1

<400> SEQUENCE: 312

Gly Gly Thr Phe Ser Ser Tyr Asp Ile Ser
1               5                   10

```
<210> SEQ ID NO 313
<211> LENGTH: 17
<212> TYPE: PRT
<213> ORGANISM: Artificial Sequence
<220> FEATURE:
<223> OTHER INFORMATION: mAb CDRH2

<400> SEQUENCE: 313

Arg Ile Ile Pro Ser Phe Gly Ala Ala Asn Tyr Ala Gln Lys Phe Gln
1               5                   10                  15
Gly

<210> SEQ ID NO 314
<211> LENGTH: 6
<212> TYPE: PRT
<213> ORGANISM: Artificial Sequence
<220> FEATURE:
<223> OTHER INFORMATION: mAb CDRH2

<400> SEQUENCE: 314

Ile Pro Ser Phe Gly Ala
1               5

<210> SEQ ID NO 315
<211> LENGTH: 12
<212> TYPE: PRT
<213> ORGANISM: Artificial Sequence
<220> FEATURE:
<223> OTHER INFORMATION: mAb CDRH3

<400> SEQUENCE: 315

Asp Asp Gly Glu Gly Trp Thr Pro Pro Phe Gly Tyr
1               5                   10

<210> SEQ ID NO 316
<211> LENGTH: 5
<212> TYPE: PRT
<213> ORGANISM: Artificial Sequence
<220> FEATURE:
<223> OTHER INFORMATION: mAb CDRH1

<400> SEQUENCE: 316

Ser Tyr Ala Met Asn
1               5

<210> SEQ ID NO 317
<211> LENGTH: 7
<212> TYPE: PRT
<213> ORGANISM: Artificial Sequence
<220> FEATURE:
<223> OTHER INFORMATION: mAb CDRH1

<400> SEQUENCE: 317

Gly Phe Thr Phe Ser Ser Tyr
1               5

<210> SEQ ID NO 318
<211> LENGTH: 10
<212> TYPE: PRT
<213> ORGANISM: Artificial Sequence
<220> FEATURE:
<223> OTHER INFORMATION: mAb CDRH1

<400> SEQUENCE: 318

Gly Phe Thr Phe Ser Ser Tyr Ala Met Asn
```

```
<210> SEQ ID NO 319
<211> LENGTH: 17
<212> TYPE: PRT
<213> ORGANISM: Artificial Sequence
<220> FEATURE:
<223> OTHER INFORMATION: mAb CDRH2

<400> SEQUENCE: 319

Ser Ile Ser Gly Gly Gly Arg Ser Thr Tyr Tyr Ala Asp Ser Val Lys
1               5                   10                  15
Gly

<210> SEQ ID NO 320
<211> LENGTH: 6
<212> TYPE: PRT
<213> ORGANISM: Artificial Sequence
<220> FEATURE:
<223> OTHER INFORMATION: mAb CDRH2

<400> SEQUENCE: 320

Ser Gly Gly Gly Arg Ser
1               5

<210> SEQ ID NO 321
<211> LENGTH: 15
<212> TYPE: PRT
<213> ORGANISM: Artificial Sequence
<220> FEATURE:
<223> OTHER INFORMATION: mAb CDRH3

<400> SEQUENCE: 321

Asp Leu Ser Pro Ser Asp Val Gly Trp Gly Tyr Gly Phe Asp Ile
1               5                   10                  15

<210> SEQ ID NO 322
<211> LENGTH: 17
<212> TYPE: PRT
<213> ORGANISM: Artificial Sequence
<220> FEATURE:
<223> OTHER INFORMATION: mAb CDRH2

<400> SEQUENCE: 322

Ala Ile Ser Gly Gly Gly Arg Ser Thr Tyr Tyr Ala Asp Ser Val Lys
1               5                   10                  15
Gly

<210> SEQ ID NO 323
<211> LENGTH: 12
<212> TYPE: PRT
<213> ORGANISM: Artificial Sequence
<220> FEATURE:
<223> OTHER INFORMATION: mAb CDRH1

<400> SEQUENCE: 323

Arg Ala Ser Gln Ser Val Ser His Ser Tyr Leu Ala
1               5                   10

<210> SEQ ID NO 324
<211> LENGTH: 7
<212> TYPE: PRT
<213> ORGANISM: Artificial Sequence
<220> FEATURE:
<223> OTHER INFORMATION: mAb CDRH2
```

```
<400> SEQUENCE: 324

Gly Ala Ser Phe Arg Ala Ala
1               5

<210> SEQ ID NO 325
<211> LENGTH: 9
<212> TYPE: PRT
<213> ORGANISM: Artificial Sequence
<220> FEATURE:
<223> OTHER INFORMATION: mAb CDRH3

<400> SEQUENCE: 325

Gln Gln Tyr Gly Ser Glu Pro Tyr Thr
1               5

<210> SEQ ID NO 326
<211> LENGTH: 12
<212> TYPE: PRT
<213> ORGANISM: Artificial Sequence
<220> FEATURE:
<223> OTHER INFORMATION: mAb CDRH1

<400> SEQUENCE: 326

Arg Ala Ser Gln Ser Val Thr Ser Ser Gln Leu Ala
1               5                   10

<210> SEQ ID NO 327
<211> LENGTH: 10
<212> TYPE: PRT
<213> ORGANISM: Artificial Sequence
<220> FEATURE:
<223> OTHER INFORMATION: mAb CDRH3

<400> SEQUENCE: 327

Gln Gln Tyr Gly Ser Ser Leu Leu Ile Thr
1               5                   10

<210> SEQ ID NO 328
<211> LENGTH: 12
<212> TYPE: PRT
<213> ORGANISM: Artificial Sequence
<220> FEATURE:
<223> OTHER INFORMATION: mAb CDRH1

<400> SEQUENCE: 328

Arg Ala Ser Gln Ala Val Asp Ser Ser Asp Leu Ala
1               5                   10

<210> SEQ ID NO 329
<211> LENGTH: 7
<212> TYPE: PRT
<213> ORGANISM: Artificial Sequence
<220> FEATURE:
<223> OTHER INFORMATION: mAb CDRH2

<400> SEQUENCE: 329

Asp Ala Tyr Thr Arg Pro Ser
1               5

<210> SEQ ID NO 330
<211> LENGTH: 9
<212> TYPE: PRT
<213> ORGANISM: Artificial Sequence
<220> FEATURE:
<223> OTHER INFORMATION: mAb CDRH3

<400> SEQUENCE: 330
```

```
Gln Gln Tyr Gly Ser Ser Pro Leu Thr
1               5

<210> SEQ ID NO 331
<211> LENGTH: 11
<212> TYPE: PRT
<213> ORGANISM: Artificial Sequence
<220> FEATURE:
<223> OTHER INFORMATION: mAb CDRH1

<400> SEQUENCE: 331

Arg Ala Ser Gln Ser Val Ser Ser Asn Leu Ala
1               5                   10

<210> SEQ ID NO 332
<211> LENGTH: 7
<212> TYPE: PRT
<213> ORGANISM: Artificial Sequence
<220> FEATURE:
<223> OTHER INFORMATION: mAb CDRH2

<400> SEQUENCE: 332

Asp Ala Tyr Thr Arg Ala Thr
1               5

<210> SEQ ID NO 333
<211> LENGTH: 8
<212> TYPE: PRT
<213> ORGANISM: Artificial Sequence
<220> FEATURE:
<223> OTHER INFORMATION: mAb CDRH3

<400> SEQUENCE: 333

Gln Gln Tyr Gly Ser Pro Tyr Thr
1               5

<210> SEQ ID NO 334
<211> LENGTH: 7
<212> TYPE: PRT
<213> ORGANISM: Artificial Sequence
<220> FEATURE:
<223> OTHER INFORMATION: mAb CDRH2

<400> SEQUENCE: 334

Asp Thr Phe Thr Arg Ala Thr
1               5

<210> SEQ ID NO 335
<211> LENGTH: 9
<212> TYPE: PRT
<213> ORGANISM: Artificial Sequence
<220> FEATURE:
<223> OTHER INFORMATION: mAb CDRH3

<400> SEQUENCE: 335

Gln Gln Tyr Gly Ser Ser Pro Pro Thr
1               5

<210> SEQ ID NO 336
<211> LENGTH: 11
<212> TYPE: PRT
<213> ORGANISM: Artificial Sequence
<220> FEATURE:
<223> OTHER INFORMATION: mAb CDRH1

<400> SEQUENCE: 336
```

Arg Ala Ser Gln Asp Val Ser Asp Leu Leu Ala
1               5                   10

<210> SEQ ID NO 337
<211> LENGTH: 9
<212> TYPE: PRT
<213> ORGANISM: Artificial Sequence
<220> FEATURE:
<223> OTHER INFORMATION: mAb CDRH3

<400> SEQUENCE: 337

Gln Gln Tyr Ala Ser Ser Pro Ile Thr
1               5

<210> SEQ ID NO 338
<211> LENGTH: 11
<212> TYPE: PRT
<213> ORGANISM: Artificial Sequence
<220> FEATURE:
<223> OTHER INFORMATION: mAb CDRH1

<400> SEQUENCE: 338

Arg Ala Ser Gln Lys Val Ser Asp Leu Leu Ala
1               5                   10

<210> SEQ ID NO 339
<211> LENGTH: 9
<212> TYPE: PRT
<213> ORGANISM: Artificial Sequence
<220> FEATURE:
<223> OTHER INFORMATION: mAb CDRH3

<400> SEQUENCE: 339

Gln Gln Tyr Thr Gly Ser Pro Ile Thr
1               5

<210> SEQ ID NO 340
<211> LENGTH: 11
<212> TYPE: PRT
<213> ORGANISM: Artificial Sequence
<220> FEATURE:
<223> OTHER INFORMATION: mAb CDRH1

<400> SEQUENCE: 340

Arg Ala Ser Leu Ser Val Ser Asp Leu Leu Ala
1               5                   10

<210> SEQ ID NO 341
<211> LENGTH: 7
<212> TYPE: PRT
<213> ORGANISM: Artificial Sequence
<220> FEATURE:
<223> OTHER INFORMATION: mAb CDRH2

<400> SEQUENCE: 341

Asp Ala Tyr Ser Arg Ala Thr
1               5

<210> SEQ ID NO 342
<211> LENGTH: 9
<212> TYPE: PRT
<213> ORGANISM: Artificial Sequence
<220> FEATURE:
<223> OTHER INFORMATION: mAb CDRH3

<400> SEQUENCE: 342

Gln Gln Tyr Ser Ser Asn Pro Ile Thr

```
1               5

<210> SEQ ID NO 343
<211> LENGTH: 11
<212> TYPE: PRT
<213> ORGANISM: Artificial Sequence
<220> FEATURE:
<223> OTHER INFORMATION: mAb CDRH1

<400> SEQUENCE: 343

Arg Ala Ser Gly Ser Val Ser Asp Leu Leu Ala
1               5                   10

<210> SEQ ID NO 344
<211> LENGTH: 9
<212> TYPE: PRT
<213> ORGANISM: Artificial Sequence
<220> FEATURE:
<223> OTHER INFORMATION: mAb CDRH3

<400> SEQUENCE: 344

Gln Gln Tyr Ala Ser Tyr Pro Ile Thr
1               5

<210> SEQ ID NO 345
<211> LENGTH: 11
<212> TYPE: PRT
<213> ORGANISM: Artificial Sequence
<220> FEATURE:
<223> OTHER INFORMATION: mAb CDRH1

<400> SEQUENCE: 345

Arg Ala Ser Gln Ser Val Ser Asp Leu Leu Ala
1               5                   10

<210> SEQ ID NO 346
<211> LENGTH: 7
<212> TYPE: PRT
<213> ORGANISM: Artificial Sequence
<220> FEATURE:
<223> OTHER INFORMATION: mAb CDRH2

<400> SEQUENCE: 346

Asp Ala Phe Ser Arg Ala Thr
1               5

<210> SEQ ID NO 347
<211> LENGTH: 9
<212> TYPE: PRT
<213> ORGANISM: Artificial Sequence
<220> FEATURE:
<223> OTHER INFORMATION: mAb CDRH3

<400> SEQUENCE: 347

Gln Gln Tyr Gly Thr Pro Pro Ile Thr
1               5

<210> SEQ ID NO 348
<211> LENGTH: 11
<212> TYPE: PRT
<213> ORGANISM: Artificial Sequence
<220> FEATURE:
<223> OTHER INFORMATION: mAb CDRH1

<400> SEQUENCE: 348

Arg Ala Ser Glu Ser Val Ser Asp Leu Leu Ala
1               5                   10
```

```
<210> SEQ ID NO 349
<211> LENGTH: 9
<212> TYPE: PRT
<213> ORGANISM: Artificial Sequence
<220> FEATURE:
<223> OTHER INFORMATION: mAb CDRH3

<400> SEQUENCE: 349

Gln Gln Tyr Ser Ala Ser Pro Ile Thr
1               5

<210> SEQ ID NO 350
<211> LENGTH: 11
<212> TYPE: PRT
<213> ORGANISM: Artificial Sequence
<220> FEATURE:
<223> OTHER INFORMATION: mAb CDRH1

<400> SEQUENCE: 350

Arg Ala Ser Gln Ser Val Ser Ser Leu Leu Ala
1               5                   10

<210> SEQ ID NO 351
<211> LENGTH: 5
<212> TYPE: PRT
<213> ORGANISM: Artificial Sequence
<220> FEATURE:
<223> OTHER INFORMATION: linker peptide

<400> SEQUENCE: 351

Ser Gly Gly Gly Gly
1               5

<210> SEQ ID NO 352
<211> LENGTH: 5
<212> TYPE: PRT
<213> ORGANISM: Artificial Sequence
<220> FEATURE:
<223> OTHER INFORMATION: linker peptide

<400> SEQUENCE: 352

Gly Gly Gly Gly Ser
1               5

<210> SEQ ID NO 353
<211> LENGTH: 6
<212> TYPE: PRT
<213> ORGANISM: Artificial Sequence
<220> FEATURE:
<223> OTHER INFORMATION: linker peptide

<400> SEQUENCE: 353

Ser Gly Gly Gly Gly Ser
1               5
```